(12) United States Patent
Tomigahara et al.

(10) Patent No.: US 7,691,883 B2
(45) Date of Patent: Apr. 6, 2010

(54) CINNAMOYL COMPOUND AND USE OF THE SAME

(75) Inventors: Yoshitaka Tomigahara, Toyonaka (JP); Kiyoshi Higashi, Osaka (JP); Junya Takahashi, Kawabe-gun (JP); Chizuko Takahashi, Osaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 649 days.

(21) Appl. No.: 10/572,639

(22) PCT Filed: Sep. 16, 2004

(86) PCT No.: PCT/JP2004/013987

§ 371 (c)(1),
(2), (4) Date: Mar. 17, 2006

(87) PCT Pub. No.: WO2005/028463

PCT Pub. Date: Mar. 31, 2005

(65) Prior Publication Data

US 2007/0265228 A1    Nov. 15, 2007

(30) Foreign Application Priority Data

Sep. 17, 2003  (JP)  ............... 2003-324149
Sep. 17, 2003  (JP)  ............... 2003-324153

(51) Int. Cl.
*A61K 31/44*  (2006.01)
*A61K 31/366*  (2006.01)
*C07D 309/38*  (2006.01)
*C07D 405/12*  (2006.01)

(52) U.S. Cl. .............. 514/336; 514/459; 546/282.1; 549/291

(58) Field of Classification Search ......... 514/336, 514/459; 546/282.1; 549/291
See application file for complete search history.

(56) References Cited

U.S. PATENT DOCUMENTS

2006/0211680 A1   9/2006  Tomigahara et al.

FOREIGN PATENT DOCUMENTS

| DE | 2728243 A | * | 1/1979 |
| JP | 41-1412 B | * | 2/1966 |
| WO | WO 97/35565 A1 | * | 10/1997 |
| WO | WO 01/28493 A2 | * | 4/2001 |
| WO | 2004/056365 | | 7/2004 |
| WO | 2005/028439 | | 3/2005 |

OTHER PUBLICATIONS

* Cited in the ISR of priority document.*
Supplementary European Search Report issued Mar. 4, 2009 in corresponding European Application No. 04 77 3377.
J. Shiue et al., "Phenyl-Carbonyl Coupling Reactions Promoted by Samarium Diiodide and Hexamethylphosphoramide," Journal of Organic Chemistry (1997), vol. 62, No. 14, pp. 4643-4649.
J. Breitenbucher et al., "Solid-phase synthesis of 4-aryl-1,4-dihydropyridines via the Hantzsch three component condensation," Tetrahedron Letters (2000), vol. 41, pp. 4311-4315.

* cited by examiner

*Primary Examiner*—Taofiq A Solola
(74) *Attorney, Agent, or Firm*—Wenderoth, Lind & Ponack, LLP.

(57) ABSTRACT

The present invention relates to a cinnamoyl compound represented by the formula (I):

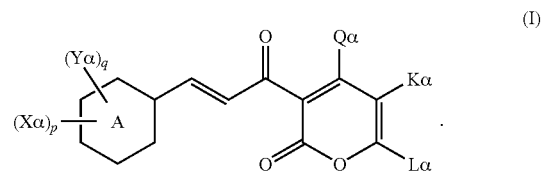

27 Claims, No Drawings

US 7,691,883 B2

CINNAMOYL COMPOUND AND USE OF THE SAME

This application is a U.S. national stage of International Application No. PCT/JP2004/013987 filed Sep. 16, 2004.

TECHNICAL FIELD

The present invention relates to a cinnamoyl compound and use of the same.

BACKGROUND ART

In diseases and disorders such as hepatic cirrhosis, interstitial pulmonary disease, chronic renal failure (or disease resulting in chronic renal failure), hyperplasia scar after inflammation, postoperative scars or burn scars, scleroderma, arteriosclerosis, hypertension and the like, excessive accumulation of an extracellular matrix, a representative of which is collagen, causes fibrosis and sclerosis of tissues, resulting in decreased functions, cicatrization and the like in the organs or tissues. Such excessive accumulation of an extracellular matrix is induced by increased production of collagen due to a breakdown of balance between biosynthesis and degradation of collagen and the like. In fact, it has been observed that expression of a collagen gene, in particular, a Type I collagen gene has been increased in a fibrotic tissue [e.g. J. Invest. Dermatol., 94, 365, (1990) and Proc. Natl. Acad. Sci. USA, 88, 6642, (1991)]. It has been also observed that the amount of TGF-β, which is a cytokine, has been increased in a fibrotic tissue [e.g. J. Invest. Dermatol., 94, 365, (1990) and Proc. Natl. Acad. Sci. USA, 88, 6642, (1991)]. It has been shown that TGF-β has increased expression of a Type I collagen gene and been involved in increased production of collagen and, consequently, fibrosis of a tissue [e.g. Lab. Invest., 63, 171, (1990) and J. Invest. Dermatol., 94, 365, (1990)]. It has been also shown that by administering an anti-TGF-β antibody or a soluble anti-TGF-β receptor to a model animal of tissue fibrosis, improvement of tissue fibrosis has been achieved and thereby the tissue function has been also improved [e.g. Diabetes, 45, 522-530, (1996), Proc. Natl. Acad. Sci. USA, 96, 12719-12724, (1999) and Proc. Natl. Acad. Sci. USA, 97, 8015-8020, (2000)]. It has been also known that by administering a compound which suppressively acts on intracellular signal transduction via TGF-β, improvement in fibrosis of a tissue has been achieved and thereby the tissue function has been also improved [e.g. Autoimmunity, 35, 277-282, (2002), J. Hepatol., 37, 331-339, (2002) and Life Sci., 71, 1559-1606, (2002)].

Thus, there is a need for development and provision of a drug which improves fibrosis of a tissue by decreasing expression of a Type I collagen gene in the tissue to reduce accumulation of collagen (i.e. a collagen accumulation-suppressing agent and a fibrosing disease-treating agent).

DISCLOSURE OF THE INVENTION

Under these circumstances, the present inventors have studied intensively and, as a result, found out that compounds represented by the following formulas (I) to (XXXVIII) have the ability to suppress transcription of I type collagen gene. Thus, the present invention has been completed.

That is, the present invention provides:

1. A cinnamoyl compound represented by the formula (I):

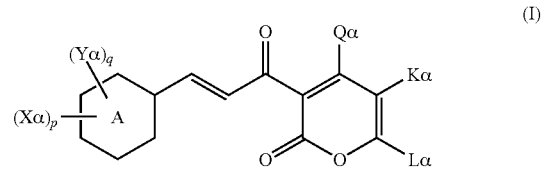

wherein

I. A represents a benzene ring or a pyridine ring; and in $(Y_\alpha)_q$, $Y_\alpha$ is a substituent on a carbon atom and represents a group included in the following $X_0$ group or $Y_0$ group, q represents 0, 1, 2, 3 or 4, and $Y_\alpha$s are the same or different when q is 2 or more and the adjacent two same or different $Y_\alpha$s together may form a group included in the $Z_0$ group to be fused to the A ring when q is 2 or more; and in $(X_\alpha)_p$, $X_\alpha$ represents a substituent on a carbon atom which does not belong to the following $X_0$ group, $Y_0$ group and $Z_0$ group, p represents 1, 2, 3, 4 or 5, and $X_\alpha$s may be the same or different when p is 2 or more; and the sum of p and q is 5 or less;

(1) the $X_0$ group: a $M_a$-group, wherein $M_a$ represents a $R_b$-group (wherein $R_b$ represents a C1-C10 alkyl group optionally substituted with a halogen atom), a halogen atom, a nitro group, a cyano group, a hydroxy group, a $R_c$—$B_a$—$R_d$- group (wherein $R_c$ represents a C1-C10 alkyl group optionally substituted with a halogen atom, $B_a$ represents an oxy group, a thio group, a sulfinyl group or a sulfonyl group, and $R_d$ represents a single bond or a C1-C10 alkylene group), a HO$R_d$- group (wherein $R_d$ is as defined above), a $R_e$—CO—$R_d$- group (wherein $R_e$ represents a hydrogen atom, or a C1-C10 alkyl group optionally substituted with a halogen atom, and $R_d$ is as defined above), a $R_e$—CO—O—$R_d$- group (wherein $R_e$ and $R_d$ are as defined above), a $R_e$O—CO—$R_d$- group (wherein $R_e$ and $R_d$ are as defined above), a HO—CO—CH=CH— group, a $R_e R_e'$N—$R_d$- group (wherein $R_e$ and $R_e'$ are the same or different, $R_e$ is as defined above, $R_e'$ has the same meaning as $R_e$ has, and $R_d$ is as defined above), a $R_e$—CO—N$R_e'$—$R_d$- group (wherein $R_e$, $R_e'$ and $R_d$ are as defined above), a $R_b$O—CO—N($R_e$)—$R_d$- group (wherein $R_b$, $R_e$ and $R_d$ are as defined above), a $R_e R_e'$N—CO—$R_d$- group (wherein $R_e$, $R_e'$ and $R_d$ are as defined above), a $R_e R_e'$N—CO—N$R_e''$—$R_d$- group (wherein $R_e$, $R_e'$ and $R_e''$ are the same or different, $R_e$ and $R_e'$ are as defined above, $R_e''$ has the same meaning as $R_e$ has, and $R_d$ is as defined above), a $R_e R_e'$N—C(=N$R_e''$)—N$R_e'''$—$R_d$- group (wherein $R_e$, $R_e'$, $R_e''$ and $R_e'''$ are the same or different, $R_e$, $R_e'$ and $R_e''$ are as defined above, $R_e'''$ has the same meaning as $R_e$ has, and $R_d$ is as defined above), a $R_b$—SO$_2$—N$R_e$—$R_d$- group (wherein $R_b$, $R_e$ and $R_d$ are as defined above), a $R_e R_e'$N—SO$_2$—$R_d$- group (wherein $R_e$, $R_e'$ and $R_d$ are as defined above), a C2-C10 alkenyl group or a C2-C10 alkynyl group;

(2) the $Y_0$ group: a $M_{b0}$-$R_d$- group, wherein $M_{b0}$ represents a $M_{c0}$- group

[wherein $M_{co}$ represents a $M_{do}$-$R_d'$- group [wherein $M_{do}$ represents a 6 to 10-membered aryl group optionally substituted with a $M_a$- group (wherein $M_a$ is as defined above), a 5 to 10-membered heteroaryl group optionally substituted with a $M_a$-group (wherein $M_a$ is as defined above), a 3 to 10-membered cyclic hydrocarbon or heterocyclic group optionally substituted with a $M_a$- group (wherein $M_a$ is as defined above) and optionally containing an unsaturated bond, a ($b_0$)- group

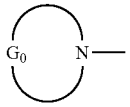

($b_0$)

(in the ($b_0$)- group, $G_0$ forms an optionally substituted, saturated or unsaturated, nonaromatic 5 to 14-membered cyclic hydrocarbon or heterocyclic ring), a ($c_0$)- group

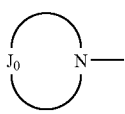

($c_0$)

(in the ($C_0$)- group, $J_0$ forms a 5 to 7-membered aromatic ring optionally containing a nitrogen atom), a ($d_0$)- group

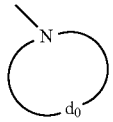

($d_0$)

[wherein $d_0$ forms a 5 to 12-membered hydrocarbon ring which is substituted with a carbonyl group or a thiocarbonyl group and further which may be optionally substituted with an oxy group, a thio group, a —$NR_1$- group {wherein $R_1$ represents a hydrogen atom, a C1-C10 alkyl group, a C2-C10 alkyl group substituted with a halogen atom or a $R_2$—$B_1$— group (wherein $R_2$ represents a C1-C10 alkyl group, a C3-C10 alkenyl group or a C3-C10 alkynyl group, and $B_1$ represents an oxy group, a thio group, a sulfinyl group or a sulfonyl group), a C3-C10 alkenyl group, or a C3-C10 alkynyl group}, a sulfinyl group or a sulfonyl group] or a ($e_0$)- group

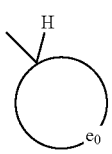

($e_0$)

{wherein $e_0$ forms a 5 to 12-membered hydrocarbon ring optionally substituted with a carbonyl group, a thiocarbonyl group, an oxy group, a thio group, a —$NR_1$— group (wherein $R_1$ is as defined above), a sulfinyl group or a sulfonyl group}; and $R_d'$ is the same as or different from $R_d$ and has the same meaning as $R_d$ has]],
a $M_{c0}$-$B_a$- group (wherein $M_{c0}$ and $B_a$ are as defined above), a $M_{c0}$-CO- group (wherein $M_{c0}$ is as defined above), a $M_{c0}$-CO—O— group (wherein $M_{c0}$ is as defined above), a $M_{c0}$O—CO- group (wherein $M_{c0}$ is as defined above), a $M_{c0}R_eN$- group (wherein $M_{c0}$ and $R_e$ are as defined above),
a $M_{c0}$-CO—$NR_e$- group (wherein $M_{c0}$ and $R_e$ are as defined above), a $M_{c0}$O—CO—$NR_e$— group (wherein $M_{c0}$ and $R_e$ are as defined above), a $M_{c0}R_eN$—CO— group (wherein $M_{c0}$ and $R_e$ are as defined above), a $M_{c0}R_eN$—CO—$NR_e'$- group (wherein $M_{c0}$, $R_e$ and $R_e'$ are as defined above), a $M_{c0}R_eN$—C(=$NR_e'$)—$NR_e''$- group (wherein $M_{c0}$, $R_e$, $R_e'$ and $R_e''$ are as defined above), a $M_{c0}$-$SO_2$—$NR_e$- group (wherein $M_{c0}$ and $R_e$ are as defined above) or a $M_{c0}R_eN$—$SO_2$- group (wherein $M_{c0}$ and $R_e$ are as defined above), and
$R_d$ is as defined above;
(3) the $Z_0$ group: a 5 to 12-membered cyclic hydrocarbon or heterocyclic ring optionally substituted with a halogen atom, a C1-C10 alkoxy group, a C3-C10 alkenyloxy group, a C3-C10 alkynyloxy group, a carbonyl group, a thiocarbonyl group, an oxy group, a thio group, a sulfinyl group or a sulfonyl group, which is an aromatic or nonaromatic and monocyclic or fused ring and which is fused to the A ring;
II. $Q_\alpha$ represents an optionally substituted hydroxy group, or an optionally substituted amino group;
III. $K_\alpha$ and $L_\alpha$ are the same or different, and represent a hydrogen atom, or a substituent on a carbon atom, or $K_\alpha$ and $L_\alpha$ may form a C1-C10 alkylene group optionally having a substituent or a C1-C10 alkenylene group optionally having a substituent; and
the term "as defined above" used for the same symbols among plural substituents means that the plural substituents independently represent the same meaning as that described above and, among the plural substituents, although the selection range of substituents to be selected is the same, selected substituents may be the same or different as long as they are selected within the range;

2. A cinnamoyl compound represented by the formula (II):

(II)

wherein
I. A represents a benzene ring or a pyridine ring;
II. in $(X_{A0})_p$, $X_{A0}$ is a substituent on a carbon atom and represents a group included in any group of the following $A_0$ to $N_0$ groups, p represents 1, 2, 3, 4 or 5, and when p is 2 or more, $X_{A0}$s are the same or different;
(1) the $A_0$ group:
a $D_1$-$R_4$- group [wherein $D_1$ represents a ($R_1$—(O)$_k$—) $A_1N$—(O)$_k$- group [wherein $R_1$ represents a hydrogen atom, or a C1-C10 alkyl group, or a C2-C10 alkyl group substituted with a halogen atom or a $R_2$—$B_1$-group (wherein $R_2$ represents a C1-C10 alkyl group, a C3-C10 alkenyl group or a C3-C10 alkynyl group, and $B_1$ represents an oxy group, a thio group, a sulfinyl group or a sulfonyl group), or a C3-C10 alkenyl group, or a C3-C10 alkynyl group, k represents 0 or 1, $A_1$ represents a $R_3$—(CHR$_0$)$_m$—($B_2$—$B_3$)$_{m'}$- group {wherein $R_3$ represents a hydrogen atom, or a C1-C10 alkyl group optionally substituted with a halogen atom or a $R_2$—$B_1$— group (wherein $R_2$ and $B_1$ are as defined above), or a C2-C10 alkenyl group, or a C2-C10 alkynyl group, $R_0$ represents a hydrogen atom, a C1-C10 alkyl group or a C2-C10 haloalkyl group, m represents 0 or 1, $B_2$ represents a single bond, an oxy group, a thio group or a —N((O)$_n$$R_1'$)- group (wherein $R_1'$ is the same as or different from $R_1$, and has the same meaning as $R_1$ has, and n represents 0 or 1), $B_3$ represents a carbonyl group, a thiocarbonyl group or a sulfonyl group, m' represents 0 or 1, and when $B_3$ is a sulfonyl group, it does not occur that m is 0 and $R_3$ is a hydrogen atom at the same time}, and k' represents 0 or 1], and $R_4$ represents a C1-C10 alkylene group, provided that a $R_0'R_0''N$—$R_4$- group (wherein $R_0'$ and $R_0''$ are the same as or different from $R_0$ and have the same meaning as $R_0$ has, and $R_4$ is as defined above) is excluded], a $D_2$-$R_4$- group [wherein $D_2$ represents a cyano group, a $R_1R_1'NC(=N-(O)_n-A_1)$- group (wherein $R_1$, $R_1'$, n and $A_1$ are as defined above), an $A_1N=C(-OR_2)$- group (wherein $A_1$ and $R_2$ are as defined above) or a $NH_2$—CS- group, and $R_4$ is as defined above], a $D_3$-$R_4$- group [wherein $D_3$ represents a nitro group or a $R_1OSO_2$- group (wherein $R_1$ is as defined above), and $R_4$ is as defined above], or a $R_1OSO_2$- group [wherein $R_1$ is as defined above];

(2) the $B_0$ group: an $(a_0)$- group (a₀)

in the $(a_0)$- group, $E_0$ forms an optionally substituted, saturated or unsaturated, aromatic or nonaromatic 5 to 14-membered cyclic hydrocarbon or heterocyclic ring, and $R_1$ is as defined above;

(3) the $C_0$ group: a C2-C10 alkenyl group substituted with a halogen atom, a $R_2$—$B_1$- group (wherein $R_2$ and $B_1$ are as defined above), a $D_4$-$R_4$- group [wherein $D_4$ represents a hydroxy group or an $A_1$-O- group (wherein $A_1$ is as defined above), and $R_4$ is as defined above], a $D_5$- group [wherein $D_5$ represents a $O=C(R_3)$- group (wherein $R_3$ is as defined above), an $A_1$-$(O)_n$—$N=C(R_3)$- group (wherein $A_1$, n and $R_3$ are as defined above), a $R_1$—$B_0$—CO—$R_4$—$(O)_n$—$N=C(R_3)$- group {wherein $R_1$, $R_4$, n and $R_3$ are as defined above, and $B_0$ represents an oxy group, a thio group or a —N$((O)_m R_1')$— group (wherein $R_1'$ and m are as defined above)}, a $D_2$-$R_4$—$(O)_n$—$N=C(R_3)$- group (wherein $D_2$, $R_4$, n and $R_3$ are as defined above) or a $R_1A_1N$—$N=C(R_3)$- group (wherein $R_1$, $A_1$ and $R_3$ are as defined above)], a $R_1A_1N$—O—$R_4$- group (wherein $R_1$, $A_1$ and $R_4$ are as defined above), a $R_1(A_1-(O)_n-)N$- group (wherein $R_1$, $A_1$ and n are as defined above), a $D_2$- group (wherein $D_2$ is as defined above) or a $D_3$- group (wherein $D_3$ is as defined above);

(4) the $D_0$ group: a C2-C10 alkynyl group substituted with a $(b_0)$-$R_4$- group (in $(b_0)$ (b₀)

$G_0$ forms an optionally substituted, saturated or unsaturated, nonaromatic 5 to 14-membered cyclic hydrocarbon or heterocyclic ring), a $(c_0)$-$R_4$- group (in $(c_0)$ (c₀)

$J_0$ forms an aromatic 5 to 7-membered ring optionally containing a nitrogen atom and $R_4$ is as defined above), a halogen atom, a $R_2$—$B_1$—$R_4$- group (wherein $R_2$, $B_1$ and $R_4$ are as defined above), a $D_4$-$R_4$- group (wherein $D_4$ and $R_4$ are as defined above), a $D_5$- group (wherein $D_5$ is as defined above), a $D_1$-$R_4$- group (wherein $D_1$ and $R_4$ are as defined above), a $D_2$- group (wherein $D_2$ is as defined above) or a $D_3$-$R_4$- group (wherein $D_3$ and $R_4$ are as defined above);

(5) the $E_0$ group: an $A_2$-CO—$R_5$- group, provided that $R_5$ is not a vinylene group when $A_2$ is a hydroxy group, wherein $A_2$ represents (i) an $A_3$-$B_4$- group wherein $A_3$ represents a hydrogen atom, or a C1-C10 alkyl group, or a C2-C10 haloalkyl group, or a C2-C10 alkenyl group optionally substituted with a halogen atom, or a C3-C10 alkynyl group optionally substituted with a halogen atom, or a $R_{a0}$—$(R_4)_m$- group (wherein $R_{a0}$ represents an optionally substituted 5 to 7-membered aryl group or heteroaryl group, and $R_4$ and m are as defined above), or a C1-C10 alkyl group substituted with a $(b_0)$-$R_4$- group (wherein $(b_0)$ and $R_4$ are as defined above), a $(c_0)$-$R_4$- group (wherein $(c_0)$ and $R_4$ are as defined above), a $R_2$—$B_1$—$R_4$- group (wherein $R_2$, $B_1$ and $R_4$ are as defined above), a $D_4$-$R_4$- group (wherein $D_4$ and $R_4$ are as defined above), a $D_5$- group (wherein $D_5$ is as defined above), a $D_1$-$R_4$- group (wherein $D_1$ and $R_4$ are as defined above), a $D_2$- group (wherein $D_2$ is as defined above), a $D_3$-$R_4$- group (wherein $D_3$ and $R_4$ are as defined above) or an $A_4$-$SO_2$—$R_4$- group {wherein $A_4$ represents a $(b_0)$- group (wherein $(b_0)$ is as defined above), a $(c_0)$- group (wherein $(c_0)$ is as defined above) or a $R_1R_1'N$- group (wherein $R_1$ and $R_1'$ are as defined above), and $R_4$ is as defined above}, and $B_4$ represents an oxy group, a thio group or a —N$((O)_m R_1)$- group (wherein $R_1$ and m are as defined above), provided that $A_3$ is not a hydrogen atom when $B_4$ is a thio group;

(ii) a $R_1$—$B_4$—CO—$R_4$—$B_4'$- group, wherein $R_1$, $B_4$ and $R_4$ are as defined above, $B_4'$ is the same as or different from $B_4$ and has the same meaning as $B_4$ has, provided that $R_2$ is not a hydrogen atom when $B_4$ is a thio group, or a $D_2$-$R_4$—$B_4$- group, wherein $D_2$, $R_4$ and $B_4$ are as defined above;

(iii) a $R_2$—$SO_2$—$NR_1$- group, wherein $R_2$ is as defined above, provided that a hydrogen atom is excluded, and $R_1$ is as defined above;

(iv) a $(b_0)$- group, wherein $(b_0)$ is as defined above;

(v) a $(c_0)$- group, wherein $(c_0)$ is as defined above; or (vi) a $R_1A_1N$—$NR_1'$- group, wherein $R_1$, $A_1$ and $R_1'$ are as defined above; and $R_5$ represents a C2-C10 alkenylene group optionally substituted with a halogen atom or a C2-C10 alkynylene group;

(6) the $F_0$ group: an $A_5$-$B_5$—$R_6$- group wherein $A_5$ represents a C2-C10 alkyl group substituted with a $D_4$- group (wherein $D_4$ is as defined above), a $D_1$- group (wherein $D_1$ is as defined above), a $D_3$- group (wherein $D_3$ is as defined above) or an $A_4$-$SO_2$- group (wherein $A_4$ is as defined above), or a C1-C10 alkyl group substituted with a $R_2$—$B_1$- group (wherein $R_2$ and $B_1$ are as defined above), a $D_2$- group (wherein $D_2$ is as defined above), a $D_5$- group (wherein $D_5$ is as defined above) or an $A_2$-CO- group (wherein $A_2$ is as defined above), $B_5$ represents a $B_1$- group (wherein $B_1$ is as defined above) or a —$NA_1$- group (wherein $A_1$ is as defined above), and $R_6$ represents a single bond or a C1-C10 alkylene group;

(7) the $G_0$ group: an $A_6$-$B_5$—$R_6$- group wherein $A_6$ represents an $(a_0)$-$R_4$- group (wherein $(a_0)$ and $R_4$ are as defined above), or a C2-C10 alkenyl group, or a C2-C10 alkynyl group, or a C2-C10 alkenyl group substituted with a halogen atom, a $R_2$—$B_1$- group (wherein $R_2$ and $B_1$ are as defined above), a $D_5$- group (wherein $D_5$ is as defined above), a $D_2$- group (wherein $D_2$ is as defined above) or an $A_2$-CO- group (wherein $A_2$ is as defined above), or a C2-C10 alkynyl group substituted with a halogen atom, a $R_2$—$B_1$- group (wherein $R_2$ and $B_1$ are as defined above), a $D_5$- group (wherein $D_5$ is as defined above), $D_2$- group (wherein $D_2$ is as defined above) or an $A_2$-CO- group (wherein $A_2$ is as defined above), or a C3-C10 alkenyl group substituted with a $(b_0)$- group (wherein $(b_0)$ is as defined above), a $(c_0)$- group (wherein $(c_0)$ is as defined above), a $D_4$- group (wherein $D_4$ is as defined above), a $D_1$- group (wherein $D_1$ is as defined above) or a $D_3$- group (wherein $D_3$ is as defined above), or a C3-C10 alkynyl group substituted with a $D_4$- group (wherein $D_4$ is as defined above), a $D_1$- group (wherein $D_1$ is as defined above) or a $D_3$- group (wherein $D_3$ is as defined above), and $B_5$ and $R_6$ are as defined above;

(8) the $H_0$ group:

a $D_2$-N(—$(O)_n$-$A_1$)-$R_6$- group (wherein $D_2$, n, $A_1$ and $R_6$ are as defined above), a $D_2$- group (wherein $D_2$ is as defined above, provided that a cyano group is excluded), a $R_1(R_1'(O)_n)N$—$CR_1''$=N—$R_6$- group (wherein $R_1$, $R_1'$, n and $R_6$ are as defined above, $R_1''$ is the same as or different from $R_1$ and has the same meaning as that of $R_1$), a $R_1$—$(O)_n$—N=$CR_1'$—$NR_2$—$R_6$- group (wherein $R_1$, n, $R_1'$, $R_2$ and $R_6$ are as defined above), a $R_2$—$B_3$—$NR_1$—CO—$NR_1'$—$R_6$- group (wherein $R_2$, $B_3$, $R_1$, $R_1'$ and $R_6$ are as defined above), a $D_2$-CO—$NR_1$—$R_6$- group (wherein $D_2$, $R_1$ and $R_6$ are as defined above) or an $A_2$-COCO—$NR_1$—$R_6$- group (wherein $A_2$, $R_1$ and $R_6$ are as defined above);

(9) the $I_0$ group:

an $A_7$-$B_6$—N$((O)_n R_1)$—$R_6$- group [wherein $A_7$ represents a C2-C10 alkenyl group optionally substituted with a halogen atom, or a C2-C10 alkynyl group, or a C3-C10 haloalkynyl group, or a $R_2$—$B_1$—$R_4$- group (wherein $R_2$, $B_1$ and $R_4$ are as defined above), or a $D_4$-$R_4$- group (wherein $D_4$ and $R_4$ are as defined above), or a $D_5$-$R_4$- group (wherein $D_5$ and $R_4$ are as defined above), or a $D_1$-$R_4$- group (wherein $D_1$ and $R_4$ are as defined above), or a $(b_0)$-$R_4$- group (wherein $(b_0)$ and $R_4$ are as defined above), or a $(c_0)$-$R_4$- group (wherein $(c_0)$ and $R_4$ are as defined above), or a $D_2$-$R_4$- group (wherein $D_2$ and $R_4$ are as defined above), or a $D_3$-$R_4$- group (wherein $D_3$ and $R_4$ are as defined above), or an $A_4$-$SO_2$—$R_4$- group (wherein $A_4$ and $R_4$ are as defined above), or an $A_2$-CO—$R_4$- group (wherein $A_2$ and $R_4$ are as defined above), $B_6$ represents a carbonyl group or a thiocarbonyl group, and n, $R_1$ and $R_6$ are as defined above], an $A_8$-CS—N$((O)_n R_1)$—$R_6$- group [wherein $A_8$ represents a hydrogen atom or a C1-C10 alkyl group optionally substituted with a halogen atom, and n, $R_1$ and $R_4$ are as defined above], an $A_7'$-$B_2'$—$B_3$—N$((O)_n R_1)$—$R_6$- group [wherein $A_7'$ represents a C3-C10 alkenyl group optionally substituted with a halogen atom, or a C3-C10 alkynyl group optionally substituted with a halogen atom, or a $R_2$—$B_1$—$R_4'$- group (wherein $R_2$ and $B_1$ are as defined above, and $R_4'$ represents a C2-C10 alkylene group), or a $D_4$-$R_4'$- group (wherein $D_4$ and $R_4'$ are as defined above), or a $D_1$-$R_4'$- group (wherein $D_1$ and $R_4'$ are as defined above), or a $(b_0)$-$R_4'$- group (wherein $(b_0)$ and $R_4'$ are as defined above), or a $(c_0)$-$R_4'$- group (wherein $(c_0)$ and $R_4'$ are as defined above), or a $D_2$-$R_4$— group (wherein $D_2$ and $R_4$ are as defined above), or a $D_3$-$R_4'$- group (wherein $D_3$ and $R_4'$ are as defined above), or an $A_2$-CO—$R_4$- group (wherein $A_2$ and $R_4$ are as defined above), $B_2'$ represents an oxy group, a thio group or a —N$((O)_{n'} R_1')$- group (wherein n' is the same as or different from n and has the same meaning as that of n, and $R_1'$ is as defined above), and $B_3$, n, $R_1$ and $R_6$ are as defined above], an $A_8'$-$B_2'$—CS—N$((O)_n R_1)$—$R_6$- group [wherein $A_8'$ represents a C1-C10 alkyl group or a C2-C10 haloalkyl group, $B_2'$ is as defined above, and n, $R_1$ and $R_6$ are as defined above], an $A_8'$-S—$B_3'$—N$((O)_n R_1)$—$R_6$- group [wherein $A_8'$, n, $R_1$ and $R_6$ are as defined above, and $B_3'$ represents a carbonyl group or a sulfonyl group] or an $A_7''$-$SO_2$—N$((O)_n R_1)$—$R_6$- group [wherein $A_7''$ represents a C2-C10 alkenyl group, or a C3-C10 alkenyl group substituted with a halogen atom, or a C3-C10 alkynyl group optionally substituted with a halogen atom, or a $R_2$—$B_1$—$R_4'$- group (wherein $R_2$, $B_1$ and $R_4'$ are as defined above), or a $D_4$-$R_4'$- group (wherein $D_4$ and $R_4'$ are as defined above), or a $D_5$-$R_4'$- group (wherein $D_5$ and $R_4$ are as defined above), or a $D_1$-$R_4'$- group (wherein $D_1$ and $R_4'$ are as defined above), or a $(b_0)$-$R_4'$- group (wherein $(b_0)$ and $R_4'$ are as defined above), or a $(c_0)$-$R_4'$- group (wherein $(c_0)$ and $R_4'$ are as defined above), or a $D_2$-$R_4$- group (wherein $D_2$ and $R_4$ are as defined above), or a $NO_2$—$R_4$- group (wherein $R_4$ is as defined above), or an $A_2$-CO—$R_4$- group (wherein $A_2$ and $R_4$ are as defined above), and n, $R_1$ and $R_6$ are as defined above];

(10) the $J_0$ group:

an $A_7$-CO- group (wherein $A_7$ is as defined above), an $A_9$-CS- group (wherein $A_9$ represents $A_7$ or $A_8$), an $A_9'(O)_m N=C(A_9)$- group (wherein $A_9'$ represents $A_7'$ or $A_8'$, and m and $A_9$ are as defined above), a $D_2$-CO- group (wherein $D_2$ is as defined above), an $A_2$-COCO- group (wherein $A_2$ is as defined above), an $A_9$-CO—$B_1'$—$R_6$- group (wherein $A_9$ and $R_6$ are as defined above, and $B_1'$ represents an oxy group or a thio group, provided that $A_9$ is not $A_8$ when $B_1'$ is an oxy group), an $A_9$-CS—$B_1'$—$R_6$- group (wherein $A_9$, $B_1'$ and $R_6$ are as defined above), an $A_7''$-$SO_2$—$B_1'$—$R_6$- group (wherein $A_7''$, $B_1'$ and $R_6$ are as defined above), an $A_8$-$SO_2$—$B_1'$—$R_6$- group (wherein $A_8$, $B_1'$ and $R_6$ are as defined above, provided that $A_8$ is not a hydrogen atom), an $A_9'$-$B_2'$—$B_3$—$B_1'$—$R_6$- group (wherein $A_9'$, $B_2'$, $B_3$, $B_1'$ and $R_6$ are as defined above), or a C2-C10 alkenyl group substituted with a $(b_0)$- group (wherein $(b_0)$ is as defined above) or a $(c_0)$- group (wherein $(c_0)$ is as defined above);

(11) the $K_0$ group: an $A_{10}$-N$((O)_n R_1)$—CO—$R_6$- group wherein $A_{10}$ represents a hydrogen atom (provided that n is not 0), an $A_7''$-$SO_2$- group (wherein $A_7''$ is as defined above), an $A_8$-$SO_2$- group (wherein $A_8$ is as defined above, provided that $A_8$ is not a hydrogen atom), an $A_9'O$- group (wherein $A_9'$ is as defined above, provided that n is not 1), an $A_9'$- group (wherein $A_9'$ is as defined above, provided that $A_8'$ is excluded when n is 0), a $R_2OCH_2$- group (wherein $R_2$ is as defined above), an $A_2$-CO—$R_4$- group (wherein $A_2$ and $R_4$ are as defined above) or an $A_2$-CO—CH(CH$_2$CO-$A_2$)- group (wherein $A_2$ is as defined above), and n, $R_1$ and $R_6$ are as defined above;

(12) the L₀ group:

an A₁₀'-N((O)ₙR₁)—SO₂—R₆- group [wherein A₁₀' represents a hydrogen atom (provided that n is not 0), an A₉'O- group (wherein A₉' is as defined above, provided that n is not 1), an A₉'- group (wherein A₉' is as defined above, provided that A₈' is excluded when n is 0), a R₂—CO- group (wherein R₂ is as defined above), an A₂-CO—R₄- group (wherein A₂ and R₄ are as defined above) or an A₂-CO—CH(CH₂CO-A₂)- group (wherein A₂ is as defined above), and n, R₁ and R₆ are as defined above], an A₉"R₁N—SO₂—N((O)ₙR₁')—R₆- group [wherein A₉" represents a hydrogen atom or an A₉'- group (wherein A₉' is as defined above, and R₁, n, R₁' and R₆ are as defined above] or a (b₀)-SO₂—N((O)ₙR₁')—R₆- group [wherein (b₀), n, R₁' and R₆ are as defined above];

(13) the M₀ group:

a R₁(R₂S)C=N—R₆- group (wherein R₁, R₂ and R₆ are as defined above), a R₂B(R₂'B')C=N—R₆- group (wherein R₂ and R₆ are as defined above, R₂' is the same as or different from R₂ and has the same meaning as that of R₂, and B and B' are the same or different and represent an oxy group or a thio group), a R₁R₁'N—(R₂S)C=N—R₆- group (wherein R₁, R₁', R₂ and R₆ are as defined above), a R₁N=C(SR₂)—NR₂'—R₆- group (wherein R₁, R₂, R₂' and R₆ are as defined above) or a R₁(R₁'O)N—R₆- group (wherein R₁, R₁' and R₆ are as defined above);

(14) the N₀ group: a A₁₁-P(=O)(OR₁')—R₄- group wherein A₁₁ represents a R₁- group (wherein R₁ is as defined above), a R₁O—R₆- group (wherein R₁ and R₆ are as defined above) or a R₁OCO—CHR₀- group (wherein R₁ and R₀ are as defined above), and R₁' and R₄ are as defined above;

III. in (Y_{A0})_q, Y_{A0} is a substituent on a carbon atom and represents a group included in the following X₀ group and Y₀ group, q represents 0, 1, 2, 3 or 4, the sum of p (wherein p is as defined above) and q is 5 or less, Y_{A0}s are the same as or different when q is 2 or more, and the adjacent two same or different Y_{A0} may form a group included in the Z₀ group to be fused to the A ring when q is 2 or more;

(1) the X₀ group: a M_a- group, wherein M_a represents a R_b- group (wherein R_b represents a C1-C10 alkyl group optionally substituted with a halogen atom), a halogen atom, a nitro group, a cyano group, a hydroxy group, a R_c—B_a—R_d- group (wherein R_c represents a C1-C10 alkyl group optionally substituted with a halogen atom, B_a represents an oxy group, a thio group, a sulfinyl group or a sulfonyl group, and R_d represents a single bond or a C1-C10 alkylene group), a HOR_d- group (wherein R_d is as defined above), a R_e—CO—R_d- group (wherein R_e represents a hydrogen atom, or a C1-C10 alkyl group optionally substituted with a halogen atom, and R_d is as defined above), a R_e—CO—O—R_d- group (wherein R_e and R_d are as defined above), a R_eO—CO—R_d- group (wherein R_e and R_d are as defined above), a HO—CO—CH=CH- group, a R_eR_e'N—R_d- group (wherein R_e and R_e' are the same or different, R_e is as defined above, R_e' has the same meaning as R_e has, and R_d is as defined above), a R_e—CO—NR_e'—R_d- group (wherein R_e, R_e' and R_d are as defined above), a R_bO—CO—N(R_e)—R_d- group (wherein R_b, R_e and R_d are as defined above), a R_eR_e'N—CO—R_d- group (wherein R_e, R_e' and R_d are as defined above), a R_eR_e'N—CO—NR_e"—R_d- group (wherein R_e, R_e' and R_e" are the same or different, R_e and R_e' are as defined above, R_e" has the same meaning as R_e has, and R_d is as defined above), a R_eR_e'N—C(=NR_e")—NRe'"—R_d- group (wherein R_e, R_e', R_e" and R_e'" are the same or different, R_e, R_e' and R_e" are as defined above, R_e'" has the same meaning as R_e has, and R_d is as defined above), a R_b—SO₂—NR_e—R_d- group (wherein R_b, R_e and R_d are as defined above), a R_eR_e'N—SO₂—R_d- group (wherein R_e, R_e' and R_d are as defined above), a C2-C10 alkenyl group or a C2-C10 alkynyl group;

(2) the Y₀ group: a M_{b0}-R_d- group, wherein M_{b0} represents a M_{c0}- group

[wherein M_{c0} represents a M_{d0}-R_d'- group [wherein M_{d0} represents a 6 to 10-membered aryl group optionally substituted with a M_a- group (wherein M_a is as defined above), a 5 to 10-membered heteroaryl group optionally substituted with a M_a- group (wherein M_a is as defined above), a 3 to 10-membered cyclic hydrocarbon or heterocyclic group which is optionally substituted with a M_a- group (wherein M_a is as defined above) and which optionally contains an unsaturated bond, or a (b_o)- group

(wherein (b_o) forms as defined above), a (c_o)- group

(wherein (c_o) forms as defined above), a (d_0)-group

{wherein d_o forms a 5 to 12-membered hydrocarbon ring which is substituted with a carbonyl group or a thiocarbonyl group and further which may be optionally substituted with an oxy group, a thio group, a —NR₁- group (wherein R₁ is as defined above), a sulfinyl group or a sulfonyl group} or a (e₀)- group

{wherein e₀ forms a 5 to 12-membered hydrocarbon ring optionally substituted with a carbonyl group, a thiocarbonyl group, an oxy group, a thio group, a —NR₁— group (wherein R₁ is as defined above), a sulfinyl group or a sulfonyl group}, and R_d' is the same as or different from R_d and has the same meaning as R_d has]], a $M_{c0}$-$B_a$- group (wherein $M_{c0}$ and $B_a$ are as defined above), a $M_{c0}$-CO- group (wherein $M_{c0}$ is as defined above), a $M_{c0}$-CO—O- group (wherein $M_{c0}$ is as defined above), a $M_{c0}$O—CO- group (wherein $M_{c0}$ is as defined above), a $M_{c0}R_eN$- group (wherein $M_{c0}$ and $R_e$ are as defined above), a $M_{c0}$-CO—$NR_e$- group (wherein $M_{c0}$ and Re are as defined above), a $M_{c0}$O—CO—$NR_e$- group (wherein $M_{c0}$ and $R_e$ are as defined above), a $M_{c0}R_eN$—CO- group (wherein $M_{c0}$ and $R_e$ are as defined above), a $M_{c0}R_eN$—CO—$NR_e'$- group (wherein $M_{c0}$, $R_e$ and $R_e'$ are as defined above), a $M_{c0}R_eN$—C(=$NR_e'$)—$NR_e''$- group (wherein $M_{c0}$, $R_e$, $R_e'$ and $R_e''$ are as defined above), a $M_{c0}$-$SO_2$—$NR_e$- group (wherein $M_{c0}$ and $R_e$ are as defined above) or a $M_{c0}R_eN$—$SO_2$- group (wherein $M_{c0}$ and $R_e$ are as defined above), and $R_d$ is as defined above;

(3) the $Z_0$ group: a 5 to 12-membered cyclic hydrocarbon or heterocyclic ring optionally substituted with a halogen atom, a C1-C10 alkoxy group, a C3-C10 alkenyloxy group, a C3-C10 alkynyloxy group, a carbonyl group, a thiocarbonyl group, an oxy group, a thio group, a sulfinyl group or a sulfonyl group, which is an aromatic or nonaromatic and monocyclic or fused ring and which is fused to the A ring;

IV. $Q_{A0}$ represents a hydroxyl group, a ($b_0$)- group (wherein ($b_0$) is as defined above), an $A_9$-$B_6$—$B_c$- group [wherein $A_9$ and $B_6$ are as defined above, and $B_c$ represent an oxy group or a —N(($O)_mR_1$)- group (wherein m and $R_1$ are as defined above), provided that $B_c$ is not a sulfonyl group when $A_9$ is a hydrogen atom], an $A_7''$-$SO_2$—$B_c$- group (wherein $A_7''$ and $B_c$ are as defined above), an $A_8$-$SO_2$—$B_c$- group (wherein $A_8$ and $B_c$ are as defined above, provided that $A_8$ is not a hydrogen atom), a $R_1R_1'N$—$SO_2$—$B_c$- group (wherein $R_1$, $R_1'$ and $B_c$ are as defined above), a ($b_0$)-$SO_2$—$B_c$- group (wherein ($b_0$) and $B_c$ are as defined above), an $A_9'$-$B_c$- group (wherein $A_9'$ and $B_c$ are as defined above), a $D_5$-$R_4$—$B_c$- group (wherein $D_5$, $R_4$ and $B_c$ are as defined above), a $M_{c0}$-$B_3$—$B_c$- group (wherein $M_{c0}$, $B_3$ and $B_c$ are as defined above) or a $M_{c0}$-$B_c$- group (wherein $M_{c0}$ and $B_c$ are as defined above);

V. $K_{A0}$ represents a hydrogen atom, a halogen atom, or a C10 alkyl group, $L_{A0}$ represents a hydrogen atom, or a $M_{b0}$- group ($M_{b0}$ is as defined above), or $K_{A0}$ and $L_{A0}$ may form a C1-C10 alkylene group, or a C1-C10 alkenylene group optionally substituted with single or the same or different plural $M_a$ groups; and the term "as defined above" used for the same symbols among plural substituents means that the plural substituents independently represent the same meaning as that described above and, among the plural substituents, although the selection range of substituents to be selected is the same, selected substituents may be the same or different as long as they are selected within the range;

3. A cinnamoyl compound represented by the formula (III):

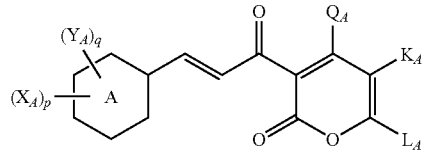

(III)

wherein

I. A represents a benzene ring or a pyridine ring;

II. in $(X_A)_p$, $X_A$ is a substituent on a carbon atom and represents a group included in any group or the following A to N groups, p represents 1, 2, 3, 4 or 5, and, $X_A$s are the same or different when p is 2 or more, (1) the A group:

a $D_1$-$R_4$- group, wherein $D_1$ represents a ($R_1$—$(O)_k$-$(A_1N$—$(O)_{k'}$- group [wherein $R_1$ represents a hydrogen atom, or a C1-C10 alkyl group, or a C2-C10 alkyl group substituted with a halogen atom or a $R_2$—$B_1$- group (wherein $R_2$ represents a C1-C10 alkyl group, a C3-C10 alkenyl group or a C3-C10 alkynyl group, and $B_1$ represents an oxy group, a thio group, a sulfinyl group or a sulfonyl group), or a C3-C10 alkenyl group, or a C3-C10 alkynyl group, k represents 0 or 1, $A_1$ represents a $R_3$—$(CHR_0)_m$—$(B_2$—$B_3)_{m'}$- group {wherein $R_3$ represents a hydrogen atom, or a C1-C10 alkyl group optionally substituted with a halogen atom or a $R_2$—$B_1$- group (wherein $R_2$ and $B_1$ are as defined above), or a C2-C10 alkenyl group, or a C2-C10 alkynyl group, $R_0$ represents a hydrogen atom, a C1-C10 alkyl group or a C2-C10 haloalkyl group, m represents 0 or 1, $B_2$ represents a single bond, an oxy group, a thio group or a —N(($O)_nR_1'$)- group (wherein $R_1'$ is the same as or different from $R_1$ and has the same meaning as $R_1$ has, and n represents 0 or 1), $B_3$ represents a carbonyl group, a thiocarbonyl group or a sulfonyl group, m' represents 0 or 1, and when $B_3$ is a sulfonyl group, it does not occur that m is 0 and $R_3$ is a hydrogen atom at the same time}, and k' represents 0 or 1], and $R_4$ represents a C1-C10 alkylene group, provided that a $R_0'R_0''N$—$R_4$-group (wherein $R_0'$ and $R_0''$ are the same as or different from $R_0$ and has the same meaning as $R_0$ has, and $R_4$ is as defined above) is excluded, a $D_2$-$R_4$- group, wherein $D_2$ represents a cyano group, a $R_1R_1'NC$(=$N$—$(O)_n$-$A_1$)-group (wherein $R_1$, $R_1'$, n and $A_1$ are as defined above), an $A_1N$=$C(-OR_2)$-group (wherein $A_1$ and $R_2$ are as defined above) or a $NH_2$—CS-group, and $R_4$ is as defined above, a $D_3$-$R_4$- group, wherein $D_3$ represents a nitro group or a $R_1OSO_2$- group (wherein $R_1$ is as defined above), and $R_4$ is as defined above, or a $R_1OSO_2$- group, wherein $R_1$ is as defined above;

(2) the B group: an (a)-group

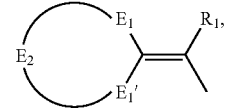

(a)

in (a), $E_1$ and $E_1'$ represent a methylene group optionally substituted with a C1-C10 alkyl group or a C1-C10 alkoxy group, or a carbonyl group, provided that $E_1$ and $E_1'$ are not a carbonyl group at the same time, $E_2$ represents a C2-C10 alkylene group optionally substituted with an oxy group, a thio group, a sulfinyl group, a sulfonyl group or a —$NR_1'$- group (wherein $R_1'$ is as defined above), or a C3-C10 alkenylene group optionally substituted with an oxy group, a thio group, a sulfinyl group, a sulfonyl group or a —$NR_1'$- group (wherein $R_1'$ is as defined above), and $R_1$ is as defined above;

(3) the C group: a C2-C10 alkenyl group substituted with a halogen atom, a $R_2$—$B_1$- group (wherein $R_2$ and $B_1$ are as defined above), a $D_4$-$R_4$- group [wherein $D_4$ represents a hydroxyl group or an $A_1$-O- group (wherein $A_1$ is as defined above), and $R_4$ is as defined above], a $D_5$- group [wherein $D_5$ represents an O=$C(R_3)$- group (wherein $R_3$ is as defined above), an $A_1$-$(O)_n$—N=C($R_3$)- group (wherein $A_1$, n and $R_3$ are as defined above), a $R_1$—$B_0$—CO—$R_4$—$(O)_n$—N=C($R_3$)- group {wherein $R_1$, $R_4$, n and $R_3$ are as defined above, and $B_0$ represents an oxy group, a thio group or a —N$((O)_m R_1')$— group (wherein $R_1'$ and m are as defined above)}, a $D_2$-$R_4$—$(O)_n$—N=C($R_3$)- group (wherein $D_2$, $R_4$, n and $R_3$ are as defined above) or a $R_1 A_1 N$—N=C($R_3$)- group (wherein $R_1$, $A_1$ and $R_3$ are as defined above)], a $R_1 A_1 N$—O—$R_4$- group (wherein $R_1$, $A_1$ and $R_4$ are as defined above), a $R_1$ ($A_1$-(O)n-)N- group (wherein $R_1$, $A_1$ and n are as defined above), a $D_2$- group (wherein $D_2$ is as defined above) or a $D_3$- group (wherein $D_3$ is as defined above);

(4) the D group: a C2-C10 alkynyl group substituted with a (b)-$R_4$- group [wherein, in (b)

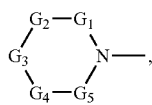
(b)

$G_1$, $G_2$, $G_4$ and $G_5$ represent a methylene group which is connected with the adjacent atom via a single bond and which may be optionally substituted with a methyl group, or a methine group which is connected with the adjacent atom via a double bond and which may be optionally substituted with a methyl group, and $G_3$ represents a single bond, a double bond, a C1-C10 alkylene group optionally substituted with a methyl group, an oxy group, a thio group, a sulfinyl group, a sulfonyl group or a —$NR_1$- group (wherein $R_1$ is as defined above), or a C2-C10 alkenylene group optionally substituted with a methyl group, an oxy group, a thio group, a sulfinyl group, a sulfonyl group or a —$NR_1$- group (wherein $R_1$ is as defined above); and $R_4$ is as defined above], a (c)-$R_4$- group (wherein, in (c)

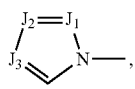
(c)

$J_1$, $J_2$ and $J_3$ are the same or different, and represent a methine group optionally substituted with a methyl group, or a nitrogen atom; and $R_4$ is as defined above), a halogen atom, a $R_2$—$B_1$—$R_4$- group (wherein $R_2$, $B_1$ and $R_4$ are as defined above), a $D_4$-$R_4$- group (wherein $D_4$ and $R_4$ are as defined above), a $D_5$- group (wherein $D_5$ is as defined above), a $D_1$-$R_4$- group (wherein $D_1$ and $R_4$ are as defined above), a $D_2$- group (wherein $D_2$ is as defined above) or a $D_3$-$R_4$- group (wherein $D_3$ and $R_4$ are as defined above);

(5) the E group: an $A_2$-CO—$R_5$- group, provided that $R_5$ is not a vinylene group when $A_2$ is a hydroxyl group, wherein $A_2$ represents (i) an $A_3$-$B_4$- group wherein $A_3$ represents a hydrogen atom, or a C1-C10 alkyl group, or a C2-C10 haloalkyl group, or a C2-C10 alkenyl group optionally substituted with a halogen atom, or a C3-C10 alkynyl group optionally substituted with a halogen atom, or $R_a$—$(R_4)_m$- group (wherein $R_a$ represents a phenyl group, a pyridyl group, a furyl group or a thienyl group, which may be optionally substituted with a halogen atom, a C1-C10 alkyl group, a C1-C10 alkoxy group or a nitro group, and $R_4$ and m are as defined above), or a C1-C10 alkyl group substituted with a (b)-$R_4$- group (wherein (b) and $R_4$ are as defined above), a (c)-$R_4$- group (wherein (c) and $R_4$ are as defined above), a $R_2$—$B_1$—$R_4$- group (wherein $R_2$, $B_1$ and $R_4$ are as defined above), a $D_4$-$R_4$- group (wherein $D_4$ and $R_4$ are as defined above), a $D_5$- group (wherein $D_5$ is as defined above), a $D_1$-$R_4$- group (wherein $D_1$ and $R_4$ are as defined above), a $D_2$- group (wherein $D_2$ is as defined above), a $D_3$-$R_4$- group (wherein $D_3$ and $R_4$ are as defined above) or an $A_4$-$SO_2$—$R_4$- group {wherein $A_4$ represents a (b)- group (wherein (b) is as defined above), a (c)- group (wherein (c) is as defined above) or a $R_1 R_1'N$- group (wherein $R_1$ and $R_1'$ are as defined above), and $R_4$ is as defined above}, and $B_4$ represents an oxy group, a thio group or a —N$((O)_m R_1)$- group (wherein $R_1$ and m are as defined above), provided that $A_3$ is not a hydrogen atom when $B_4$ is a thio group, (ii) a $R_1$—$B_4$—CO—$R_4$—$B_4'$- group wherein $R_1$, $B_4$ and $R_4$ are as defined above, $B_4'$ is the same as or different from $B_4$ and has the same meaning as $B_4$ has, provided that $R_2$ is not a hydrogen atom when $B_4$ is a thio group, or a $D_2$-$R_4$—$B_4$-group, wherein $D_2$, $R_4$ and $B_4$ are as defined above, (iii) a $R_2$—$SO_2$—$NR_1$- group wherein $R_2$ is as defined above, provided that a hydrogen atom is excluded; and $R_1$ is as defined above, (iv) a (b)- group, wherein (b) is as defined above, (v) a (c)- group, wherein (c) is as defined above, or (vi) a $R_1 A_1 N$—$NR_1'$- group, wherein $R_1$, $A_1$ and $R_1'$ are as defined above, and $R_5$ represents a C2-C10 alkenylene group optionally substituted with a halogen atom, or a C2-C10 alkynylene group;

(6) the F group: an $A_5$-$B_5$—$R_6$- group wherein $A_5$ represents a C2-C10 alkyl group substituted with a $D_4$- group (wherein $D_4$ is as defined above), a $D_1$- group (wherein $D_1$ is as defined above), a $D_3$- group (wherein $D_3$ is as defined above) or an $A_4$-$SO_2$- group (wherein $A_4$ is as defined above), or a C1-C10 alkyl group substituted with a $R_2$—$B_1$- group (wherein $R_2$ and $B_1$ are as defined above), a $D_2$- group (wherein $D_2$ is as defined above), a $D_5$- group (wherein $D_5$ is as defined above) or an $A_2$-CO- group (wherein $A_2$ is as defined above), $B_5$ represents a $B_1$- group (wherein $B_1$ is as defined above) or a —$NA_1$- group (wherein $A_1$ is as defined above), and $R_6$ represents a single bond or a C1-C10 alkylene group;

(7) the G group: an $A_6$-$B_5$—$R_6$- group wherein $A_6$ represents an (a) —$R_4$- group (wherein (a) and $R_4$ are as defined above), or a C2-C10 alkenyl group, or a C2-C10 alkynyl group, or a C2-C10 alkenyl group substituted with a halogen atom, a $R_2$—$B_1$- group (wherein $R_2$ and $B_1$ are as defined above), a $D_5$- group (wherein $D_5$ is as defined above), a $D_2$- group (wherein $D_2$ is as defined above) or an $A_2$-CO- group (wherein $A_2$ is as define above), or a C2-C10 alkynyl group substituted with a halogen atom, a $R_2$—$B_1$- group (wherein $R_2$ and $B_1$ are as defined above), a $D_5$- group (wherein $D_5$ is as defined above), a $D_2$- group (wherein $D_2$ is as defined above) or an $A_2$-CO- group (wherein $A_2$ is as defined above), or a C3-C10 alkenyl group substituted with a (b)- group (wherein (b) is as defined above), a (c)- group (wherein (c) is as defined above), a $D_4$- group (wherein $D_4$ is as defined above), a $D_1$- group (wherein $D_1$ is as defined above) or a $D_3$- group (wherein $D_3$ is as defined above), or a C3-C10 alkynyl group substituted with a $D_4$- group (wherein $D_4$ is as defined above), a $D_1$- group (wherein $D_1$ is as defined above) or a $D_3$- group (wherein $D_3$ is as defined above), and $B_5$ and $R_6$ are as defined above;

(8) the H group:

a $D_2$-N(—(O)$_n$-A$_1$)-R$_6$- group (wherein $D_2$, n, $A_1$ and $R_6$ are as defined above), a $D_2$- group (wherein $D_2$ is as defined above, provided that a cyano group is excluded), a $R_1(R_1'(O)_n)N—CR_1''=N—R_6$- group (wherein $R_1$, $R_1'$, n and $R_6$ are as defined above, $R_1''$ is the same as or different from $R_1$ and has the same meaning as $R_1$ has), a $R_1—(O)_n—N=CR_1'—NR_2—R_6$- group (wherein $R_1$, n, $R_1'$, $R_2$ and $R_6$ are as defined above), a $R_2—B_3—NR_1—CO—NR_1'—R_6$- group (wherein $R_2$, $B_3$, $R_1$, $R_1'$ and $R_6$ are as defined above), a $D_2—CO—NR_1—R_6$- group (wherein $D_2$, $R_1$ and $R_6$ are as defined above) or an $A_2—COCO—NR_1—R_6$- group (wherein $A_2$, $R_1$ and $R_6$ are as defined above);

(9) the I group:

an $A_7-B_6—N((O)_nR_1)—R_6$- group [wherein $A_7$ represents a C2-C10 alkenyl group optionally substituted with a halogen atom, or a C2-C10 alkynyl group, or a C3-C10 haloalkynyl group, or a $R_2—B_1—R_4$- group (wherein $R_2$, $B_1$ and $R_4$ are as defined above), or a $D_4$-$R_4$- group (wherein $D_4$ and $R_4$ are as defined above), or a $D_5$-$R_4$- group (wherein $D_5$ and $R_4$ are as defined above), or a $D_1$-$R_4$- group (wherein $D_1$ and $R_4$ are as defined above), or a (b)-$R_4$- group (wherein (b) and $R_4$ are as defined above), or a (c)-$R_4$- group (wherein (c) and $R_4$ are as defined above), or a $D_2$-$R_4$- group (wherein $D_2$ and $R_4$ are as defined above), or a $D_3$-$R_4$- group (wherein $D_3$ and $R_4$ are as defined above), or an $A_4$-$SO_2$—$R_4$- group (wherein $A_4$ and $R_4$ are as defined above), or an $A_2$-CO—$R_4$- group (wherein $A_2$ and $R_4$ are as defined above), $B_6$ represents a carbonyl group or a thiocarbonyl group, and n, $R_1$ and $R_6$ are as defined above], an $A_8$-CS—N$((O)_nR_1)$—$R_6$- group [wherein $A_8$ represents a hydrogen atom or a C1-C10 alkyl group optionally substituted with a halogen atom, and n, $R_1$ and $R_6$ are as defined above], an $A_7'$-$B_2'$—$B_3$—N$((O)_nR_1)$—$R_6$- group [wherein $A_7'$ represents a C3-C10 alkenyl group optionally substituted with a halogen atom, or a C3-C10 alkynyl group optionally substituted with a halogen atom, or a $R_2$—$B_1$—$R_4'$- group (wherein $R_2$ and $B_1$ are as defined above, and $R_4'$ represents a C2-C10 alkylene group), or a $D_4$-$R_4'$- group (wherein $D_4$ and $R_4'$ are as defined above), or a $D_1$-$R_4'$- group (wherein $D_1$ and $R_4'$ are as defined above), or a (b)-$R_4'$- group (wherein (b) and $R_4'$ are as defined above), or a (c)-$R_4'$- group (wherein (c) and $R_4'$ are as defined above), or a $D_2$-$R_4'$— group (wherein $D_2$ and $R_4'$ are as defined above), or a $D_3$-$R_4'$— group (wherein $D_3$ and $R_4'$ are as defined above), or an $A_2$-CO—$R_4'$- group (wherein $A_2$ and $R_4'$ are as defined above), $B_2'$ represents an oxy group, a thio group or a —N$((O)_{n'}R_1')$- group (wherein n' is the same as or different from n and has the same meaning as n has, and $R_1'$ is as defined above, and $B_3$, n, $R_1$ and $R_6$ are as defined above], an $A_8'$-$B_2'$—CS—N$((O)_nR_1)$—$R_4$- group [wherein $A_8'$ represents a C1-C10 alkyl group or a C2-C10 haloalkyl group, $B_2'$ is as defined above, and n, $R_1$ and $R_6$ are as defined above], an $A_8'$-S—$B_3'$—N$((O)_nR_1)$—$R_6$- group [wherein $A_8'$, n, $R_1$ and $R_6$ are as defined above, and $B_3'$ represents a carbonyl group or a sulfonyl group] or an $A_7''$-$SO_2$—N$((O)_nR_1)$—$R_6$- group [wherein $A_7''$ represents a C2-C10 alkenyl group, or a C3-C10 alkenyl group substituted with a halogen atom, or a C3-C10 alkynyl group optionally substituted with a halogen atom, or a $R_2$—$B_1$—$R_4'$- group (wherein $R_2$, $B_1$ and $R_4'$ are as defined above), or a $D_4$-$R_4'$— group (wherein $D_4$ and $R_4'$ are as defined above), or a $D_5$-$R_4$— group (wherein $D_5$ and $R_4$ are as defined above), or a $D_1$-$R_4'$— group (wherein $D_1$ and $R_4'$ are as defined above), or a (b) —$R_4'$- group (wherein (b) and $R_4'$ are as defined above), or a (c)-$R_4'$- group (wherein (c) and $R_4'$ are as defined above), or a $D_2$-$R_4$- group (wherein $D_2$ and $R_4$ are as defined above), or a $NO_2$—$R_4$- group (wherein $R_4$ is as defined above), or an $A_2$-CO—$R_4$- group (wherein $A_2$ and $R_4$ are as defined above), and n, $R_1$ and $R_4$ are as defined above];

(10) the J group:

an $A_7$-CO- group (wherein $A_7$ is as defined above), an $A_9$-CS- group (wherein $A_9$ represents $A_7$ or $A_8$), an $A_9'(O)_mN=C(A_9)$- group (wherein $A_9'$ represents $A_7'$ or $A_8'$, and m and $A_9$ are as defined above), a $D_2$-CO- group (wherein $D_2$ is as defined above), an $A_2$-COCO- group (wherein $A_2$ is as defined above), an $A_9$-CO—$B_1'$—$R_6$- group (wherein $A_9$ and $R_6$ are as defined above, and $B_1'$ represents an oxy group or a thio group, provided that $A_9$ is not $A_8$ when $B_1'$ is an oxy group), an $A_9$-CS—$B_1'$—$R_6$- group (wherein $A_9$, $B_1'$ and $R_6$ are as defined above), an $A_7''$-$SO_2$—$B_1'$—$R_6$- group (wherein $A_7''$, $B_1'$ and $R_6$ are as defined above), an $A_8$-$SO_2$—$B_1'$—$R_6$- group (wherein $A_8$, $B_1'$ and $R_6$ are as defined above, provided that $A_8$ is not a hydrogen atom), an $A_9'$-$B_2'$—$B_3$—$B_1'$—$R_6$- group (wherein $A_9'$, $B_2'$, $B_3$, $B_1'$ and $R_6$ are as defined above), or a C2-C10 alkenyl group substituted with a (b)- group (wherein (b) is as defined above) or a (c)- group (wherein (c) is as defined above);

(11) the K group: an $A_{10}$-N$((O)_nR_1)$—CO—$R_6$- group wherein $A_{10}$ represents a hydrogen atom (provided that n is not 0), an $A_7''$-$SO_2$- group (wherein $A_7''$ is as defined above), an $A_8$-$SO_2$- group (wherein $A_8$ is as defined above, provided that $A_8$ is not a hydrogen atom), an $A_9'$O- group (wherein $A_9'$ is as defined above, provided that n is not 1), an $A_9'$- group (wherein $A_9'$ is as defined above, provided that $A_8'$ is excluded when n is 0), a $R_2OCH_2$- group (wherein $R_2$ is as defined above), an $A_2$-CO—$R_4$- group (wherein $A_2$ and $R_4$ are as defined above) or an $A_2$-CO—CH(CH$_2$CO-A$_2$)- group (wherein $A_2$ is as defined above), and n, $R_1$ and $R_6$ are as defined above;

(12) the L group:

an $A_{10}'$-N$((O)_nR_1)$—$SO_2$—$R_6$- group [wherein $A_{10}'$ represents a hydrogen atom (provided that n is not 0), an $A_9'$O- group (wherein $A_9'$ is as defined above, provided that n is not 1), an $A_9'$- group (wherein $A_9'$ is as defined above, provided that $A_8'$ is excluded when n is 0), a $R_2$—CO- group (wherein $R_2$ is as defined above), an $A_2$-CO—$R_4$- group (wherein $A_2$ and $R_4$ are as defined above) or an $A_2$-CO—CH(CH$_2$CO-A$_2$)- group (wherein $A_2$ is as defined above), and n, $R_1$ and $R_6$ are as defined above], an $A_9''R_1N$—$SO_2$—N$((O)_nR_1')$—$R_6$- group [wherein $A_9''$ represents a hydrogen atom or an $A_9'$- group (wherein $A_9'$ is as defined above), and $R_1$, n, $R_1'$ and $R_6$ are as defined above] or a (b)-$SO_2$—N$((O)_nR_1')$—$R_6$- group [wherein (b), n, $R_1'$ and $R_6$ are as defined above];

(13) the M group:

a $R_1(R_2S)C=N$—$R_6$- group (wherein $R_1$, $R_2$ and $R_6$ are as defined above), a $R_2B(R_2'B')C=N$—$R_6$- group (wherein $R_2$ and $R_6$ are as defined above, $R_2'$ is the same as or different from $R_2$ and has the same meaning as $R_2$ has, and B and B' are the same or different and represent an oxy group or a thio group), a $R_1R_1'N$—$(R_2S)C=N$—$R_6$- group (wherein $R_1$, $R_1'$, $R_2$ and $R_6$ are as defined above), a $R_1N=C(SR_2)$—$NR_2'$—$R_6$- group (wherein $R_1$, $R_2$, $R_2'$ and $R_6$ are as defined above) or a $R_1(R_1'O)N$—$R_6$- group (wherein $R_1$, $R_1'$ and $R_6$ are as defined above);

(14) the N group: an $A_{11}$-P(=O)($OR_1'$)—$R_4$- group
wherein $A_{11}$ represents a $R_1$- group (wherein $R_1$ is as defined above), a $R_1O$—$R_6$- group (wherein $R_1$ and $R_6$ are as defined above) or a $R_1OCO$—$CHR_0$- group (wherein $R_1$ and $R_0$ are as defined above), and $R_1'$ and $R_4$ are as defined above;

III. in $(Y_A)_q$, $Y_A$ is a substituent on a carbon atom and represents a group included in the following X group or Y group, q represents 0, 1, 2, 3 or 4, the sum of p (wherein p is as defined above) and q is 5 or less, $Y_A$s are the same or different when q is 2 or more, and the adjacent two same or different $Y_A$s together may form a group included in the Z group to be fused to the A ring when q is 2 or more, (1) the X group: a $M_a$- group
wherein $M_a$ represents a $R_b$- group (wherein $R_b$ represents a C1-C10 alkyl group optionally substituted with a halogen atom), a halogen atom, a nitro group, a cyano group, a $R_c$—$B_a$—$R_d$- group (wherein $R_c$ represents a C1-C10 alkyl group optionally substituted with a halogen atom, $B_a$ represents an oxy group, a thio group, a sulfinyl group or a sulfonyl group, and $R_d$ represents a single bond or a C1-C10 alkylene group), a $HOR_d$- group (wherein $R_d$ is as defined above), a $R_e$—CO—$R_d$- group (wherein $R_e$ represents a hydrogen atom, or a C1-C10 alkyl group optionally substituted with a halogen atom, and $R_d$ is as defined above), a $R_e$—CO—O—$R_d$- group (wherein $R_e$ and $R_d$ are as defined above), a $R_eO$—CO—$R_d$- group (wherein $R_e$ and $R_d$ are as defined above), a HO—CO—CH=CH- group, a $R_eR_e'N$—$R_d$- group (wherein $R_e$ and $R_e'$ are the same or different, $R_e$ is as defined above, $R_e'$ has the same meaning as $R_e$ has, and $R_d$ is as defined above), a $R_e$—CO—$NR_e'$—$R_d$- group (wherein $R_e$, $R_e'$ and $R_d$ are as defined above), a $R_bO$—CO—N($R_e$)—$R_d$- group (wherein $R_b$, $R_e$ and $R_d$ are as defined above), a $R_eR_e'N$—CO—$R_d$- group (wherein $R_e$, $R_e'$ and $R_d$ are as defined above), a $R_eR_e'N$—CO—$NR_e''$—$R_d$- group (wherein $R_e$, $R_e'$ and $R_e''$ are the same or different, $R_e$ and $R_e'$ are as defined above, $R_e''$ has the same meaning as $R_e$ has, and $R_d$ is as defined above), a $R_eR_e'N$—C(=$NR_e''$)—$NR_e'''$—$R_d$- group (wherein $R_e$, $R_e'$, $R_e''$ and $R_e'''$ are the same or different, $R_e$, $R_e'$ and $R_e''$ are as defined above, $R_e'''$ has the same meaning as $R_e$ has, and $R_d$ is as defined above), a $R_b$—$SO_2$—$NR_e$—$R_d$- group (wherein $R_b$, $R_e$ and $R_d$ are as defined above), a $R_eR_e'N$—$SO_2$—$R_d$- group (wherein $R_e$, $R_e'$ and $R_d$ are as defined above), a C2-C10 alkenyl group or a C2-C10 alkynyl group;

(2) the Y group: a $M_b$-$R_d$-group, wherein $M_b$ represents a $M_c$-group
[wherein $M_c$ represents a $M_d$-$R_d'$- group [wherein $M_d$ represents a phenyl group optionally substituted with a $M_a$- group (wherein $M_a$ is as defined above), a pyridyl group optionally substituted with a $M_a$- group (wherein $M_a$ is as defined above), a naphthyl group optionally substituted with a $M_a$- group (wherein $M_a$ is as defined above), a (b)- group (wherein (b) is as defined above), a (c)- group (wherein (c) is as defined above), a (d)- group

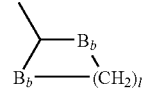

(d)

(wherein l is 2, 3 or 4, $B_b$ represents an oxy group or a thio group) or an (e)- group

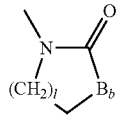

(e)

(wherein l and $B_b$ are as defined above), and $R_d'$ is the same as or different from $R_d$ and has the same meaning as $R_d$ has]],
a $M_c$-$B_a$- group (wherein $M_c$ and $B_a$ are as defined above), a $M_c$-CO- group (wherein $M_c$ is as defined above), a $M_c$-CO—O— group (wherein $M_c$ is as defined above), a $M_cO$—CO- group (wherein $M_c$ is as defined above), a $M_cR_eN$- group (wherein $M_c$ and $R_e$ are as defined above), a $M_c$-CO—$NR_e$- group (wherein $M_c$ and $R_e$ are as defined above), a $M_cO$—CO—$NR_e$- group (wherein $M_c$ and $R_e$ are as defined above), a $M_cR_eN$—CO- group (wherein $M_c$ and $R_e$ are as defined above), a $M_cR_eN$—CO—$NR_e'$- group (wherein $M_c$, $R_e$ and $R_e'$ are as defined above), a $M_cR_eN$—C(=$NR_e'$)—$NR_e''$- group (wherein $M_c$, $R_e$, $R_e'$ and $R_e''$ are as defined above), a $M_c$-$SO_2$—$NR_e$- group (wherein $M_c$ and $R_e$ are as defined above) or a $M_cR_eN$—$SO_2$- group (wherein $M_c$ and $R_e$ are as defined above), and
$R_d$ is as defined above;

(3) the Z group:
a —N=C($Y_a$)—$Y_a'$- group (wherein $Y_a$ represents a hydrogen atom, or a C1-C10 alkyl group optionally substituted with a halogen atom, or a C1-C10 alkoxy group, and $Y_a'$ represents an oxy group, a thio group, or an imino group optionally substituted with a C1-C10 alkyl group), a —$Y_b$—$Y_b'$—$Y_b''$- group (wherein $Y_b$ and $Y_b''$ are the same or different, and represent a methylene group, an oxy group, a thio group, a sulfinyl group, or an imino group optionally substituted with a C1-C10 alkyl group, and $Y_b'$ represents a C1-C4 alkylene group optionally substituted with a halogen atom, or a C1-C4 alkylene group optionally having an oxo group) or a —$Y_c$—O—$Y_c'$—O- group (wherein $Y_c$ and $Y_c'$ are the same or different, and represent a C1-C10 alkylene group);

IV. $Q_A$ represents a hydroxyl group, a (b)- group (wherein (b) is as defined above), an $A_9$-$B_6$—$B_c$- group [wherein $A_9$ and $B_6$ are as defined above, and $B_c$ represents an oxy group or a —N((O)$_m R_1$)- group (wherein m and $R_1$ are as defined above), provided that $B_c$ is not a sulfonyl group when $A_9$ is a hydrogen atom], an $A_7''$-$SO_2$—$B_c$- group (wherein $A_7''$ and $B_c$ are as defined above), an $A_8$-$SO_2$—$B_c$- group (wherein $A_8$ and $B_c$ are as defined above, provided that $A_8$ is not a hydrogen atom), a $R_1R_1'N$—$SO_2$—$B_c$- group (wherein $R_1$, $R_1'$ and $B_c$ are as defined above), a (b)-$SO_2$—$B_c$- group (wherein (b) and $B_c$ are as defined above), an $A_9'$-$B_c$- group (wherein $A_9'$ and $B_c$ are as defined above), a $D_5$-$R_c$—$B_c$- group (wherein $D_5$, $R_4$ and $B_c$ are as defined above), a $M_c$-$B_3$—$B_c$- group (wherein $M_c$, $B_3$ and $B_c$ are as defined above) or a $M_c$-$B_c$- group (wherein $M_c$ and $B_c$ are as defined above);

V. $K_A$ represents a hydrogen atom, a halogen atom or a C1-C10 alkyl group, $L_A$ represents a hydrogen atom, a C1-C10 alkyl group or a $M_b$-group ($M_b$ is as defined above), or $K_A$ and $L_A$ may form a C1-C10 alkylene group or a —C($M_a'$)=C($M_a''$)-C($M_a'''$)=C($M_a''''$)-group ($M_a'$, $M_a''$, $M_a'''$ and $M_a''''$ are the same or different, are the same as or different from $M_a$, and represent a hydrogen atom or $M_a$); and the term "as defined above" used for the same symbols among plural substituents means that the plural substituents independently represent the same meaning as that described above and, among the plural substituents, although the selection range of substituents to be selected is the same, selected substituents may be the same or different as long as they are selected within the range;

4. A cinnamoyl compound represented by the formula (IV):

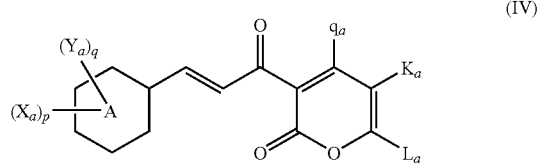

(IV)

wherein

A represents a benzene ring or a pyridine ring, $X_a$ is a substituent on a carbon atom, and represents a C1-C10 alkyl group substituted with a cyano group; a C1-C10 alkyl group substituted with a tetrahydropyran-4-ylidene group; a C2-C10 alkenyl group substituted with a halogen atom or a cyano group; a C2-C10 alkenyl group substituted with a C1-C10 alkoxycarbonyl group; a C3-C10 alkynyl group substituted with a hydroxyl group; an $a_0$-$r_1$-b-$r_1$'- group {wherein $a_0$ represents a methyl group substituted with a C1-C10 alkylthio group, a methyl group substituted with a C1-C10 alkylsulfinyl group, a methyl group substituted with a C1-C10 alkylsulfonyl group, a C2-C10 alkenyl group, a C2-C10 alkynyl group, a $r_2$O—CO- group (wherein $r_2$ represents a C1-C10 alkyl group, or a C2-C10 alkyl group substituted with a hydroxyl group), a carboxyl group, a rr'N—CO- group (wherein r and r' are the same or different, and represent a hydrogen atom or a C1-C10 alkyl group), an $a_1$-NH—CO— group (wherein $a_1$ represents a C2-C10 alkyl group substituted with a C1-C10 alkoxy group), an $a_1$'-CO- group (wherein $a_1$' represents a morpholino group), a rr'N—CH$_2$- group (wherein r and r' are as defined above), a $r_0$-(O)$_l$—CONH—CH$_2$- group (wherein $r_0$ represents a C1-C10 alkyl group, and l represents 0 or 1), a r-OCH$_2$- group (wherein r is as defined above), a $r_0$-CO- group (wherein $r_0$ is as defined above), a cyano group, or a sulfomethyl group, $r_1$ represents a C1-C10 alkylene group, $r_1$' represents a single bond or a C1-C10 alkylene group, and b represents an oxy group, a thio group, a sulfinyl group, a sulfonyl group or a imino group}; an $a_2$-y-CO—NH- group (wherein $a_2$ represents a C2-C10 alkyl group substituted with a C1-C10 alkoxy group, and y represents an oxy group or an imino group); a $r_0$O—COCO—NH- group (wherein $r_0$ is as defined above); an $a_3$-z-NH— group (wherein $a_3$ represents a C2-C10 alkenyl group, or a C1-C10 alkyl group substituted with a C1-C10 alkoxy group, a C1-C10 alkoxycarbonyl group, a carboxy group or a cyano group, and z represents a carbonyl group or a sulfonyl group); an $a_4$-NHCO- group {wherein $a_4$ represents a C1-C10 alkoxy group, or a C3-C10 alkenyloxy group, or a $r_0$-SO$_2$— group (wherein $r_0$ is as defined above), or a C2-C10 alkyl group substituted with a hydroxyl group or a C1-C10 alkoxy group, or a C1-C10 alkyl group substituted with a rO—CO— group (wherein r is as defined above), a cyano group or an aminocarbonyl group, or a rO—CO-(rO—COCH$_2$)CH- group (wherein r is as defined above)}; an $a_5$-NHSO$_2$- group (wherein $a_5$ represents a C2-C10 alkyl group substituted with a C1-C10 alkoxy group); a $r_0$ON═CH- group (wherein $r_0$ is as defined above); a $r_0$NHCSNH- group (wherein $r_0$ is as defined above); a $r_0$NHC(═S$r_0$')═N- group (wherein $r_0$ is as defined above, $r_0$' is the same as the different from $r_0$ and has the same meaning as $r_0$ has); or a $(r_0O)_2P$(═O)CH$_2$- group (wherein $r_0$ is as defined above);

p represents 1, 2 or 3, and when p is 2 or more, $X_a$s are the same or different;

$Y_a$ represents a halogen atom, a nitro group, a $r_0$CO—NH- group (wherein $r_0$ is as defined above), a C1-C10 alkyl group or a C1-C10 alkoxy group;

q represents 0, 1 or 2, and when q is 2 or more, $Y_a$s are the same or different;

$q_a$ represents a $r_a$-O- group {wherein $r_a$ represents a hydrogen atom, a C1-C10 alkyl group, a C3-C10 alkenyl group, a C3-C10 alkynyl group, a C1-C10 alkyl group substituted with a $r_0r_0$'N—CH$_2$- group (wherein $r_0$ and $r_0$' are as defined above), a rOCH$_2$- group (wherein r is as defined above), a $r_0$-CO- group (wherein $r_0$ is as defined above), a C1-C10 alkoxycarbonyl group, a carboxy group, an aminocarbonyl group or a cyano group, or a $r_3$-$r_1$-group (wherein $r_3$ represents a phenyl group or a pyridyl group, and $r_1$ is as defined above)}; a piperidino group; a morpholino group; or a $r_4r_4$'N- group (wherein $r_4$ and $r_4$' are the same or different, and represent a hydrogen atom, a C1-C10 alkyl group, a C3-C10 alkenyl group, a C3-C10 alkynyl group, or a C2-C10 alkyl group substituted with a C1-C10 alkoxy group, provided that $r_4$ and $r_4$' are not a hydrogen atom at the same time);

$K_a$ represents a hydrogen atom, a halogen atom or a C1-C10 alkyl group, and $L_a$ represents a hydrogen atom or a C1-C10 alkyl group; or $K_a$ and $L_a$ together may form a C1-C10 alkylene group or a 1,3-butadienylene group;

the term "as defined above" used for the same symbols among plural substituents means that the plural substituents independently represent the same meaning as that described above and, among the plural substituents, although the selection range of substituents to be selected is the same, selected substituents may be the same or different as long as they are selected within the range;

5. A cinnamoyl compound represented by the formula (V):

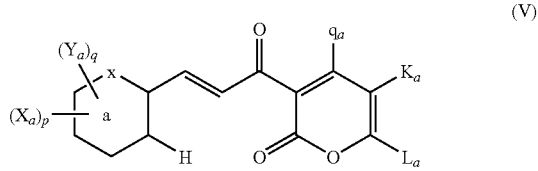

(V)

wherein a represents a benzene ring or a pyridine ring;

x represents a methine group or a nitrogen atom;

$X_a$ is a substituent on a carbon atom, and represents a C1-C10 alkyl group substituted with a cyano group; a C1-C10 alkyl group substituted with a tetrahydropyran-4-ylidene group; a C2-C10 alkenyl group substituted with a halogen atom or a cyano group; a C2-C10 alkenyl group substituted with a C1-C10 alkoxycarbonyl group; a C3-C10 alkynyl group substituted with a hydroxyl group; an $a_0$-$r_1$-b-$r_1$'- group {wherein $a_0$ represents a methyl group substituted with a C1-C10 alkylthio group, a methyl group substituted with a C1-C10 alkylsulfinyl group, a methyl group substituted with a C1-C10 alkylsulfonyl group, a C2-C10 alkenyl group, a C2-C10 alkynyl group, a $r_2$O—CO- group (wherein $r_2$ represents a C1-C10 alkyl group, or a C2-C10 alkyl group substituted with a hydroxyl group), a carboxyl group, a rr'N—CO- group (wherein r and r' are the same or different, and represent a hydrogen atom or a C1-C10 alkyl group), an $a_1$-NH—CO— group (wherein $a_1$ represents a C2-C10 alkyl group substituted with a C1-C10 alkoxy group), an $a_1'$-CO- group (wherein $a_1'$ represents a morpholino group), a rr'N—CH$_2$— group (wherein r and r' are as defined above), a $r_0$-(O)$_l$—CONH—CH$_2$- group (wherein $r_0$ represents a C1-C10 alkyl group, and l represents 0 or 1), a r-OCH$_2$- group (wherein r is as defined above), a $r_0$-CO- group (wherein $r_0$ is as defined above), a cyano group, or a sulfomethyl group, $r_1$ represents a C1-C10 alkylene group, $r_1'$ represents a single bond or a C1-C10 alkylene group, and b represents an oxy group, a thio group, a sulfinyl group, a sulfonyl group or a imino group}; an $a_2$-y-CO—NH- group (wherein $a_2$ represents a C2-C10 alkyl group substituted with a C1-C10 alkoxy group, and y represents an oxy group or an imino group); a $r_0$O—COCO—NH- group (wherein $r_0$ is as defined above); an $a_3$-z-NH— group (wherein $a_3$ represents a C2-C10 alkenyl group, or a C1-C10 alkyl group substituted with a C1-C10 alkoxy group, a C1-C10 alkoxycarbonyl group, a carboxy group or a cyano group, and z represents a carbonyl group or a sulfonyl group); an $a_4$-NHCO- group {wherein $a_4$ represents a C1-C10 alkoxy group, or a C3-C10 alkenyloxy group, or a $r_0$-SO$_2$— group (wherein $r_0$ is as defined above), or a C2-C10 alkyl group substituted with a hydroxyl group or a C1-C10 alkoxy group, or a C1-C10 alkyl group substituted with a rO—CO— group (wherein r is as defined above), a cyano group or an aminocarbonyl group, or a rO—CO-(rO—COCH$_2$)CH- group (wherein r is as defined above)}; an $a_5$-NHSO$_2$- group (wherein $a_5$ represents a C2-C10 alkyl group substituted with a C1-C10 alkoxy group); a $r_0$ON=CH- group (wherein $r_0$ is as defined above); a $r_0$NHCSNH- group (wherein $r_0$ is as defined above); a $r_0$NHC(—S$r_0'$)=N- group (wherein $r_0$ is as defined above, $r_0'$ is the same as the different from $r_0$ and has the same meaning as $r_0$ has); or a $(r_0O)_2P(=O)CH_2$- group (wherein $r_0$ is as defined above);

p represents 1, 2 or 3, and when p is 2 or more, $X_a$s are the same or different;

$Y_a$ represents a halogen atom, a nitro group, a $r_0$CO—NH- group (wherein $r_0$ is as defined above), a C1-C10 alkyl group or a C1-C10 alkoxy group;

q represents 0, 1 or 2, and when q is 2 or more, $Y_a$s are the same or different;

$q_a$ represents a $r_a$-O- group {wherein $r_a$ represents a hydrogen atom, a C1-C10 alkyl group, a C3-C10 alkenyl group, a C3-C10 alkynyl group, a C1-C10 alkyl group substituted with a $r_0r_0'$N—CH$_2$- group (wherein $r_0$ and $r_0'$ are as defined above), a rOCH$_2$- group (wherein r is as defined above), a $r_0$-CO- group (wherein $r_0$ is as defined above), a C1-C10 alkoxycarbonyl group, a carboxy group, an aminocarbonyl group or a cyano group, or a $r_3$-$r_1$-group (wherein $r_3$ represents a phenyl group or a pyridyl group, and $r_1$ is as defined above)}; a piperidino group; a morpholino group; or a $r_4r_4'$N- group (wherein $r_4$ and $r_4'$ are the same or different, and represent a hydrogen atom, a C1-C10 alkyl group, a C3-C10 alkenyl group, a C3-C10 alkynyl group, or a C2-C10 alkyl group substituted with a C1-C10 alkoxy group, provided that $r_4$ and $r_4'$ are not a hydrogen atom at the same time);

$t_a$ represents a $r_b$- group (wherein $r_b$ is the same as or different from $r_a$, and has the same meaning as $r_a$ has) or a $r_3'$- group (wherein $r_3'$ is the same as or different from $r_3$, and has the same meaning as $r_3$ has);

$K_a$ represents a hydrogen atom, a halogen atom or a C1-C10 alkyl group, and $L_a$ represents a hydrogen atom or a C1-C10 alkyl group; or $K_a$ and $L_a$ together may form a C1-C10 alkylene group or a 1,3-butadienylene group;

the term "as defined above" used for the same symbols among plural substituents means that the plural substituents independently represent the same meaning as that described above and, among the plural substituents, although the selection range of substituents to be selected is the same, selected substituents may be the same or different as long as they are selected within the range;

6. A 2H-pyran-2-one compound represented by the formula (VI):

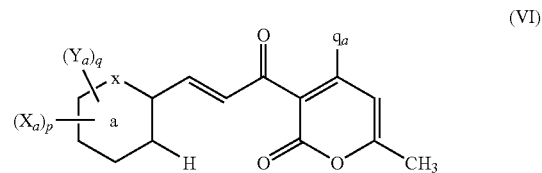

(VI)

wherein
a represents a benzene ring or a pyridine ring;
x represents a methine group or a nitrogen atom;
$X_a$ is a substituent on a carbon atom, and represents a C1-C10 alkyl group substituted with a cyano group; a C1-C10 alkyl group substituted with a tetrahydropyran-4-ylidene group; a C2-C10 alkenyl group substituted with a halogen atom or a cyano group; a C2-C10 alkenyl group substituted with a C1-C10 alkoxycarbonyl group; a C3-C10 alkynyl group substituted with a hydroxyl group; an $a_0$-$r_1$-b-$r_1'$- group {wherein $a_0$ represents a methyl group substituted with a C1-C10 alkylthio group, a methyl group substituted with a C1-C10 alkylsulfinyl group, a methyl group substituted with a C1-C10 alkylsulfonyl group, a C2-C10 alkenyl group, a C2-C10 alkynyl group, a $r_2$O—CO- group (wherein $r_2$ represents a C1-C10 alkyl group, or a C2-C10 alkyl group substituted with a hydroxyl group), a carboxyl group, a rr'N—CO- group (wherein r and r' are the same or different, and represent a hydrogen atom or a C1-C10 alkyl group), an $a_1$-NH—CO— group (wherein $a_1$ represents a C2-C10 alkyl group substituted with a C1-C10 alkoxy group), an $a_1'$-CO- group (wherein $a_1'$ represents a morpholino group), a rr'N—CH$_2$— group (wherein r and r' are as defined above), a $r_0$-(O)$_l$—CONH—CH$_2$- group (wherein $r_0$ represents a C1-C10 alkyl group, and l represents 0 or 1), a r-OCH$_2$- group (wherein r is as defined above), a $r_0$-CO- group (wherein $r_0$ is as defined above), a cyano group, or a sulfomethyl group, $r_1$ represents a C1-C10 alkylene group, $r_1'$ represents a single bond or a C1-C10 alkylene group, and b represents an oxy group, a thio group, a sulfinyl group, a sulfonyl group or a imino group}; an $a_2$-y-CO—NH- group (wherein $a_2$ represents a C2-C10 alkyl group substituted with a C1-C10 alkoxy group, and y represents an oxy group or an imino group); a $r_0$O—COCO—NH- group (wherein $r_0$ is as defined above); an $a_3$-z-NH— group (wherein $a_3$ represents a C2-C10 alkenyl group, or a C1-C10 alkyl group substituted with a C1-C10 alkoxy group, a C1-C10 alkoxycarbonyl group, a carboxy group or a cyano group, and z represents a carbonyl group or a sulfonyl group); an $a_4$-NHCO- group {wherein $a_4$ represents a C1-C10 alkoxy group, or a C3-C10 alkenyloxy group, or a $r_0$-SO$_2$— group (wherein $r_0$ is as defined above), or a C2-C10 alkyl group substituted with a hydroxyl group or a C1-C10 alkoxy group, or a C1-C10 alkyl group substituted with a rO—CO— group (wherein r is as defined above), a cyano group or an aminocarbonyl group, or a rO—CO-(rO—COCH$_2$)CH- group (wherein r is as defined above)}; an $a_5$-NHSO$_2$- group (wherein $a_5$ represents a C2-C10 alkyl group substituted with a C1-C10 alkoxy group); a $r_0$ON=CH- group (wherein $r_0$ is as defined above); a $r_0$NHCSNH- group (wherein $r_0$ is as defined above); a r$_0$NHC(—Sr$_0$')=N- group (wherein r$_0$ is as defined above, r$_0$' is the same as the different from r$_0$ and has the same meaning as r$_0$ has); or a (r$_0$O)$_2$P(=O)CH$_2$- group (wherein r$_0$ is as defined above);

p represents 1, 2 or 3, and when p is 2 or more, X$_a$s are the same or different;

Y$_a$ represents a halogen atom, a nitro group, a r$_0$CO—NH- group (wherein r$_0$ is as defined above), a C1-C10 alkyl group or a C1-C10 alkoxy group;

q represents 0, 1 or 2, and when q is 2 or more, Y$_a$s are the same or different;

q$_a$ represents a r$_a$-O- group {wherein r$_a$ represents a hydrogen atom, a C1-C10 alkyl group, a C3-C10 alkenyl group, a C3-C10 alkynyl group, a C1-C10 alkyl group substituted with a r$_0$r$_0$'N—CH$_2$- group (wherein r$_0$ and r$_0$' are as defined above), a rOCH$_2$- group (wherein r is as defined above), a r$_0$-CO- group (wherein r$_0$ is as defined above), a C1-C10 alkoxycarbonyl group, a carboxy group, an aminocarbonyl group or a cyano group, or a r$_3$-r$_1$-group (wherein r$_3$ represents a phenyl group or a pyridyl group, and r$_1$ is as defined above)}; a piperidino group; a morpholino group; or a r$_4$r$_4$'N- group (wherein r$_4$ and r$_4$' are the same or different, and represent a hydrogen atom, a C1-C10 alkyl group, a C3-C10 alkenyl group, a C3-C10 alkynyl group, or a C2-C10 alkyl group substituted with a C1-C10 alkoxy group, provided that r$_4$ and r$_4$' are not a hydrogen atom at the same time);

the term "as defined above" used for the same symbols among plural substituents means that the plural substituents independently represent the same meaning as that described above and, among the plural substituents, although the selection range of substituents to be selected is the same, selected substituents may be the same or different as long as they are selected within the range;

7. A 2H-pyran-2-one compound represented by the formula (VII):

(VII)

wherein

X$_a$' represents a C1-C10 alkyl group substituted with a cyano group, or a C2-C10 alkenyl group substituted with a halogen atom or a cyano group, or an a$_0$'-r$_1$-O-group {a$_0$' represents a methyl group substituted with a C1-C10 alkylthio group, a C2-C10 alkenyl group, a C2-C10 alkynyl group, a HOCH$_2$-group or a cyano group, and r$_1$ represents a C1-C10 alkylene group}, or an a$_6$-CONH-group (a$_6$ represents a C1-C10 alkyl group substituted with a C1-C10 alkoxy group, or a C2-C10 alkoxy group substituted with a C1-C10 alkoxy group), or an a$_7$-NHCO-group (a$_7$ represents a C2-C10 alkyl group substituted with a C1-C10 alkoxy group, or a C1-C10 alkyl group substituted with a C1-C10 alkoxycarbonyl group); q$_a$' represents an amino group substituted with a C3-C10 alkynyl group, a piperidino group, a morpholino group or a r$_a$'-O-group (r$_a$' represents a hydrogen atom, a C1-C10 alkyl group or a C3-C10 alkenyl group).

8. A 2H-1-benzopyran-2-one compound represented by the formula (VIII):

(VIII)

wherein
a represents a benzene ring or a pyridine ring;
x represents a methine group or a nitrogen atom;
X$_a$ is a substituent on a carbon atom, and represents a C1-C10 alkyl group substituted with a cyano group; a C1-C10 alkyl group substituted with a tetrahydropyran-4-ylidene group; a C2-C10 alkenyl group substituted with a halogen atom or a cyano group; a C2-C10 alkenyl group substituted with a C1-C10 alkoxycarbonyl group; a C3-C10 alkynyl group substituted with a hydroxyl group; an a$_0$-r$_1$-b-r$_1$'- group {wherein a$_0$ represents a methyl group substituted with a C1-C10 alkylthio group, a methyl group substituted with a C1-C10 alkylsulfinyl group, a methyl group substituted with a C1-C10 alkylsulfonyl group, a C2-C10 alkenyl group, a C2-C10 alkynyl group, a r$_2$O—CO- group (wherein r$_2$ represents a C1-C10 alkyl group, or a C2-C10 alkyl group substituted with a hydroxyl group), a carboxyl group, a rr'N—CO- group (wherein r and r' are the same or different, and represent a hydrogen atom or a C1-C10 alkyl group), an a$_1$-NH—CO— group (wherein a$_1$ represents a C2-C10 alkyl group substituted with a C1-C10 alkoxy group), an a$_1$'-CO- group (wherein a$_1$' represents a morpholino group), a rr'N—CH$_2$— group (wherein r and r' are as defined above), a r$_0$-(O)$_l$— CONH—CH$_2$- group (wherein r$_0$ represents a C1-C10 alkyl group, and l represents 0 or 1), a r-OCH$_2$- group (wherein r is as defined above), a r$_0$-CO- group (wherein r$_0$ is as defined above), a cyano group, or a sulfomethyl group, r$_1$ represents a C1-C10 alkylene group, r$_1$' represents a single bond or a C1-C10 alkylene group, and b represents an oxy group, a thio group, a sulfinyl group, a sulfonyl group or a imino group}; an a$_2$-y-CO—NH- group (wherein a$_2$ represents a C2-C10 alkyl group substituted with a C1-C10 alkoxy group, and y represents an oxy group or an imino group); a r$_0$O—COCO—NH- group (wherein r$_0$ is as defined above); an a$_3$-z-NH— group (wherein a$_3$ represents a C2-C10 alkenyl group, or a C1-C10 alkyl group substituted with a C1-C10 alkoxy group, a C1-C10 alkoxycarbonyl group, a carboxy group or a cyano group, and z represents a carbonyl group or a sulfonyl group); an a$_4$-NHCO- group {wherein a$_4$ represents a C1-C10 alkoxy group, or a C3-C10 alkenyloxy group, or a r$_0$-SO$_2$— group (wherein r$_0$ is as defined above), or a C2-C10 alkyl group substituted with a hydroxyl group or a C1-C10 alkoxy group, or a C1-C10 alkyl group substituted with a rO—CO— group (wherein r is as defined above), a cyano group or an aminocarbonyl group, or a rO—CO-(rO—COCH$_2$)CH- group (wherein r is as defined above)}; an a$_5$-NHSO$_2$- group (wherein a$_5$ represents a C2-C10 alkyl group substituted with a C1-C10 alkoxy group); a r$_0$ON=CH- group (wherein r$_0$ is as defined above); a r$_0$NHCSNH- group (wherein r$_0$ is as defined above); a r$_0$NHC(—Sr$_0$')=N- group (wherein r$_0$ is as defined above, r$_0$' is the same as the different from r$_0$ and has the same meaning as r$_0$ has); or a (r$_0$O)$_2$P(=O)CH$_2$- group (wherein r$_0$ is as defined above);

p represents 1, 2 or 3, and when p is 2 or more, X$_a$s are the same or different;

$Y_a$ represents a halogen atom, a nitro group, a $r_0CO-NH$-group (wherein $r_0$ is as defined above), a C1-C10 alkyl group or a C1-C10 alkoxy group;

q represents 0, 1 or 2, and when q is 2 or more, $Y_a$s are the same or different;

$q_a$ represents a $r_a$-O- group {wherein $r_a$ represents a hydrogen atom, a C1-C10 alkyl group, a C3-C10 alkenyl group, a C3-C10 alkynyl group, a C1-C10 alkyl group substituted with a $r_0r_0'N-CH_2$- group (wherein $r_0$ and $r_0'$ are as defined above), a $rOCH_2$- group (wherein r is as defined above), a $r_0$-CO- group (wherein $r_0$ is as defined above), a C1-C10 alkoxycarbonyl group, a carboxy group, an aminocarbonyl group or a cyano group, or a $r_3$-$r_1$-group (wherein $r_3$ represents a phenyl group or a pyridyl group, and $r_1$ is as defined above)}; a piperidino group; a morpholino group; or a $r_4r_4'N$-group (wherein $r_4$ and $r_4'$ are the same or different, and represent a hydrogen atom, a C1-C10 alkyl group, a C3-C10 alkenyl group, a C3-C10 alkynyl group, or a C2-C10 alkyl group substituted with a C1-C10 alkoxy group, provided that $r_4$ and $r_4'$ are not a hydrogen atom at the same time);

$t_a$ represents a $r_b$- group (wherein $r_b$ is the same as or different from $r_a$, and has the same meaning as $r_a$ has) or a $r_3'$- group (wherein $r_3'$ is the same as or different from $r_3$, and has the same meaning as $r_3$ has);

$K_a$ represents a hydrogen atom, a halogen atom or a C1-C10 alkyl group, and $L_a$ represents a hydrogen atom or a C1-C10 alkyl group; or $K_a$ and $L_a$ together may form a C1-C10 alkylene group or a 1,3-butadienylene group;

the term "as defined above" used for the same symbols among plural substituents means that the plural substituents independently represent the same meaning as that described above and, among the plural substituents, although the selection range of substituents to be selected is the same, selected substituents may be the same or different as long as they are selected within the range;

9. A 2H-1-benzopyran-2-one compound represented by the formula (IX):

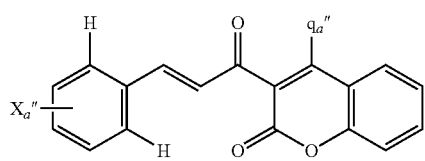

wherein $X_a''$ represents a C1-C10 alkoxy group substituted with a cyano group or a hydroxymethyl group, or an $a_6$-CONH- group ($a_6$ represents a C1-C10 alkyl group substituted with a C1-C10 alkoxy group, or a C2-C10 alkoxy group substituted with a C1-C10 alkoxy group), or an $a_7$-NHCO-group ($a_7$ represents a C2-C10 alkyl group substituted with a hydroxy group, or a C2-C10 alkyl group substituted with a C1-C10 alkoxy group, or a C1-C10 alkyl group substituted with a C1-C10 alkoxycarbonyl group), and $q_a''$ represents a hydroxy group, a C1-C10 alkoxy group or a piperidino group;

10. A 2H-pyran-2-one compound represented by the formula (X):

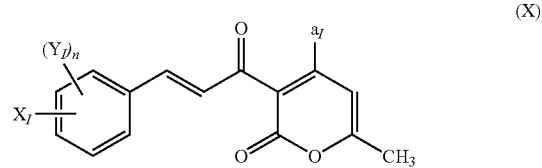

wherein $X_I$ represents a C2-C4 alkenyl group substituted with a cyano group, an $A_I$-$R_I$—O-group ($A_I$ represents a C1-C4 alkylthio group, a C2-C4 alkenyl group, a C2-C4 alkynyl group, a C1-C4 alkoxycarbonyl group, a carboxy group or a cyano group, and $R_I$ represents a C1-C4 alkylene group), an $A_{II}$-$(y)_m$-z-NH-group ($A_{II}$ represents a C2-C4 alkenyl group, or a C1-C4 alkyl group substituted with a C1-C4 alkoxy group, a C1-C4 alkoxycarbonyl group, a carboxy group or a cyano group, y represents an oxy group or an imino group, z represents a carbonyl group or a sulfonyl group, and m represents 0 or 1) or an $A_{III}$-NHCO-group ($A_{III}$ represents a methanesulfonyl group, or a C1-C4 alkyl group substituted with a hydroxy group, a C1-C4 alkoxy group, a C1-C4 alkoxycarbonyl group, a carboxy group or a cyano group), $a_I$ represents a hydroxy group, a C1-C4 alkoxy group, a C2-C4 alkenyloxy group, a C2-C4 alkynyloxy group, a C1-C4 alkylamino group, a C2-C4 alkenylamino group, a C2-C4 alkynylamino group, a morpholino group or a piperidino group, $Y_I$ represents a halogen atom, a nitro group, a C1-C4 alkyl group or a C1-C4 alkoxy group, n represents 0, 1 or 2 and, when n is 2, $Y_I$s may be different;

11. A 2H-1-benzopyran-2-one compound represented by the formula (XI):

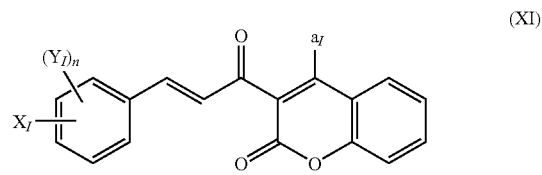

wherein $X_I$ represents a C2-C4 alkenyl group substituted with a cyano group, an $A_I$-$R_I$—O-group ($A_I$ represents a C1-C4 alkylthio group, a C2-C4 alkenyl group, a C2-C4 alkynyl group, a C1-C4 alkoxycarbonyl group, a carboxy group or a cyano group, and $R_I$ represents a C1-C4 alkylene group), an $A_{II}$-$(y)_m$-z-NH-group ($A_{II}$ represents a C2-C4 alkenyl group, or a C1-C4 alkyl group substituted with a C1-C4 alkoxy group, a C1-C4 alkoxycarbonyl group, a carboxy group or a cyano group, y represents an oxy group or an imino group, z represents a carbonyl group or a sulfonyl group, and m represents 0 or 1) or an $A_{III}$-NHCO-group ($A_{III}$ represents a methanesulfonyl group, or a C1-C4 alkyl group substituted with a hydroxy group, a C1-C4 alkoxy group, a C1-C4 alkoxycarbonyl group, a carboxy group or a cyano group), $a_I$ represents a hydroxy group, a C1-C4 alkoxy group, a C2-C4 alkenyloxy group, a C2-C4 alkynyloxy group, a C1-C4 alkylamino group, a C2-C4 alkenylamino group, a C2-C4 alkynylamino group, a morpholino group or a piperidino group, $Y_I$ represents a halogen atom, a nitro group, a C1-C4 alkyl group or a C1-C4 alkoxy group, n represented 0, 1 or 2 and, when n is 2, $Y_I$'s may be different;

12. A 2H-pyran-2-one compound represented by the formula (XII):

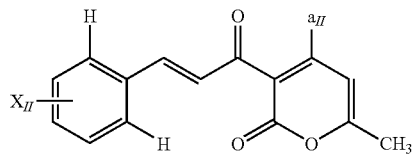

wherein $X_{II}$ represents an allyloxy group, a propargyloxy group, a cyanomethoxy group, a methoxyacetylamino group, a methoxycarbonylmethylaminocarbonyl group or a 2-cyanoethenyl group, and $a_{II}$ represents a hydroxy group, a methoxy group or a morpholino group;

13. A 2H-1-benzopyran-2-one compound represented by the formula (XIII):

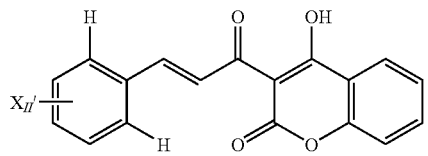

wherein $X_{II}'$ represents a cyanomethoxy group, a methoxyacetylamino group or a 2-hydroxyethylaminocarbonyl group;

14. A 2H-pyran-2-one compound represented by the formula (XIV):

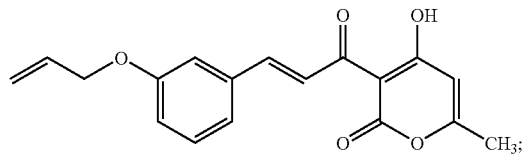

15. A 2H-pyran-2-one compound represented by the formula (XV):

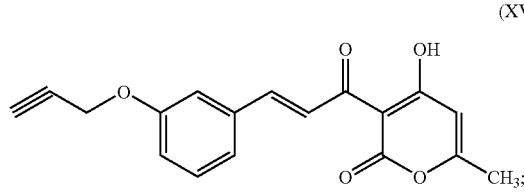

16. A 2H-pyran-2-one compound represented by the formula (XVI):

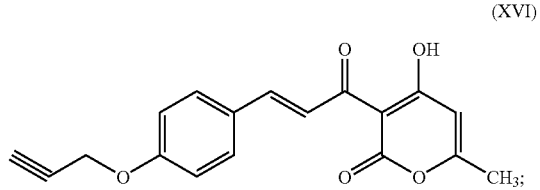

17. A 2H-pyran-2-one compound represented by the formula (XVII):

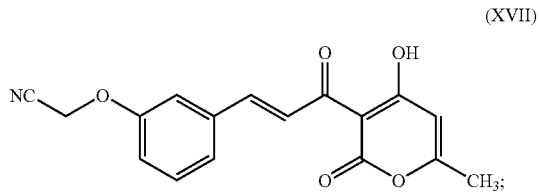

18. A 2H-pyran-2-one compound represented by the formula (XVIII):

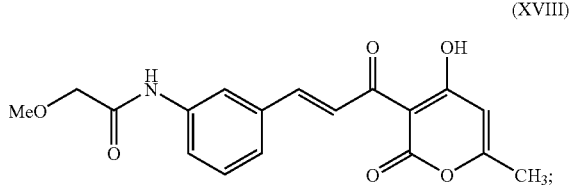

19. A 2H-pyran-2-one compound represented by the formula (XIX):

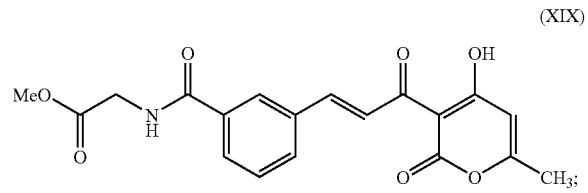

20. A 2H-pyran-2-one compound represented by the formula (XX):

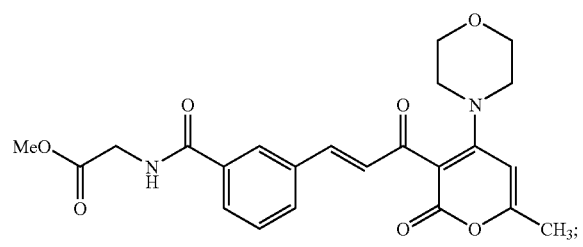

21. A 2H-pyran-2-one compound represented by the formula (XXI):

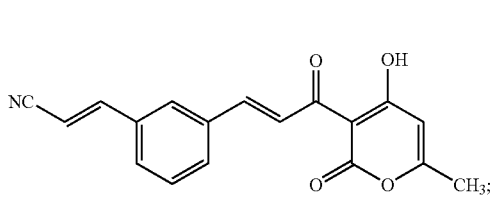
(XXI)

22. A 2H-pyran-2-one compound represented by the formula (XXII):

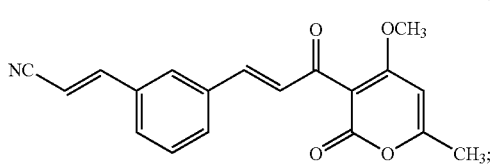
(XXII)

23. A 2H-a-benzopyran-2-one compound represented by the formula (XXIII):

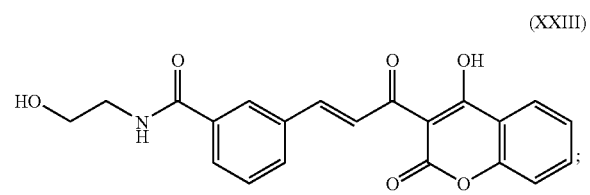
(XXIII)

24. A 2H-a-benzopyran-2-one compound represented by the formula (XXIV):

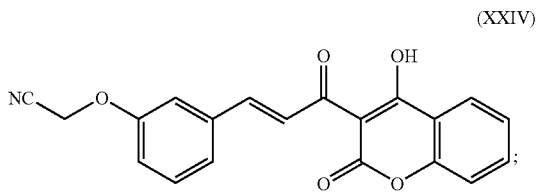
(XXIV)

25. A 2H-1-benzopyran-2-one compound represented by the formula (XXV):

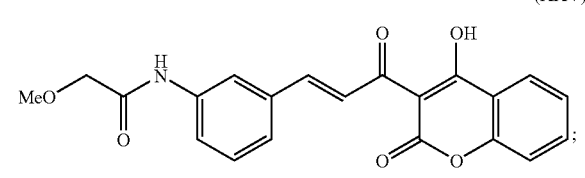
(XXV)

26. A benzaldehyde derivative represented by the formula (XXVI-1):

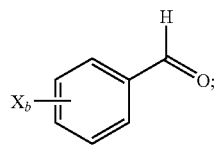
(XXVI-1)

[wherein $X_b$ represents a MeO—COCH$_2$NHCO-group, a MeOCH$_2$CHO—CO—NH-group, a MeOCH$_2$CH$_2$NH—CO—NH-group, a MeSO$_2$NH—CO-group, a NCCH$_2$NH—CO-group, a F$_2$C=CH-group, a MeO—CO-(MeO—COCH$_2$—)CH-group, a MeOCH$_2$CH$_2$NH—SO$_2$-group, a MeO—NHCO-group or a CH$_2$=CHCH$_2$O—NHCO-group.];

the formula (XXVI-2):

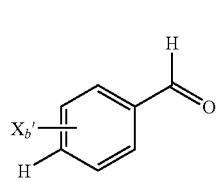
(XXVI-2)

[wherein $X_b'$ represents a MeOCH$_2$CO—NH-group or a MeOCH$_2$CH$_2$NH—CO-group.];

the formula (XXVI-3):

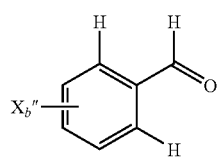
(XXVI-3)

[wherein $X_b''$ represents a MeSCH$_2$CH$_2$O-group, a HOCH$_2$CH$_2$OCH$_2$-group or a NC—CH$_2$CH$_2$-group.] or the formula (XXVI-4):

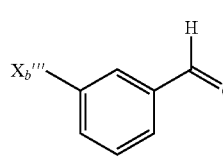
(XXVI-4)

[wherein $X_b'''$ represents a NCCH=CH-group, a H$_2$NCOCH$_2$O-group, a MeCOCH$_2$O-group, a CH$_3$O—COCH$_2$SCH$_2$-group, a tetrahydropyran-4-ylidenemethyl group, a CH$_3$O—COCO—NH-group or a (CH$_3$O)$_2$P(=O)CH$_2$-group.]; or 6-formyl-2-[(2-methoxyethyl)aminocarbonyl]pyridine;

27. A benzaldehyde derivative represented by the formula (XXVII):

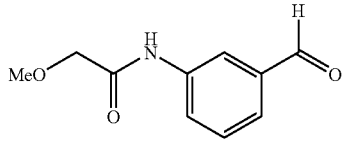
(XXVII)

28. A benzaldehyde derivative represented by the formula (XXVIII):

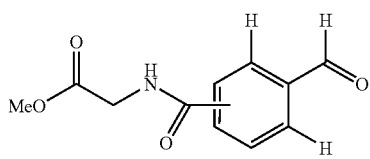
(XXVIII)

29. A benzaldehyde derivative represented by the formula (XXIX):

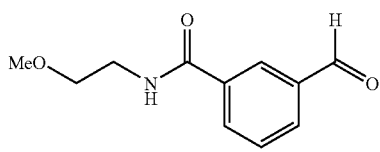
(XXIX)

30. A benzaldehyde derivative represented by the formula (XXX):

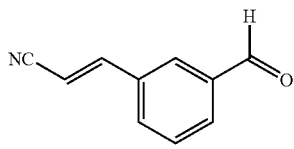
(XXX)

31. A benzaldehyde derivative represented by the formula (XXXI):

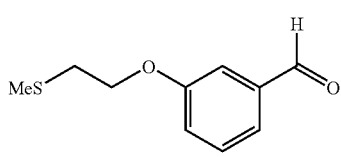
(XXXI)

32. A benzaldehyde derivative represented by the formula (XXXII):

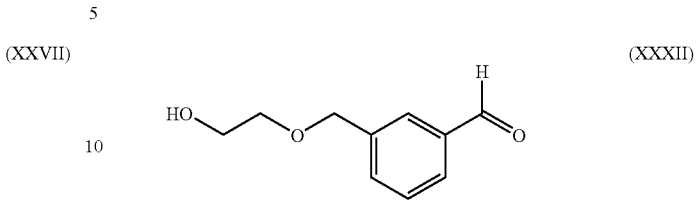
(XXXII)

33. A benzaldehyde derivative represented by the formula (XXXIII):

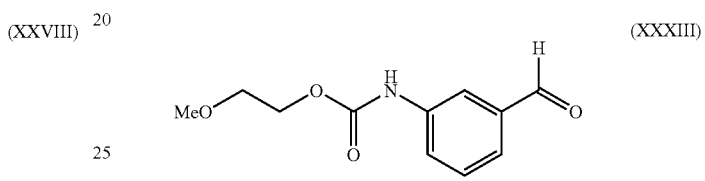
(XXXIII)

34. A benzaldehyde derivative represented by the formula (XXXIV):

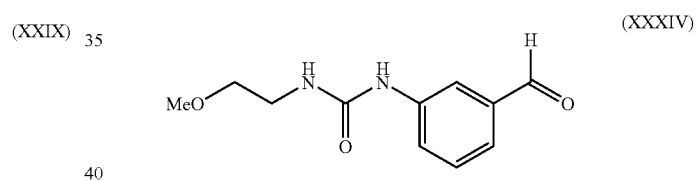
(XXXIV)

35. A benzaldehyde derivative represented by the formula (XXXV):

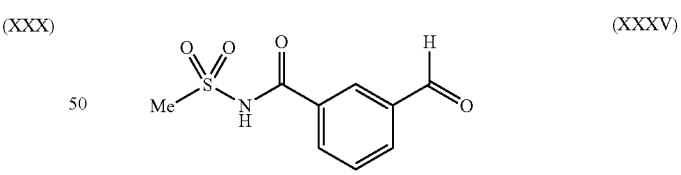
(XXXV)

36. A benzaldehyde derivative represented by the formula (XXXVI):

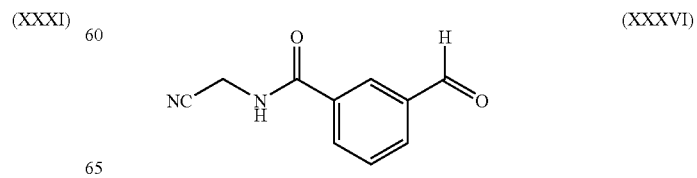
(XXXVI)

37. A benzaldehyde derivative represented by the formula (XXXVII):

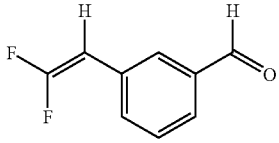
(XXXVII)

38. A benzaldehyde derivative represented by the formula (XXXVIII):

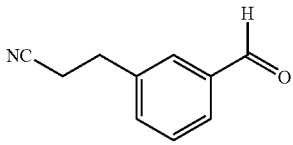
(XXXVIII)

39. A benzaldehyde derivative represented by the formula (XXXIX):

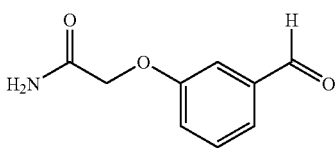
(XXXIX)

40. A benzaldehyde derivative represented by the formula (XL):

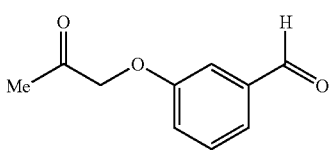
(XL)

41. A benzaldehyde derivative represented by the formula (XLI):

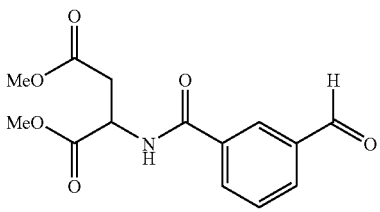
(XLI)

42. A pyridinecarbaldehyde derivative represented by the formula (XLII):

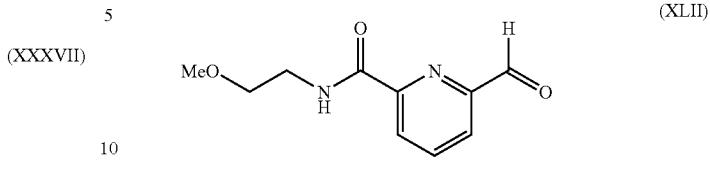
(XLII)

43. A benzaldehyde derivative represented by the formula (XLIII):

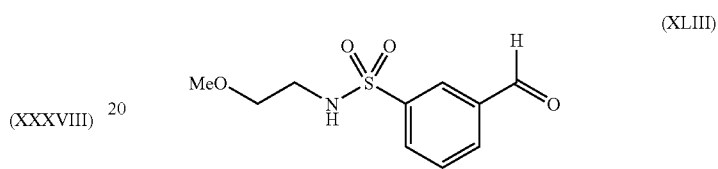
(XLIII)

44. A benzaldehyde derivative represented by the formula (XLIV):

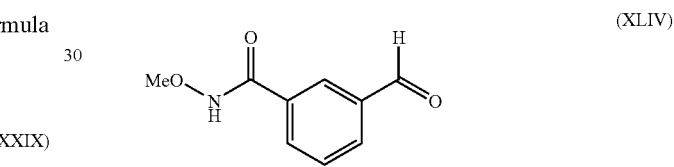
(XLIV)

45. A benzaldehyde derivative represented by the formula (XLV):

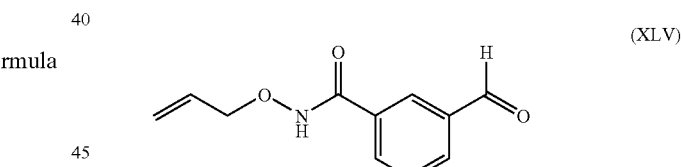
(XLV)

46. A process for producing a cynnamoyl compound represented by the formula (XLVI-1):

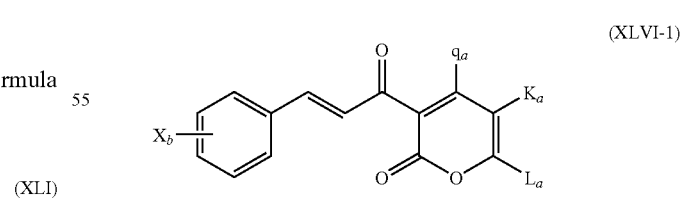
(XLVI-1)

wherein $X_b$ represents a MeO—COCH$_2$NHCO-group, a MeOCH$_2$CH$_2$O—CO—NH-group, a MeOCH$_2$CH$_2$NH—CO—NH-group, a MeSO$_2$NH—CO-group, a NCCH$_2$NH—CO-group, a F$_2$C═CH-group, a MeO—CO-(MeO—COCH$_2$—)CH-group, a MeOCH$_2$CH$_2$NH—SO$_2$-group, a MeO—NHCO-group or a CH═CHCH$_2$O—NHCO-group, and $q_a$, $K_a$ and $L_a$ are as defined below, the formula (XLVI-2):

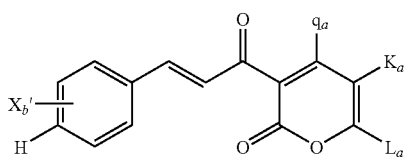
(XLVI-2)

wherein $X_b'$ represents a MeOCH$_2$CO—NH-group or a MeOCH$_2$CH$_2$NH—CO-group, $q_a$, $K_a$ and $L_a$ are as defined below, the formula (XLVI-3):

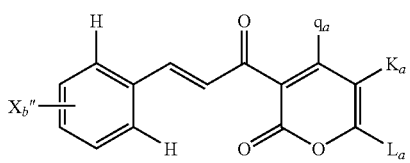
(XLVI-3)

wherein $X_b''$ represents a MeSCH$_2$CH$_2$O-group, a HOCH$_2$CH$_2$OCH$_2$-group or a NC—CH$_2$CH$_2$-group, and $q_a$, $K_a$ and $L_a$ are as defined below, the formula (XLVI-4):

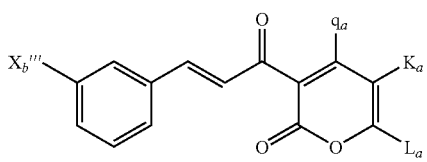
(XLVI-4)

wherein $X_b'''$ represents a NCCH=CH-group, a H$_2$NCOCH$_2$O-group, a MeCOCH$_2$O-group, a CH$_3$O—COCH$_2$SCH$_2$-group, a tetrahydropyran-4-ylidenemethyl group, a CH$_3$O—COCO—NH-group or a (CH$_3$O)$_2$P(=O)CH$_2$-group, and $q_a$, $K_a$ and $L_a$ are as defined below, or the formula (XLVI-5):

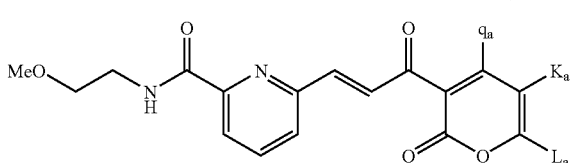
(XLVI-5)

wherein $q_a$, $K_a$ and $L_a$ are as defined below, which comprises reacting a benzaldehyde derivative represented by the formula (XXVI-1), the formula (XXVI-2), the formula (XXVI-3) or the formula (XXVI-4), or 6-formyl-2-[(2-methoxyethyl)aminocarbonyl]pyridine as defined in the above item 26, with a compound represented by the formula (XLVI):

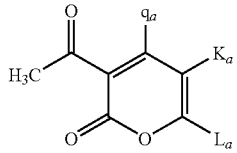
(XLVI)

wherein $q_a$ represents a $r_a$-O-group {wherein $r_a$ represents a hydrogen atom; a C1-C10 alkyl group; a C3-C10 alkenyl group; a C3-C10 alkynyl group; a C1-C10 alkyl group substituted with a $r_0r_0'$N—CH$_2$- group (wherein $r_0$ and $r_0'$ are the same or different, and represent a C1-C10 alkyl group), a rOCH$_2$-group (wherein r represents a hydrogen atom or a C1-C10 alkyl group), a $r_0$-CO- group (wherein $r_0$ is as defined above), a C1-C10 alkoxycarbonyl group, a carboxy group, an aminocarbonyl group or a cyano group; or a $r_3$-$r_1$-group (wherein $r_3$ represents a phenyl group or a pyridyl group, and $r_1$ represents a C1-C10 alkylene group)}, a piperidino group, a morpholino group, or a $r_4r_4'$N- group (wherein $r_4$ and $r_4'$ are the same or different, and represent a hydrogen atom, a C1-C10 alkyl group, a C3-C10 alkenyl group, a C3-C10 alkynyl group, or a C2-C10 alkyl group substituted with a C1-C10 alkoxy group, provided that $r_4$ and $r_4'$ are not a hydrogen atom at the same time), $K_a$ represents a hydrogen atom, a halogen atom or a C1-C10 alkyl group, and $L_a$ represents a hydrogen atom or a C1-C10 alkyl group, or $K_a$ and $L_a$ together may form a C1-C10 alkylene group or a 1,3-butadienylene group, and the term "as defined above (or below)" used for the same symbols among plural substituents means that the plural substituents independently represent the same meaning as that described above (or below) and, among the plural substituents, although the selection range of substituents to be selected is the same, selected substituents may be the same or different as long as they are selected within the range;

47. A process for producing a cinnamoyl compound represented by the formula (XLVII″):

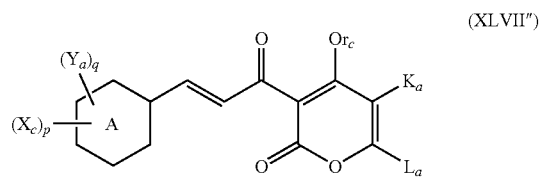
(XLVII″)

wherein A, $X_c$, $Y_a$, p, q, $r_c$, $K_a$ and $L_a$ are as defined below, and the term "as defined above (or below)" used for the same symbols among plural substituents means that the plural substituents independently represent the same meaning as that described above (or below) and, among the plural substituents, although the selection range of substituents to be selected is the same, selected substituents may be the same or different as long as they are selected within the range; which comprises reacting a cinnamoyl compound represented by the formula (XLVII):

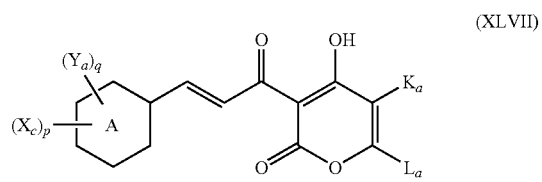
(XLVII)

wherein

A represents a benzene ring or a pyridine ring, $X_c$ is a substituent on a carbon atom, and represents a C1-C10 alkyl group substituted with a cyano group; a C1-C10 alkyl group substituted with a tetrahydropyran-4-ylidene group; a C2-C10 alkenyl group substituted with a halogen atom or a cyano group; a C2-C10 alkenyl group substituted with a C1-C10 alkoxycarbonyl group; a C2-C10 alkynyl group substituted with a hydroxylmethyl group; an $a_{0c}$-$r_1$-b-$r_1$'- group {wherein $a_{0c}$ represents a methyl group substituted with a C1-C10 alkylthio group, a methyl group substituted with a C1-C10 alkylsulfinyl group, a methyl group substituted with a C1-C10 alkylsulfonyl group, a C2-C10 alkenyl group, a C2-C10 alkynyl group, a $r_2$O—CO- group (wherein $r_2$ represents a C1-C10 alkyl group, or a C2-C10 alkyl group substituted with a hydroxyl group), a rr'N—CO— group (wherein r and r' are the same or different, and represent a hydrogen atom or a C1-C10 alkyl group), an $a_1$-NH—CO- group (wherein $a_1$ represents a C2-C10 alkyl group substituted with a C1-C10 alkoxy group), an $a_1$'-CO- group (wherein $a_1$' represents a morpholino group), a rr'N—CH$_2$— group (wherein r and r' are as defined above), a $r_0$-(O)$_l$—CONH—CH$_2$- group (wherein $r_0$ represents a C1-C10 alkyl group, and l represents 0 or 1), a r-OCH$_2$- group (wherein r is as defined above), a $r_0$-CO- group (wherein $r_0$ is as defined above), or a cyano group, $r_1$ represents a C1-C10 alkylene group, $r_1$' represents a single bond or a C1-C10 alkylene group, and b represents an oxy group, a thio group, a sulfinyl group, a sulfonyl group or a imino group}; an $a_2$-y-CO—NH- group (wherein $a_2$ represents a C2-C10 alkyl group substituted with a C1-C10 alkoxy group, and y represents an oxy group or an imino group); a $r_0$O—COCO—NH- group (wherein $r_0$ is as defined above); an $a_3$-z-NH- group (wherein $a_3$ represents a C2-C10 alkenyl group, or a C1-C10 alkyl group substituted with a C1-C10 alkoxy group, a C1-C10 alkoxycarbonyl group or a cyano group, and z represents a carbonyl group or a sulfonyl group); an $a_4$-NHCO- group {wherein $a_4$ represents a C1-C10 alkoxy group, or a C3-C10 alkenyloxy group, or a $r_0$-SO$_2$- group (wherein $r_0$ is as defined above), or a C2-C10 alkyl group substituted with a hydroxyl group or a C1-C10 alkoxy group, or a C1-C10 alkyl group substituted with a $r_0$O—CO- group (wherein $r_0$ is as defined above), a cyano group or an aminocarbonyl group, or a $r_0$O—CO-($r_0$O—COCH$_2$)CH- group (wherein $r_0$ is as defined above)}; an $a_5$-NHSO$_2$- group (wherein $a_5$ represents a C2-C10 alkyl group substituted with a C1-C10 alkoxy group); a $r_0$ON=CH- group (wherein $r_0$ is as defined above); a $r_0$NHCSNH— group (wherein $r_0$ is as defined above); a $r_0$NHC(—S$r_0$')=N— group (wherein $r_0$ is as defined above, $r_0$' is the same as the different from $r_0$ and has the same meaning as $r_0$ has); or a ($r_0$O)$_2$P(=O)CH$_2$- group (wherein $r_0$ is as defined above);

p represents 1, 2 or 3, and when p is 2 or more, $X_c$s are the same or different;

$Y_a$ represents a halogen atom, a nitro group, a $r_0$CO—NH- group (wherein $r_0$ is as defined above), a C1-C10 alkyl group or a C1-C10 alkoxy group;

q represents 0, 1 or 2, and when q is 2 or more, $Y_a$s are the same or different;

$K_a$ represents a hydrogen atom, a halogen atom or a C1-C10 alkyl group, and $L_a$ represents a hydrogen atom or a C1-C10 alkyl group, or $K_a$ and $L_a$ together may form a C1-C10 alkylene group or a 1,3-butadienylene group, and the term "as defined above" used for the same symbols among plural substituents means that the plural substituents independently represent the same meaning as that described above and, among the plural substituents, although the selection range of substituents to be selected is the same, selected substituents may be the same or different as long as they are selected within the range, with a compound represented by the formula (XLVII'):

$$r_c\text{-V} \qquad (XLVII')$$

wherein $r_c$ represents a $t_c$'-group {wherein $t_c$' represents a C1-C10 alkyl group; a C3-C10 alkenyl group; a C3-C10 alkynyl group; a C1-C10 alkyl group substituted with a $r_0 r_0$'N—CH$_2$- group (wherein $r_0$ and $r_0$' are as defined above), a rOCH$_2$- group (wherein r is as defined above), a $r_0$-CO— group (wherein $r_0$ is as defined above), a C1-C10 alkoxycarbonyl group, an aminocarbonyl group or a cyano group; or a $r_3$-$r_1$- group (wherein $r_3$ represents a phenyl group or a pyridyl group, and $r_1$ is as defined above)}, and V represents a leaving group, and the term "as defined above" used for the same symbols among plural substituents means that the plural substituents independently represent the same meaning as that described above and, among the plural substituents, although the selection range of substituents to be selected is the same, selected substituents may be the same or different as long as they are selected within the range;

48. A process for producing a cinnamoyl compound represented by the formula (XLVIII'):

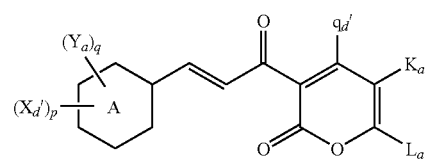

(XLVIII')

wherein

A is as defined below, $X_d$' is a substituent on a carbon atom, and represents an $a_{0d}$'-$r_1$-b-$r_1$'- group (wherein $a_{0d}$' represents a carboxy group, and $r_1$, $r_1$' and b are as defined below), a HO—COCO—NH- group, an $a_{3d}$'-z-NH- group (wherein $a_{3d}$' represents a C1-C10 alkyl group substituted with a carboxy group, and z is as defined below), or an $a_{4d}$'-NHCO- group (wherein $a_{4d}$' represents a C1-C10 alkyl group substituted with a carboxy group, or a HO—CO—(HO—COCH$_2$)CH- group), p is as defined below and, and when p is 2 or more, $X_d$' s are the same or different, $Y_a$ and q are as defined below, $q_d$' represents a $r_d$"-O- group {wherein $r_d$" represents a hydrogen atom; a C1-C10 alkyl group; a C3-C10 alkenyl group; a C3-C10 alkynyl group; a C1-C10 alkyl group substituted with a $r_0 r_0$'N—CH$_2$- group (wherein $r_0$ and $r_0$' are as defined below), a rOCH$_2$- group (wherein r is as defined below), a $r_0$-CO- group (wherein $r_0$ is as defined below), a carboxy group, an aminocarbonyl group or a cyano group; or a $r_3$-$r_1$- group (wherein $r_3$ represents a phenyl group or a pyridyl group, and $r_1$ is as defined below)}, a piperidino group, a morpholino group, or a $r_4 r_4$'N- group (wherein $r_4$ and $r_4$' are as defined below, provided that they are not hydrogen atom at the same time), $K_a$ and $L_a$ are as defined below, and the term "as defined above (or below)" used for the same symbols among plural substituents means that the plural substituents independently represent the same meaning as that described above (or below) and, among the plural substituents, although the selection range of substituents to be selected is the same, selected substituents may be the same or different as long as they are selected within the range;

which comprises hydrolyzing a cinnamoyl compound represented by the formula (XLVIII):

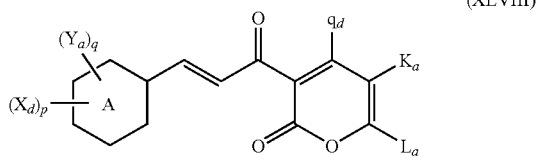

(XLVIII)

wherein

A represents a benzene ring or a pyridine ring, $X_d$ is a substituent on a carbon atom, and represents an $a_{0d}$-$r_1$-b-$r_1$'- group {wherein $a_{0d}$ represents a $r_2$O—CO— group (wherein $r_2$ represents a C1-C10 alkyl group, or a C2-C10 alkyl group substituted with a hydroxy group), $r_1$ represents a C1-C10 alkylene group, $r_1$' represents a single bond or a C1-C10 alkylene group, and b represents an oxy group, a thio group, a sulfinyl group, a sulfonyl group or an imino group}, a $r_0$O—COCO—NH- group (wherein $r_0$ represents a C1-C10 alkyl group), an $a_{3d}$-z-NH- group (wherein $a_{3d}$ represents a C1-C10 alkyl group substituted with a C1-C10 alkoxycarbonyl group, and z represents a carbonyl group or a sulfonyl group), or an $a_{4d}$-NHCO- group {wherein $a_{4d}$ represents a C1-C10 alkyl group substituted with a $r_0$O—CO— group (wherein $r_0$ is as defined above), or a $r_0$O—CO-($r_0$O—COCH$_2$)CH- group (wherein $r_0$ is as defined above)}, p represents 1, 2 or 3, and when p is 2 or more, $X_d$s are the same or different, $Y_a$ represents a halogen atom, a nitro group, a $r_0$CO—NH- group (wherein $r_0$ is as defined above), a C1-C10 alkyl group or a C1-C10 alkoxy group, q represents 0, 1 or 2, and when q is 2 or more, $Y_a$s are the same or different;

$q_d$ represents a $r_d$-O- group {wherein $r_d$ represents a hydrogen atom, a C1-C10 alkyl group, a C3-C10 alkenyl group, a C3-C10 alkynyl group, a C1-C10 alkyl group substituted with a $r_0r_0$'N—CH$_2$- group (wherein $r_0$ is as defined above, and $r_0$' is the same as or different from $r_0$ and has the same meaning as $r_0$ has), a rOCH$_2$- group (wherein r is as defined above), a $r_0$-CO- group (wherein $r_0$ is as defined above), a C1-C10 alkoxycarbonyl group, a carboxy group, an aminocarbonyl group or a cyano group, or a $r_3$-$r_1$-group (wherein $r_3$ represents a phenyl group or a pyridyl group, and $r_1$ is as defined above)}; a piperidino group; a morpholino group; or a $r_4r_4$'N- group (wherein $r_4$ and $r_4$' represent a hydrogen atom, a C1-C10 alkyl group, a C3-C10 alkenyl group, a C3-C10 alkynyl group, or a C2-C10 alkyl group substituted with a C1-C10 alkoxy group, provided that they are not a hydrogen atom at the same time), $K_a$ represents a hydrogen atom, a halogen atom or a C1-C10 alkyl group, and $L_a$ represents a hydrogen atom or a C1-C10 alkyl group, or $K_a$ and $L_a$ together may form a C1-C10 alkylene group or a 1,3-butadienylene group, the term "as defined above" used for the same symbols among plural substituents means that the plural substituents independently represent the same meaning as that described above and, among the plural substituents, although the selection range of substituents to be selected is the same, selected substituents may be the same or different as long as they are selected within the range;

49. A process for producing a cinnamoyl compound represented by the formula (XLIX"):

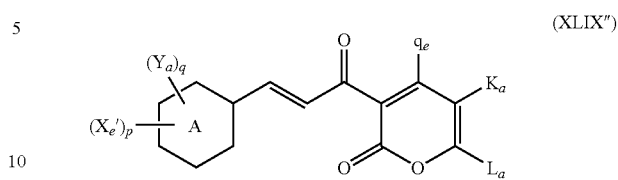

(XLIX")

wherein $X_e$' represents an $a_{0e}$'-$r_1$"-b"- group {wherein $a_{0e}$' represents an $a_{0e}$- group (wherein $a_{0e}$ is as defined below), a 3-sulfopropyl group or a 4-sulfobutyl group, and $r_1$" and b" are as defined below}, and A, $Y_a$, p, q, $q_e$, $K_a$ and $L_a$ are as defined below, and the term "as defined above (or below)" used for the same symbols among plural substituents means that the plural substituents independently represent the same meaning as that described above (or below) and, among the plural substituents, although the selection range of substituents to be selected is the same, selected substituents may be the same or different as long as they are selected within the range;

which comprises reacting a cinnamoyl compound represented by the formula (XLIX):

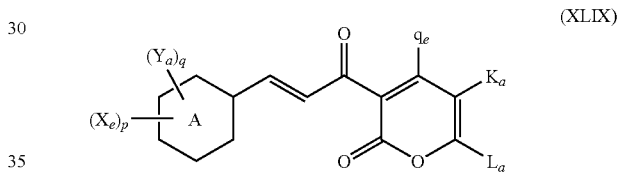

(XLIX)

wherein

A represents a benzene ring or a pyridine ring, $X_e$ is a substituent on a carbon atom, and represents a H-b"- group (wherein b" represents an oxy group or a thio group), p represents 1, 2 or 3 and, when p is 2 or more, $X_e$s are the same or different, $Y_a$ represents a halogen atom, a nitro group, a $r_0$CO—NH- group (wherein $r_0$ is a C1-C10 alkyl group), a C1-C10 alkyl group or a C1-C10 alkoxy group, q represents 0, 1 or 2, and when q is 2 or more, $Y_a$s are the same or different;

$q_e$ represents a $r_e$-O- group {wherein $r_e$ represents a C1-C10 alkyl group, a C3-C10 alkenyl group, a C3-C10 alkynyl group, a C1-C10 alkyl group substituted with a $r_0r_0$'N—CH$_2$- group (wherein $r_0$ is as defined above, and $r_0$' is the same as or different from $r_0$ and has the same meaning as $r_0$ has), a rOCH$_2$- group (wherein r represents a hydrogen atom or a C1-C10 alkyl group), a $r_0$-CO- group (wherein $r_0$ is as defined above), a C1-C10 alkoxycarbonyl group, an aminocarbonyl group or a cyano group, or a $r_3$-$r_1$- group (wherein $r_3$ represents a phenyl group or a pyridyl group, and $r_1$ represents a C1-C10 alkylene group)}; a piperidino group; a morpholino group; or a $r_4r_4$'N- group (wherein $r_4$ and $r_4$' represent a hydrogen atom, a C1-C10 alkyl group, a C3-C10 alkenyl group, a C3-C10 alkynyl group, or a C2-C10 alkyl group substituted with a C1-C10 alkoxy group, provided that they are not a hydrogen atom at the same time), $K_a$ represents a hydrogen atom, a halogen atom or a C1-C10 alkyl group, and $L_a$ represents a hydrogen atom or a C1-C10 alkyl group, or $K_a$ and $L_a$ together may form a C1-C10 alkylene group or a 1,3-butadienylene group, and the term "as defined above" used for the same symbols among plural substituents means that the plural substituents independently represent the same meaning as that described above and, among the plural substituents, although the selection range of substituents to be selected is the same, selected substituents may be the same or different as long as they are selected within the range, with a compound represented by the formula (XLIX'):

(XLIX')

wherein $a_{0e}$ represents a methyl group substituted with a C1-C10 alkylthio group, a methyl group substituted with a C1-C10 alkylsulfinyl group, a methyl group substituted with a C1-C10 alkylsulfonyl group, a C2-C10 alkenyl group, a C2-C10 alkynyl group, a $r_2$O—CO- group (wherein $r_2$ represents a C1-C10 alkyl group, or a C2-C10 alkyl group substituted with a hydroxy group), a rr'N—CO- group (wherein r and r' are the same or different, and represent a hydrogen atom or a C1-C10 alkyl group), an $a_1$-NH—CO- group (wherein $a_1$ represents a C2-C10 alkyl group substituted with a C1-C10 alkoxy group), an $a_1$'-CO- group (wherein $a_1$' represents a morpholino group), a rr'N—CH$_2$- group (wherein r is as defined above, r' is the same as or different from r and has the same meaning as r has), a $r_0$-(O)$_1$—CONH—CH$_2$- group (wherein $r_0$ is as defined above, and l represents 0 or 1), a r-OCH$_2$- group (wherein r is as defined above), a $r_0$-CO— group (wherein $r_0$ is as defined above) or a cyano group, $r_1$" is the same as or different from $r_1$ and has the same meaning as $r_1$ has, and V' represents a leaving group or a hydroxy group, or 1,3-propanesultone or 1,4-butanesultone the term "as defined above" used for the same symbols among plural substituents means that the plural substituents independently represent the same meaning as that described above and, among the plural substituents, although the selection range of substituents to be selected is the same, selected substituents may be the same or different as long as they are selected within the range;

50. Use of a compound according to any one of the above items 1 to 25 as an active ingredient for suppressing transcription of a Type I collagen gene;

51. A composition for suppressing transcription of a Type I collagen gene, which comprises a compound according to any one of the above items 1 to 25 and an inert carrier;

52. Use of a compound according to any one of the above items 1 to 25 as an active ingredient for decreasing expression of a Type I collagen gene to induce a reduction in accumulation of collagen and thereby improving tissue fibrosis;

53. A composition for improving tissue fibrosis, which comprises a compound according to any one of the above items 1 to 25 and an inert carrier;

54. A method for improving tissue fibrosis, which comprises administering an effective amount of a compound according to any one of the above items 1 to 25 to a mammal in need thereof;

55. Use of a compound according to any one of the above items 1 to 25 as an active ingredient for suppressing the activity of TGF-β;

56. A composition for suppressing the activity of TGF-β, which comprises a compound according to any one of the above items 1 to 25 and an inert carrier;

57. Use of a compound according to any one of the above items 1 to 25 as an active ingredient for inhibiting a promoting effect of TGF-β on transition to a hair regression phase to induce extension of a hair growth phase and thereby providing hair-growing effect;

58. A composition for hair growth which comprises a compound according to any one of the above items 1 to 25 and an inert carrier;

59. A method for growing hair, which comprises administering an effective amount of a compound according to any one of the above items 1 to 25 to a mammal in need thereof;

60. Use of a compound according to any one of the above items 1 to 25 as an active ingredient for treating chronic renal failure;

61. An agent for treating chronic renal failure, which comprises a compound according to any one of the above items 1 to 25 and an inert carrier;

62. Use of a compound according to the above item 2 as an active ingredient for suppressing transcription of a Type I collagen gene;

63. A composition for suppressing transcription of a Type I collagen gene, which comprises a compound according to the above item 2 and an inert carrier;

64. Use of a compound according to the above item 3 as an active ingredient for suppressing transcription of a Type I collagen gene;

65. A composition for suppressing transcription of a Type I collagen gene, which comprises a compound according to the above item 3 and an inert carrier;

66. Use of a compound according to the above item 4 as an active ingredient for suppressing transcription of a Type I collagen gene;

67. A composition for suppressing transcription of a Type I collagen gene, which comprises a compound according to the above item 4 and an inert carrier;

68. Use of a compound according to the above item 10 as an active ingredient for suppressing transcription of a Type I collagen gene;

69. A composition for suppressing transcription of a Type I collagen gene, which comprises a compound according to the above item 10 and an inert carrier;

70. Use of a compound according to the above item 11 as an active ingredient for suppressing transcription of a Type I collagen gene;

71. A composition for suppressing transcription of a Type I collagen gene, which comprises a compound according to the above item 11 and an inert carrier;

72. Use of a compound according to the above item 14 to 25 as an active ingredient for suppressing transcription of a Type I collagen gene;

73. A composition for suppressing transcription of a Type I collagen gene, which comprises a compound according to the above item 14 to 25 and an inert carrier; and the like.

BEST MODE FOR CARRYING OUT THE INVENTION

The present invention will be explained in detail below.

In the present invention, a saturated hydrocarbon group in an alkyl group, a haloalkyl group, an alkoxy group, an alkoxycarbonyl group, an alkylthio group, an alkylsulfinyl group, an alkylsulfonyl group and an alkylene group may be branched, and a part or all of carbon atoms thereof may form a ring. An unsaturated hydrocarbon group in an alkenyl group, an alkenyloxy group, an alkynyl group, an alkynyloxy group, an alkenylene group and an alkynylene group may be branched, a part or all of carbon atoms thereof may form a ring, and the number of unsaturated bonds thereof may be singular or plural.

In the present invention, examples of an alkyl group include a methyl group, an ethyl group, an isopropyl group, a cyclohexyl group, a cyclopropylmethyl group and the like. Examples of a haloalkyl group include a 2,2,2-trifluoroethyl group and the like. Examples of an alkoxy group include a methoxy group, an ethoxy group, a cyclopentyloxy group, a 2-cyclohexylethoxy group and the like. Examples of an alkylthio group include a methylthio group and the like. Examples of an alkylsulfinyl group include a methylsulfinyl group and the like. Examples of an alkylsulfonyl group include a methylsulfonyl group and the like. Examples of an alkylene group include a methylene group, an ethylethylene group, a 1,4-cyclohexylene group and the like. Examples of an alkenyl group include a vinyl group, a 2-propenyl group, a 3-methyl-2-butenyl group, a 1,3-butadienyl group, a 3-cyclohexenyl group and the like. Examples of an alkynyl group include an ethynyl group, a 2-propynyl group, a 2-penten-4-ynyl group and the like. Examples of an alkenylene group include a vinylene group, a propenylene group, a 1,3-butadienylene group and the like. Examples of an alkynylene group include an ethynylene group, a propynylene group and the like.

In the present invention, examples of a halogen atom include a fluorine atom, a chlorine atom, a bromine atom and an iodine atom.

In the present invention, a pyridyl group includes a 2-pyridyl group, a 3-pyridyl group and a 4-pyridyl group. A furyl group includes a 2-furyl group and a 3-furyl group. A thienyl group includes a 2-thienyl group and a 3-thienyl group. A naphthyl group includes a 1-naphthyl group and a 2-naphthyl group.

In the present invention, examples of a leaving group include an alkylsulfonyloxy group such as a mesyloxy group and the like, an arylsulfonyloxy group such as a tosyloxy group and the like, an alkoxysulfonyloxy group such as a methoxysulfonyloxy group and the like, and a halogen atom such as a bromine atom and the like.

When the A ring is a pyridine ring in the cinnamoyl compound represented by the formula (I), (II), (III) and (IV) (hereinafter, referred to as the present compound (I), (II), (III) and (IV), respectively, in some cases), and when the a ring is a pyridine ring in the cinnamoyl compound represented by the formula (V), a 2H-pyran-2-one compound represented by the formula (VI) and a 2H-1-benzopyran-2-one compound represented by the formula (VIII) (hereinafter, referred to as the present compound (V), (VI) and (VIII), respectively, in some cases), in the case where a ring is a pyridine ring and x is a nitrogen atom, a N-oxide thereof is also included.

In the present compound (V), (VI) and (VIII), when x is a methine group, a methine group has no substituent.

The present compound (I) to (VI) and (VIII), a 2H-pyran-2-one compound represented by the formula (VII) (hereinafter, referred to as the present compound (VII) in some cases), a 2H-1-benzopyran-2-one compound represented by the formula (IX), a 2H-pyran-2-one compound represented by the formula (X), a 2H-1-benzopyran-2-one compound represented by the formula (XI), a 2H-pyran-2-one compound represented by the formula (XII) and a 2H-1-benzopyran-2-one compound represented by the formula (XIII) (hereinafter, referred to as the present compound (VII), (IX), (X), (XI), (XII) and (XIII), respectively, in some cases), a 2H-pyran-2-one compound represented by the formula (XIV) to (XXII) (hereinafter, referred to as the present compound (XIV) to (XXII), respectively, in some cases) and a 2H-1-benzopyran-2-one compound represented by the formula (XXIII) to (XXV) (hereinafter, referred to as the present compound (XXIII) to (XXV), respectively, in some cases) represent a pharmacologically acceptable salt thereof at the same time. A pharmacologically acceptable salt represents a salt with an inorganic acid, a salt with an organic acid, a salt with an inorganic base or a salt with an organic base, of the present compound (I) to (XXV) (hereinafter, referred to as the present compound in some cases). Examples of a salt with an inorganic acid include hydrochloride, hydrobromide and the like, examples of a salt with an organic acid include acetate, benzoate and the like, examples of a salt with an inorganic base include a potassium salt, a sodium salt and the like, and examples of a salt with an organic base include a pyridine salt, a morpholine salt and the like.

$X_{40}$, $Y_{40}$, $Q_{40}$, $K_{40}$ and $L_{40}$ in the present compound (II) are independently represented by groups represented by $D_1$, $D_2$, $D_3$, $D_4$, $D_5$, $R_0$, $R_0'$, $R_2''$, $R_1$, $R_1'$, $R_1''$, $R_2$, $R_2'$, $R_3$, $R_4$, $R_4'$, $R_5$, $R_6$, $A_1$, $A_2$, $A_3$, $A_4$, $A_5$, $A_6$, $A_7$, $A_7'$, $A_7''$, $A_8$, $A_8'$, $A_9$, $A_9'$, $A_9''$, $A_{10}$, $A_{10}'$, $A_{11}$, B, B', $B_0$, $B_1$, $B_1'$, $B_2$, $B_2'$, $B_3$, $B_3'$, $B_4$, $B_4'$, $B_5$, $B_6$, $(a_0)$, $(b_0)$, $(c_0)$, $(d_0)$, $(e_0)$, $M_a$, $M_a'$, $M_a''$, $M_a'''$, $M_a''''$, $M_{b0}$, $M_{c0}$, $M_{d0}$, $R_{a0}$, $R_b$, $R_c$, $R_d$, $R_d'$, $R_e$, $R_e'$, $R_e''$, $R_e'''$, $B_a$, $B_b$, $B_c$, $Y_a$, $Y_a'$, $Y_b$, $Y_b'$, $Y_b''$, $Y_c$ and $Y_c'$, and integers represented by k, k', l, m, m', n and n'.

$X_4$, $Y_4$, $Q_4$, $K_4$ and $L_4$ in the present compound (III) are independently represented by groups represented by $D_1$, $D_2$, $D_3$, $D_4$, $D_5$, $R_0$, $R_0'$, $R_2''$, $R_1$, $R_1'$, $R_1''$, $R_2$, $R_2'$, $R_3$, $R_4$, $R_4'$, $R_5$, $R_6$, $A_1$, $A_2$, $A_3$, $A_4$, $A_5$, $A_6$, $A_7$, $A_7'$, $A_7''$, $A_8$, $A_8'$, $A_9$, $A_9'$, $A_9''$, $A_{10}$, $A_{10}'$, $A_{11}$, B, B', $B_0$, $B_1$, $B_1'$, $B_2$, $B_2'$, $B_3$, $B_3'$, $B_4$, $B_4'$, $B_5$, $B_6$, (a), (b), (c), (d), (e), $M_a$, $M_a'$, $M_a''$, $M_a'''$, $M_a''''$, $M_b$, $M_c$, $M_d$, $R_a$, $R_b$, $R_c$, $R_d$, $R_d'$, $R_e$, $R_e'$, $R_e''$, $R_e'''$, $B_a$, $B_b$, $B_c$, $Y_a$, $Y_a'$, $Y_b$, $Y_b'$, $Y_b''$, $Y_c$ and $Y_c'$, and integers represented by k, k', l, m, m', n and n'.

$X_a$, $Y_a$ and $q_a$ in the present compound (IV), (V), (VI) and (VIII) are independently represented by groups represented by $a_0$, $a_1$, $a_1'$, $a_2$, $a_3$, $a_4$, $a_5$, b, r, r', $r_0$, $r_0'$, $r_1$, $r_1'$, $r_2$, $r_3$, $r_4$, $r_4'$, ra, y and z, and an integer represented by l.

In the present invention, $X_c$, $Y_a$ and $r_c$ in (XLVII), (XLVII') and (XLVII'') are independently represented by groups represented by $a_{0c}$, $a_1$, $a_1'$, $a_2$, $a_3$, $a_4$, $a_5$, b, r, r', $r_0$, $r_0'$, $r_1$, $r_1'$, $r_2$, $r_3$, y and z, and an integer represented by l.

In the present invention, $X_d$, $X_d'$, $Y_a$, $q_d$ and $q_d'$ in (XLVIII) and (XLVIII') are independently represented by groups represented by $a_{0d}$, $a_{0d}'$, $a_{3d}$, $a_{3d}'$, $a_{4d}$, $a_{4d}'$, b, $r_0$, $r_0'$, $r_1$, $r_1'$, $r_2$, $r_3$, $r_4$, $r_4'$, $r_d$, $r_d''$ and z.

In the present invention, $X_e$, $X_e'$, $Y_a$ and $q_e$ in (XLIX) and (XLIX'') are independently represented by groups represented by $a_{0e}$, $a_1$, $a_1'$, b'', r, r', $r_0$, $r_0'$, $r_1$, $r_1''$, $r_2$, $r_3$, $r_4$, $r_4'$ and $r_e$, and an integer represented by l.

In the $Y_0$ group of substituents which may be selected as $Y_a$ of the present compound (I), the "6 to 10-membered aryl group" represents a monocyclic or fused aromatic hydrocarbon group, and includes a phenyl group, a 1-naphthyl group, a 2-naphthyl group, a 6-indanyl group and the like. The "5 to 10-membered heteroaryl group" represents a monocyclic or fused aromatic heterocyclic group, and includes a 2-furyl group, a 3-furyl group, a 2-thienyl group, a 3-thienyl group, a 2-pyridyl group, a 3-pyridyl group, a 4-pyridyl group, a 2-quinolyl group and the like. The "3 to 10-membered cyclic hydrocarbon or heterocyclic group optionally containing an unsaturated bond" includes a monocyclic ring or a fused ring, for example, includes a 2-cyclohexenyl group, a 2-morpholinyl group, a 4-piperidyl group and the like, and may be substituted with a single or same or different plural aforementioned $M_a$-groups.

In the $Z_0$ group of substituents which may be selected as $Y_\alpha$ of the present compound (I), the "group which is fused to the A ring" may have single or same or different plural atoms or groups selected from a halogen atom, a C1-C10 alkoxy group, a C3-C10 alkenyloxy group, a C3-C10 alkynyloxy group, a carbonyl group, a thiocarbonyl group, an oxy group, a thio group, a sulfinyl group and a sulfonyl group.

In $R_{a0}$ of the $E_0$ group of substituents which may be selected as $X_{A0}$ of the present compound (II), the "optionally substituted 5 to 7-membered aryl group or heteroaryl group" represents a monocyclic or fused aromatic hydrocarbon group or a monocyclic or fused aromatic heterocyclic group, and includes a phenyl group, a 1-naphthyl group, a 2-naphthyl group, a 6-indanyl group, a 2-furyl group, a 3-furyl group, a 2-thienyl group, a 3-thienyl group, a 2-pyridyl group, a 3-pyridyl group, a 4-pyridyl group, a 2-quinolyl group and the like. Said group may be substituted with single or same or different plural aforementioned $M_a$-groups.

In $(d_0)$ of the $Y_0$ group of substituents which may be selected as $Y_\alpha$ and $Y_{A0}$ of the present compounds (I) and (II), the "5 to 12-membered hydrocarbon ring which is substituted with a carbonyl group or a thiocarbonyl group and further which may be optionally substituted with an oxy group, a thio group, a —$NR_1$- group (wherein $R_1$ is as defined above), a sulfinyl group or a sulfonyl group" represents a 5 to 12-membered hydrocarbon ring in which one or more carbon atoms are substituted with a carbonyl group or a thiocarbonyl group and further one or more carbon atoms may be substituted with a group or groups, which may be the same or different, selected from an oxy group, a thio group, a —$NR_1$- group (wherein $R_1$ is as defined above), a sulfinyl group and a sulfonyl group.

In $(e_0)$ of the $Y_0$ group of substituents which may be selected as $Y_\alpha$ and $Y_{A0}$ of the present compounds (I) and (II), the "5 to 12-membered hydrocarbon ring optionally substituted with a carbonyl group, a thiocarbonyl group, an oxy group, a thio group, a —$NR_1$- group (wherein $R_1$ is as defined above), a sulfinyl group or a sulfonyl group" represents a 5 to 12-membered hydrocarbon ring in which one or more carbon atoms may be substituted with a group or groups, which may be the same or different, selected from a carbonyl group, a thiocarbonyl group, an oxy group, a thio group, a —$NR_1$- group (wherein $R_1$ is as defined above), a sulfinyl group and a sulfonyl group.

In (a) of the B group of substituents which may be selected as $X_A$ of the present compound (III), the "C2-C10 alkylene group optionally substituted with an oxy group, a thio group, a sulfinyl group, a sulfonyl group or a —$NR_1$'— group (wherein $R_1$' is as defined above)" represents a C2-C10 alkylene group in which one or more carbon atoms may be substituted with a group or groups, which may be the same or different, selected from an oxy group, a thio group, a sulfinyl group, a sulfonyl group and a —$NR_1$'- group (wherein $R_1$' is as defined above). The "C3-C10 alkenylene group optionally substituted with an oxy group, a thio group, a sulfinyl group, a sulfonyl group or a —$NR_1$'- group (wherein $R_1$' is as defined above)" represents a C3-C10 alkenylene group in which one or more carbon atoms may be substituted with a group or groups, which may be the same or different, selected from an oxy group, a thio group, a sulfinyl group, a sulfonyl group and a —$NR_1$'- group (wherein $R_1$' is as defined above).

In (b) of the D group of substituents which may be selected as $X_A$ of the present compound (III), the "C1-C10 alkylene group optionally substituted with a methyl group, an oxy group, a thio group, a sulfinyl group, a sulfonyl group or a —$NR_1$- group (wherein $R_1$ is as defined above)" represents a C2-C10 alkylene group in which one or more carbon atoms may be substituted with a methyl group or in which one or more carbon atoms may be substituted with a group or groups, which may be the same or different, selected from an oxy group, a thio group, a sulfinyl group, a sulfonyl group and a —$NR_1$- group (wherein $R_1$ is as defined above). The "C2-C10 alkenylene group optionally substituted with a methyl group, an oxy group, a thio group, a sulfinyl group, a sulfonyl group or a —$NR_1$- group (wherein $R_1$ is as defined above)" represents a C2-C10 alkenylene group in which one or more carbon atoms may be substituted with a methyl group or in which one or more carbon atoms may be substituted with a group or groups, which may be the same or different, selected from an oxy group, a thio group, a sulfinyl group, a sulfonyl group and a —$NR_1$- group (wherein $R_1$ is as defined above).

Groups belonging to the $X_0$ group, the $Y_0$ group and the $Z_0$ group which may be selected as $Y_\alpha$ of the present compound (I) will be exemplified in the following Table X, Table Y and Table Z, respectively.

Groups belonging to the $A_0$ group, the $B_0$ group, the $C_0$ group, the $D_0$ group, the $E_0$ group, the $F_0$ group, the G0 group, the $H_0$ group, the $I_0$ group, the $J_0$ group, the $K_0$ group, the $L_0$ group, the $M_0$ group and the $N_0$ group which may be selected as $X_{A0}$ of the present compound (II) will be exemplified in the following Table A, Table B, Table C, Table D, Table E, Table F, Table G, Table H, Table I, Table J, Table K, Table L, Table M and Table N, respectively. Groups belonging to the $X_0$ group, the $Y_0$ group and the $Z_0$ group which may be selected as $Y_{A0}$ will be exemplified in the following Table X, Table Y and Table Z, respectively. $Q_0$ and $T_0$ will be exemplified in the following Table Q and Table T, respectively.

Groups belonging to the A group, the B group, the C group, the D group, the E group, the F group, the G group, the H group, the I group, the J group, the K group, the L group, the M group and the N group which may be selected as $X_A$ of the present compound (III) will be exemplified in the following Table A, Table B, Table C, Table D, Table E, Table F, Table G, Table H, Table I, Table J, Table K, Table L, Table M and Table N, respectively. Groups belonging to the X group, the Y group and the Z group which may be selected as $Y_A$ will be exemplified in the following Table X, Table Y and Table Z, respectively. Q and T will be exemplified in the following Table Q and Table T.

Groups belonging to the aforementioned $A_0$ to $N_0$ groups and A to N groups will be exemplified in the following Table A to Table N. When said groups have geometrical isomers, all of the geometrical isomers are included, and when said groups have tautomers, all of the tautomers are included.

Groups belonging to the $A_0$ group and the A group will be exemplified in Table A.

TABLE A

| No. | Group |
|---|---|
| A-1 | —$CH_2ONH_2$ |
| A-2 | —$CH_2ON(CH_3)_2$ |
| A-3 | —$CH_2ONHCOCH_3$ |
| A-4 | —$CH_2NHOCH_2CH\!=\!CH_2$ |

TABLE A-continued

| No. | Group |
|---|---|
| A-5 | —CH$_2$CN |
| A-6 | —CH$_2$CH$_2$CN |
| A-7 | —CH$_2$CH$_2$C(=NH)NH$_2$ |
| A-8 | —CH$_2$CH$_2$C(=NCH$_2$C=CH)N(CH$_3$)$_2$ |
| A-9 | —CH$_2$C(=NH)NHCOCH$_3$ |
| A-10 | —CH$_2$C(=NOCOCH$_3$)—NH$_2$ |
| A-11 | —CH$_2$C(=NCOCH$_3$)—OCH$_3$ |
| A-12 | —CH$_2$CSNH$_2$ |
| A-13 | —CH$_2$NO$_2$ |
| A-14 | —CH$_2$SO$_3$H |
| A-15 | —SO$_3$H |

Groups belonging to the B$_0$ group and the B group will be exemplified in Table B.

TABLE B

| No. | Group |
|---|---|
| B-1 | 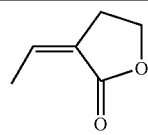 |
| B-2 | 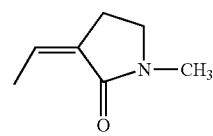 |
| B-3 | 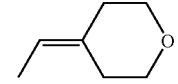 |
| B-4 | 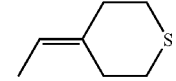 |
| B-5 | 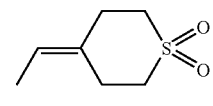 |
| B-6 |  |

Groups belonging to the C$_0$ group and the C group will be exemplified in Table C.

TABLE C

| No. | Group |
|---|---|
| C-1 | —CH=CF$_2$ |
| C-2 | —CH=CHOCH$_3$ |
| C-3 | —CH=CHSCH$_3$ |
| C-4 | —CH=CHSOCH$_3$ |
| C-5 | —CH=CHSO$_2$CH$_3$ |
| C-6 | —CH=CHCH$_2$OH |
| C-7 | —CH=CHCH$_2$OCOCH$_3$ |
| C-8 | —CH=CHCHO |
| C-9 | —CH=CHCH=NCH$_2$CH=CH$_2$ |
| C-10 | —CH=CHCH=NOH |
| C-11 | —CH=CHCH=NOCH$_2$COOCH$_3$ |
| C-12 | —CH=CHCH=NOCH$_2$CN |
| C-13 | —CH=CHCH=NN(CH$_3$)$_2$ |
| C-14 | —CH=CHCH=NNHCOCH$_3$ |

TABLE C-continued

| No. | Group |
|---|---|
| C-15 | —CH=CHCOCH$_3$ |
| C-16 | —CH=C(CH$_3$)COCH$_3$ |
| C-17 | —CH=CHCOCF$_3$ |
| C-18 | —CH=CHCH$_2$ON(CH$_3$)$_2$ |
| C-19 | —CH=CHCH$_2$ON(SO$_2$CH$_3$)CH$_3$ |
| C-20 | —CH=CHCH$_2$N(CH$_2$CH=CH$_2$)$_2$ |
| C-21 | —CH=CHCH$_2$N(OH)CH$_3$ |
| C-22 | —CH=CHNHCOCH$_3$ |
| C-23 | —CH=CHCN |
| C-24 | —CH=CHC(=NH)N(CH$_3$)$_2$ |
| C-25 | —CH=CHC(=NH)NHOCH$_3$ |
| C-26 | —CH=CHCSNH$_2$ |
| C-27 | —CH=CHNO$_2$ |
| C-28 | —CH=CHSO$_3$H |

Groups belonging to the D$_0$ group and the D group will be exemplified in Table D.

TABLE D

| No. | Group |
|---|---|
| D-1 | 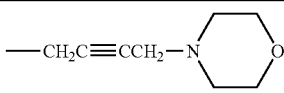 |
| D-2 | 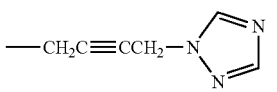 |
| D-3 | —C=Cl |
| D-4 | —C=CCH$_2$SCH$_3$ |
| D-5 | —C=CC(CH$_3$)$_2$OH |
| D-6 | —C=CCH$_2$OCOOCH$_3$ |
| D-7 | —C=CCH=NCH$_3$ |
| D-8 | —C=CCH=NOCH$_3$ |
| D-9 | —C=CCH=NN(CH$_3$)$_2$ |
| D-10 | —C=CCH$_2$ON(CH$_3$)$_2$ |
| D-11 | —C=CCH$_2$N(CH$_3$)$_2$ |
| D-12 | —C=CCH$_2$CH$_2$NO$_2$ |

Groups belonging to the E$_0$ group and the E group will be exemplified in Table E.

TABLE E

| No. | Group |
|---|---|
| E-1 | —CH=CHCOOCH$_3$ |
| E-2 | —CH=CHCOOC$_2$H$_5$ |
| E-3 | —CH=CHCOOCH$_2$CH$_2$Cl |
| E-4 | —CH=CHCOOCH$_2$CF$_3$ |
| E-5 | —CH=CHCOOCH$_2$CH=CH$_2$ |
| E-6 | —CH=CHCOOCH$_2$C=CH |
| E-7 | 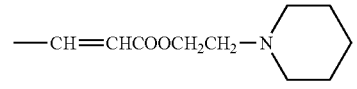 |
| E-8 | 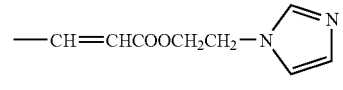 |
| E-9 | —CH=CHCOOCH$_2$CH$_2$OCH$_3$ |
| E-10 | —CH=CHCOOCH$_2$CH$_2$SCH$_3$ |
| E-11 | —CH=CHCOOCH$_2$CH$_2$SOCH$_3$ |
| E-12 | —CH=CHCOOCH$_2$CH$_2$SO$_2$CH$_3$ |
| E-13 | —CH=CHCOOCH$_2$CH$_2$OH |
| E-14 | —CH=CHCOOCH$_2$CH$_2$OSO$_2$N(CH$_3$)$_2$ |
| E-15 | —CH=CHCOOCH$_2$CH$_2$COCH$_3$ |

TABLE E-continued

| No. | Group |
|---|---|
| E-17 | —CH=CHCOOCH$_2$CH$_2$ON(CH$_3$)$_2$ |
| E-18 | —CH=CHCOOCH$_2$CH$_2$N(CH$_3$)$_2$ |
| E-19 | —CH=CHCOOCH$_2$CH$_2$N(OC$_2$H$_5$)C$_2$H$_5$ |
| E-20 | —CH=CHCOOCH$_2$CH$_2$NHCOCH$_3$ |
| E-21 | —CH=CHCOOCH$_2$CH$_2$N(CH$_3$)COCH$_3$ |
| E-22 | —CH=CHCOOCH$_2$CH$_2$NHCOOCH$_2$CH$_2$OCH$_3$ |
| E-23 | —CH=CHCOOCH$_2$CH$_2$NHCOSCH$_2$CH=CH$_2$ |
| E-24 | —CH=CHCOOCH$_2$CH$_2$NHCONHC$_2$H$_5$ |
| E-25 | —CH=CHCOOCH$_2$CH$_2$NHCON(CH$_3$)$_2$ |
| E-26 | —CH=CHCOOCH$_2$CH$_2$NHCON(OCH$_3$)CH$_3$ |
| E-27 | —CH=CHCOOCH$_2$CH$_2$NHCSNHCH$_2$CH$_2$Cl |
| E-28 | —CH=CHCOOCH$_2$CH$_2$NHSO$_2$N(CH$_3$)$_2$ |
| E-29 | —CH=CHCOOCH$_2$CH$_2$CN |
| E-30 | —CH=CHCOOCH$_2$CH$_2$NO$_2$ |
| E-31 | —CH=CHCOOCH$_2$CH$_2$SO$_3$H |
| E-32 | —CH=CHCONHCH$_2$CH$_2$SO$_2$—N(piperidine) |
| E-33 | —CH=CHCONHCH$_2$CH$_2$SO$_2$N(CH$_3$)$_2$ |
| E-34 | —CH=CHCOSCH$_3$ |
| E-35 | —CH=CHCON(CH$_3$)CH$_2$C=CH |
| E-36 | —CH=CHCON(OCH$_3$)CH$_3$ |
| E-37 | —CH=CHCONHOCH$_3$ |
| E-38 | —CH=CHCONHOCH$_2$CH=CH$_2$ |
| E-39 | —CH=CHCOOCH$_2$COOCH$_3$ |
| E-40 | —CH=CHCOSCH$_2$COOCH$_3$ |
| E-41 | —CH=CHCONHCH$_2$COOCH$_3$ |
| E-42 | —CH=CHCONHCH$_2$CON(CH$_3$)$_2$ |
| E-43 | —CH=CHCONHCH$_2$CN |
| E-44 | —CH=CHCONHCH$_2$C(=NH)N(CH$_3$)CH$_2$CH=CH$_2$ |
| E-45 | —CH=CHCONHCH$_2$C(=NH)NHOH |
| E-46 | —CH=CHCONHSO$_2$CH$_3$ |
| E-47 | —CH=CHCO—N(pyrrolidine) |
| E-48 | —CH=CHCO—N(pyrrole) |
| E-49 | —CH=CHCO—N(piperidine) |
| E-50 | —CH=CHCO—N(tetrahydropyridine) |
| E-51 | —CH=CHCO—N(morpholine) |
| E-52 | —CH=CHCO—N(2,6-dimethylmorpholine) |
| E-53 | —CH=CHCO—N(thiomorpholine) |
| E-54 | —CH=CHCO—N(thiomorpholine S-oxide) |
| E-55 | —CH=CHCO—N(thiomorpholine S,S-dioxide) |
| E-56 | —CH=CHCO—N(4-methylpiperazine) |
| E-57 | —CH=CHCO—N(azepane) |
| E-58 | —CH=CHCO—NH-(4-pyridyl) |
| E-59 | —CH=CHCONHN(CH$_3$)$_2$ |
| E-60 | —CH=CHCONHNHCOOC$_2$H$_5$ |
| E-61 | —CH=CHCONHNHCSNH(c)C$_6$H$_{11}$ |
| E-62 | —CH=CFCOOCH$_3$ |

Groups belonging to the F$_0$ group and the F group will be exemplified in Table F.

TABLE F

| No. | Group |
|---|---|
| F-1 | —OCH$_2$CH$_2$OH |
| F-2 | —OCH$_2$CH$_2$CH$_2$OH |
| F-3 | —CH$_2$OCH$_2$CH$_2$OH |
| F-4 | —OCH$_2$CH$_2$OCON(CH$_3$)$_2$ |
| F-5 | —OCH$_2$CH$_2$ONH$_2$ |
| F-6 | —OCH$_2$CH$_2$N(CH$_3$)$_2$ |
| F-7 | —OCH$_2$CH$_2$CH$_2$N(CH$_3$)$_2$ |
| F-8 | —OCH$_2$CH$_2$N(OCH$_3$)CH$_3$ |
| F-9 | —OCH$_2$CH$_2$NH$_2$ |
| F-10 | —OCH$_2$CH$_2$NHCOCH$_3$ |
| F-11 | —OCH$_2$CH$_2$N(CH$_3$)COCH$_3$ |
| F-12 | —OCH$_2$CH$_2$NHCOO(t)C$_4$H$_9$ |
| F-13 | —OCH$_2$CH$_2$NHCOSCH$_2$CH=CH$_2$ |
| F-14 | —OCH$_2$CH$_2$NHCONHC$_2$H$_5$ |
| F-15 | —OCH$_2$CH$_2$NHCON(CH$_3$)$_2$ |
| F-16 | —OCH$_2$CH$_2$NHCON(OCH$_3$)CH$_3$ |
| F-17 | —OCH$_2$CH$_2$NHCSNHCH$_2$CH$_2$Cl |
| F-18 | —OCH$_2$CH$_2$NO$_2$ |
| F-19 | —OCH$_2$CH$_2$SO$_3$H |
| F-20 | —OCH$_2$CH$_2$CH$_2$SO$_3$H |
| F-21 | —OCH$_2$CH$_2$CH$_2$CH$_2$SO$_3$H |
| F-22 | —OCH$_2$CH$_2$NHSO$_2$N(CH$_3$)$_2$ |
| F-23 | —OCH$_2$CH$_2$SO$_2$—N(morpholine) |
| F-24 | —OCH$_2$CH$_2$OCH$_3$ |
| F-25 | —OCH$_2$CH$_2$SCH$_3$ |
| F-26 | —OCH$_2$CH$_2$SOCH$_3$ |
| F-27 | —OCH$_2$CH$_2$SO$_2$CH$_3$ |
| F-28 | —OCH$_2$CN |
| F-29 | —OCH$_2$C(=NH)NH$_2$ |
| F-30 | —OCH$_2$CSNH$_2$ |
| F-31 | —OCH$_2$COCH$_3$ |
| F-32 | —OCH$_2$COCF$_3$ |
| F-33 | —OCH$_2$CHO |

TABLE F-continued

| No. | Group |
|---|---|
| F-34 | —OCH$_2$CH=NOCH$_2$C≡CH |
| F-35 | —OCH$_2$CH=NN(CH$_3$)$_2$ |
| F-36 | —OCH$_2$COOH |
| F-37 | —OCH$_2$COOCH$_3$ |
| F-38 | —OCH$_2$COOCH$_2$CH$_2$Cl |
| F-39 | —OCH$_2$COOCH$_2$CH=CH$_2$ |
| F-40 | —OCH$_2$COOCH$_2$C≡CH |
| F-41 | —OCH$_2$COOCH$_2$CH$_2$—N(piperidine) |
| F-42 | —OCH$_2$COOCH$_2$CH$_2$—N(imidazole) |
| F-43 | —OCH$_2$COOCH$_2$CH$_2$OCH$_3$ |
| F-44 | —OCH$_2$COOCH$_2$CH$_2$SCH$_3$ |
| F-45 | —OCH$_2$COOCH$_2$CH$_2$SOCH$_3$ |
| F-46 | —OCH$_2$COOCH$_2$CH$_2$SO$_2$CH$_3$ |
| F-47 | —OCH$_2$COOCH$_2$CH$_2$OH |
| F-48 | —OCH$_2$COO(CH$_2$)$_9$OH |
| F-49 | —OCH$_2$COOCH$_2$CH$_2$OSO$_2$N(CH$_3$)$_2$ |
| F-50 | —OCH$_2$COOCH$_2$CH$_2$COCH$_3$ |
| F-51 | —OCH$_2$COOCH$_2$CH$_2$ON(CH$_3$)$_2$ |
| F-52 | —OCH$_2$COOCH$_2$CH$_2$N(CH$_3$)$_2$ |
| F-53 | —OCH$_2$COOCH$_2$CH$_2$N(OC$_2$H$_5$)C$_2$H$_5$ |
| F-54 | —OCH$_2$COOCH$_2$CH$_2$NHCOCH$_3$ |
| F-55 | —OCH$_2$COOCH$_2$CH$_2$N(CH$_3$)COCH$_3$ |
| F-56 | —OCH$_2$COOCH$_2$CH$_2$NHCOOCH$_2$CH$_2$OCH$_3$ |
| F-57 | —OCH$_2$COOCH$_2$CH$_2$NHCOSCH$_2$CH=CH$_2$ |
| F-58 | —OCH$_2$COOCH$_2$CH$_2$NHCONHC$_2$H$_5$ |
| F-59 | —OCH$_2$COOCH$_2$CH$_2$NHCON(CH$_3$)$_2$ |
| F-60 | —OCH$_2$COOCH$_2$CH$_2$NHCON(OCH$_3$)CH$_3$ |
| F-61 | —OCH$_2$COOCH$_2$CH$_2$NHCSNHCH$_2$Cl |
| F-62 | —OCH$_2$COOCH$_2$CH$_2$NHSO$_2$N(CH$_3$)$_2$ |
| F-63 | —OCH$_2$COOCH$_2$CH$_2$CN |
| F-64 | —OCH$_2$COOCH$_2$CH$_2$NO$_2$ |
| F-65 | —OCH$_2$COOCH$_2$CH$_2$SO$_3$H |
| F-66 | —OCH$_2$CONHCH$_2$CH$_2$SO$_2$—N(piperidine) |
| F-67 | —OCH$_2$CONHCH$_2$CH$_2$SO$_2$N(CH$_3$)$_2$ |
| F-68 | —OCH$_2$COSCH$_3$ |
| F-69 | —OCH$_2$CONH$_2$ |
| F-70 | —OCH$_2$CONHCH$_3$ |
| F-71 | —OCH$_2$CON(CH$_3$)$_2$ |
| F-72 | —OCH$_2$CON(CH$_3$)CH$_2$C≡CH |
| F-73 | —OCH$_2$CON(OCH$_3$)CH$_3$ |
| F-74 | —OCH$_2$CONHOCH$_3$ |
| F-75 | —OCH$_2$CONHOCH$_2$CH=CH$_2$ |
| F-76 | —OCH$_2$COOCH$_2$COOCH$_3$ |
| F-77 | —OCH$_2$COSCH$_2$COOCH$_3$ |
| F-78 | —OCH$_2$CONHCH$_2$COOCH$_3$ |
| F-79 | —OCH$_2$CONHCH$_2$CON(CH$_3$)$_2$ |
| F-80 | —OCH$_2$CONHCH$_2$CN |
| F-81 | —OCH$_2$CONHCH$_2$C(=NH)NH$_2$ |
| F-82 | —OCH$_2$CONHSO$_2$CH$_3$ |
| F-83 | —OCH$_2$CO—N(thiomorpholine) |
| F-84 | —OCH$_2$CONHN(CH$_3$)$_2$ |
| F-85 | —OCH$_2$CONHNHCOOC$_2$H$_5$ |
| F-86 | —OCH$_2$CONHNHCSNH(c)C$_6$H$_{11}$ |
| F-87 | —SCH$_2$CN |
| F-88 | —CH$_2$SCH$_2$COOCH$_3$ |
| F-89 | —CH$_2$SOCH$_2$COOCH$_3$ |
| F-90 | —CH$_2$SO$_2$CH$_2$COOCH$_3$ |
| F-91 | —NHCH$_2$COOCH$_3$ |
| F-92 | —NHCH$_2$CH$_2$N(CH$_3$)$_2$ |
| F-93 | —N(COCH$_3$)CH$_2$CH$_2$OH |
| F-94 | —CH$_2$OCH$_2$COOCH$_3$ |

Groups belonging to the G$_0$ group and the G group will be exemplified in Table G.

TABLE G

| No. | Group |
|---|---|
| G-1 | (methoxymethylene-dihydrofuran-2(3H)-one) |
| G-2 | (methoxymethylene-1-methylpyrrolidin-2-one) |
| G-3 | (methoxymethylene-tetrahydropyran) |
| G-4 | (methoxymethylene-tetrahydrothiopyran) |
| G-5 | (methoxymethylene-tetrahydrothiopyran 1,1-dioxide) |
| G-6 | (methoxymethylene-1-methylpiperidine) |
| G-7 | —OCH$_2$CH=CH$_2$ |
| G-8 | —OCH$_2$C≡CH |
| G-9 | —OCH$_2$CH=CHCl |
| G-10 | —SCH=CHOCH$_3$ |
| G-11 | —SO$_2$CH=CHOCH$_3$ |
| G-12 | —OCH=CHCOCH$_3$ |
| G-13 | —OCH=CHCHO |
| G-14 | —OCH=CHCH=NCH$_2$CH=CH$_2$ |
| G-15 | —OCH=CHCH=NOCH$_3$ |
| G-16 | —OCH=CHCH=NN(CH$_3$)$_2$ |
| G-17 | —OCH=CHCN |
| G-18 | —OCH=CHC(=NH)NH$_2$ |
| G-19 | —OCH=CHCOOH |
| G-20 | —OCH$_2$C≡CCOOH |
| G-21 | —OCH=CHCOOCH$_3$ |
| G-22 | —OCH=CHCOOCH$_2$CH$_2$Cl |
| G-23 | —OCH=CHCOOCH$_2$CH=CH$_2$ |
| G-24 | —OCH=CHCOOCH$_2$C≡CH |
| G-25 | —OCH=CHCOOCH$_2$CH$_2$—N(piperidine) |
| G-26 | —OCH=CHCOOCH$_2$CH$_2$—N(imidazole) |

TABLE G-continued

| | |
|---|---|
| G-27 | —OCH=CHCOOCH$_2$CH$_2$OCH$_3$ |
| G-28 | —OCH=CHCOOCH$_2$CH$_2$SCH$_3$ |
| G-29 | —OCH=CHCOOCH$_2$CH$_2$SOCH$_3$ |
| G-30 | —OCH=CHCOOCH$_2$CH$_2$SO$_2$CH$_3$ |
| G-31 | —OCH=CHCOOCH$_2$CH$_2$OH |
| G-32 | —OCH=CHCOOCH$_2$CH$_2$OSO$_2$N(CH$_3$)$_2$ |
| G-33 | —OCH=CHCOOCH$_2$CH$_2$COCH$_3$ |
| G-34 | —OCH=CHCOOCH$_2$CH$_2$ON(CH$_3$)$_2$ |
| G-35 | —OCH=CHCOOCH$_2$CH$_2$N(CH$_3$)$_2$ |
| G-36 | —OCH=CHCOOCH$_2$CH$_2$N(OC$_2$H$_5$)C$_2$H$_5$ |
| G-37 | —OCH=CHCOOCH$_2$CH$_2$NHCOCH$_3$ |
| G-38 | —OCH=CHCOOCH$_2$CH$_2$N(CH$_3$)COCH$_3$ |
| G-39 | —OCH=CHCOOCH$_2$CH$_2$NHCOOCH$_2$CH$_2$OCH$_3$ |
| G-40 | —OCH=CHCOOCH$_2$CH$_2$NHCOSCH$_2$CH=CH$_2$ |
| G-42 | —OCH=CHCOOCH$_2$CH$_2$NHCONHC$_2$H$_5$ |
| G-42 | —OCH=CHCOOCH$_2$CH$_2$NHCON(CH$_3$)$_2$ |
| G-43 | —OCH=CHCOOCH$_2$CH$_2$NHCON(OCH$_3$)CH$_3$ |
| G-44 | —OCH=CHCOOCH$_2$CH$_2$NHCSNHCH$_2$CH$_2$Cl |
| G-45 | —OCH=CHCOOCH$_2$CH$_2$NHSO$_2$N(CH$_3$)$_2$ |
| G-46 | —OCH=CHCOOCH$_2$CH$_2$C(=NH)NH$_2$ |
| G-47 | —OCH=CHCOOCH$_2$CH$_2$NO$_2$ |
| G-48 | —OCH=CHCOOCH$_2$CH$_2$SO$_3$H |
| G-49 | —OCH=CHCONHCH$_2$CH$_2$SO$_2$—N(piperidine) |
| G-50 | —OCH=CHCONHCH$_2$CH$_2$SO$_2$N(CH$_3$)$_2$ |
| G-51 | —OCH=CHCOSCH$_3$ |
| G-52 | —OCH=CHCON(CH$_3$)CH$_2$C≡CH |
| G-53 | —OCH=CHCON(OCH$_3$)CH$_3$ |
| G-54 | —OCH=CHCONHOCH$_3$ |
| G-55 | —OCH=CHCONHOCH$_2$CH=CH$_2$ |
| G-56 | —OCH=CHCONHCH$_2$COOCH$_3$ |
| G-57 | —OCH=CHCONHCH$_2$CON(CH$_3$)$_2$ |
| G-58 | —OCH=CHCONHSO$_2$CH$_3$ |
| G-59 | —OCH=CHCO—N(thiomorpholine) |
| G-60 | —OCH=CHCONHN(CH$_3$)$_2$ |
| G-61 | —OCH=CHCONHNHCOOC$_2$H$_5$ |
| G-62 | —OCH=CHCONHNHCSNH(c)C$_6$H$_{11}$ |
| G-63 | —OCH=CHCH$_2$—N(morpholine) |
| G-64 | —OCH=CHCH$_2$—N(imidazole) |
| G-65 | —OCH=CHCH$_2$OCH$_3$ |
| G-66 | —OCH=CHCH$_2$SCH$_3$ |
| G-67 | —OCH=CHCH$_2$SOCH$_3$ |
| G-68 | —OCH=CHCH$_2$SO$_2$CH$_3$ |
| G-69 | —OCH=CHCH$_2$OH |
| G-70 | —OCH=CHCH$_2$COOCH$_3$ |
| G-71 | —OCH$_2$C≡CCH$_2$OH |
| G-72 | —OCH=CHCH$_2$ON(CH$_3$)$_2$ |
| G-73 | —OCH=CHCH$_2$N(CH$_3$)$_2$ |
| G-74 | —OCH=CHCH$_2$N(CH$_2$CH=CH$_2$)$_2$ |
| G-75 | —OCH=CHCH$_2$N(OH)CH$_3$ |
| G-76 | —OCH=CHCH$_2$NO$_2$ |
| G-77 | —OCH=CHCH$_2$SO$_3$H |
| G-73 | —SCH$_2$CH=CH$_2$ |
| G-79 | —SOCH$_2$CH=CH$_2$ |
| G-80 | —SO$_2$CH$_2$CH=CH$_2$ |
| G-81 | —SCH=CHCOOH |
| G-82 | —CH$_2$NHCH=CHCOOH |
| G-83 | —CH$_2$OCH$_2$CH=CH$_2$ |
| G-84 | —CH$_2$OCH=CHCOOH |

Groups belonging to the H$_0$ group and the H group will be exemplified in Table H.

TABLE H

| No. | Group |
|---|---|
| H-1 | —CH$_2$NHCN |
| H-2 | —N(COCH$_3$)CN |
| H-3 | —NHC(=NH)NHOH |
| H-4 | —NHC(=NH)N(CH$_2$CH=CH$_2$)CH$_3$ |
| H-5 | —C(=NH)NHCH$_2$CH=CH$_2$ |
| H-6 | —N=CHN(CH$_3$)$_2$ |
| H-7 | —N(CH$_3$)C(CH$_3$)=NOCH$_2$C≡CH |
| H-8 | —NHCONHCOCH$_3$ |
| H-9 | —NHCONHSO$_2$CH$_3$ |
| H-10 | —NHCOCN |
| H-11 | —NHCOCOOCH$_3$ |

Groups belonging to the I$_0$ group and the I group will be exemplified in Table I.

TABLE I

| No. | Group |
|---|---|
| I-1 | —NHCOCH=CH$_2$ |
| I-2 | —NHCSCH=CH$_2$ |
| I-3 | —NHCOCF=CH$_2$ |
| I-4 | —NHCO=CH |
| I-5 | —NHCOCH$_2$OCH$_3$ |
| I-6 | —NHCOCH$_2$SCH$_3$ |
| I-7 | —NHCOCH$_2$COCH$_3$ |
| I-8 | —NHCOCH$_2$OH |
| I-9 | —NHCOCH$_2$ONH$_2$ |
| I-10 | —NHCOCH$_2$N(CH$_3$)CH$_2$C≡CH |
| I-11 | —NHCOCH$_2$NHCOCH$_3$ |
| I-12 | —NHCOCH$_2$COOCH$_3$ |
| I-13 | —NHCOCH$_2$CN |
| I-14 | —NHCOCH$_2$NO$_2$ |
| I-15 | —NHCOCH$_2$SO$_3$H |
| I-16 | —NHCOCH$_2$SO$_2$N(CH$_3$)$_2$ |
| I-17 | —NHCSCH$_3$ |
| I-18 | —NHCSCH$_2$N(CH$_3$)$_2$ |
| I-19 | —NHCOOCH$_2$CH$_2$OCH$_3$ |
| I-20 | —NHCOOCH$_2$CN |
| I-21 | —NHCOOCH$_2$CH$_2$NO$_2$ |
| I-22 | —NHCOOCH$_2$CH$_2$NHCOCH$_3$ |
| I-23 | —NH(CS)OCH$_3$ |
| I-24 | —NH(CO)SCH$_3$ |
| I-24 | —NHCONHCH$_2$CH$_2$OCH$_3$ |
| I-25 | —NHCSNHCH$_3$ |
| I-26 | —NHSO$_2$CH=CH$_2$ |
| I-27 | —NHSO$_2$CH$_2$CH=CH$_2$ |
| I-28 | —NHSO$_2$CH$_2$C≡CH |
| I-29 | —NHSO$_2$CH$_2$COCH$_3$ |
| I-30 | —NHSO$_2$CH$_2$CN |
| I-31 | —NHSO$_2$CH$_2$NO$_2$ |
| I-32 | —NHSO$_2$CH$_2$COOH |
| I-33 | —NHSO$_2$CH$_2$COOCH$_3$ |

Groups belonging to the J$_0$ group and the J group will be exemplified in Table J.

TABLE J

| No. | Group |
|---|---|
| J-1 | —COCH=CH$_2$ |
| J-2 | —COC≡CH |
| J-3 | —COC≡CCF$_3$ |
| J-4 | —COCH$_2$SCH$_3$ |
| J-5 | —COCH$_2$OH |
| J-6 | —COCH$_2$N(CH$_3$)$_2$ |
| J-7 | —CSCH$_3$ |
| J-8 | —CSCF$_3$ |
| J-9 | —CH=NCH$_3$ |
| J-10 | —CH=NOCH$_3$ |

TABLE J-continued

| No. | Group |
|---|---|
| J-11 | —COCN |
| J-12 | —COC(=NH)NH$_2$ |
| J-13 | —COCOOCH$_3$ |
| J-14 | —CH$_2$OCON(CH$_3$)$_2$ |

Groups belonging to the $K_0$ group and the K group will be exemplified in Table K.

TABLE K

| No. | Group |
|---|---|
| K-1 | —CONHSO$_2$CH$_3$ |
| K-2 | —CONHOH |
| K-3 | —CONHOCH$_3$ |
| K-4 | —CONHOCH$_2$CH=CH$_2$ |
| K-5 | —CONHCH$_2$CH$_2$OH |
| K-6 | —CONHCH$_2$CH$_2$OCH$_3$ |
| K-7 | —CONHCH$_2$OCH$_3$ |
| K-8 | —CONHCH$_2$CH=CH$_2$ |
| K-9 | —CONHCH$_2$C≡CH |
| K-10 | —CONHCH$_2$CN |
| K-11 | —CONHCH$_2$COOH |
| K-12 | —CONHCH$_2$COOCH$_3$ |
| K-13 | —CONHCH$_2$CONH$_2$ |
| K-14 | —CONHCH$_2$CONHCH$_3$ |
| K-15 | —CONHCH$_2$CONH(CH$_3$)$_2$ |
| K-16 | —CONHCH(CH$_2$COOH)COOH |
| K-17 | —CONHCH(CH$_2$COOCH$_3$)COOCH$_3$ |

Groups belonging to the $L_0$ and the L group will be exemplified in Table L.

TABLE L

| No. | Group |
|---|---|
| L-1 | —SO$_2$NHOH |
| L-2 | —SO$_2$NHOCH$_3$ |
| L-3 | —SO$_2$NHOCH$_2$CH=CH$_2$ |
| L-4 | —SO$_2$NHCH$_2$CH$_2$OCH$_3$ |
| L-5 | —SO$_2$NHCH$_2$CH=CH$_2$ |
| L-6 | —SO$_2$NHCH$_2$C≡CH |
| L-7 | —SO$_2$NHCH$_2$CN |
| L-8 | —SO$_2$NHCOCH$_3$ |
| L-9 | —SO$_2$NHCH$_2$COOH |
| L-10 | —SO$_2$NHCH$_2$COOCH$_3$ |
| L-11 | —SO$_2$NHCH$_2$CONH$_2$ |
| L-12 | —SO$_2$NHCH$_2$CONHCH$_3$ |
| L-13 | —SO$_2$NHCH$_2$CON(CH$_3$)$_2$ |
| L-14 | —SO$_2$NHCH(CH$_2$COOH)COOH |
| L-15 | —NHSO$_2$N(CH$_3$)$_2$ |

Groups belonging to the $M_0$ group and the M group will be exemplified in Table M.

TABLE M

| No. | Group |
|---|---|
| M-1 | —N=C(—SCH$_3$)CH$_3$ |
| M-2 | —N=C(—OCH$_3$)OCH$_3$ |
| M-3 | —N=C(—SCH$_3$)OCH$_3$ |
| M-4 | —N=C(—SCH$_3$)SCH$_3$ |
| M-5 | —N=C(—SCH$_3$)NHCH$_3$ |
| M-6 | —N(CH$_3$)C(—SCH$_3$)=NCH$_3$ |
| M-7 | —N(CH$_3$)OCH$_2$CH=CH$_2$ |
| M-8 | —N(CH$_2$CH=CH$_2$)OCH$_2$CH=CH$_2$ |

Groups belonging to the $N_0$ group and the N group will be exemplified in Table N.

TABLE N

| No. | Group |
|---|---|
| N-1 | —CH$_2$P(=O)(OH)$_2$ |
| N-2 | —CH$_2$P(=O)(OCH$_3$)$_2$ |
| N-3 | —CH$_2$P(=O)(OCH$_3$)—CH$_3$ |
| N-4 | —CH$_2$P(=O)(OCH$_3$)—CH(OH)CH$_3$ |
| N-5 | —CH$_2$P(=O)(OCH$_3$)—CH$_2$CH$_2$OH |
| N-6 | —CH$_2$P(=O)(OCH$_3$)—CH$_2$COOCH$_3$ |

Groups belonging to the aforementioned $X_0$ to $Z_0$ groups and X to Z groups will be exemplified in the following Table X to Table Z. When said groups have geometrical isomers, all of the geometrical isomers are included, and when said groups have tautomers, all of the tautomers are included.

Groups belonging to the $X_0$ group and the X group will be exemplified in Table X.

TABLE X

| No. | Group |
|---|---|
| X-1 | —CH$_3$ |
| X-2 | —C$_2$H$_5$ |
| X-3 | —CF$_3$ |
| X-4 | —CH=CHCH$_3$ |
| X-5 | —CH$_2$CH=CH$_2$ |
| X-6 | —C≡CH |
| X-7 | —F |
| X-8 | —Cl |
| X-9 | —Br |
| X-10 | —NO$_2$ |
| X-11 | —CN |
| X-12 | —OCH$_3$ |
| X-13 | —SCH$_3$ |
| X-14 | —SOC$_4$H$_9$ |
| X-15 | —SO$_2$C$_4$H$_9$ |
| X-16 | —OCHF$_2$ |
| X-17 | —OCF$_3$ |
| X-18 | —OCF$_2$CHF$_2$ |
| X-19 | —SCF$_3$ |
| X-20 | —CH$_2$OCH$_3$ |
| X-21 | —COCH$_3$ |
| X-22 | —OCOCH$_3$ |
| X-23 | —COOH |
| X-24 | —COOCH$_3$ |
| X-25 | —CH=CHCOOH |
| X-26 | —N(CH$_3$)$_2$ |
| X-27 | —NHCOCH$_3$ |
| X-28 | —NHCOOCH$_3$ |
| X-29 | —CONH$_2$ |
| X-30 | —CON(CH$_3$)$_2$ |
| X-31 | —NHCON(CH$_3$)$_2$ |
| X-32 | —NHC(=NH)NH$_2$ |
| X-33 | —NHSO$_2$CF$_3$ |
| X-34 | —SO$_2$N(CH$_3$)$_2$ |

Groups belonging to the $Y_0$ group and the Y group will be exemplified in Table Y.

TABLE Y

| No. | Group |
|---|---|
| Y-1 | 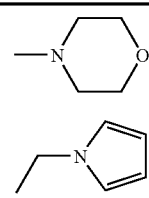 |
| Y-2 | |

TABLE Y-continued

| No. | Group |
|---|---|
| Y-3 | 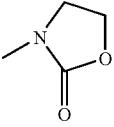 |
| Y-4 | 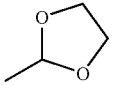 |
| Y-5 | 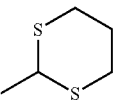 |
| Y-6 | 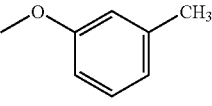 |
| Y-7 | 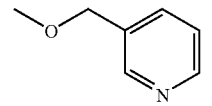 |
| Y-8 | 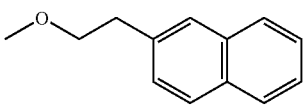 |
| Y-9 | 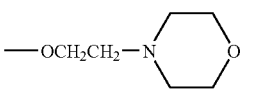 |
| Y-10 | 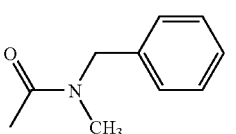 |

The A ring fused to the $Z_0$ group or the Z group will be exemplified in Table Z.

TABLE Z

| No. | Group |
|---|---|
| Z-1 | 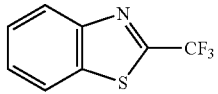 |
| Z-2 | 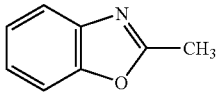 |
| Z-3 | 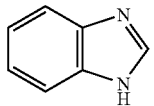 |

TABLE Z-continued

| No. | Group |
|---|---|
| Z-4 | 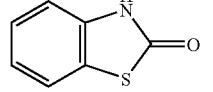 |
| Z-5 | 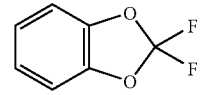 |
| Z-6 | 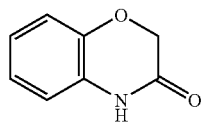 |
| Z-7 | 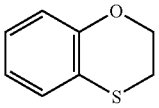 |
| Z-8 | 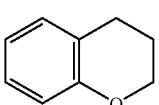 |
| Z-9 | 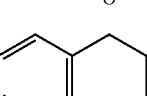 |
| Z-10 | 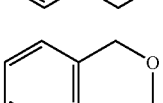 |

$Q_{A0}$ and $Q_A$ will be exemplified in Table Q.

TABLE Q

| No. | Group |
|---|---|
| Q-1 | —OH |
| Q-2 | 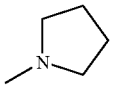 |
| Q-3 | 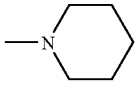 |
| Q-4 | 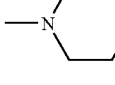 |
| Q-5 | —OCOCH$_3$ |
| Q-6 | —OSO$_2$N(CH$_3$)$_2$ |
| Q-7 | —NHCH$_2$CH=CH$_2$ |
| Q-8 | —NHCH$_2$C≡CH |
| Q-9 | —NHCH$_2$CH$_2$CH$_3$ |
| Q-10 | —OCH$_3$ |
| Q-11 | —OCH$_2$CH$_2$(c)C$_6$H$_{11}$ |
| Q-12 | —OCH$_2$CH=CH$_2$ |
| Q-13 | —OCH$_2$C≡CH |
| Q-14 | —OCH$_2$COOH |
| Q-15 | —OCH$_2$COOCH$_3$ |

TABLE Q-continued

| No. | Group |
|---|---|
| Q-16 | —OCH$_2$CONH$_2$ |
| Q-17 | —OCH$_2$CN |
| Q-18 | —OCH$_2$CH$_2$OH |
| Q-19 | —OCH$_2$CH$_2$OCH$_3$ |
| Q-20 | —OCH$_2$CH$_2$N(CH$_3$)$_2$ |
| Q-21 | —OCH$_2$COCH$_3$ |
| Q-22 | —OCOC$_6$H$_5$ |
| Q-23 | —OCH$_2$C$_6$H$_5$ |
| Q-24 | 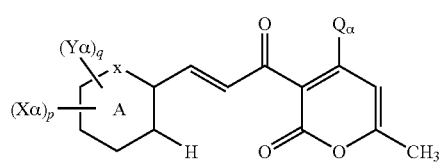 (3-Cl-benzyloxy) |
| Q-25 | (3-CH$_3$-benzyloxy) |
| Q-26 | (4-OCH$_3$-benzyloxy) |

$T_{A0}$ and $T_A$ will be exemplified in Table T.

TABLE T

| No. | Group |
|---|---|
| T-1 | —H |
| T-2 | —CH$_3$ |
| T-3 | —CH$_2$CH$_2$(c)C$_6$H$_{11}$ |
| T-4 | —CH$_2$CH=CH$_2$ |
| T-5 | —CH$_2$C≡CH |
| T-6 | —CH$_2$C$_6$H$_5$ |
| T-7 | —CH$_2$COOH |
| T-8 | —CH$_2$COOCH$_3$ |
| T-9 | —CH$_2$CONH$_2$ |
| T-10 | —CH$_2$CN |
| T-11 | —CH$_2$CH$_2$OH |
| T-12 | —CH$_2$CH$_2$OCH$_3$ |
| T-13 | —CH$_2$CH$_2$N(CH$_3$)$_2$ |
| T-14 | —CH$_2$COCH$_3$ |
| T-15 | —CH$_2$CF$_3$ |
| T-16 | —Ph |
| T-17 | (2-pyridylmethyl) |

Examples of the present compound (I) include a 2H-pyran-2-one compound represented by the formula (I'):

(I')

$$\text{structure with } (Y_\alpha)_q, (X_\alpha)_p, A, Q_\alpha, CH_3$$

[wherein A, X$_\alpha$, Y$_\alpha$, p, q and Q$_\alpha$ are as defined above, and x represents a methine group or a nitrogen atom.]

In the 2H-pyran-2-one compound (I'), when x is a methine group, the methine group has no substituent. Specifically, in the 2H-pyran-2-one compound (I'), there is exemplified the case where Q$_\alpha$ is an optionally substituted hydroxy group.

Examples of the present compound (II) include a 2H-pyran-2-one compound represented by the formula (II'):

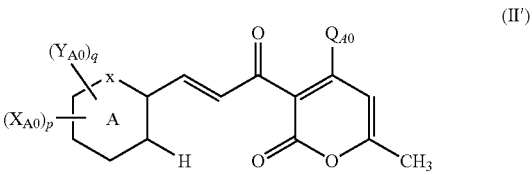

(II')

[wherein A, X$_{A0}$, Y$_{A0}$, p, q and X$_{A0}$ are as defined above, and x represents a methine group or a nitrogen atom.]

In the 2H-pyran-2-one compound (II'), when x is a methine group, the methine group has no substituent. Specifically, in the 2H-pyran-2-one compound (II'), there is exemplified the case where Q$_{A0}$ is a hydroxy group, an A$_9$'-O-group (A$_9$' is as defined above) or a M$_c$-O-group (M$_c$ is as defined above).

Examples of the present compound (III) include a 2H-pyran-2-one compound represented by the formula (III'):

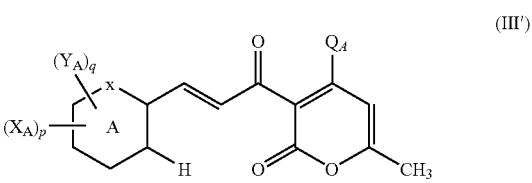

(III')

[wherein A, X$_A$, Y$_A$, p, q and Q$_A$ are as defined above, and x represents a methine group or a nitrogen atom.]

In the 2H-pyran-2-one compound (III'), when x is a methine group, the methine group has no substituent. Specifically, in the 2H-pyran-2-one compound (III'), there is exemplified the case where Q$_A$ is a hydroxy group, an A$_9$'-O-group (A$_9$' is as defined above) or a M$_c$-O-group (M$_c$ is as defined above). Further, specifically, in a 2H-pyran-2-one compound (III'), when Q$_A$ is a hydroxy group, an A$_9$'-O-group (A$_9$' is as defined above) or a M$_c$-O-group (M$_c$ is as defined above), a X$_A$-group represents a substituent belonging to a F group, an I group or a K group.

Examples of the present compound (IV) include that wherein q$_a$ is a r$_a$-O-group (r$_a$ is as defined above).

Examples of the present compound (V) include that wherein q$_a$ is a r$_a$-O-group (r$_a$ is as defined above).

Examples of the present compound (VI) include that wherein q$_a$ is a r$_a$-O-group (r$_a$ is as defined above).

Examples of the present compound (VII) include that wherein q$_a$' is a r$_a$'-O-group (r$_a$' is as defined above).

Examples of the present compound (VIII) include that wherein q$_a$ is a r$_a$-O-group (r$_a$ is as defined above).

Examples of the present compound (IX) include that wherein q$_a$" is a hydroxy group or a C1-C10 alkoxy group.

Examples of the present compound (X) include a 2H-pyran-2-one compound represented by the formula (X'):

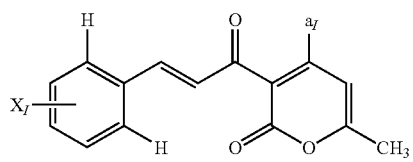

[wherein X₁ and a₁ are as defined above.]

Examples of the present compound (X₁) include a 2H-1-benzopyran-2-one compound represented by the formula (X₁'):

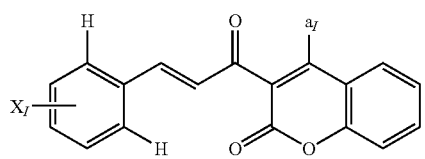

[wherein X₁ and a₁ are as defined above.]

Among the present compound (I), examples of typical compounds include a 2H-pyran-2-one compound represented by the formula (XIV):

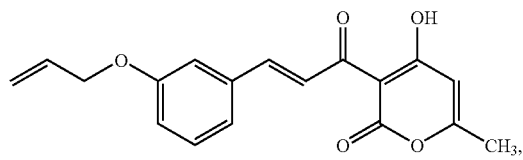

a 2H-pyran-2-one compound represented by the formula (XV):

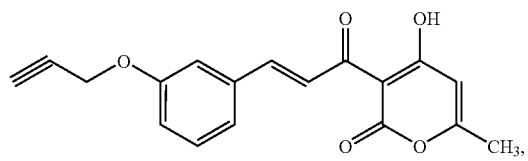

a 2H-pyran-2-one compound represented by the formula (XVI):

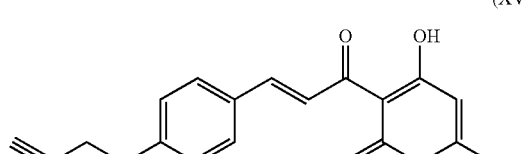

a 2H-pyran-2-one compound represented by the formula (XVII):

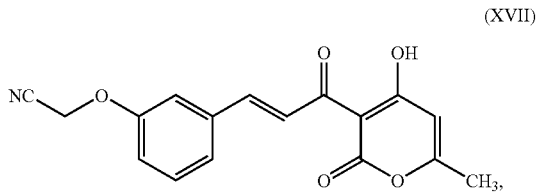

a 2H-pyran-2-one compound represented by the formula (XVIII):

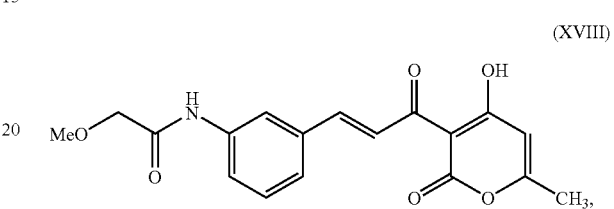

a 2H-pyran-2-one compound represented by the formula (XIX):

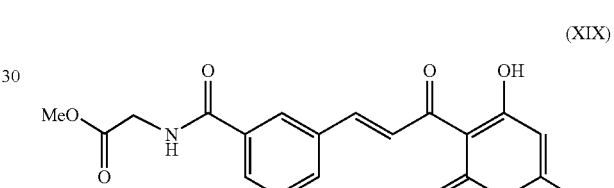

a 2H-pyran-2-one compound represented by the formula (XX):

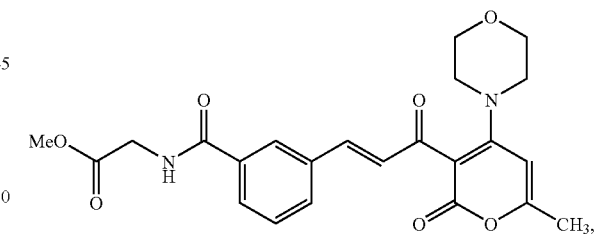

a 2H-pyran-2-one compound represented by the formula (XXI):

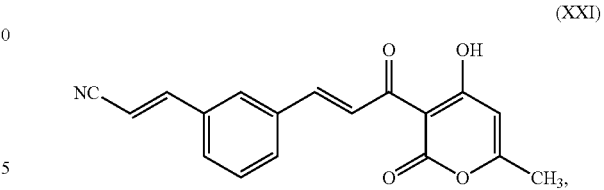

a 2H-pyran-2-one compound represented by the formula (XXII):

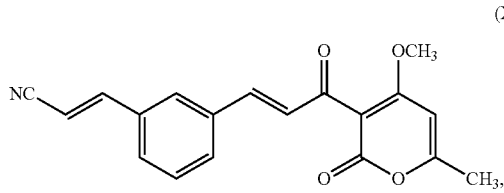

a 2H-1-benzopyran-2-one compound represented by the formula (XXIII):

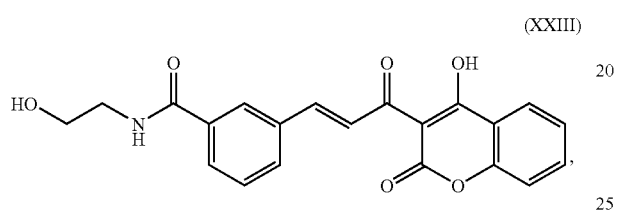

a 2H-1-benzopyran-2-one compound represented by the formula (XXIV):

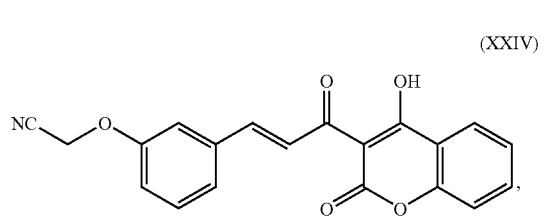

a 2H-1-benzopyran-2-one compound represented by the formula (XXV):

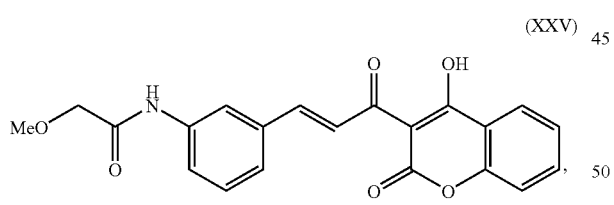

and the like.

The present compounds are novel compounds. Although JP09227547 and WO00/20371 disclose compounds having a certain conceptional skeleton, they do not describe concretely a compound having a structure similar to that of the present compounds. In addition, in these publications, there is no description regarding a suppressing effect on transcription of a Type I collagen gene in tissues and then a suppressing effect on accumulation of collagen.

[Production Process A of the Present Compound]

The present compound (I) can be produced by reacting a compound represented by the formula (α) (wherein A, $X_\alpha$, $Y_\alpha$, p and q are as defined above) and a compound represented by the formula (α') (wherein $Q_\alpha$, $K_\alpha$ and $L_\alpha$ are as defined above) (see Indian J. Chem. (1974), 12, 956 and JP50046666).

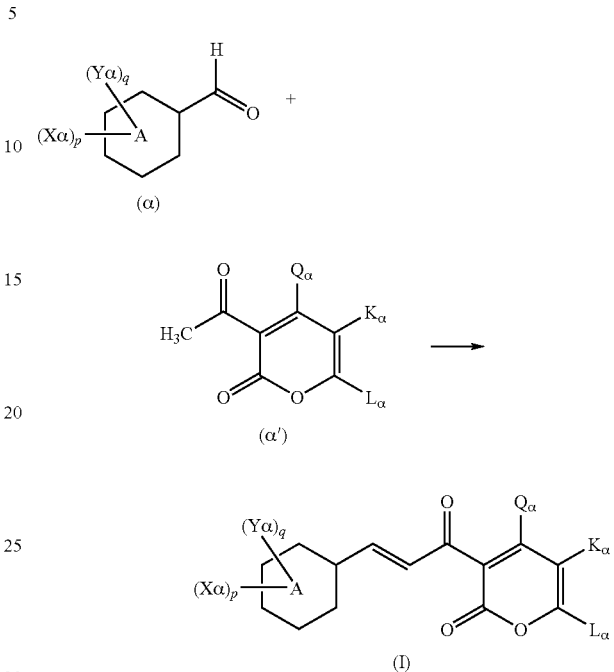

The present compound (II) can be produced by reacting a compound represented by the formula (A0) (wherein A, $X_{A0}$, $Y_{A0}$, p and q are as defined above) and a compound represented by the formula (A0') (wherein $Q_{A0}$, $K_{A0}$ and $L_{A0}$ are as defined above), as described above.

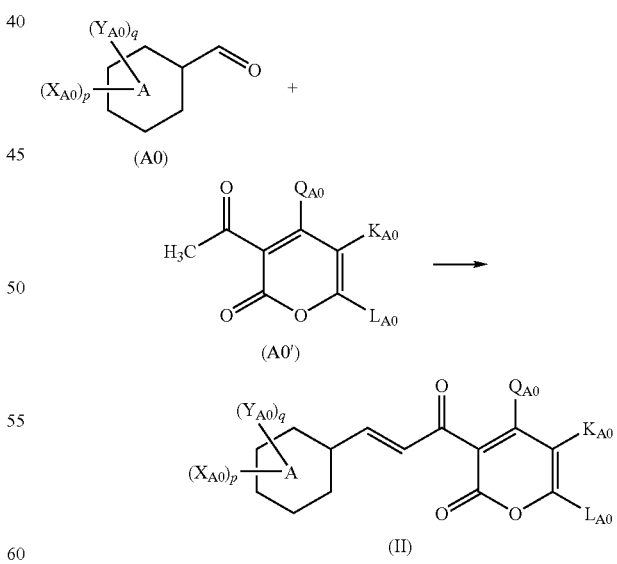

The present compound (III) can be produced by reacting a compound represented by the formula (A) (wherein A, $X_A$, $Y_A$, P and q are as defined above) and a compound represented by the formula (A') (wherein $Q_A$, $K_A$ and $L_A$ are as defined above), as described above.

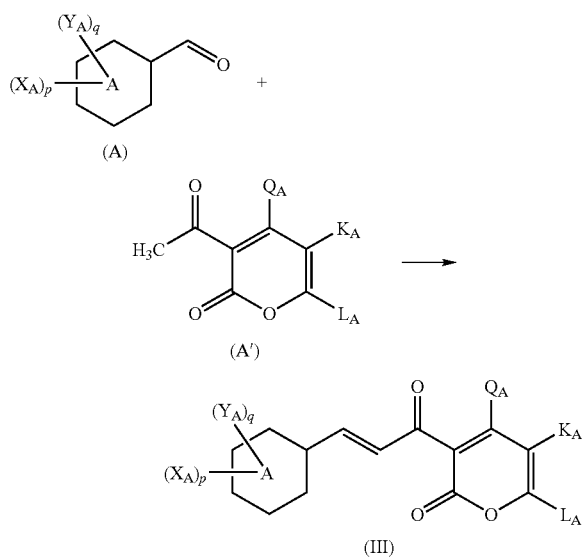

The present compound (IV) can be produced by reacting a compound represented by the formula (a) (wherein A, $X_a$, $Y_a$, p and q are as defined above) and a compound represented by the formula (a') (wherein $Q_a$, $K_a$ and $L_a$ are as defined above), as described above.

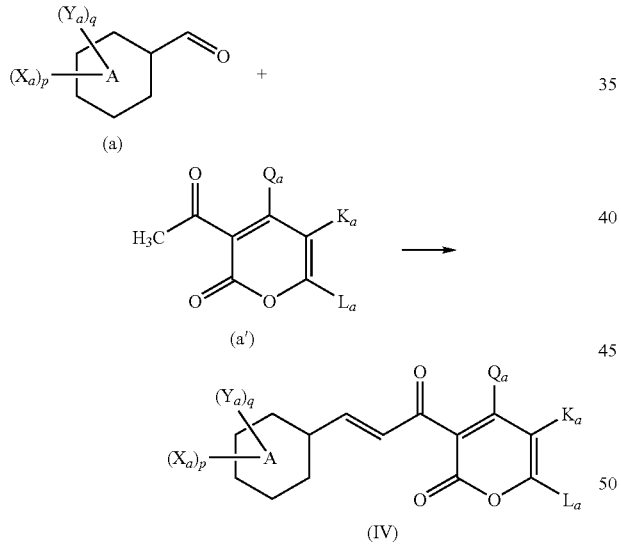

Although a part of a compound represented by the formula (a) is described, for example, in the document (EP330645) and known, the benzaldehyde derivatives represented by the formula (XXVI-1), (XXVI-2), (XXVI-3) and (XXVI-4) (hereinafter, referred to as the present benzaldehyde derivatives in some cases), and 6-formyl-2-[(2-methoxyethyl)aminocarbonyl]pyridine (hereinafter, referred to as the present pyridinecarbaldehyde derivative in some cases) have not been reported yet, and are a novel substance.

The present benzaldehyde derivative can be produced, for example, by reacting a compound represented by the formula (XXVI-a):

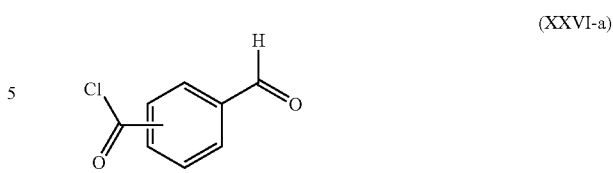

with glycine methyl ester. In the reaction, a range of a reaction temperature is usually room temperature to a solvent refluxing temperature, and a range of a reaction time is usually instant to about 24 hours. The reaction is performed usually in the presence of a base, and examples of the base to be used include organic bases such as pyridine, triethylamine, N,N-dimethylaniline, tributylamine, N-methylmorpholine and the like, inorganic bases such as sodium hydroxide, potassium hydroxide, potassium carbonate and the like. The amount of a reagent to be supplied to the reaction is such that glycine methyl ester is usually 1 to 2 mole, and a base is usually 1 to 7 mole per 1 mole of a compound (XXVI-a). In the reaction, a solvent is not necessarily required, but the reaction is performed usually in the presence of a solvent. Examples of the solvent which can be used in the reaction include aliphatic hydrocarbons such as hexane, petroleum ether and the like, aromatic hydrocarbons such as benzene, toluene and the like, halogenated hydrocarbons such as chloroform, dichloroethane and the like, ethers such as diethyl ether, dioxane, tetrahydrofuran and the like, ketones such as acetone, methyl ethyl ketone and the like, esters such as ethyl acetate, diethyl carbonate and the like, nitrites such as acetonitrile, isobutylnitrile and the like, amides such as formamide, N,N-dimethylformamide and the like, sulfur compounds such as dimethyl sulfoxide and the like, and a mixture thereof. The reaction mixture after completion of the reaction is subjected to conventional post-treatment such as extraction with an organic solvent, washing with water, concentration of the organic layer under reduced pressure and the like and, if necessary, is purified by a procedure such as chromatography, recrystallization and the like, thereby, the objective present compound can be obtained.

In addition, the present benzaldehyde derivative can be produced, for example, by oxidizing a compound represented by the formula (XXVI-b):

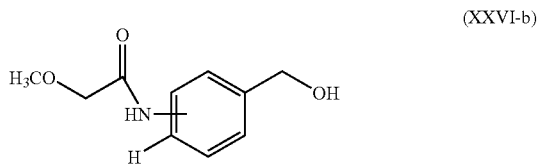

using dimethyl sulfoxide which has been activated with oxalyl chloride, in the presence of a base such as triethylamine and the like in dichloromethane (SYNTHESIS (1981), 165).

A compound represented by the formula (XXVI-b) can be produced, for example, by reacting a compound represented by the formula (XXVI-c):

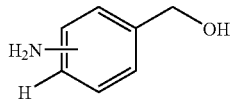

(XXVI-c)

with methoxyacetyl chloride. The reaction of the compound (XXVI-c) and methoxyacetyl chloride can be performed as in the aforementioned reaction of the compound (XXVI-a) and glycine methyl ester.

In addition, the present benzaldehyde derivative can be produced, for example, by reacting a compound represented by the formula (XXVI-d):

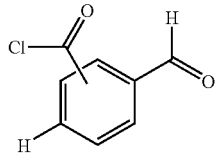

(XXVI-d)

with 2-methoxyethylamine. The reaction of the compound (XXVI-d) and 2-methoxyethylamine can be performed as in the aforementioned reaction of the compound (XXVI-a) and glycine methyl ester.

The compound (XXVI-d) is described, for example, in the document such as J. Medicinal Chem. (2001), 44, 362, and is known.

The present pyridinecarbaldehyde derivative can be produced by reacting a compound represented by the formula (XXVI-e):

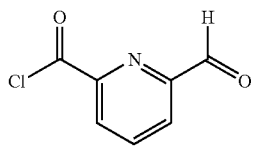

(XXVI-e)

with 2-methoxyethylamine. The reaction of the compound (XXVI-e) and 2-methoxyethylamine can be performed as in the aforementioned reaction of the compound (XXVI-a) and glycine methyl ester. The compound (XXVI-e) can be produced by reacting 2-carboxy-6-formylpyridine with a chlorinating agent such as phosphoryl chloride, thionyl chloride and phosphorus trichloride. In the reaction, a range of the reaction temperature is usually room temperature to a solvent refluxing temperature, and a range of the reaction time is usually instant to about 24 hours. The amount of a reagent to be supplied to the reaction is such that a chlorinating agent is usually 1 to 10 moles per 1 mole of 2-carboxy-6-formylpyridine. In the reaction, a solvent is not necessarily required, and the reaction is performed usually in the presence of a solvent. Examples of the solvent which can be used in the reaction include aliphatic hydrocarbons such as hexane, petroleum ether and the like, aromatic hydrocarbons such as benzene, toluene and the like, halogenated hydrocarbons such as chloroform, dichloroethane and the like, ethers such as diethyl ether, dioxane, tetrahydrofuran and the like, and a mixture thereof. After completion of the reaction, volatile substances can be distilled off under reduced pressure to obtain the compound (XXVI-e). 2-Carboxy-6-formylpyridine is described, for example, in the document such as Bioorg. Medicinal Chem. Letters (2003) 13, 609 and is known.

Among the present compound (IV), cinnamoyl compounds represented by the formula (XLVI-1), (XLVI-2), (XLVI-3), (XLVI-4) and (XLVI-5) can be produced by reacting the present benzaldehyde derivative or the present pyridinecarbaldehyde derivative with the compound (XLVI).

[Production Process B of the Present Compound]

Among the present compounds, a cinnamoyl compound represented by the formula (XLVII″) can be produced by reacting a cinnamoyl compound represented by the formula (XLVII) and a compound represented by the formula (XLVII′).

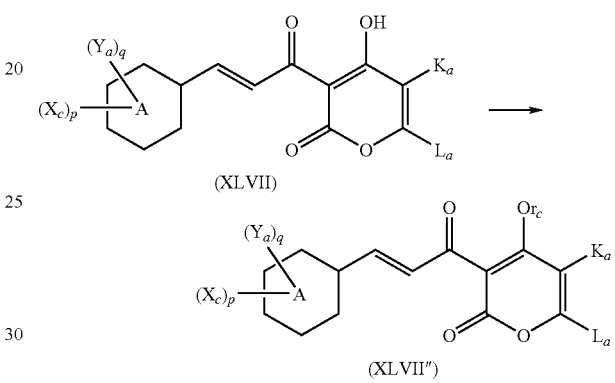

Examples of the reaction process include a process for reacting the compound (XLVII) and the compound (XLVII′) in the presence of a base.

The reaction of the compound (XLVII) and the compound (XLVII′) in the presence of a base is performed usually in a solvent. Examples of the solvent which is used in the reaction include acid amides such as N,N-dimethylformamide, N,N-dimethylacetamide and the like, sulfoxides such as dimethyl sulfoxide and the like, phosphoric acid amide compounds such as hexamethylphosphoramide and the like, and ketones such as acetone, methyl ethyl ketone and the like.

Examples of the base used in the reaction include alkali metal hydrides such as sodium hydride, potassium hydride and the like, carbonates of an alkali metal such as potassium carbonate and the like, and silver oxide.

Examples of the compound (XLVII′) include alkylsulfonic acid esters such as methyl methanesulfonate and the like, arylsulfonic acid esters such as p-toluenesulfonic acid methyl ester, p-toluenesulfonic acid 2-methoxyethyl ester and the like, sulfate esters such as dimethyl sulfate and the like, and halides such as methyl iodide, 2-chloroethyldimethylamine, allyl bromide, propargyl bromide, methyl bromoacetate, bromoacetonitrile, 2-bromoethanol, benzyl bromide, bromoacetone and the like.

The amount of a reagent used in the reaction is such a ratio that a base is usually 1 mole to 2 moles, and the compound (XLVII′) is usually 1 mole to 2 moles relative to 1 mole of the compound (XLVII).

The reaction temperature is usually in a range of 0° C. to 100° C., and a reaction time is usually in a range of 1 hour to 200 hours.

After completion of the reaction, the reaction mixture is extracted with an organic solvent, and the organic layer is subjected to a post-treatment procedure such as drying, concentration and the like, thereby, the cinnamoyl compound (XLVII") can be isolated. The isolated compound (XLVII") can be also further purified by chromatography, recrystallization or the like.

[Production Process C of the Present Compound]

Among the present compounds, a cinnamoyl compound represented by the formula (XLVIII') can be produced by hydrolyzing a cinnamoyl compound represented by the formula (XLVIII).

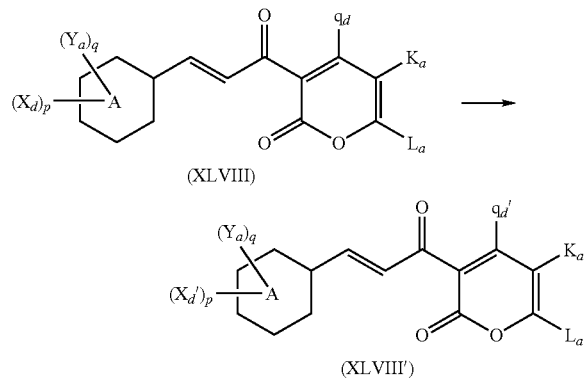

Hydrolysis of the cinnamoyl compound (XLVIII) is performed usually in a solvent in the presence of an acid or a base. Examples of the solvent used in the reaction include water, alcohols such as methanol, ethanol and the like, ketones such as acetone, methyl ethyl ketone and the like, and a mixture thereof.

Examples of the acid used in the reaction include inorganic acids such as hydrochloric acid, sulfuric acid, hydrobromic acid and the like, and organic acids such as p-toluenesulfonic acid and the like.

Examples of the base used in the reaction include alkali metal hydroxides such as sodium hydroxide, potassium hydroxide and the like, and carbonates of an alkali metal such as sodium carbonate, potassium carbonate and the like.

The amount of a reagent used in the reaction is such a ratio that a base is usually 1 mole to 10 moles per 1 mole of the compound (XLVIII).

The reaction temperature is usually in a range of 0° C. to a solvent refluxing temperature, and the reaction time is usually in a range of 1 hour to 200 hours.

After completion of the reaction, the reaction mixture is extracted with an organic solvent, and the organic layer is subjected to a post-treatment procedure such as drying, concentration and the like, thereby, the cinnamoyl compound (XLVIII') can be isolated. The isolated compound (XLVIII') can be also further purified by chromatography, recrystallization or the like.

[Production Process D of the Present Compound]

Among the present compounds, a cinnamoyl compound represented by the formula (XLIX") can be produced by reacting a cinnamoyl compound represented by the formula (XLIX) with a compound represented by the formula (XLIX'), 1,3-propanesultone or 1,4-butanesultone.

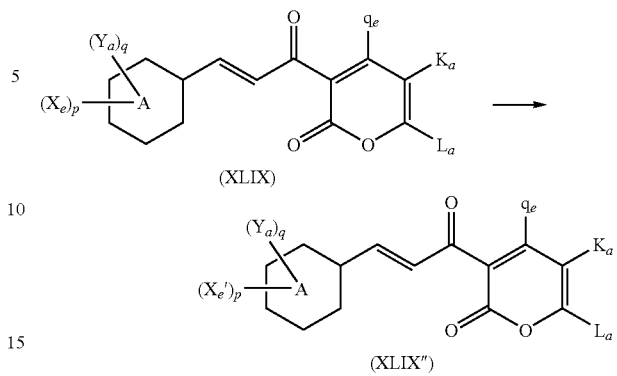

Examples of the reaction process include a process for reacting the compound (XLIX) with a compound which is the compound (XLIX') in which V' is a leaving group, 1,3-propanesultone or 1,4-butanesultone in the presence of a base.

The reaction of the compound (XLIX) with the compound which is the compound (XLIX') in which V' is a leaving group, 1,3-propanesultone or 1,4-butanesultone in the presence of a base can be performed as in the aforementioned reaction of the compound (XLVII) and the compound (XLVII').

Examples of the compound which is the compound (XLIX') in which V' is a leaving group include alkylsulfonic acid esters such as 2-methoxyethyl methanesulfonate and the like, arylsulfonic acid esters such as p-toluenesulfonic acid 2-methoxyethyl ester and the like, and halides such as 2-chloroethyldimethylamine, allyl bromide, propargyl bromide, methyl bromoacetate, bromoacetonitrile, 2-bromoethanol, bromoacetone and the like.

In addition, examples of the reaction process include a reaction for subjecting the compound (XLIX), and the compound which is a compound (XLIX') in which V' is a hydroxy group to a dehydrating reaction in the presence of triphenylphosphine and azodicarboxylic acid ester.

The reaction is performed usually in a solvent, and examples of the solvent used in the reaction include ethers such as tetrahydrofuran and the like. Examples of azodicarboxylic acid ester include diethyl azodicarboxylate.

The amount of a reagent used in the reaction is such a ratio that triphenylphosphine and azodicarboxylic acid ester is usually 1 mole to 2 moles, and the compound (XLIX') is usually 1 mole to 2 moles per 1 mole of the compound (XLIX).

The reaction temperature is usually in a range of 0° C. to room temperature, and the reaction time is usually in a range of 1 hour to 200 hours.

After completion of the reaction, the reaction mixture is extracted with an organic solvent, and the organic layer is subjected to a post-treatment procedure such as drying, isolation and the like, thereby, the cinnamoyl compound (XLIX") can be isolated. The isolated compound (XLIX") can be also further purified by chromatography, recrystallization or the like.

Table 1 exemplifies the benzaldehyde derivatives (XXVI-1), (XXVI-2), (XXVI-3) and (XXVI-4) represented by compound numbers (a) to (p), and (r) to (x), and the pyridinecarbaldehyde derivative represented by a compound number (q).

TABLE 1

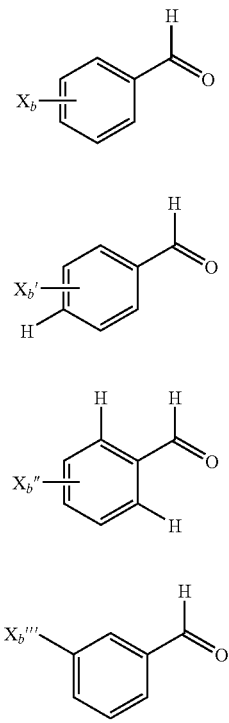

(XXVI-1)

(XXVI-2)

(XXVI-3)

(XXVI-4)

| Compound No. | $X_b$, $X_b'$, $X_b''$ or $X_b'''$ |
|---|---|
| (a) | 3-NHCOCH$_2$OCH$_3$ |
| (b) | 3-CONHCH$_2$COOCH$_3$ |
| (c) | 4-CONHCH$_2$COOCH$_3$ |
| (d) | 3-CONHCH$_2$CH$_2$OCH$_3$ |
| (e) | 3-CH=CHCN |
| (f) | 3-OCH$_2$CH$_2$SCH$_3$ |
| (g) | 3-CH$_2$OCH$_2$CH$_2$OH |
| (h) | 3-NHCOOCH$_2$CH$_2$OCH$_3$ |
| (i) | 3-NHCONHCH$_2$CH$_2$OCH$_3$ |
| (j) | 3-CONHSO$_2$CH$_3$ |
| (k) | 3-CONHCH$_2$CN |
| (l) | 3-CH=CF$_2$ |
| (m) | 3-CH$_2$CH$_2$CN |

TABLE 1-continued

| | |
|---|---|
| (n) | 3-OCH$_2$CONH$_2$ |
| (o) | 3-OCH$_2$COCH$_3$ |
| (p) | 3-CONHCH(CO$_2$CH$_3$)CH$_2$CO$_2$CH$_3$ |

| Compound No. | Pyridinecarbaldehyde compound |
|---|---|
| (q) | MeO‐CH$_2$CH$_2$NHC(O)‐pyridine‐CHO |

| Compound No. | $X_b$, $X_b'$, $X_b''$ or $X_b'''$ |
|---|---|
| (r) | 3-SO$_2$NHCH$_2$CH$_2$OCH$_3$ |
| (s) | 3-CONHOCH$_3$ |
| (t) | 3-CONHOCH$_2$CH=CH$_2$ |
| (u) | 3-CH$_2$SCH$_2$COOCH$_3$ |
| (v) | 3-CH= (tetrahydropyran-4-ylidene) |
| (w) | 3-NHCOCOOCH$_3$ |
| (x) | 3-CH$_2$P(=O)(OCH$_3$)$_2$ |

Among the present compound (IV), the present compound (IVa) represented by compound numbers (1a) to (88a) is exemplified in Table 2a.

TABLE 2a

The present compound (IVa):

(IVa)

$(Y_a)_q$ — A — CH=CH—C(O)— [pyranone ring with $Or_a$, =O, CH$_3$]

$(X_a)_p$

In Table 2a, in compound numbers (1a) to (75a), (77a) to (79a) and (81a) to (88a), A represents a benzene ring.

| Compound No. | $X_a$ and $Y_a$ | $r_a$ |
|---|---|---|
| (1a) | 3-CH=CHCN | —H |
| (2a) | 3-CH=CHCN | —CH$_3$ |
| (3a) | 3-OCH$_2$CH$_2$SCH$_3$ | —H |
| (4a) | 3-OCH$_2$CH=CH$_2$ | —H |
| (5a) | 3-OCH$_2$CH=CH$_2$ | —CH$_3$ |
| (6a) | 2-OCH$_2$C≡CH | —H |
| (7a) | 3-OCH$_2$C≡CH | —H |
| (8a) | 3-OCH$_2$C≡CH | —CH$_3$ |
| (9a) | 4-OCH$_2$C≡CH | —H |
| (10a) | 4-OCH$_2$C≡CH | —CH$_3$ |
| (11a) | 3-OCH$_2$COOCH$_3$ | —H |
| (12a) | 3-OCH$_3$,4-OCH$_2$COOCH$_3$ | —H |
| (13a) | 3-OCH$_2$COOH | —H |
| (14a) | 3-OCH$_2$CN | —H |
| (15a) | 3-OCH$_2$CN | —CH$_3$ |
| (16a) | 4-OCH$_2$CN | —H |
| (17a) | 3-CH$_3$,4-OCH$_2$CN | —H |
| (18a) | 3-NO$_2$,4-OCH$_2$CN | —H |
| (19a) | 3-F,4-OCH$_2$CN,5-OCH$_3$ | —H |

-continued

| | | |
|---|---|---|
| (20a) | 3-NHCOCH=CH$_2$ | —H |
| (21a) | 3-NHCOCH$_2$OCH$_3$ | —H |
| (22a) | 3-NHCOCH$_2$OCH$_3$ | —CH$_3$ |
| (23a) | 4-NHCOCH$_2$OCH$_3$ | —H |
| (24a) | 3-NHCOOCH$_2$CH$_2$OCH$_3$ | —H |
| (25a) | 3-NHCOOCH$_2$CH$_2$OCH$_3$ | —CH$_3$ |
| (26a) | 3-NHCONHCH$_2$CH$_2$OCH$_3$ | —H |
| (27a) | 3-NHSO$_2$CH$_2$COOCH$_3$ | —H |
| (28a) | 3-NHSO$_2$CH$_2$COOH | —H |
| (29a) | 3-NHCOCH$_2$CN | —H |
| (30a) | 3-CONHSO$_2$CH$_3$ | —H |
| (31a) | 3-CONHCH$_2$CH$_2$OH | —H |
| (32a) | 4-CONHCH$_2$CH$_2$OH | —H |
| (33a) | 3-CONHCH$_2$COOCH$_3$ | —H |
| (34a) | 4-CONHCH$_2$COOCH$_3$ | —H |
| (35a) | 3-CONHCH$_2$CH$_2$OCH$_3$ | —H |
| (36a) | 4-CONHCH$_2$CH$_2$OCH$_3$ | —H |
| (37a) | 3-CONHCH$_2$COOH | —H |
| (38a) | 3-CONHCH$_2$CN | —H |
| (39a) | 3-OCH$_2$OCN(CH$_3$)$_2$ | —H |
| (40a) | 3-OCH$_2$CH$_2$CH$_2$N(CH$_3$)$_2$ | —H |
| (41a) | 3-OCH$_2$CH$_2$OH | —H |
| (42a) | 3-CH=CF$_2$ | —H |
| (43a) | 3-CH=CF$_2$ | —CH$_3$ |
| (44a) | 3-CH$_2$CH$_2$CN | —H |
| (45a) | 3-CH$_2$CH$_2$CN | —CH$_3$ |
| (46a) | 3-OCH$_2$CH$_2$SOCH$_3$ | —H |
| (47a) | 3-OCH$_2$CH$_2$SO$_2$CH$_3$ | —H |
| (48a) | 3-CH$_2$OCH$_2$CH$_2$OH | —H |
| (49a) | 3-OCH$_2$CH$_2$CH$_2$OH | —H |
| (50a) | 3-OCH$_2$CH$_2$CH$_2$OH | —CH$_3$ |
| (51a) | 3-OCH$_2$CH$_2$OCH$_3$ | —H |
| (52a) | 3-OCH$_2$CH$_2$NH$_2$ | —H |
| (53a) | 3-OCH$_2$CH$_2$NHCOCH$_3$ | —H |
| (54a) | 3-OCH$_2$CH$_2$NHCOOC(CH$_3$)$_3$ | —H |
| (55a) | 3-OCH$_2$CH$_2$N(CH$_3$)$_2$ | —H |
| (56a) | 3-OCH$_2$CH$_2$SO$_3$H | —H |
| (57a) | 3-OCH$_2$CH$_2$CH$_2$SO$_3$Na | —Na |
| (58a) | 3-OCH$_2$COO(CH$_2$)$_9$—OH | —H |
| (59a) | 4-OCH$_2$OCOCH$_3$ | —H |
| (60a) | 3-OCH$_2$COOH•pyridine | —H |
| (61a) | 4-OCH$_2$COOH | —H |
| (62a) | 3-OCH$_2$CONH$_2$ | —H |
| (63a) | 3-Br,4-OCH$_2$COOCH$_3$ | —H |
| (64a) | 3-CH$_3$,4-OCH$_2$COOCH$_3$ | —H |
| (65a) | 3-NHCOCH$_3$,4-OCH$_2$CN | —H |
| (66a) | 3-OCH$_2$COCH$_3$ | —H |
| (67a) | 3-CH$_2$SCH$_2$COOCH$_3$ | —H |
| (68a) | 3-CH$_2$SOCH$_2$COOCH$_3$ | —H |
| (69a) | 3-CH$_2$SO$_2$CH$_2$COOCH$_3$ | —H |
| (70a) | 3-NHSO$_2$CH$_2$CH=CH$_2$ | —H |
| (71a) | 3-NHCH$_2$CH$_2$N(CH$_3$)$_2$ | —H |
| (72a) | 4-CONHCH$_2$COOH | —H |
| (73a) | 3-CONHCH$_2$CONH$_2$ | —H |
| (74a) | 3-CONHCH(CO$_2$CH$_3$)—CH$_2$CO$_2$CH$_3$ | —H |
| (75a) | 3-CONHCH(CO$_2$H)—CH$_2$OC$_2$H | —H |

| Compound No. | (IVa) |
|---|---|
| (76a) | 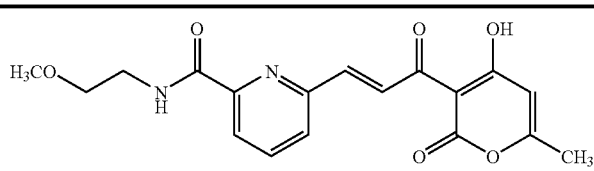 |

| Compound No. | X$_a$ and Y$_a$ | r$_a$ |
|---|---|---|
| (77a) | 3-SO$_2$NHCH$_2$CH$_2$OCH$_3$ | —H |
| (78a) | 3-CONHOCH$_3$ | —H |
| (79a) | 3-CONHOCH$_2$CH=CH$_2$ | —H |

-continued

| Compound No. | (IVa) |
|---|---|
| (80a) | 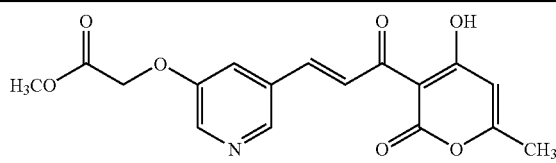 |

| Compound No. | $X_a$ and $Y_a$ | $r_a$ |
|---|---|---|
| (81a) | 3-CH= 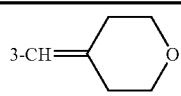 | —H |
| (82a) | 3-C≡CC(CH₃)₂OH | —H |
| (83a) | 3-CH=CHCOOCH₃ | —H |
| (84a) | 3-NHCOCOOCH₃ | —H |
| (85a) | 3-CH=NOCH₃ | —H |
| (86a) | 3-NHCSNHCH₃ | —H |
| (87a) | 3-N=C(—SCH₃)NHCH₃ | —H |
| (88a) | 3-CH₂P(=O)(OCH₃)₂ | —H |

Among the present compound (IV), the present compound (IVb) represented by compound numbers (1b) to (21b) is exemplified in Table 2b.

TABLE 2b

The present compound (IVb):

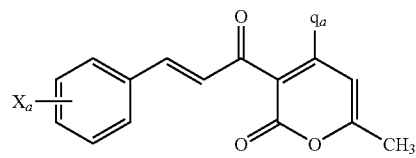 (IVb)

| Compound No. | $X_a$ | $q_a$ |
|---|---|---|
| (1b) | 3-OCH₂CH=CH₂ | —OCH₂CH=CH₂ |
| (2b) | 3-OCH₂C≡CH | —OCH₂CH=CH₂ |
| (3b) | 3-OCH₂COOCH₃ | —OCH₂C≡CH |
| (4b) | 3-OCH₂COOCH₃ | —OCH₂COOCH₃ |
| (5b) | 3-OCH₂COOH | —OCH₂COOH |
| (6b) | 3-OCH₂CONH₂ | —OCH₂CONH₂ |
| (7b) | 3-OCH₂COOCH₃ | —OCH₂CN |
| (8b) | 3-OCH₂COOH | —OCH₂CH₂OH |
| (9b) | 3-OCH₂COOCH₃ | —OCH₂Ph |
| (10b) | 3-OCH₂COOH | —OCH₂Ph |
| (11b) | 3-OCH₂COOCH₃ | —OCH₂CH₂N(CH₃)₂ |
| (12b) | 3-OCH₂COOCH₃ | —OCH₂COCH₃ |
| (13b) | 3-OCH₂COOCH₃ | —OCH₂CH₂OCH₃ |
| (14b) | 3-OCH₂CH₂SCH₃ | 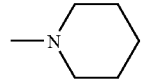 |
| (15b) | 2-OCH₂C≡CH | 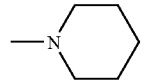 |
| (16b) | 3-CONHCH₂COOCH₃ | 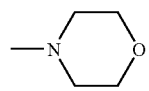 |

TABLE 2b-continued

The present compound (IVb):

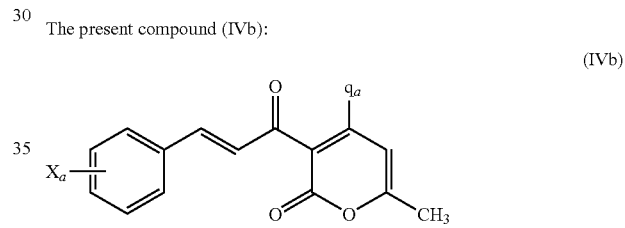 (IVb)

| Compound No. | $X_a$ | $q_a$ |
|---|---|---|
| (17b) | 3-NHCOCH₂OCH₃ |  |
| (18b) | 3-NHCOOCH₂CH₂OCH₃ | 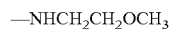 |
| (19b) | 3-CONHCH₂COOCH₃ | 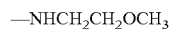 |
| (20b) | 3-CH=CHCN | —NHCH₂C≡CH |
| (21b) | 3-OCH₂CONHCH₂CH₂OCH₃ | —NHCH₂CH₂OCH₃ |

Among the present compound (IV), the present compound (IVc) represented by the compound numbers (1c) to (3c) is exemplified in Table 2c.

TABLE 2c

The present compound (IVc):

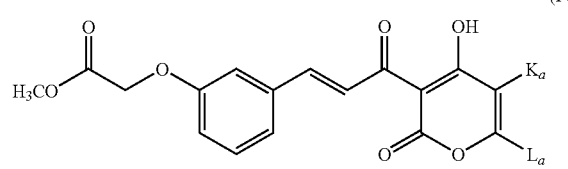

| Compound No. | Compound |
|---|---|
| (1c) | 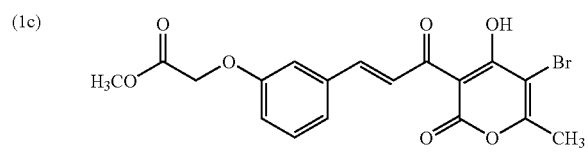 |
| (2c) | 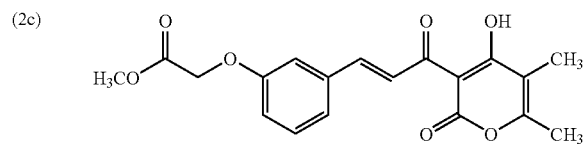 |

TABLE 2c-continued

The present compound (IVc):

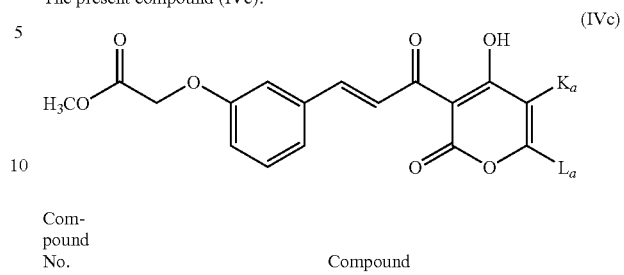

| Compound No. | Compound |
|---|---|
| (3c) | 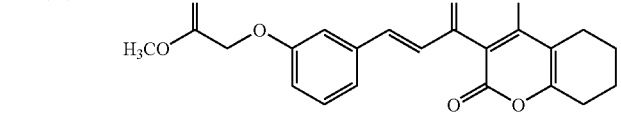 |

Among the present compound (IV), the present compound (IVd) represented by compound numbers (1d) to (88d) is exemplified in Table 2d.

TABLE 2d

The present compound (IVd):

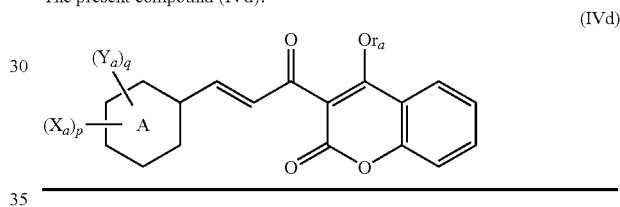

In Table 2d, in compound numbers (1d) to (75d), (77d) to (79d) and (81d) to (88d), A represents a benzene ring.

| Compound No. | $X_a$ and $Y_a$ | $r_a$ |
|---|---|---|
| (1d) | 3-CH=CHCN | —H |
| (2d) | 3-CH=CHCN | —CH$_3$ |
| (3d) | 3-OCH$_2$CH$_2$SCH$_3$ | —H |
| (4d) | 3-OCH$_2$CH=CH$_2$ | —H |
| (5d) | 3-OCH$_2$CH=CH$_2$ | —CH$_3$ |
| (6d) | 2-OCH$_2$C≡CH | —H |
| (7d) | 3-OCH$_2$C≡CH | —H |
| (8d) | 3-OCH$_2$C≡CH | —CH$_3$ |
| (9d) | 4-OCH$_2$C≡CH | —H |
| (10d) | 4-OCH$_2$C≡CH | —CH$_3$ |
| (11d) | 3-OCH$_2$COOCH$_3$ | —H |
| (12d) | 3-OCH$_3$,4-OCH$_2$COOCH$_3$ | —H |
| (13d) | 3-OCH$_2$COOH | —H |
| (14d) | 3-OCH$_2$CN | —H |
| (15d) | 3-OCH$_2$CN | —CH$_3$ |
| (16d) | 4-OCH$_2$CN | —H |
| (17d) | 3-CH$_3$,4-OCH$_2$CN | —H |
| (18d) | 3-NO$_2$,4-OCH$_2$CN | —H |
| (19d) | 3-F,4-OCH$_2$CN,5-OCH$_3$ | —H |
| (20d) | 3-NHCOCH=CH$_2$ | —H |
| (21d) | 3-NHCOCH$_2$OCH$_3$ | —H |
| (22d) | 3-NHCOCH$_2$OCH$_3$ | —CH$_3$ |
| (23d) | 4-NHCOCH$_2$OCH$_3$ | —H |
| (24d) | 3-NHCOOCH$_2$CH$_2$OCH$_3$ | —H |
| (25d) | 3-NHCOOCH$_2$CH$_2$OCH$_3$ | —CH$_3$ |
| (26d) | 3-NHCONHCH$_2$CH$_2$OCH$_3$ | —H |
| (27d) | 3-NHSO$_2$CH$_2$COOCH$_3$ | —H |
| (28d) | 3-NHSO$_2$CH$_2$COOH | —H |

-continued

| | | |
|---|---|---|
| (29d) | 3-NHCO$_2$CH$_2$CN | —H |
| (30d) | 3-CONHSO$_2$CH$_3$ | —H |
| (31d) | 3-CONHCH$_2$CH$_2$OH | —H |
| (32d) | 4-CONHCH$_2$CH$_2$OH | —H |
| (33d) | 3-CONHCH$_2$COOCH$_3$ | —H |
| (34d) | 4-CONHCH$_2$COOCH$_3$ | —H |
| (35d) | 3-CONHCH$_2$CH$_2$OCH$_3$ | —H |
| (36d) | 4-CONHCH$_2$CH$_2$OCH$_3$ | —H |
| (37d) | 3-CONHCH$_2$COOH | —H |
| (38d) | 3-CONHCH$_2$CN | —H |
| (39d) | 3-OCH$_2$CON(CH$_3$)$_2$ | —H |
| (40d) | 3-OCH$_2$CH$_2$CH$_2$N(CH$_3$)$_2$ | —H |
| (41d) | 3-OCH$_2$CH$_2$OH | —H |
| (42d) | 3-CH=CF$_2$ | —H |
| (43d) | 3-CH=CF$_2$ | —CH$_3$ |
| (44d) | 3-CH$_2$CH$_2$CN | —H |
| (45d) | 3-CH$_2$CH$_2$CN | —CH$_3$ |
| (46d) | 3-OCH$_2$CH$_2$SOCH$_3$ | —H |
| (47d) | 3-OCH$_2$CH$_2$SO$_2$CH$_3$ | —H |
| (48d) | 3-CH$_2$OCH$_2$CH$_2$OH | —H |
| (49d) | 3-OCH$_2$CH$_2$CH$_2$OH | —H |
| (50d) | 3-OCH$_2$CH$_2$CH$_2$OH | —CH$_3$ |
| (51d) | 3-OCH$_2$CH$_2$OCH$_3$ | —H |
| (52d) | 3-OCH$_2$CH$_2$NH$_2$ | —H |
| (53d) | 3-OCH$_2$CH$_2$NHCOCH$_3$ | —H |
| (54d) | 3-OCH$_2$CH$_2$NHCOOC(CH$_3$)$_3$ | —H |
| (55d) | 3-OCH$_2$CH$_2$N(CH$_3$)$_2$ | —H |
| (56d) | 3-OCH$_2$CH$_2$SO$_3$H | —H |
| (57d) | 3-OCH$_2$CH$_2$SO$_3$Na | —Na |
| (58d) | 3-OCH$_2$COO(CH$_2$)$_9$—OH | —H |
| (59d) | 4-OCH$_2$COOCH$_3$ | —H |
| (60d) | 3-OCH$_2$COOH•pyridine | —H |
| (61d) | 4-OCH$_2$COOH | —H |
| (62d) | 3-OCH$_2$CONH$_2$ | —H |
| (63d) | 3-Br,4-OCH$_2$COOCH$_3$ | —H |
| (64d) | 3-CH$_3$,4-OCH$_2$COOCH$_3$ | —H |
| (65d) | 3-NHCOCH$_3$,4-OCH$_2$CN | —H |
| (66d) | 3-OCH$_2$COCH$_3$ | —H |
| (67d) | 3-CH$_2$SCH$_2$COOCH$_3$ | —H |
| (68d) | 3-CH$_2$SOCH$_2$COOCH$_3$ | —H |
| (69d) | 3-CH$_2$SO$_2$CH$_2$COOCH$_3$ | —H |
| (70d) | 3-NHSO$_2$CH$_2$CH=CH$_2$ | —H |
| (71d) | 3-NHCH$_2$CH$_2$N(CH$_3$)$_2$ | —H |
| (72d) | 4-CONHCH$_2$COOH | —H |
| (73d) | 3-CONHCH$_2$CONH$_2$ | —H |
| (74d) | 3-CONHCH(CO$_2$CH$_3$)—CH$_2$CO$_2$CH$_3$ | —H |
| (75d) | 3-CONHCH(CO$_2$H)—CH$_2$CO$_2$H | —H |

| Compound No. | (IVd) |
|---|---|
| (76d) | ![structure] |

| Compound No. | X$_a$ and Y$_a$ | r$_a$ |
|---|---|---|
| (77d) | 3-SO$_2$NHCH$_2$CH$_2$OCH$_3$ | —H |
| (78d) | 3-CONHOCH$_3$ | —H |
| (79d) | 3-CONHOCH$_2$CH=CH$_2$ | —H |

| Compound No. | (IVd) |
|---|---|
| (80d) | ![structure] |

-continued

| Compound No. | $X_a$ and $Y_a$ | $r_a$ |
|---|---|---|
| (81d) | 3-CH=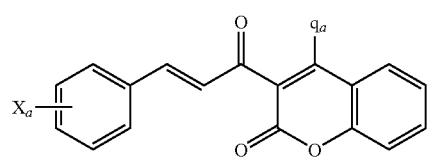 (tetrahydropyran-4-ylidene) | —H |
| (82d) | 3-C≡CC(CH$_3$)$_2$OH | —H |
| (83d) | 3-CH=CHCOOCH$_3$ | —H |
| (84d) | 3-NHCOCOOCH$_3$ | —H |
| (85d) | 3-CH=NOCH$_3$ | —H |
| (86d) | 3-NHCSNHCH3 | —H |
| (87d) | 3-N=C(—SCH$_3$)NHCH$_3$ | —H |
| (88d) | 3-CH$_2$P(=O)(OCH$_3$)$_2$ | —H |

Among the present compound (IV), the present compound (IVe) represented by compound numbers (1e) to (21e) is exemplified in Table 2e.

TABLE 2e

The present compound (IVe):

(IVe)

| Compound No. | $X_a$ | $q_a$ |
|---|---|---|
| (1e) | 3-OCH$_2$CH=CH$_2$ | —OCH$_2$CH=CH$_2$ |
| (2e) | 3-OCH$_2$C≡CH | —OCH$_2$CH=CH$_2$ |
| (3e) | 3-OCH$_2$COOCH$_3$ | —OCH$_2$C≡CH |
| (4e) | 3-OCH$_2$COOCH$_3$ | —OCH$_2$COOCH$_3$ |
| (5e) | 3-OCH$_2$COOH | —OCH$_2$COOH |
| (6e) | 3-OCH$_2$CONH$_2$ | —OCH$_2$CONH$_2$ |
| (7e) | 3-OCH$_2$COOCH$_3$ | —OCH$_2$CN |
| (8e) | 3-OCH$_2$COOH | —OCH$_2$CH$_2$OH |
| (9e) | 3-OCH$_2$COOCH$_3$ | —OCH$_2$Ph |
| (10e) | 3-OCH$_2$COOH | —OCH$_2$Ph |
| (11e) | 3-OCH$_2$COOCH$_3$ | —OCH$_2$CH$_2$N(CH$_3$)$_2$ |
| (12e) | 3-OCH$_2$COOCH$_3$ | —OCH$_2$COCH$_3$ |
| (13e) | 3-OCH$_2$COOCH$_3$ | —OCH$_2$CH$_2$OCH$_3$ |
| (14e) | 3-OCH$_2$CH$_2$SCH$_3$ | —N(piperidinyl) |
| (15e) | 2-OCH$_2$C≡CH | —N(piperidinyl) |
| (16e) | 3-CONHCH$_2$COOCH$_3$ | —N(piperidinyl) |
| (17e) | 3-NHCOCH$_2$OCH$_3$ | —N(piperidinyl) |
| (18e) | 3-NHCOOCH$_2$CH$_2$OCH$_3$ | —N(piperidinyl) |
| (19e) | 3-CONHCH$_2$COOCH$_3$ | —N(morpholinyl) |
| (20e) | 3-CH=CHCN | —NHCH$_2$C≡CH |
| (21e) | 3-OCH$_2$CONHCH$_2$CH$_2$OCH$_3$ | —NHCH$_2$CH$_2$OCH$_3$ |

The present compound has the ability to suppress transcription of a Type I collagen gene. The ability is important in improving tissue fibrosis because it decreases expression of a Type I collagen gene to induce a reduction in accumulation of collagen. Therefore, the present compound can be utilized as an active ingredient of a composition (medicament, cosmetic, food additive etc.) which can improve tissue fibrosis by decreasing expression of a Type I collagen gene to induce a reduction in accumulation of collagen.

A disease to which the transcription-suppressing composition of the present invention and the fibrosis-improving composition of the present invention can be applied includes, for example, a disease in which excessive accumulation of collagen causes fibrosis and then sclerosis of tissues, resulting in decreased function, cicatrization and the like in the tissues such as organs (i.e. fibrosing disease etc.). Specifically, the disease includes diseases and disorders such as hepatic cirrhosis, interstitial pulmonary disease, chronic renal failure (or disease resulting in chronic renal failure), hyperplasia scar after inflammation, postoperative scars or burn scars, scleroderma, arteriosclerosis, hypertension and the like. Incidentally, as an example of hepatic cirrhosis, it has been already known that C type or B type hepatitis virus induces chronic inflammation and then increased production of TGF-β, and thereby, hepatic fibrosis (particularly, accumulation of type I and type III collagen) is induced to cause hepatic cirrhosis (e.g. see Clin. Liver Dis., 7, 195-210 (2003)). As an example of interstitial pulmonary disease, it has been thought that pneumonia caused by mites, viruses, tubercle bacilli or the like induces increased production of TGF-β and then pulmonary fibrosis, and thereby interstitial pulmonary disease is caused. For chronic renal failure such as diabetic nephropathy and IgA nephropathy, it has been already suggested that diabetic nephropathy is caused by increased level of TGF-β in renal glomeruli due to hyperglycemia and thereby induction of renal fibrosis (particularly accumulation of Type I and Type IV collagen), and IgA nephropathy is caused by induction of nephritis due to accumulation of IgA in renal glomeruli followed by increased level of TGF-β, and thereby induction of renal fibrosis (particularly accumulation of Type I and Type IV collagen) (e.g. see Am. J. Physiol. Renal Phsiol., 278, F830-F838 (2000), Kidney Int. 64.149-159 (2003)). A db/db mouse, a diabetic nephropathy model animal, develops hyperglycemia by overeating because it has a mutation in a leptin receptor for suppressing ingestion, and then spontaneously develops diabetes. In the db/db mouse, the blood glucose concentration is about 4 times higher than a normal mouse, and fibrosis of renal glomeruli and increased level of TGF-β are found (e.g. see Am. J. Pathol., 158, 1653-1663 (2001)). An anti-Thy-1 rat, an IgA nephropathy model animal, is produced by administering an anti-Thy-1 antibody to a normal rat to artificially cause renal fibrosis. It has been shown that renal fibrosis is suppressed by administering an anti-TGF-β receptor antibody to the model animal (e.g. see Kidney Int., 60, 1745-1755 (2001)). Although the cause of scleroderma is unknown, it has been found that skin fibrosis is improved by administering a TGF-β inhibitor to a Tsk mouse, which is a model animal therefor (e.g. see J. Invest. Dermatol., 118.461-470 (2001)). Thus, a compound which suppresses the activity of TGF-β can be utilized as an active ingredient of a composition (medicament, cosmetic, food additive etc.) for inhibiting the collagen synthesis-promoting activity of TGF-β to suppress tissue fibrosis and thereby providing a fibrosing disease therapeutic effect.

Such transcription-suppressing composition and fibrosis-improving composition of the present invention comprise the present compound and an inert carrier. Such composition usually comprises 0.01% by weight to 99.99% by weight of the present compound and 99.99% by weight to 0.01% by weight of an inert carrier. The inert carrier is a pharmaceutically acceptable carrier or excipient. The transcription-suppressing composition and fibrosis-improving composition of the present invention may further comprise pharmaceutical additives, cosmetic additives, food additives and the like.

The present compound also inhibits the ability of TGF-β to promote transcription of a Type I collagen gene, as shown in Example 4 below. That is, the present compound is a TGF-β antagonist having the ability to suppress the activity of TGF-β. Therefore, the present compound can be also utilized as an active ingredient of a composition for suppressing the activity of TGF-β. It has been known that TGF-β has the ability to promote transition from a growth phase (hereinafter, also referred to as hair growth phase in some cases) to a regression phase (hereinafter, also referred to as a hair regression phase in some cases) in the hair life cycle [J. Invest. Dermatol., 111, 948-954 (1998), FASEB J., 16, 1967-1969 (2002)]. Further, it has been reported that an anti-TGF-β antibody, Fetuin, which is a TGF-β inhibitor, and the like antagonize the suppressing-activity of TGF-β on hair extension and exhibit a promoting-effect on hair extension [J. Invest. Dermaton., 118, 993-997 (2002), JP-A 2000-342296]. Therefore, the present compound (and a TGF-β activity-suppressing composition containing the present compound as an active ingredient) may be utilized for inhibiting a promoting effect of TGF-β on transition to a hair regression phase to induce extension of a hair growth phase and thereby providing a hair-growing effect.

Such TGF-β suppressing composition and hair-growing composition of the present invention comprise the present compound and an inert carrier. Such composition usually comprises 0.01% by weight to 99.99% by weight of the present compound and 99.99% by weight to 0.01% by weight of an inert carrier. The inert carrier is a pharmaceutically acceptable carrier or excipient. The TGF-β suppressing composition and hair-growing composition of the present invention may further comprise pharmaceutical additives, cosmetic additives, food additives and the like.

A pharmaceutically acceptable carrier, excipient, pharmaceutical additive, food additive, cosmetic additive, a medicament additive, and the like contained in the above-described composition can be appropriately selected depending on the specific use thereof. In addition, the composition may be in a form of various solids, liquids and the like depending on the specific use thereof.

For example, when the present compound is used as an active ingredient of a medicament, specific examples of the medicament include oral preparations such as powders, fine granules, granules, tablets, syrups, capsules, suspensions, emulsions, extracts and pills; and parenteral preparations such as injections, transdermal absorbing agents such as external liquids and ointments, suppositories and local preparations.

Oral preparations can be prepared using carriers or excipients, and pharmaceutical additives such as binders, disintegrants, surfactants, lubricants, glidants, diluents, preservatives, coloring agents, flavors, stabilizers, humectants, antiseptics, antioxidants and the like, for example, gelatin, sodium alginate, starch, corn starch, white sugar, lactose, glucose, mannit, carboxymethylcellulose, dextrin, polyvinylpyrrolidone, crystalline cellulose, soybean lecithin, sucrose, fatty acid ester, talc, magnesium stearate, polyethylene glycol, magnesium silicate, anhydrous silicic acid and the like, according to a conventional method.

A dose of the oral preparation varies depending on the age, sex and weight of a mammal to be administered, the severity of disease, the kind and dosage form of the composition of the present invention, and the like. Usually, in the case of oral administration, about 1 mg to about 2 g per day, preferably about 5 mg to about 1 g per day of the active ingredient may be administered to an adult human. The daily dose may be also administered at one time or in several divided doses.

Among parenteral preparations, an injection can be prepared using such as a water-soluble solvent such as physiological saline or sterilized water Ringer solution, a water-insoluble solvent such as vegetable oil or fatty acid ester, an isotonic agent such as glucose or sodium chloride, pharmaceutical additives such as a solubilizer, a stabilizer, an antiseptic, a suspending agent and an emulsifying agent, and the like, according to a conventional method. A transdermal absorbing agent such as external liquid or a gel-like ointment, a suppository for rectal administration and the like can be also prepared according to a conventional method. For administering such parenteral preparations, they may be administered by injection (subcutaneously, intravenously etc.), transdermally, or rectally. A local preparation can be prepared, for example, by incorporating the present compound into a pellet of a sustained-release polymer such as ethylene vinyl acetate polymer. The pellet may be surgically transplanted into a tissue to be treated.

A dose of the parenteral preparation varies depending on the age, sex and weight of a mammal to be administered, the severity of disease, the kind and dosage form of the composition of the present invention, and the like. Usually, in the case of administration by injection, about 0.1 mg to about 500 mg of the active ingredient may be administered to an adult human. The daily dose may be also administered at one time or in several divided doses.

When the present compound is used by adding to cosmetics, specific examples of the form of a cosmetic with comprises the present compound include liquid, emulsion, cream, lotion, ointment, gel, aerosol, mousse and the like. Lotion can be prepared using cosmetic additives such as a suspending agent, an emulsifier, a preservative and the like, according to a conventional method.

A dose of the cosmetic varies depending on the age, sex and weight of a mammal to be administered, the severity of disease, the kind and dosage form of the composition of the present invention, and the like. Usually, about 0.01 mg to about 50 mg of the active ingredient may be administered to an adult human. The daily dose may be also administered at one time or in several divided doses.

When the present compound is used as a food additive, specific examples of the form of a food which comprises the additive include powder, a tablet, a beverage, an edible gel or a mixed liquid of the gel and syrup, for example, general beverage and food and luxury food and beverage such as seasonings, Japanese confectionaries, western confectioneries, ice confectioneries, beverage, spreads, pastes, pickles, bottled or canned products, processed domestic animal meats, processed fish meats or marine product, processed dairy or egg products, processed vegetables, processed fruits, processed cereals and the like. Alternatively, the present compound can be also added to feeds or provenders for rearing animals such as livestocks, poultry, honey bee, silkworm, fish and the like.

A dose of the food varies depending on the age, sex and weight of a mammal to be administered, the severity of disease, the kind and dosage form of the composition of the present invention, and the like. Usually, about 0.1 mg to about 500 mg of the active ingredient may be administered to an adult human. The daily dose may be also administered at one time or in several divided doses.

EXAMPLE

The following Examples further illustrate the present invention.

Example 1

Synthesis of the Present Benzaldehyde Derivative and the Present Pyridinecarbaldehyde Derivative Will Be Described in Examples 1-1 to 1-24

Example 1-1

Synthesis of the Present Benzaldehyde Derivative [Compound No. (a)]

To a mixture of 12.31 g of 3-aminobenzyl alcohol, 160 ml of tetrahydrofuran and 12.41 g of triethylamine was added a solution of 11.42 g of methoxyacetyl chloride in 40 ml of tetrahydrofuran at 10° C. After stirred at room temperature for 1.5 hours, insolubles were filtered and the filtrate was concentrated under reduced pressure. The resulting residue was dissolved in 200 ml of ethyl acetate. The organic layer washed successively with water, diluted hydrochloric acid and an aqueous saturated sodium chloride solution, dried over anhydrous magnesium sulfate, and then concentrated. The residue was subjected to silica gel column chromatography to obtain 15.88 g of oily (3-methoxyacetylamino)benzyl alcohol.

$^1$H-NMR (400 MHz, CDCl$_3$) δ (ppm): 1.83 (t, 1H, J=5.1 Hz), 3.50 (s, 3H), 4.01 (s, 2H), 4.69 (d, 2H, J=4.4 Hz), 7.13 (dd, 1H, J=0.5, 7.1 Hz), 7.33 (t, 1H, J=7.8 Hz), 7.50 (dd, 1H, J=1.0, 8.1 Hz), 7.59 (s, 1H), 8.26 (broad s, 1H).

To a mixture of 11.40 g of oxalyl chloride and 200 ml of dichloromethane was added dropwise a solution of 14 ml of dimethyl sulfoxide in 30 ml of dichloromethane at −60° C. for 15 minutes. After stirred at −60° C. for 10 minutes, a solution of 15.88 g of 3-(methoxyacetylamino)benzyl alcohol in 70 ml of dichloromethane was added dropwise at −60° C. for 20 minutes. After stirred at −60° C. for 10 minutes, 24.82 g of triethylamine was added dropwise at −60° C. for 20 minutes. After stirred at room temperature for 45 minutes, 500 ml of water was added to the reaction solution, followed by extraction with 300 ml of ethyl acetate. The organic layer washed with an aqueous saturated sodium chloride solution, dried over anhydrous magnesium sulfate, and then concentrated to obtain 14.93 g of 3-(methoxyacetylamino)benzaldehyde [Compound No. (a)] as a white crystal.

$^1$H-NMR (400 MHz, CDCl$_3$) δ (ppm): 3.53 (s, 3H), 4.05 (s, 2H), 7.52 (t, 1H, J=7.8 Hz), 7.65 (d, 1H, J=7.6 Hz), 7.93 (d, 1H, J=8.0 Hz), 8.06 (s, 1H), 8.41 (broad s, 1H), 10.01 (s, 1H).

Example 1-2

Synthesis of the Present Banzaldehyde Derivative [Compound No. (b)]

To a mixture of 200 ml of tetrahydrofuran, 26.00 g of pyridine and 20.70 g of glycine methyl ester hydrochloride was added a solution of 16.00 g of 3-formylbenzoic acid chloride in 20 ml of tetrahydrofuran at 10° C. After stirred at room temperature for 60 hours, insolubles were filtered and the filtrate was concentrated under reduced pressure. The resulting residue was subjected to silica gel column chromatography to obtain 4.23 g of oily 3-[[(methyoxycarbonylmethyl)amino]carbonyl]benzaldehyde [Compound No. (b)].

$^1$H-NMR (400 MHz, CDCl$_3$) δ (ppm): 3.83 (s, 3H), 4.29 (d, 2H, J=4.9 Hz), 6.78 (broad s, 1H), 7.65 (t, 1H, J=7.6 Hz), 8.04 (d, 1H, J=7.6 Hz), 8.11 (d, 1H, J=7.6 Hz), 8.31 (s, 1H), 10.08 (s, 1H).

Example 1-3

Synthesis of the Present Benzaldehyde Derivative [Compound No. (c)]

According to the same manner as that of Example 1-2 except that 15.40 g of 4-formylbenzoic acid chloride was used in place of 3-formylbenzoic acid chloride, 5.79 g of 4-[[(methoxycarbonylmethyl)amino]carbonyl]benzaldehyde [Compound No. (c)] was obtained as a pale yellow solid.

$^1$H-NMR (400 MHz, CDCl$_3$) δ (ppm): 3.83 (s, 3H), 4.29 (s, 2H), 6.73 (broad s, 1H), 7.97 (s, 4H), 10.09 (s, 1H).

Example 1-4

Synthesis of the Present Benzaldehyde Derivative [Compound No. (d)]

To a mixture of 200 ml of tetrahydrofuran, 16.70 g of triethylamine and 12.40 g of 2-methoxyethylamine was added a solution of 16.00 g of 3-formylbenzoic acid chloride in 20 ml of tetrahydrofuran at room temperature. After stirred at room temperature for 6 hours, insolubles were filtered and the filtrate was concentrated under reduced pressure. The resulting residue was subjected to silica gel column chromatography to obtain 10.79 g of oily 3-[(2-methoxyethyl)aminocarbonyl]benzaldehyde [Compound No. (d)].

$^1$H-NMR (400 MHz, CDCl$_3$) δ (ppm): 3.41 (s, 3H), 3.59 (t, 2H, J=4.6 Hz), 3.69 (dt, 2H, J=5.3, 5.4 Hz), 7.64 (t, 1H, J=7.6 Hz), 8.03 (dt, 1H, J=1.2, 7.6 Hz), 8.10 (dt, 1H, J=1.2, 7.8 Hz), 8.27 (s, 1H), 10.08 (s, 1H).

Example 1-5

Synthesis of the Present Benzaldehyde Derivative [Compound No. (e)]

To a mixture of 3.73 g of sodium hydride (60% oily) and 150 ml of dimethylformamide was added dropwise a solution of 16.53 g of diethyl cyanomethylphosphonate in 12 ml of dimethylformamide under ice-cooling. After stirred at room temperature for 1 hour, a solution of 14.85 g of 3-([1,3]dioxolan-2-yl)benzaldehyde in 40 ml of dimethylformamide was added. After stirred at 50° C. for 30 minutes, ice water was added to the mixture, followed by extraction with ethyl acetate. The organic layer was washed with an aqueous saturated sodium chloride solution, dried over anhydrous sodium sulfate, and then concentrated under reduced pressure. The resulting residue was subjected to silica gel column chromatography to obtain 11.91 g of a cis-trans isomer mixture of oily 2-[3-(2-cyanoethenyl)phenyl]-[1,3]dioxolane.

11.91 g of the cis-trans isomer mixture of 2-[3-(2-cyanoethenyl)phenyl]-[1,3]dioxolane was dissolved in 180 ml of tetrahydrofuran, and thereto 40 ml of 6 N hydrochloric acid was added dropwise under ice-cooling. After stirred at room temperature overnight, the reaction solution was concentrated under reduced pressure, and extracted with t-butyl methyl ether and then ethyl acetate. The organic layers were combined, and washed successively with an aqueous saturated sodium bicarbonate solution and then an aqueous saturated sodium chloride solution. After dried over anhydrous magnesium sulfate, crystals obtained by concentration under reduced pressured were filtered to obtain 4.90 g of trans-3-(2-cyanoethenyl)benzaldehyde [Compound No. (e)] as a white solid.

$^1$H-NMR (400 MHz, CDCl$_3$) δ (ppm): 5.96 (d, 1H, J=16.8 Hz), 7.47 (d, 1H, J=16.8 Hz), 7.59-7.63 (m, 1H), 7.71 (d, 1H, J=7.6 Hz), 7.93-7.97 (m, 2H), 10.05 (s, 1H).

Example 1-6

Synthesis of the Present Benzaldehyde Derivative [Compound No. (f)]

To a mixture of 1.00 g of 3-hydroxybenzaldehyde, 25 ml of tetrahydrofuran, 2.40 g of triphenylphosphine and 0.78 ml of 2-methylthioethanol was added dropwise 3.50 ml of diethyl azodicarboxylate (40% toluene solution), and the mixture was stirred at room temperature for 15.5 hours. The reaction solution was concentrated under reduced pressure, and the resulting residue was subjected to silica gel column chromatography to obtain 0.71 g of oily 3-(2-methylthioethoxy)benzaldehyde [Compound No. (f)].

$^1$H-NMR (300 MHz, CDCl$_3$) δ (ppm): 2.23 (s, 3H), 2.91 (t, 2H, J=6.0 Hz), 4.22 (t, 2H, J=6.0 Hz), 7.17-7.21 (m, 1H), 7.39-7.47 (m, 3H), 9.98 (s, 1H).

Example 1-7

Synthesis of the Present Benzaldehyde Derivative (Compound No. (g))

A mixture of 1.99 g of 3-(bromomethyl)benzaldehyde, 0.80 g of sodium hydroxide and 8 ml of ethylene glycol was heated at 55° C. for 6 hours. After water was added, the mixture was extracted with chloroform and then washed with an aqueous saturated sodium chloride solution. After dried over anhydrous sodium sulfate and then concentration under reduced pressure, the resulting residue was subjected to silica gel column chromatography to obtain 0.79 g of oily 3-[(2-hydroxyethoxy)methyl]benzaldehyde [Compound No. (g)].

$^1$H-NMR (270 MHz, CDCl$_3$) δ (ppm): 2.00 (broad s, 1H), 3.59-3.80 (m, 4H), 4.65 (s, 2H), 7.51-7.56 (m, 1H), 7.63 (d, 1H, J=7.4 Hz), 7.82 (d, 1H, J=7.4 Hz), 7.87 (s, 1H), 10.03 (s, 1H).

Example 1-8

Synthesis of the Present Benzaldehyde Derivative [Compound No. (h)]

To a solution of 15.0 g of 3-aminobenzyl alcohol in 120 ml of tetrahydrofuran was added dropwise a solution of 18 ml of 2-methoxyethyl chloroformate in 70 ml of tetrahydrofuran under ice-cooling. After stirred for 30 minutes under ice-cooling and then at room temperature for 30 minutes, additional 2 ml of 2-methoxyethyl chloroformate was added, and the mixture was stirred at room temperature for 1 hour. After ethyl acetate was added, the mixture was washed successively with an aqueous saturated sodium bicarbonate solution and then an aqueous saturated sodium chloride solution, dried over anhydrous magnesium sulfate, and then concentrated to obtain 30.2 g of 3-[(2-methoxyethoxy)carbonylamino]benzyl alcohol.

$^1$H-NMR (400 MHz, CDCl$_3$) δ (ppm): 1.82 (t, 1H, J=5.2 Hz), 3.41 (s, 3H), 3.63-3.65 (m, 2H), 4.31-4.34 (m, 2H), 4.67 (d, 2H, J=5.2 Hz), 6.77 (broad s, 1H), 7.05-7.08 (m, 1H), 7.27-7.31 (m, 2H), 7.40 (s, 1H).

To a mixture of 13 ml of oxalyl chloride and 400 ml of dichloromethane was added dropwise a solution of 23 ml of dimethyl sulfoxide in 40 ml of dichloromethane at −60° C. for 15 minutes. After stirred at −60° C. for 10 minutes, a solution of 30.2 g of 3-[(2-methoxyethoxy)carbonylamino]benzyl alcohol in 100 ml of dichloromethane was added dropwise at −60° C. for 25 minutes. After stirred at −60° C. for 20 minutes, 56 ml of triethylamine was added dropwise at −60° C. for 15 minutes. After stirred at room temperature for 45 minutes, water was added to the reaction solution, followed by extraction with ethyl acetate. The organic layer washed successively with water and then an aqueous saturated sodium chloride solution. After dried over anhydrous magnesium sulfate and then concentration, the resulting crude crystals were washed with t-butyl methyl ether and then dried to obtain 17.55 g of 3-[(2-methoxyethoxy)carbonylamino]benzaldehyde [Compound No. (h)] as a white solid.

$^1$H-NMR (400 MHz, CDCl$_3$) δ (ppm): 3.43 (s, 3H), 3.65-3.67 (m, 2H), 4.35-4.37 (m, 2H), 6.84 (broad s, 1H), 7.48 (t, 1H, J=6.8 Hz), 7.59 (d, 1H, J=6.8 Hz), 7.67 (d, 1H, J=6.8 Hz), 7.90 (s, 1H), 9.99 (s, 1H).

Example 1-9

Synthesis of the Present Benzaldehyde Derivative [Compound No. (i)]

To a solution of 1.23 g of 3-aminobenzyl alcohol in 12 ml of tetrahydrofuran was added dropwise a solution of 1.32 ml of phenyl chloroformate in 5 ml of tetrahydrofuran under ice-cooling. After stirred at room temperature for 30 minutes, a solvent was distilled off under reduced pressure, and the resulting residue was dissolved in 10 ml of dimethyl sulfoxide. 2.2 ml of 2-methoxyethylamine was added, and the mixture was stirred at 70° C. for 40 minutes. This was cooled to room temperature, ethyl acetate and water were added, and the layers were separated. Water was distilled off from the aqueous layer under reduced pressure, and sodium chloride was added, followed by extraction with ethyl acetate. After dried over anhydrous magnesium sulfate and then concentration, the resulting residue was subjected to silica gel column chromatography to obtain 0.67 g of oily 3-[(2-methoxyethyl) aminocarbonylamino]benzyl alcohol.

$^1$H-NMR (270 MHz, CDCl$_3$) δ (ppm): 3.33 (s, 3H), 3.36 (t, 2H, J=5.4 Hz), 3.45 (t, 2H, J=5.4 Hz), 4.53 (d, 2H, J=5.4 Hz), 5.88 (t, 1H, J=5.4 Hz), 6.93 (d, 1H, J=5.4 Hz), 7.16 (d, 1H, J=7.6 Hz), 7.21 (s, 1H), 7.27 (d, 1H, J=5.4 Hz), 7.64 (s, 1H), 8.00 (s, 1H).

To a mixture of 2.64 g of oxalyl chloride and 50 ml of dichloromethane was added dropwise a solution of 3.24 g of dimethyl sulfoxide in 30 ml of dichloromethane at −60° C. for 10 minutes. After stirred at −60° C. for 20 minutes, a solution of 3.72 g of 3-[(2-methoxyethyl)aminocarbonylamino]benzyl alcohol in 30 ml of dichloromethane was added dropwise at −60° C. for 1 hour. After stirred at −60° C. for 15 minutes, 9.24 g of triethylamine was added dropwise at −60° C. for 25 minutes. After stirred at room temperature for 1 hour, water was added to the reaction solution, and the layers were separated. The organic layer washed with an aqueous saturated sodium chloride solution, dried over anhydrous sodium sulfate, and then concentrated to obtain 2.79 g of 3-[(2-methoxyethyl)aminocarbonylamino]benzaldehyde [Compound No. (i)] as a white crystal.

$^1$H-NMR (270 MHz, CDCl$_3$) δ (ppm): 3.38 (s, 3H), 3.43-3.48 (m, 2H), 3.53 (t, 2H, J=4.3 Hz), 5.75 (broad s, 1H), 7.40 (t, 1H, J=7.8 Hz), 7.50 (d, 1H, J=7.6 Hz), 7.71 (d, 1H, J=7.8 Hz), 7.80 (s, 1H), 7.81 (s, 1H), 9.92 (s, 1H).

Example 1-10

Synthesis of the Present Benzaldehyde Derivative [Compound No. (j)]

A mixture of 10.18 g of 3-formylbenzoic acid, 6.99 g of methanesulfonamide, 200 ml of dichloromethane, 8.95 g of dimethylaminopyridine, 15.22 g of dicyclohexylcarbodiimide and 100 ml of tetrahydrofuran was stirred at room temperature. The reaction solution was concentrated under reduced pressure, dissolved in ethyl acetate, a 1 N aqueous sodium hydroxide solution was added, and the layers were separated. To the aqueous layer was added 2 N hydrochloric acid to adjust to pH 1, this was extracted with ethyl acetate, dried over anhydrous sodium sulfate, and then concentrated to obtain 4.01 g of 3-[(methanesulfonyl)aminocarbonyl]benzaldehyde [Compound No. (j)] as a white solid.

$^1$H-NMR (270 MHz, DMSO-d$_6$) δ (ppm): 3.38 (s, 3H), 7.75 (t, 1H, J=7.6 Hz), 8.14-8.23 (m, 2H), 8.46 (s, 1H), 10.08 (s, 1H), 12.39 (broad s, 1H).

Example 1-11

Synthesis of the Present Benzaldehyde Derivative [Compound No. (k)]

To a mixture of 1.93 g of cyanoacetamide sulfate and 5 ml of water was added dropwise a solution of 3.34 g of 3-formylbenzoic acid chloride in 7 ml of toluene under ice-cooling. 2.93 g of sodium carbonate was added, and this was stirred at room temperature for 2 hours. The resulting crystals were filtered and washed successively with water, toluene and t-butyl methyl ether to obtain 1.80 g of 3-[(cyanomethyl)aminocarbonyl]benzaldehyde [Compound No. (k)].

$^1$H-NMR (400 MHz, CDCl$_3$+DMSO-d$_6$ (1 drop)) δ (ppm): 4.34 (d, 2H, J=5.4 Hz), 7.64-7.67 (m, 1H), 8.03-8.05 (m, 1H), 8.23-8.26 (m, 1H), 8.46-8.47 (m, 1H), 9.11 (broad s, 1H), 10.09 (s, 1H).

Example 1-12

Synthesis of the Present Benzaldehyde Derivative [Compound No. (l)]

To a mixture of 0.67 g of magnesium and 10 ml of tetrahydrofuran was added a catalytic amount of iodine, and added dropwise a solution of 6.0 g of 1-bromo-3-(2,2-difluoroethenyl)benzene in 20 ml of tetrahydrofuran at 55° C. After stirred at room temperature for 15 minutes, a solution of 3.98 g of 1-formylpiperidine in 5 ml of tetrahydrofuran was added dropwise. This was heated under reflux for 15 minutes, and ice water and 10% hydrochloric acid were added, followed by extraction with t-butyl methyl ether. The organic layer washed with an aqueous saturated sodium chloride solution, dried over anhydrous magnesium sulfate and then concentrated. The resulting residue was subjected to silica gel column chromatography to obtained 1.13 g of oily 3-(2,2-difluoroethenyl)benzaldehyde [Compound No. (l)].

$^1$H-NMR (400 MHz, CDCl$_3$) δ (ppm): 5.36 (dd, 1H, J=3.4, 25.9 Hz), 7.52 (t, 1H, J=7.6 Hz), 7.59 (d, 1H, J=7.8 Hz), 7.75 (d, 1H, J=7.6 Hz), 7.83 (s, 1H), 10.01 (s, 1H).

Example 1-13

Synthesis of the Present Benzaldehyde Derivative [Compound No. (m)]

To a solution of 4.48 g of a cis-trans isomer mixture of 2-[3-(2-cyanoethenyl)phenyl]-[1,3]dioxolane in 100 ml of ethyl acetate was added 0.60 g of 5% palladium carbon to perform hydrogenation. The catalyst was filtered by filtration with Celite, and the filtrate was concentrated under reduced pressure to obtain 3.52 g of 2-[3-(2-cyanoethyl)phenyl]-[1,3]dioxolane.

$^1$H-NMR (400 MHz, CDCl$_3$) δ (ppm): 2.62 (t, 2H, J=7.6 Hz), 2.98 (t, 2H, J=7.6 Hz), 4.04-4.13 (m, 4H), 5.80 (s, 1H), 7.24 (d, 1H, J=7.1 Hz), 7.34-7.38 (m, 3H).

To 3.52 g of 2-[3-(2-cyanoethyl)phenyl]-[1,3]dioxolane was added 60 ml of tetrahydrofuran to dissolve this, and 20 ml of 6 N hydrochloric acid was added. After stirred at room temperature overnight and then concentrated under reduced pressure, ethyl acetate was added, and this was washed successively with an aqueous potassium carbonate solution and an aqueous saturated sodium chloride solution. After dried over anhydrous magnesium sulfate, concentration under reduced pressure afforded 2.68 g of 3-(2-cyanoethyl)benzaldehyde [Compound No. (m)].

$^1$H-NMR (400 MHz, CDCl$_3$) δ (ppm): 2.69 (t, 2H, J=7.3 Hz), 3.06 (t, 2H, J=7.3 Hz), 7.53-7.56 (m, 2H), 7.76-7.82 (m, 2H), 10.02 (s, 1H).

Examples 1-14

Synthesis of the Present Benzaldehyde Derivative [Compound No. (n)]

To a mixture of 12.21 g of 3-hydroxybenzaldehyde, 14.00 g of 2-chloroacetamide and 60 ml of dimethylformamide was added 20.70 g of potassium carbonate, and this was heated to stir at 90° C. for 2 hours. After cooled to room temperature, insolubles were filtered and the filtrate was concentrated under reduced pressure. The resulting residue was dissolved in tetrahydrofuran by heating. Insolubles were filtered and the filtrate was concentration under reduced pressure. The resulting crude crystals were washed with a mixed solution of tetrahydrofuran and t-butyl methyl ether and dried to obtain 13.05 g of 3-(aminocarbonylmethoxy)benzaldehyde [Compound No. (n)] as a crystal.

$^1$H-NMR (300 MHz, DMSO-d$_6$) δ (ppm): 4.53 (s, 2H), 7.29-7.60 (m, 6H), 9.98 (s, 1H).

Example 1-15

Synthesis of the Present Benzaldehyde Derivative [Compound No. (o)]

To a mixture of 3.05 g of 3-hydroxybenzaldehyde, 2.3 ml of bromoacetone and 30 ml of dimethylformamide was added 4.15 g of potassium carbonate, and this was heated and stirred at 70° C. for 30 minutes. After cooled to room temperature, insolubles were filtered and the filtrate was concentrated under reduced pressure. Water was added to the resulting residue, and then extracted with ethyl acetate. The organic layer washed successively with water and an aqueous saturated sodium chloride solution, dried over anhydrous magnesium sulfate, and then concentrated. The resulting residue was subjected to silica gel column chromatography to obtain 0.76 g of oily 3-(2-oxo-propoxy)benzaldehyde [Compound No. (o)].

$^1$H-NMR (270 MHz, DMSO-d$_6$) δ (ppm): 2.18 (s, 3H), 4.94 (s, 2H), 7.23-7.30 (m, 1H), 7.37-7.38 (m, 1H), 7.49-7.53 (m, 2H), 9.97 (s, 1H).

Example 1-16

Synthesis of the Present Benzaldehyde Derivative [Compound No. (p)]

A mixture of 30 ml of tetrahydrofuran, 12 ml of triethylamine and 4.11 g of aspartic acid dimethyl ester hydrochloride was added dropwise to a solution of 3.50 g of 3-formylbenzoic acid chloride in 30 ml of tetrahydrofuran at 10° C. After stirred at room temperature for 6 hours, insolubles were filtered and the filtrate was concentrated under reduced pressure. The resulting residue was subjected to silica gel column chromatography to obtain 3.01 g of oily 2-[3-formyl-(benzoylamino)]succinic acid dimethyl ester [Compound No. (p)].

$^1$H-NMR (270 MHz, DMSO-d$_6$) δ (ppm): 2.82-3.03 (m, 2H), 3.39 (s, 3H), 3.44 (s, 3H), 4.84-4.92 (m, 1H), 7.68-7.95 (m, 1H), 8.12-8.18 (m, 2H), 8.39 (s, 1H), 9.18 (d, 1H, J=8.1 Hz), 10.09 (s, 1H).

Example 1-17

Synthesis of the Present Pyridinecarbaldehyde Derivative [Compound No. (q)]

A mixture of 5.15 g of 2-carboxy-6-formylpyridine and 50 ml of thionyl chloride was stirred under reflux for 1 hour and then concentrated under reduced pressure. The resulting acid chloride was dissolved in 30 ml of tetrahydrofuran, and the solution was added dropwise to a mixture of 30 ml of tetrahydrofuran, 3.12 g of triethylamine and 2.31 g of 2-methoxyethylamine under ice-cooling. After allowed to stand at room temperature overnight, this was concentrated under reduced pressure, and the resulting residue was subjected to silica gel column chromatography to obtain 3.28 g of 6-formyl-2-[(2-methoxyethyl)aminocarbonyl]pyridine [Compound No. (q)] as a white solid.

$^1$H-NMR (270 MHz, CDCl$_3$) δ (ppm): 3.43 (s, 3H), 3.56-3.65 (m, 2H), 3.70-3.76 (m, 2H), 8.02-8.12 (m, 2H), 8.34 (broad s, 1H), 8.43-8.46 (m, 1H), 10.11 (s, 1H).

Example 1-18

Synthesis of the Present Benzaldehyde Derivative [Compound No. (r)]

To a solution of 4.0 g of 3-[(2-methoxyethyl)aminosulfonyl]benzoic acid in 200 ml of tetrahydrofuran was added dropwise a solution of 1.07 M borane-tetrahydrofuran complex in 43.5 ml of tetrahydrofuran under ice-cooling, and this was stirred for 30 minutes, and stirred at room temperature overnight. After 40 ml of methanol was added dropwise under ice-cooling, 100 ml of 2 N hydrochloric acid was added dropwise. After warmed to room temperature, the solvent was distilled off under reduced pressure, followed by extraction with ethyl acetate. The organic layer was dried over anhydrous magnesium sulfate, and concentrated under reduced pressure to obtain 3.0 g of oily 3-[(2-methoxyethyl)aminosulfonyl]benzyl alcohol.

$^1$H-NMR (270 MHz, DMSO-d$_6$) δ (ppm): 2.86-2.92 (m, 2H), 3.16 (s, 3H), 3.27-3.33 (m, 2H), 4.58 (d, 2H, J=5.6 Hz), 5.42 (t, 1H, J=5.6 Hz), 7.50-7.78 (m, 5H).

To a mixture of 1.71 g of oxalyl chloride and 30 ml of dichloromethane was added dropwise a solution of 2.3 g of dimethyl sulfoxide in 4 ml of dichloromethane at −60° C. for 35 minutes. After stirred at −60° C. for 20 minutes, a solution of 3.0 g of 3-[(2-methoxyethyl)aminosulfonyl]benzyl alcohol in 22 ml of dichloromethane was added dropwise at −60° C. for 1.5 hours. After stirred at −60° C. for 1 hour, 5.1 ml of triethylamine was added dropwise at −60° C. for 25 minutes. After stirred at room temperature for 3 hours, water was added to the reaction solution, and the layers were separated. The organic layer washed with water, dried over anhydrous sodium sulfate, and then concentrated. The resulting residue was subjected to silica gel column chromatography to obtain 2.07 g of oily 3-[(2-methoxyethyl)aminosulfonyl]benzaldehyde [Compound No. (r)].

$^1$H-NMR (300 MHz, CDCl$_3$) δ (ppm): 3.15-3.20 (m, 2H), 3.28 (s, 3H), 3.41-3.44 (m, 2H), 5.00 (t, 1H, J=6.0 Hz), 7.72 (t, 1H, J=7.5 Hz), 8.09-8.15 (m, 2H), 8.37 (s, 1H), 10.09 (s, 1H).

Example 1-19

Synthesis of the Present Benzaldehyde Derivative [Compound No. (s)]

To a solution of 5.63 g of 3-([1,3]dioxolan-2-yl)benzoic acid in 60 ml of tetrahydrofuran were added 3.3 ml of ethyl chloroformate and 4.8 ml of triethylamine under ice-cooling. After stirred for 10 minutes under ice-cooling, insolubles were filtered. This solution was added dropwise to a mixture of 3.63 g of methoxyamine hydrochloride, 20 ml of tetrahydrofuran, 6 ml of triethylamine and 20 ml of dimethylformamide. After stirred at room temperature for 8 hours, insolubles were filtered, and the filtrate was concentrated under reduced pressure. The resulting residue was dissolved in 30 ml of tetrahydrofuran, and 15 ml of 2 N hydrochloric acid was added dropwise, followed by stirring at room temperature for 8 hours. 20 ml of a 2 N aqueous sodium hydroxide solution was added dropwise under ice-cooling, and this was extracted with ethyl acetate. The organic layer washed with an aqueous saturated sodium chloride solution, dried over anhydrous sodium sulfate, and concentrated. The residue was subjected to silica gel column chromatography to obtain 1.50 g of 3-(methoxyaminocarbonyl)benzaldehyde [Compound No. (s)] as a white solid.

$^1$H-NMR (270 MHz, DMSO-$d_6$) δ (ppm): 3.73 (s, 3H), 7.72 (t, 1H, J=7.7 Hz), 8.05-8.10 (m, 2H), 8.28 (s, 1H), 10.07 (s, 1H), 11.98 (broad s, 1H).

Example 1-20

Synthesis of the Present Benzaldehyde Derivative [Compound No. (t)]

According to the same manner as that of Example 1-19 except that 4.93 g of allyloxyamine hydrochloride was used in place of methoxyamine hydrochloride, 1.55 g of 3-(allyloxyaminocarbonyl)benzaldehyde [Compound No. (t)] was obtained as a white solid.

$^1$H-NMR (270 MHz, DMSO-$d_6$) δ (ppm): 4.44 (d, 2H, J=5.9 Hz), 5.26-5.40 (m, 2H), 5.94-6.09 (m, 1H), 7.72 (t, 1H, J=7.7 Hz), 8.04-8.10 (m, 2H), 8.27 (s, 1H), 10.07 (s, 1H), 11.90 (broad s, 1H).

Example 1-21

Synthesis of the Present Benzaldehyde Derivative [Compound No. (u)]

To a mixture of 1.00 g of 3-(bromomethyl)benzaldehyde and 20 ml of ethanol were added 0.65 ml of methyl thioglycolate and 0.47 g of potassium carbonate, and the mixture was stirred at room temperature for 2.5 hours. To the reaction mixture was added diethyl ether, this was washed with an aqueous saturated sodium chloride solution, dried over anhydrous sodium sulfate, and then concentrated under reduced pressure. The resulting residue was subjected to silica gel column chromatography to obtain 0.36 g of oily 3-[(methoxycarbonylmethylthio)methyl]benzaldehyde [Compound No. (u)].

$^1$H-NMR (270 MHz, CDCl$_3$) δ (ppm): 3.08 (s, 2H), 3.73 (s, 3H), 3.91 (s, 2H), 7.51 (dd, 1H, J=7.6 Hz), 7.64 (d, 1H, J=7.6 Hz), 7.78-7.81 (m, 1H), 7.86 (s, 1H), 10.02 (s, 1H).

Example 1-22

Synthesis of the Present Benzaldehyde Derivative [Compound No. (v)]

To a suspension of 4.58 g of 3-(cyanobenzyl)triphenylphosphonium bromide in 15 ml of tetrahydrofuran was added 0.73 g of sodium hydride (60% oily) under ice-cooling, and this was stirred at room temperature for 1 hour. 1.01 g of tetrahydro-4H-pyran-4-one was added thereto, this was stirred at room temperature for 1 hour, 2 ml of dimethylformamide was added, and this was further stirred at room temperature for 5 hours. Water was added to the reaction solution, and this was extracted with ethyl acetate, and washed with an aqueous saturated sodium chloride solution. After dried over anhydrous magnesium sulfate, the solvent was distilled off under reduced pressure, and the resulting residue was subjected to silica gel column chromatography to obtain 0.20 g of yellow oily 3-[(tetrahydropyran-4-ylidene)methyl]benzonitrile.

$^1$H-NMR (270 MHz, DMSO-$d_6$) δ (ppm): 2.35 (t, 2H, J=5.4 Hz), 2.43 (t, 2H, J=5.4 Hz), 3.58 (t, 2H, J=5.4 Hz), 3.68 (t, 2H, J=5.4 Hz), 6.36 (s, 1H), 7.51-7.56 (m, 2H), 7.66-7.70 (m, 2H).

To a solution of 0.20 g of 3-[(tetrahydropyran-4-ylidene)methyl]benzonitrile in 7 ml of toluene was added dropwise a 1.5 M solution of diisobutylaluminum hydride in 1.24 ml of toluene at room temperature. After stirred at room temperature for 7 hours, an aqueous ammonium chloride solution was added to the reaction solution, and this was extracted with ethyl acetate, and washed with an aqueous saturated sodium chloride solution. After dried over anhydrous magnesium sulfate, the solvent was distilled off under reduced pressure, and the resulting residue was subjected to silica gel column chromatography to obtain 0.06 g of yellow oily 3-[(tetrahydropyran-4-ylidene)methyl]benzaldehyde [Compound No. (v)].

$^1$H-NMR (270 MHz, CDCl$_3$) δ (ppm): 2.43 (t, 2H, J=5.4 Hz), 2.52 (t, 2H, J=5.4 Hz), 3.68 (t, 2H, J=5.4 Hz), 3.80 (t, 2H, J=5.4 Hz), 6.37 (s, 1H), 7.44-7.53 (m, 2H), 7.71-7.75 (m, 2H), 10.01 (s, 1H).

Example 1-23

Synthesis of the Preset Benzaldehyde Derivative [Compound No. (w)]

To a solution of 4.93 g of m-aminobenzyl alcohol in 50 ml of tetrahydrofuran was added dropwise a solution of 3.7 ml of chloroglyoxylic acid methyl ester in 20 ml of tetrahydrofuran, and this was stirred at room temperature for 1.5 hours. To the reaction solution was added water, and this was extracted with ethyl acetate, and washed with an aqueous saturated sodium chloride solution. After dried over anhydrous magnesium sulfate, the solvent was distilled off under reduced pressure, and the resulting residue was subjected to silica gel column chromatography to obtain 5.10 g of 3-[(methoxycarbonyl)carbonylamino]benzyl alcohol as a white solid.

$^1$H-NMR (270 MHz, DMSO-$d_6$) δ (ppm): 3.85 (s, 3H), 4.47 (d, 2H, J=5.7 Hz), 5.23 (t, 1H, J=5.7 Hz), 7.09 (d, 1H, J=7.6 Hz), 7.30 (t, 1H, J=7.8 Hz), 7.58 (d, 1H, J=8.1 Hz), 7.73 (s, 1H), 10.76 (s, 1H).

To a solution of 1.69 g of 3-[(methoxycarbonyl)carbonylamino]benzyl alcohol in 20 ml of acetone was added 3.47 g of manganese dioxide, this was stirred at room temperature for 2 hours, 3.92 g of manganese dioxide was further added, and this was stirred at room temperature for 18 hours. The reaction solution was filtered with Celite, the filtrate was concentrated under reduced pressure, and the resulting residue was subjected to silica gel column chromatography to obtain 0.53 g of 3-[(methoxycarbonyl)carbonylamino]benzaldehyde [Compound No. (w)] as a white solid.

$^1$H-NMR (270 MHz, DMSO-$d_6$) δ (ppm): 3.87 (s, 3H), 7.61 (t, 1H, J=7.6 Hz), 7.72 (d, 1H, J=7.8 Hz), 8.00 (d, 1H, J=8.1 Hz), 8.34 (s, 1H), 9.99 (s, 1H), 11.08 (s, 1H).

Example 1-24

Synthesis of the Present Benzaldehyde Derivative [Compound No. (x)]

A mixture of 0.60 g of 3-(bromomethyl)benzaldehyde and 0.45 ml of trimethyl phosphite was stirred at 100° C. for 3 hours. The reaction mixture was subjected to silica gel column chromatography to obtain 0.62 g of oily dimethyl (3-formylbenzyl)phosphonate [Compound No. (x)].

$^1$H-NMR (270 MHz, CDCl$_3$) δ (ppm): 3.24 (d, 2H, J=21.9 Hz), 3.70 (d, 6H, J=11.1 Hz), 7.48-7.61 (m, 2H), 7.78-7.81 (m, 2H), 10.02 (s, 1H).

Example a-1

Synthesis of the Present Compound [Compound No. (1a)] by Production Process A

A solution of 5.24 g of 3-acetyl-4-hydroxy-6-methyl-2H-pyran-2-one, 4.90 g of 3-(3-formylphenyl)-2-propenenitrile and 1.92 g of piperidine in 40 ml of chloroform was heated under refluxing for 35 minutes while water was removed with a Soxhlet's extractor filled with a molecular sieve. After cooling to room temperature, the reaction mixture washed successively with 10% hydrochloric acid, and an aqueous saturated sodium chloride solution, dried over anhydrous magnesium sulfate, and concentrated. Precipitated crystals were filtered, and the crystals were subjected to silica gel column chromatography to obtain 4.05 g of 4-hydroxy-3-[3-[3-(2-cyanoethenyl)phenyl]-1-oxo-2-propenyl]-6-methyl-2H-pyran-2-one [Compound No. (1a)] as a pale yellow crystal.

$^1$H-NMR (400 MHz, CDCl$_3$) δ (ppm): 2.30 (s, 3H), 5.94 (d, 1H, J=16.8 Hz), 5.98 (s, 1H), 7.43 (d, 1H, J=16.8 Hz), 7.45-7.50 (2H), 7.70 (s, 1H), 7.75 (d, 1H, J=6.8 Hz), 7.92 (d, 1H, J=16.0 Hz), 8.33 (d, 1H, J=15.6 Hz), 12.38 (s, 1H).

Example a-2

Synthesis of the Present Compound [Compound No. (2a)] by Production Process B

To a mixture of 20 ml of hexamethylphosphoramide and 3.50 g of 4-hydroxy-3-[3-[3-(2-cyanoethenyl)phenyl]-1-oxo-2-propenyl]-6-methyl-2H-pyran-2-one was added 0.46 g of sodium hydride (60% oily) at about 0° C., and a temperature was raised to 50° C., followed by stirring for 1 hour and 10 minutes. Then, 3.22 g of dimethyl sulfate was added thereto, and the mixture was stirred at 50° C. for 4 hours. Thereafter, the reaction mixture was added to ice water, and the mixture was extracted with ethyl acetate. The organic layer washed with an aqueous saturated sodium chloride solution, dried over anhydrous magnesium sulfate, and concentrated. The residue was subjected to silica gel column chromatography to obtain 1.12 g of 4-methoxy-3-[3-[3-(2-cyanoethenyl)phenyl]-1-oxo-2-propenyl]-6-methyl-2H-pyran-2-one [Compound No. (2a)] as a pale yellow crystal.

$^1$H-NMR (400 MHz, CDCl$_3$) δ (ppm): 2.36 (s, 3H), 3.96 (s, 3H), 5.92 (d, 1H, J=16.9 Hz), 6.15 (s, 1H), 7.20 (d, 1H, J=15.9 Hz), 7.39 (d, 1H, J=16.6 Hz), 7.41 (d, 1H, J=7.6 Hz), 7.45 (d, 1H, J=8.8 Hz), 7.60 (d, 1H, J=15.9 Hz), 7.55-7.70 (2H).

Example a-3

Synthesis of the Present Compound [Compound No. (4a)] by Production Process A

According to the same manner as that of Example a-1 except that 23.8 g of 3-allyloxybenzaldehyde was used in place of 3-(3-formylphenyl)-2-propenenitrile, 7.30 g of 4-hydroxy-3-[3-(3-allyloxyphenyl)-1-oxo-2-propenyl]-6-methyl-2H-pyran-2-one [Compound No. (4a)] was obtained as a yellow crystal.

$^1$H-NMR (400 MHz, CDCl$_6$) δ (ppm): 2.28 (s, 3H), 4.58-4.62 (2H), 5.30 (d, 1H), 5.48 (d, 1H), 5.96 (s, 1H), 6.00-6.13 (m, 1H), 6.96-7.02 (m, 1H), 7.25-7.40 (m, 3H), 7.91 (d, 1H, J=15.6 Hz), 8.28 (d, 1H, J=15.6 Hz), 12.12 (s, 1H).

Example a-4

Synthesis of the Present Compound [Compound No. (5a)]

To 20 ml of tetrahydrofuran were added 2.00 g of 4-hydroxy-3-[3-(3-allyloxyphenyl)-1-oxo-2-propenyl]-6-methyl-2H-pyran-2-one, 1.85 g of triphenylphosphine and 0.23 g of methanol, and to the mixture was added dropwise a solution of 1.23 g of diethyl azodicarboxylate in 12 ml of tetrahydrofuran. The mixture was stirred at room temperature for 18 hours, and the reaction mixture was concentrated under reduced pressure. The residue was subjected to silica gel column chromatography to obtain 0.12 g of 4-methoxy-3-[3-(3-allyloxyphenyl)-1-oxo-2-propenyl]-6-methyl-2H-pyran-2-one [Compound No. (5a)] as a yellow oil.

$^1$H-NMR (400 MHz, CDCl$_6$) δ (ppm): 2.35 (s, 3H), 3.95 (s, 3H), 4.55-4.60 (2H), 5.30 (d, 1H), 5.45 (d, 1H), 6.00-6.15 (m, 1H), 6.12 (s, 1H), 6.90-7.00 (1H), 7.10-7.20 (2H), 7.45-7.80 (3H).

Example a-5

Synthesis of the Present Compound [Compound No. (7a)] by Production Process A

According to the same manner as that of Example a-1 except that 20.00 g of 3-propargyloxybenzaldehyde was used in place of 3-(3-formylphenyl)-2-propenenitrile, 1.05 g of 4-hydroxy-3-[3-(3-propargyloxyphenyl)-1-oxo-2-propenyl]-6-methyl-2H-pyran-2-one [Compound No. (7a)] was obtained as a pale yellow crystal.

$^1$H-NMR (400 MHz, CDCl$_3$) δ (ppm): 2.32 (s, 3H), 2.56 (s, 1H), 4.74 (s, 2H), 5.97 (s, 1H), 7.00-7.10 1H), 7.30-7.40 (3H), 7.92 (d, 1H, J=15.6 Hz), 8.29 (d, 1H, J=15.6 Hz), 12.16 (s, 1H).

Example a-6

Synthesis of the Present Compound [Compound No. (8a)]

According to the same manner as that of Example a-4 except that 30.80 g of 4-hydroxy-3-[3-(3-propargyloxyphenyl)-1-oxo-2-propenyl]-6-methyl-2H-pyran-2-one was used in place of 4-hydroxy-3-[3-(3-allyloxyphenyl)-1-oxo-2-propenyl]-6-methyl-2H-pyran-2-one, 0.48 g of 4-methoxy-3-[3-(3-propargyloxyphenyl)-1-oxo-2-propenyl]-6-methyl-2H-pyran-2-one [Compound No. (8a)] was obtained as a yellow solid.

$^1$H-NMR (400 MHz, CDCl$_3$) δ (ppm): 2.35 (s, 3H), 2.53 (s, 1H), 3.93 (s, 3H), 4.71 (s, 2H), 6.12 (s, 1H), 6.95-7.40 (3H), 7.40-7.70 (3H).

Example a-7

Synthesis of the Present Compound [Compound No. (9a)] by Production Process A

According to the same manner as that of a-1 except that 10.00 g of 4-propargyloxybenzaldehyde was used in place of 3-(3-formylphenyl)-2-propenenitrile, 0.89 g of 4-hydroxy-3-[3-(4-propargyloxyphenyl)-1-oxo-2-propenyl]-6-methyl-2H-pyran-2-one [Compound No. (9a)] was obtained as a red crystal.

$^1$H-NMR (400 MHz, CDCl$_3$) δ (ppm): 2.27 (s, 3H), 2.57 (s, 1H), 4.78 (s, 2H), 5.95 (s, 1H), 7.01 (d, 2H, J=6.8 Hz), 7.68-7.70 (d, 2H), 7.94 (d, 1H, J=15.6 Hz), 8.21 (d, 1H, J=15.6 Hz), 11.90 (s, 1H).

Example a-8

Synthesis of the Present Compound [Compound No. (10a)]

According to the same manner as that of Example a-4 except that 0.82 g of 4-hydroxy-3-[3-(4-propargyloxyphenyl)-1-oxo-2-propenyl]-6-methyl-2H-pyran-2-one was used in place of 4-hydroxy-3-[3-(3-allyloxyphenyl)-1-oxo-2-propenyl]-6-methyl-2H-pyran-2-one, 0.28 g of 4-methoxy-3-[3-(4-propargyloxyphenyl)-1-oxo-2-propenyl]-6-methyl-2H-pyran-2-one [Compound No. (10a)] was obtained.

$^1$H-NMR (400 MHz, CDCl$_3$) δ (ppm): 2.34 (s, 3H), 2.54 (s, 1H), 3.92 (s, 3H), 4.73 (s, 2H), 6.11 (s, 1H), 6.97 (d, 2H, J=6.8 Hz), 7.01 (d, 1H, J=15.9 Hz), 7.53 (d, 2H, J=6.8 Hz), 7.56 (d, 1H, J=15.9 Hz).

Example a-9

Synthesis of the Present Compound [Compound No. (14a)] by Production Process A

According to the same manner as that of Example a-1 except that 0.45 g of 3-(cyanomethoxy)benzaldehyde was used in place of 3-(3-formylphenyl)-2-propenenitrile, 0.10 g of 4-hydroxy-3-[3-[3-(cyanomethoxy)phenyl]-1-oxo-2-propenyl]-6-methyl-2H-pyran-2-one [Compound No. (14a)] was obtained as a yellow crystal.

$^1$H-NMR (400 MHz, CDCl$_3$) δ (ppm): 2.30 (s, 3H), 4.83 (s, 2H), 5.98 (s, 1H), 7.04-7.08 (1H), 7.25-7.26 (1H), 7.38-7.46 (1H), 7.90 (d, 1H, J=15.6 Hz), 8.30 (d, 1H, J=15.6 Hz), 12.27 (s, 1H).

Example a-10

Synthesis of the Present Compound [Compound No. (15a)] by Production Process B

According to the same manner as that of Example a-2 except that 89.0 mg of 4-hydroxy-3-[3-[3-(cyanomethoxy)phenyl]-1-oxo-2-propenyl]-6-methyl-2H-pyran-2-one was used in place of 4-hydroxy-3-[3-[3-(2-cyanoethenyl)phenyl]-1-oxo-2-propenyl]-6-methyl-2H-pyran-2-one, 13.6 mg of 4-methoxy-3-[3-[3-(cyanomethoxy)phenyl]-1-oxo-2-propenyl]-6-methyl-2H-pyran-2-one [Compound No. (15a)] was obtained.

$^1$H-NMR (400 MHz, CDCl$_3$) δ (ppm): 2.36 (s, 3H), 3.95 (s, 3H), 4.79 (s, 2H), 6.13 (s, 1H), 7.00 (dd, 1H, J=2.4, 8.1 Hz), 7.13 (d, 1H, J=15.9 Hz), 7.15 (s, 1H), 7.30 (d, 1H, J=7.6 Hz), 7.36 (t, 1H, J=7.8 Hz), 7.57 (d, 1H, J=15.9 Hz).

Example a-11

Synthesis of the Present Compound [Compound No. (21a)] by Production Process A

According to the same manner as that of Example a-1 except that 0.19 g of 3-(methoxyacetylamino)benzaldehyde was used in place of 3-(3-formylphenyl)-2-propenenitrile, 0.15 g of 4-hydroxy-3-[3-[3-(methoxyacetylamino)phenyl]-1-oxo-2-propenyl]-6-methyl-2H-pyran-2-one [Compound No. (21a)] was obtained as a yellow crystal.

$^1$H-NMR (400 MHz, CDCl$_3$) δ (ppm): 2.29 (s, 3H), 3.53 (s, 3H), 4.03 (s, 2H), 5.96 (s, 1H), 7.39 (t, 1H, J=8.0 Hz), 7.45 (d, 1H, J=8.1 Hz), 7.71 (s, 1H), 7.84 (d, 1H, J=8.1 Hz), 7.92 (d, 1H, J=15.9 Hz), 8.28 (d, 1H, J=15.9 Hz), 8.33 (s, 1H), 12.20 (s, 1H).

Example a-12

Synthesis of the Present Compound [Compound No. (22a)]

According to the same manner as that of Example a-4 except that 0.80 g of 4-hydroxy-3-[3-[3-(methoxyacetylamino)phenyl]-1-oxo-2-propenyl]-6-methyl-2H-pyran-2-one was used in place of 4-hydroxy-3-[3-(3-allyloxyphenyl)-1-oxo-2-propenyl]-6-methyl-2H-pyran-2-one, 0.63 g of 4-methoxy-3-[3-[3-(methoxyacetylamino)phenyl]-1-oxo-2-propenyl]-6-methyl-2H-pyran-2-one [Compound No. (22a)] was obtained.

$^1$H-NMR (400 MHz, CDCl$_3$) δ (ppm): 2.35 (s, 3H), 3.52 (s, 3H), 3.94 (s, 3H), 4.02 (s, 2H), 6.12 (s, 1H), 7.11 (d, 1H, J=16.1 Hz), 7.33-7.37 (2H), 7.57 (d, 1H, J=16.1 Hz), 7.59-7.65 (1H), 7.77 (s, 1H), 8.29 (s, 1H).

Example a-13

Synthesis of the Present Compound [Compound No. (24a)] by Production Process A

According to the same manner as that of Example a-1 except that 2.23 g of 3-[(2-methoxyethoxy)carbonylamino]benzaldehyde was used in place of 3-(3-formylphenyl)-2-propenenitrile, 2.25 g of 4-hydroxy-3-[3-[3-[(2-methoxyethoxy)carbonylamino]phenyl]-1-oxo-2-propenyl]-6-methyl-2H-pyran-2-one [Compound No. (24a)] was obtained as a yellow crystal.

$^1$H-NMR (400 MHz, CDCl$_3$) δ (ppm): 2.28 (s, 3H), 3.40 (s, 3H), 3.65 (d, 2H, J=4.8 Hz), 4.33 (d, 2H, J=4.4 Hz), 5.97 (s, 1H), 7.31-7.35 (1H), 7.37 (t, 1H, J=7.6 Hz), 7.60 (d, 1H, J=7.2 Hz), 7.72 (s, 1H), 7.92 (d, 1H, J=16.0 Hz), 8.26 (d, 1H, J=16.0 Hz), 8.27 (s, 1H), 12.15 (s, 1H).

Example a-14

Synthesis of the Present Compound [Compound No. (25a)] by Production Process B

According to the same manner as that of Example a-2 except that 1.00 g of 4-hydroxy-3-[3-[3-[(2-methoxyethoxy)carbonylamino]phenyl]-1-oxo-2-propenyl]-6-methyl-2H-pyran-2-one was used in place of 4-hydroxy-3-[3-[3-(2-cyanoethenyl)phenyl]-1-oxo-2-propenyl]-6-methyl-2H-pyran-2-one, 0.44 g of 4-methoxy-3-[3-[3-[(2-methoxyethoxy)carbonylamino]phenyl]-1-oxo-2-propenyl]-6-methyl-2H-pyran-2-one [Compound No. (25a)] was obtained.

$^1$H-NMR (400 MHz, CDCl$_3$) δ (ppm): 2.35 (s, 3H), 3.42 (s, 3H), 3.65 (t, 2H, J=4.8 Hz), 3.93 (s, 3H), 4.33 (t, 2H, J=4.4 Hz), 6.11 (s, 1H), 6.74 (s, 1H), 7.08 (d, 1H, J=16.0 Hz), 7.25-7.38 (4H), 7.54 (d, 1H, J=16.4 Hz), 7.61 (s, 1H).

Example a-15

Synthesis of the Present Compound [Compound No. (33a)] by Production Process A

According to the same manner as that of Example a-1 except that 1.50 g of 3-[[(methoxycarbonylmethyl)amino]carbonyl]benzaldehyde was used in place of 3-(3-formylphenyl)-2-propenenitrile, 0.68 g of 4-hydroxy-3-[3-[3-[[(methoxycarbonylmethyl)amino]carbonyl]phenyl]-1-oxo-2-propenyl]-6-methyl-2H-pyran-2-one [Compound No. (33a)] was obtained as a yellow crystal.

$^1$H-NMR (400 MHz, CDCl$_3$) δ (ppm): 2.30 (s, 3H), 3.82 (s, 3H), 4.29 (s, 2H), 5.98 (s, 1H), 6.71 (broads, 1H), 7.52 (t, 1H, J=7.6 Hz), 7.86 (d, 2H, J=7.6 Hz), 7.96 (d, 1H, J=15.6 Hz), 8.04 (s, 1H), 8.34 (d, 1H, J=16.0 Hz)

Example a-16

Synthesis of the Present Compound [Compound No. (36a)] by Production Process A

According to the same manner as that of Example a-1 except that 1.00 g of 4-[(2-methoxyethyl)aminocarbonyl]benzaldehyde was used in place of 3-(3-formylphenyl)-2-propenenitrile, 0.12 g of 4-hydroxy-3-[3-[4-[(2-methoxyethyl)aminocarbonyl]phenyl]-1-oxo-2-propenyl]-6-methyl-2H-pyran-2-one [Compound No. (36a)] was obtained as a yellow crystal.

$^1$H-NMR (400 MHz, CDCl$_3$) δ (ppm): 2.30 (s, 3H), 3.40 (s, 3H), 3.58 (t, 1H, J=4.8 Hz), 3.65-3.75 (m, 2H), 5.98 (s, 1H), 6.55 (s, 1H), 7.74 (d, 2H, J=8.4 Hz), 7.82 (d, 2H, J=8.4 Hz), 7.94 (d, 1H, J=15.6 Hz), 8.36 (d, 1H, J=15.6 Hz).

Example a-17

Synthesis of the Present Compound [Compound No. (42a)] by Production Process A

According to the same manner as that of Example a-1 except that 1.13 g of 3-(2,2-difluoroethenyl)benzaldehyde was used in place of 3-(3-formylphenyl)-2-propenenitrile, 0.61 g of 4-hydroxy-3-[3-[3-(2,2-difluoroethenyl)phenyl]-1-oxo-2-propenyl]-6-methyl-2H-pyran-2-one [Compound No. (42a)] was obtained as a reddish brown crystal.

$^1$H-NMR (400 MHz, CDCl$_3$) δ (ppm): 2.29 (s, 3H), 5.33 (dd, 1H, J=3.7, 25.9 Hz), 5.97 (s, 1H), 7.39-7.41 (m, 2H), 7.57-7.58 (m, 2H), 7.92 (d, 1H, J=15.9 Hz), 8.30 (d, 1H, J=15.9 Hz).

Example a-18

Synthesis of the Present Compound [Compound No. (43a)] by Production Process B

According to the same manner as that of Example a-2 except that 538 mg of 4-hydroxy-3-[3-[3-(2,2-difluoroethenyl)phenyl]-1-oxo-2-propenyl]-6-methyl-2H-pyran-2-one was used in place of 4-hydroxy-3-[3-[3-(2-cyanoethenyl)phenyl]-1-oxo-2-propenyl]-6-methyl-2H-pyran-2-one, 113 mg of 4-methoxy-3-[3-[3-(2,2-difluoroethenyl)phenyl]-1-oxo-2-propenyl]-6-methyl-2H-pyran-2-one [Compound No. (43a)] was obtained as a yellow crystal.

$^1$H-NMR (400 MHz, CDCl$_3$) δ (ppm): 2.35 (s, 3H), 3.94 (s, 3H), 5.28 (dd, 1H, J=3.6, 25.9 Hz), 6.13 (s, 1H), 7.13 (d, 1H, J=15.9 Hz), 7.33-7.37 (2H), 7.43-7.47 (1H), 7.50 (s, 1H), 7.58 (d, 1H, J=15.9 Hz).

Example a-19

Synthesis of the Present Compound [Compound No. (44a)] by Production Process A

According to the same manner as that of Example a-1 except that 2.68 g of 3-(2-cyanoethyl)benzaldehyde was used in place of 3-(3-formylphenyl)-2-propenenitrile, 0.74 g of 4-hydroxy-3-[3-[3-(2-cyanoethyl)phenyl]-1-oxo-2-propenyl]-6-methyl-2H-pyran-2-one [Compound No. (44a)] was obtained as a yellow crystal.

$^1$H-NMR (400 MHz, CDCl$_3$) δ (ppm): 2.30 (s, 3H), 2.67 (t, 2H, J=7.3 Hz), 3.01 (t, 2H, J=7.3 Hz), 5.98 (s, 1H), 7.32 (d, 1H, J=7.7 Hz), 7.41 (t, 1H, J=7.7 Hz), 7.53 (s, 1H), 7.61 (d, 1H, J=7.7 Hz), 7.94 (d, 1H, J=15.8 Hz), 8.31 (d, 1H, J=15.8 Hz).

Example a-20

Synthesis of the Present Compound [Compound No. (45a)] by Production Process B

According to the same manner as that of Example a-2 except that 0.61 g of 4-hydroxy-3-[3-[3-(2-cyanoethyl)phenyl]-1-oxo-2-propenyl]-6-methyl-2H-pyran-2-one was used in place of 4-hydroxy-3-[3-[3-(2-cyanoethenyl)phenyl]-1-oxo-2-propenyl]-6-methyl-2H-pyran-2-one, 0.30 g of 4-methoxy-3-[3-[3-(2-cyanoethyl)phenyl]-1-oxo-2-propenyl]-6-methyl-2H-pyran-2-one [Compound No. (45a)] was obtained as a pale brown oil.

$^1$H-NMR (400 MHz, CDCl$_3$) δ (ppm): 2.35 (s, 3H), 2.64 (t, 2H, J=7.5 Hz), 2.97 (t, 2H, J=7.5 Hz), 3.94 (s, 3H), 6.14 (s, 1H), 7.14 (d, 1H, J=16.2 Hz), 7.23-7.27 (m, 1H), 7.33-7.40 (m, 1H), 7.42 (s, 1H), 7.47-7.49 (m, 1H), 7.59 (d, 1H, J=16.2 Hz).

Example a-21

Synthesis of the Present Compound [Compound No. (49a)] by Production Process A

According to the same manner as that of Example a-1 except that 0.50 g of 3-(3-hydroxypropoxy)benzaldehyde was used in place of 3-(3-formylphenyl)-2-propenenitrile, 95 mg of 4-hydroxy-3-[3-[3-(3-hydroxypropoxy)phenyl]-1-oxo-2-propenyl]-6-methyl-2H-pyran-2-one [Compound No. (49a)] was obtained as a yellow crystal.

$^1$H-NMR (400 MHz, CDCl$_3$) δ (ppm): 1.68 (t, 1H, J=5.3 Hz), 2.06-2.11 (m, 2H), 2.29 (s, 3H), 3.87-3.91 (m, 2H), 4.19 (t, 2H, J=6.0 Hz), 5.97 (s, 1H), 6.98-6.99 (m, 1H), 7.23-7.35 (m, 3H), 7.92 (d, 1H, J=15.9 Hz), 8.29 (d, 1H, J=15.9 Hz)

Example b-1

Synthesis of the Present Compound [Compound No. (1b)] by Production Process B

According to the same manner as that of Example a-4 except that 224 μl of allyl alcohol was used in place of methanol, 69.7 mg of 4-allyloxy-3-[3-(3-allyloxyphenyl)-1-oxo-2-propenyl]-6-methyl-2H-pyran-2-one [Compound No. (1b)] was obtained.

$^1$H-NMR (400 MHz, CDCl$_6$) δ (ppm): 2.33 (s, 3H), 4.50-4.58 (2H), 4.65-4.70 (2H), 5.25-5.35 (2H), 5.35-5.45 (2H), 5.85-6.00 (1H), 6.00-6.10 (1H), 6.07 (s, 1H), 6.90-6.95 (1H), 7.05-7.20 (1H), 7.20-7.30 (1H), 7.45-7.50 (1H), 7.50-7.60 (1H), 7.70-7.80 (1H).

Example b-2

Synthesis of the Present Compound [Compound No. (2b)] by Production Process B

According to the same manner as that of Example b-1 except that 0.93 g of 4-hydroxy-3-[3-(3-propargyloxyphenyl)-1-oxo-2-propenyl]-6-methyl-2H-pyran-2-one was used in place of 4-hydroxy-3-[3-(3-allyloxyphenyl)-1-oxo-2-propenyl]-6-methyl-2H-pyran-2-one, 0.25 g of 4-allyloxy-3-[3-(3-propargyloxyphenyl)-1-oxo-2-propenyl]-6-methyl-2H-pyran-2-one [Compound No. (2b)] was obtained.

$^1$H-NMR (400 MHz, CDCl$_3$) δ (ppm): 2.33 (s, 3H), 2.54 (s, 1H), 4.69 (2H), 4.72 (2H), 5.38 (d, 1H), 5.44 (d, 1H), 5.85-5.95 (1H), 6.07 (s, 1H), 6.98-7.02 (1H), 7.05-7.25 (1H), 7.25-7.35 (1H), 7.56 (d, 1H, J=16.1 Hz).

Example b-3

Synthesis of the Present Compound [Compound No. (14b)]

In 8 ml of chloroform were dissolved 85.7 mg of 3-acetyl-4-hydroxy-6-methyl-2H-pyran-2-one, 100 mg of 3-(2-methylthioethoxy)benzaldehyde and 30.3 mg of piperidine, and the solution was heated under refluxing for 13 hours while water was removed with a Soxhlet's extractor filled with a molecular sieve. After cooling to room temperature, the reaction mixture washed successively with 10% hydrochloric acid and an aqueous saturated sodium chloride solution, dried over anhydrous magnesium sulfate, and concentrated. Precipitated crystals were filtered, and this was subjected to silica gel column chromatography to obtain 10.1 mg of 4-piperidino-3-[3-[3-(2-methylthioethoxy)phenyl]-1-oxo-2-propenyl]-6-methyl-2H-pyran-2-one [Compound No. (14b)] as a pale yellow crystal.

$^1$H-NMR (400 MHz, CDCl$_6$) δ (ppm): 1.75-2.00 (6H), 2.19 (s, 3H), 2.23 (s, 3H), 2.89 (t, 2H, J=6.8 Hz), 3.75-4.00 (4H), 4.17 (t, 2H, J=6.8 Hz), 5.69 (s, 1H), 6.90-7.35 (5H), 7.36 (d, 1H, J=15.4 Hz).

Example b-4

Synthesis of the Present Compound [Compound No. (15b)]

According to the same manner as that of Example b-3 except that 0.40 g of 2-propargyloxybenzaldehyde was used in place of 3-(2-methylthioethoxy)benzaldehyde, 0.23 g of 4-piperidino-3-[3-(2-propargyloxyphenyl)-1-oxo-2-propenyl]-6-methyl-2H-pyran-2-one [Compound No. (15b)] was obtained as a yellow crystal.

$^1$H-NMR (400 MHz, CDCl$_3$) δ (ppm): 1.75-2.00 (6H), 2.13 (s, 3H), 2.53 (t, 1H, J=2.2 Hz), 3.70-4.00 (4H), 4.73 (d, 2H, J=2.4 Hz), 5.68 (s, 1H), 6.98 (d, 1H, J=8.3 Hz), 7.00 (t, 1H, J=7.6 Hz), 7.24 (d, 1H, J=16.4 Hz), 7.35 (dt, 1H, J=1.4, 7.8 Hz), 7.52 (dd, 1H, J=1.5, 7.6 Hz), 7.59 (d, 1H, J=15.6 Hz).

Example b-5

Syntheses of the Present Compound [Compound No. (16b)]

According to the same manner as that of Example b-3 except that 0.30 g of 3-[[(methoxycarbonylmethyl)amino] carbonyl]benzaldehyde was used in place of 3-(2-methylthioethoxy)benzaldehyde, 0.21 g of 4-piperidino-3-[3-[3-[[(methoxycarbonylmethyl)amino]carbonyl]phenyl]-1-oxo-2-propenyl]-6-methyl-2H-pyran-2-one [Compound No. (16b)] was obtained as a yellow crystal.

$^1$H-NMR (400 MHz, CDCl$_3$) δ(ppm): 1.75-1.95 (6H), 2.15 (s, 3H), 3.70-4.00 (4H), 3.81 (s, 3H), 4.26 (s, 2H), 5.69 (s, 1H), 7.05 (t, 1H, J=5.2 Hz), 7.18 (d, 1H, J=15.7 Hz), 7.36 (t, 1H, J=7.8 Hz), 7.45 (d, 1H, J=15.9 Hz), 7.59 (d, 1H, J=7.8 Hz), 7.75 (d, 1H, J=7.8 Hz), 8.02 (s, 1H).

Example b-6

Synthesis of the Present Compound [Compound No. (19b)]

According to the same manner as that of Example b-3 except that 0.81 g of 3-[[(methoxycarbonylmethyl)amino] carbonyl]benzaldehyde was used in place of 3-(3-formylphenyl)-2-propenenitrile, and 223 μl of morpholine was used in place of piperidine, 0.26 g of 4-morpholino-3-[3-[3-[[(methoxycarbonylmethyl)amino]carbonyl]phenyl]-1-oxo-2-propenyl]-6-methyl-2H-pyran-2-one [Compound No. (19b)] was obtained as a yellow crystal.

$^1$H-NMR (400 MHz, CDCl$_3$) δ (ppm): 2.17 (s, 3H), 3.79 (s, 3H), 3.90-4.10 (8H), 4.26 (d, 2H, J=4.9 Hz), 5.71 (s, 1H), 7.08 (t, 1H, J=5.4 Hz), 7.23 (d, 1H, J=15.6 Hz), 7.36 (t, 1H, J=7.8 Hz), 7.53 (d, 1H, J=15.4 Hz), 7.59 (d, 1H, J=7.8 Hz), 7.76 (d, 1H, J=7.8 Hz), 8.05 (s, 1H).

Example b-7

Synthesis of the Present Compound [Compound No. (20b)]

To a mixture of 0.20 g of 4-methoxy-3-[3-[3-(2-cyanoethenyl)phenyl]-1-oxo-2-propenyl]-6-methyl-2H-pyran-2-one and 10 ml of benzene was added 34.3 mg of propargylamine, and the mixture was heated under refluxing for 3 hours and 45 minutes. After cooling to room temperature, precipitated crystals were filtered to obtain 68.0 mg of 4-propargylamino-3-[3-[3-(2-cyanoethenyl)phenyl]-1-oxo-2-propenyl]-6-methyl-2H-pyran-2-one [Compound No. (20b)] as a pale brown powder.

$^1$H-NMR (400 MHz, DMSO-d$_6$) δ (ppm): 2.25 (s, 3H), 3.41 (s, 1H), 4.35 (d, 2H, J=3.2 Hz), 6.40 (s, 1H), 6.56 (d, 1H, J=16.4 Hz), 7.51 (t, 1H, J=8.0 Hz), 7.52 (d, 1H, J=15.6 Hz), 7.71 (d, 1H, J=16.8 Hz), 7.65-7.76 (2H), 7.91 (s, 1H), 8.06 (d, 1H, J=15.6 Hz), 11.41 (s, 1H).

Example d-1

Synthesis of the Present Compound [Compound No. (14d)] by Production Process A

In 5 ml of chloroform were dissolved 0.57 g of 3-acetyl-4-hydroxy-2H-1-benzopyran-2-one, 0.45 g of 3-(cyanomethoxy)benzaldehyde and 0.20 g of piperidine, and the solution was heated under refluxing for 1 hour and 30 minutes while water was removed with a Soxhlet's extractor filled with a molecular sieve. After cooling to room temperature, the reaction mixture washed successively with 10% hydrochloric acid and an aqueous saturated sodium chloride solution, dried over anhydrous magnesium sulfate, and concentrated. Precipitated crystals were washed with a mixture of 10 ml of dioxane and 10 ml of chloroform, and washed with 10 ml of t-butyl methyl ether to obtain 0.56 g of 4-hydroxy-3-[3-[3-(cyanomethoxy)phenyl]-1-oxo-2-propenyl]-2H-1-benzopyran-2-one [Compound No. (14d)] as a yellow crystal.

$^1$H-NMR (400 MHz, CDCl$_3$) δ (ppm): 4.83 (s, 2H), 7.08 (d, 1H, J=8.0 Hz), 7.20-7.40 (5H), 7.70 (t, 1H, J=7.1 Hz), 8.01 (d, 1H, J=15.9 Hz), 8.11 (d, 1H, J=8.1 Hz), 8.44 (d, 1H, J=15.6 Hz)

Example d-2

Synthesis of the Present Compound [Compound No. (15d)] by Production Process B

To a mixture of 5 ml of hexamethylphosphoramine and 0.40 g of 4-hydroxy-3-[3-[3-(cyanomethoxy)phenyl]-1-oxo-2-propenyl]-2H-1-benzopyran-2-one was added 52 mg of sodium hydride (60% oily), and the mixture was stirred at room temperature for 1 hour. Then, 0.17 g of dimethyl sulfate was added, and the mixture was stirred at room temperature overnight. Thereafter, the reaction mixture was added to ice water, and the mixture was extracted with ethyl acetate. The organic layer washed with an aqueous saturated sodium chloride solution, dried with anhydrous magnesium sulfate, and concentrated. The residue was subjected to silica gel column chromatography to obtain 81 mg of 4-methoxy-3-[3-[3-(cyanomethoxy)phenyl]-1-oxo-2-propenyl]-2H-1-benzopyran-2-one [Compound No. (15d)] as a pale yellow crystal.

$^1$H-NMR (400 MHz, CDCl$_3$) δ (ppm): 4.04 (s, 3H), 4.80 (s, 2H), 7.04 (d, 1H, J=5.6 Hz), 7.16 (d, 1H, J=16.1 Hz), 7.10-7.40 (5H), 7.58 (d, 1H, J=16.2 Hz), 7.60 (t, 1H), 7.93 (d, 1H, J=8.1 Hz)

Example d-3

Synthesis of the Present Compound [Compound No. (21d)] by Production Process A

In 3 ml of chloroform were dissolved 0.18 g of 3-acetyl-4-hydroxy-2H-1-benzopyran-2-one, 0.17 g of 3-(methoxyacetylamino)benzaldehyde and 60 mg of piperidine, and the solution was heated under refluxing for 1 hour and 10 minutes while water was removed with a Soxhlet's extractor filled with a molecular sieve. After cooling to room temperature, the reaction solution was concentrated under reduced pressure. The residue was subjected to silica gel column chromatography, and fractions corresponding to Rf=0.3 were collected by thin layer chromatography (silica gel, chloroform (containing 2% methanol)), and concentrated to obtain 0.30 g of 4-hydroxy-3-[3-[3-(methoxyacetylamino)phenyl]-1-oxo-2-propenyl]-2H-1-benzopyran-2-one [Compound No. (21d)].

$^1$H-NMR (400 MHz, CDCl$_3$) δ (ppm): 3.54 (s, 3H), 4.05 (s, 2H), 7.20-7.31 (2H), 7.33 (t, 1H, J=7.1 Hz), 7.49 (d, 1H, J=7.8 Hz), 7.70 (dt, 1H, J=1.7, 7.3 Hz), 7.76 (s, 1H), 7.86 (d, 1H, J=7.1 Hz), 8.03 (d, 1H, J=16.1 Hz), 8.10 (dd, 1H, J=1.7, 8.1 Hz), 8.35 (s, 1H), 8.43 (d, 1H, J=15.9 Hz), 11.21 (s, 1H).

Example d-4

Synthesis of the Present Compound [Compound (22d)]

To a mixture of 5 ml of tetrahydrofuran and 6 ml of dichloromethane were added 0.59 g of 4-hydroxy-3-[3-[3-(methoxyacetylamino)phenyl]-1-oxo-2-propenyl]-2H-1-benzopyran-2-one, 0.45 g of triphenylphosphine and 55 mg of methanol, and to the mixture was added dropwise 0.74 g of a 40% toluene solution of diethyl azodicarboxylate. The mixture was stirred at room temperature for 40 minutes, and the reaction mixture was concentrated under reduced pressure. The residue was subjected to silica gel column chromatography to obtain 0.18 g of 4-methoxy-3-[3-[3-(methoxyacetylamino)phenyl]-1-oxo-2-propenyl]-2H-1-benzopyran-2-one [Compound No. (22d)].

$^1$H-NMR (400 MHz, CDCl$_3$) δ (ppm): 3.51 (s, 3H), 4.02 (s, 3H), 4.04 (s, 2H), 7.16 (d, 1H, J=16.2 Hz), 7.29-7.39 (4H), 7.59 (d, 1H, J=16.4 Hz), 7.61 (dt, 1H, J=1.5, 8.8 Hz), 7.87 (s, 1H), 7.92 (dd, 1H, J=1.5, 8.1 Hz), 8.30 (s, 1H).

Example d-5

Synthesis of the Present Compound [Compound No. (24d)] by Production Process A

In 10 ml of chloroform were dissolved 2.04 g of 3-acetyl-4-hydroxy-2H-1-benzopyran-2-one, 2.23 g of 3-[(2-methoxyethoxy)carbonylamino]benzaldehyde and 60 mg of piperidine, and the solution was heated under refluxing for 1 hour and 30 minutes while water was removed with a Soxhlet's extractor filled with a molecular sieve. After cooled to room temperature, the reaction mixture was concentrated under reduced pressure. The residue was subjected to silica gel column chromatography, and fractions corresponding to Rf=0.3 were collected by thin layer chromatography (silica gel, hexane/acetone (1:1)), and concentrated to obtain 3.42 g of 4-hydroxy-3-[3-[3-[(2-methoxyethoxy)carbonylamino]phenyl]-1-oxo-2-propenyl]-2H-1-benzopyran-2-one [Compound No. (24d)].

$^1$H-NMR (400 MHz, DMSO-d$_6$) δ (ppm): 3.30 (s, 3H), 3.59 (t, 2H, J=3.2 Hz), 4.23 (t, 2H, J=4.6 Hz), 7.35-7.50 (5H), 7.60 (d, 1H, J=7.6 Hz), 7.82 (t, 1H, J=7.1 Hz), 7.94 (s, 1H), 7.97 (d, 1H, J=15.9 Hz), 8.06 (d, 1H, J=8.1 Hz), 8.27 (d, 1H, J=15.9 Hz), 9.97 (s, 1H).

Example d-6

Synthesis of the Present Compound [Compound No. (25d)] by Production Process B

According to the same manner as that of Example d-2 except that 2.0 g of 4-hydroxy-3-[3-[3-[(2-methoxyethoxy) carbonylamino]phenyl]-1-oxo-2-propenyl]-2H-1-benzopyran-2-one was used in place of 4-hydroxy-3-[3-[3-(cyanomethoxy)phenyl]-1-oxo-2-propenyl]-2H-1-benzopyran-2-one, 1.28 g of 4-methoxy-3-[3-[3-[(2-methoxyethoxy) carbonylamino]phenyl]-1-oxo-2-propenyl]-2H-1-benzopyran-2-one [Compound No. (25d)] was obtained.
$^1$H-NMR (400 MHz, CDCl$_3$) δ (ppm): 3.43 (s, 3H), 3.65 (t, 2H, J=4.2 Hz), 4.03 (s, 3H), 4.34 (t, 2H, J=4.4 Hz), 6.73 (s, 1H), 7.14 (d, 1H, J=16.4 Hz), 7.25-7.50 (5H), 7.56 (d, 1H, J=16.4 Hz), 7.59 (t, 1H), 7.70 (s, 1H), 7.91 (dd, 1H, J=8.8 Hz)

Example d-7

Synthesis of the Present Compound [Compound No. (32d)] by Production Process A

According to the same manner as that of Example d-1 except that 0.56 g of 4-[(2-hydroxyethyl)aminocarbonyl] benzaldehyde was used in place of 3-(cyanomethoxy)benzaldehyde, 58 mg of 4-hydroxy-3-[3-[4-[(2-hydroxyethyl)aminocarbonyl]phenyl]-1-oxo-2-propenyl]-6-methyl-2H-pyran-2-one [Compound No. (32d)] was obtained.
$^1$H-NMR (400 MHz, DMSO-d$_6$) δ (ppm): 3.35 (t, 2H, J=5.6 Hz), 3.52 (t, 2H, J=6.1 Hz), 7.40-7.55 (2H), 7.80-7.90 (3H), 7.90-8.00 (2H), 8.80-8.10 (2H), 8.32 (d, 1H, J=15.9 Hz), 8.56 (t, 1H, J=5.4 Hz).

Example d-8

Synthesis of the Present Compound [Compound No. (33d)] by Production Process A

According to the same manner as that of Example d-1 except that 1.58 g of 3-[[(methoxycarbonylmethyl)amino] carbonyl]benzaldehyde was used in place of 3-(cyanomethoxy)benzaldehyde, 0.65 g of 4-hydroxy-3-[3-[3-[[(methoxycarbonylmethyl)amino]carbonyl]phenyl]-1-oxo-2-propenyl]-6-methyl-2H-pyran-2-one [Compound No. (33d)] was obtained as a yellow crystal.
$^1$H-NMR (400 MHz, DMSO-d$_6$) δ (ppm): 3.67 (s, 3H), 4.05 (d, 2H, J=6.0 Hz), 7.40-7.48 (2H), 7.58-7.68 (1H), 7.83 (t, 1H, J=7.6 Hz), 7.90-8.00 (2H), 8.00-8.10 (2H), 8.25 (s, 1H), 8.33 (d, 1H, J=15.6 Hz), 9.15 (t, 1H, J=6.0 Hz).

Example d-9

Synthesis of the Present Compound [Compound No. (36d)] by Production Process A

According to the same manner as that of Example d-1 except that 1.60 g of 4-[(2-methoxyethyl)aminocarbonyl] benzaldehyde was used in place of 3-(cyanomethoxy)benzaldehyde, 0.68 g of 4-hydroxy-3-[3-[4-[(2-methoxyethyl)aminocarbonyl]phenyl]-1-oxo-2-propenyl]-6-methyl-2H-pyran-2-one [Compound No. (36d)] was obtained as a yellow crystal.

$^1$H-NMR (400 MHz, CDCl$_3$) δ (ppm): 3.41 (s, 3H), 3.59 (t, 2H, J=5.2 Hz), 3.69 (t, 2H, J=5.2 Hz), 6.55 (s, 1H), 7.30-7.40 (2H), 7.65-7.75 (1H), 7.78 (d, 2H, J=8.4 Hz), 7.84 (d, 2H, J=8.4 Hz), 8.04 (d, 1H, J=16.0 Hz), 8.10 (d, 1H, J=8.0 Hz), 8.50 (d, 1H, J=15.6 Hz), 11.29 (s, 1H).

Example d-10

Synthesis of the Present Compound [Compound No. (49d)] by Production Process A

According to the same manner as that of Example d-1 except that 0.50 g of 3-(3-hydroxypropoxy)benzaldehyde was used in place of 3-(cyanomethoxy)benzaldehyde, 0.54 g of 4-hydroxy-3-[3-[3-(3-hydroxypropoxy)phenyl]-1-oxo-2-propenyl]-2H-1-benzopyran-2-one [Compound No. (49d)] was obtained as a yellow crystal.
$^1$H-NMR (400 MHz, CDCl$_3$) δ (ppm): 1.71 (t, 1H, J=5.3 Hz), 2.06-2.12 (m, 2H), 3.88-3.92 (m, 2H), 4.20 (t, 2H, J=6.0 Hz), 6.99-7.01 (m, 1H), 7.25-7.36 (m, 5H), 7.67-7.71 (m, 1H), 8.02 (d, 1H, J=15.8 Hz), 8.09-8.11 (m, 1H), 8.42 (d, 1H, J=15.8 Hz).

Example d-11

Synthesis of the Present Compound [Compound No. (50d)] by Production Process B

According to the same manner as that of Example d-2 except that 267 mg of 4-hydroxy-3-[3-[3-(3-hydroxypropoxy)phenyl]-1-oxo-2-propenyl]-2H-1-benzopyran-2-one was used in place of 4-hydroxy-3-[3-[3-(cyanomethoxy)phenyl]-1-oxo-2-propenyl]-2H-1-benzopyran-2-one, 22 mg of 4-methoxy-3-[3-[3-(3-hydroxypropoxy)phenyl]-1-oxo-2-propenyl]-2H-1-benzopyran-2-one [Compound No. (50d)] was obtained.
$^1$H-NMR (400 MHz, CDCl$_3$) δ (ppm): 1.62 (t, 1H, J=5.4 Hz), 2.03-2.09 (m, 2H), 3.85-3.89 (m, 2H), 4.04 (s, 3H), 4.15 (t, 2H, J=6.1 Hz), 6.95-6.98 (m, 1H), 7.11-7.18 (m, 2H), 7.27-7.36 (m, 4H), 7.55-7.62 (m, 2H), 7.90-7.93 (m, 1H).

Example e-1

Synthesis of the Present Compound [Compound No. (17e)]

By collecting fractions corresponding to Rf=0.1 by thin layer chromatography (silica gel, chloroform (containing 2% methanol)) and concentrating them in silica gel column chromatography of Example d-3, 36.1 mg of 4-piperidino-3-[3-[3-(methoxyacetylamino)phenyl]-1-oxo-2-propenyl]-2H-1-benzopyran-2-one [Compound No. (17e)] was obtained.
$^1$H-NMR (400 MHz, CDCl$_3$) δ (ppm): 1.75-2.05 (6H), 3.50 (s, 3H), 3.85-3.95 (4H), 4.01 (s, 2H), 7.08 (d, 1H, J=15.7 Hz), 7.20-7.30 (3H), 7.33 (t, 1H, J=8.1 Hz), 7.42 (d, 1H, J=15.9 Hz), 7.51 (t, 1H, J=7.3 Hz), 7.57 (d, 1H), 7.82 (s, 1H), 8.07 (dd, 1H, J=11.5, 7.8 Hz), 8.27 (s, 1H).

Example e-2

Synthesis of the Present Compound [Compound No. (18e)]

By collecting fractions corresponding to Rf=0.1 by thin layer chromatography (silica gel, chloroform (containing 2% methanol)) and concentrating them in silica gel column chromatography of Example d-5, 0.15 g of 4-piperidino-3-[3-[3-

[(2-methoxyethoxy)carbonylamino]phenyl]-1-oxo-2-propenyl]-2H-1-benzopyran-2-one [Compound No. (18e)] was obtained.

$^1$H-NMR (400 MHz, DMSO-$d_6$) δ (ppm): 1.70-1.95 (6H), 3.31 (s, 3H), 3.55 (t, 2H, J=4.6 Hz), 3.79 (s, 2H), 3.95-4.20 (4H), 4.19 (t, 2H, J=4.4 Hz), 7.21 (d, 1H, J=8.3 Hz), 7.28-7.58 (5H), 7.69 (s, 1H), 7.85 (dd, 1H, J=1.7, 8.1 Hz), 9.79 (s, 1H).

Example 3

Preparation of a Plasmid Having a Reporter Gene Linked to a Transcription Regulatory Region for a Type I Collagen Gene $1 \times 10^8$ cells of a normal human fetal skin fibroblast (Clontech, catalogue No. CC-2509) were cultured at 37° C. overnight under 5% $CO_2$ atmosphere. After the cultured cells were washed with a sodium phosphate buffer (hereinafter, referred to as PBS) twice, 3 ml of PBS was added thereto and the cells were scraped away the wall of a vessel using a cell scraper (Nalgen, catalogue No. 179693). The scraped cells were collected by centrifugation (1,500 rpm, 4° C., 15 min), and these were suspended in 20 ml of PBS and centrifuged again. To the resulting precipitates were added 11 ml of Solution 2 and 4.8 μl of pronase of DNA Extraction Kit (Stratagene, catalogue No. 200600). After shaken at 60° C. for 1 hour, the resulting mixture was allowed to stand in ice for 10 minutes. Then, 4 ml of Solution 3 of the kit was added to the mixture. After mixed, the mixture was allowed to stand in ice for 5 minutes and then centrifuged (3,000 rpm, 4° C., 15 min) to recover a supernatant. To the recovered supernatant was added 2 μl of RNase per 1 ml of the supernatant and the mixture was allowed to stand at 37° C. for 15 minutes. To the mixture was added 2-fold volume of ethanol. After mixed, a white thread-like substance (genomic DNA) appeared and the substance was recovered. The recovered genomic DNA washed with 70% ethanol and then air-dried. The air-dried genomic DNA was dissolved in 500 μl of 10 mM Tris-HCl, 1 mM EDTA (pH 8.0) (hereinafter, referred to as TE).

The resulting genomic DNA solution (the amount equivalent to 1 μg of genomic DNA), each 1 μl (10 pmol/μl) of an oligonucleotide consisting of the nucleotide sequence represented by SEQ ID No:1 and an oligonucleotide consisting of the nucleotide sequence represented by SEQ ID No:2, 29 μL of distilled water, 5 μl of the buffer attached to TaKaRa LA Taq (TAKARA SHUZO, catalogue No. RR002A), 5 μL of a $Mg^{2+}$ solution, 5 μL of a dNTP mixture and 0.5 μl of TaKaRa LA Taq (TAKARA SHUZO, catalogue No. RR002A) were mixed. After the resulting mixed solution was incubated at 94° C. for 5 minutes, the mixed solution was subjected to 30 cycles, in which one cycle consists of incubation at 94° C. for 1 minute, at 60° C. for 1 minute and then at 72° C. for 1 minute. The mixed solution was electrophoresed on a 2% agarose gel to recover about 0.5 kb of a DNA. The recovered DNA was treated with phenol/chloroform and then precipitated with ethanol to recover the DNA. The resulting DNA was dissolved in ultrapure water. To this solution were added 2.5 μl of NheI and 2.5 μl of HindIII, and then incubated at 37° C. for 3 hours. Then, the solution was electrophoresed on a 2% agarose gel to recover about 3.5 kb of a DNA. The recovered DNA was precipitated with ethanol to recover again the DNA (hereinafter, referred to as the collagen promoter DNA).

On the other hand, the vector pGL3 (Promega, catalogue No. E1751) having the nucleotide sequence encoding firefly luciferase was digested with NheI and HindIII, and then subjected to agarose gel electrophoresis as described above to recover about 5 kb of a DNA. The recovered DNA was precipitated with ethanol to recover the DNA again. To the recovered DNA were added 44 μl of distilled water, 5 μl of Buffer attached to Alkaline Phosphatase (TAKARA SHUZO, catalogue No. 2120A) and 1 μl of Alkaline Phosphatase (TAKARA SHUZO, catalogue No. 2120A). The mixed solution was incubated at 65° C. for 30 minutes. Then, the mixed solution was treated with phenol/chloroform twice, and precipitated with ethanol to recover the DNA (hereinafter referred to as the Luc vector DNA). Then, after about 20 ng of the collagen promoter DNA and about 20 ng of the Luc vector DNA were mixed, the same amount of a DNA Ligation kit Ver2 enzyme solution was added and this was incubated overnight at 16° C. To the mixed solution was added *Escherichia coli* 5Hdα (TOYOBO, catalogue No. DNA-903), this was allowed to stand in ice for 30 minutes, and then incubated at 42° C. for 45 seconds. The resulting *Escherichia coli* was seeded on a LB plate containing 50 μg/ml ampicillin sodium (Nacalai, catalogue No. 027-39), and this was allowed to stand at 37° C. for 1 day. A single colony appeared and the colony was cultured in 2 ml of a LB medium containing 50 μg/ml ampicillin at 37° C. for 12 hours. From the resulting culture solution, a plasmid DNA was prepared using AUTOMATIC DNA ISOLATION SYSTEM PI-50 (KURABO). The nucleotide sequence of the prepared plasmid DNA was analyzed with a DNA sequencer. As a result, it was confirmed that the plasmid (hereinafter, referred to as COL-Luc) had a nucleotide sequence comprising a nucleotide sequence encoding the amino acid sequence of firefly luciferase as a reporter gene linked downstream of the nucleotide sequence −3500 to +57 (the transcription initiation point is +1) of a transcription regulatory region for a human-derived Type I collagen α2 chain gene.

Example 4

(Measurement of the Ability of a Test Compound to Regulate Transcription of a Type I Collagen Gene Using the Expression Level of a Report Gene as an Index).

$1 \times 10^6$ cells of a normal human fetal skin fibroblast were seeded on a 100 mm dish and cultured at 37° C. overnight under 5% $CO_2$ atmosphere in a Dulbecco's-MEM (Nissui Seiyaku, catalogue No. 05919) medium containing 10(v/v) % heat-inactivated bovine fetal serum (hereinafter, referred to as FBS; Gibco, catalogue No. 21140-079) (hereinafter, this medium is referred to as D-MEM(+)). Then, the medium was replaced with a Dulbecco's-MEM medium not containing FBS (hereinafter, this medium is referred to as D-MEM(−)).

To 300 μl of D-MEM(−) were added 5 μg of COL-Luc and 5 μg of pCMV-β-gal (Invitrogen, catalogue No. 10586-014), and the resulting mixed solution was allowed to stand at room temperature for 5 minutes (solution 1). To 300 μl of D-MEM (−) was added 20 μl of Lipofectine (Gibco, catalogue No. 18292-011), and the resulting mixed solution was allowed to stand at room temperature for 45 minutes (solution 2). Then, the solution 1 and the solution 2 were mixed. After the mixture was allowed to stand at room temperature for 10 minutes, 5.4 ml of D-MEM(−) was added to thereto, followed by mixing. The mixed solution was added to the normal human fetal skin fibroblasts, and the cells were cultured at 37° C. under 5% $CO_2$ atmosphere. After 6 hours, the culture supernatant was removed from the dish, and the cells were washed with PBS twice. To the dish was added 1 ml of PBS containing 0.25% trypsin, and the cells were scraped off the dish. To the scraped cells was added D-MEM(+), and these were mixed well. The mixture was dispensed into a 12-well plate at 1 ml per well, and the plate was incubated at 37° C. overnight under 5% CO$_2$ atmosphere. On the next day, each well washed with D-MEM(-) twice, and this was replaced with 1 ml of a Dulbecco's-MEM medium containing 0.1% FBS (hereinafter, this medium is referred to as D-MEM (0.1%)).

To the thus cultured cells was added 10 μl of a 100 μM solution of the present compound represented by the compound number 1a), (2a), (4a), (5a), (7a) to (10a), (14a), (15a), (21a), (22a), (24a), (25a), (33a), (36a), (1b), (2b), (14b) to (16b), (19b), (20b), (14d), (15d), (21d), (22d), (24d), (25d), (32d), (33d), (36d), (17e) or (18e) in dimethyl sulfoxide (hereinafter, DMSO) (final concentration 1 μM). As a control, only 10 μl of DMSO was added.

After one hour, 10 μl of a 0.5 μg/ml aqueous solution of TGF-β (Pepro Tech) or distilled water was added to the well, and the plate was further incubated at 37° C. for 40 hours under 5% CO$_2$ atmosphere. After the incubated cells were washed with PBS twice, 200 μl of a cell lysing agent (Toyo Inc., catalogue No. PD10) was added thereto and the cells were scraped. The scraped cells were recovered as a cell suspension, and the suspension was centrifuged (15,000 rpm, 4° C., 5 min) to recover a supernatant. The recovered supernatant was transferred to a 96-well plate at 50 μl per well, and then 50 μl of a Luc assay solution (20 mM Tricine (pH 7.8), 2.67 mM MgSO$_4$, 0.1 mM EDTA, 33.3 mM DTT, 270 μM Coenzyme A, 530 μM ATP, 470 μM Luciferin) was automatically dispensed into the plate using MICROLUMAT LB96P (manufactured by EG&G BERTHOLD). Luminescence in each well was measured (Delay: 1.6 second, Meas. Interval: 20 second).

On the other hand, 50 μl of the recovered supernatant or the cell lysing agent was added to 50 μl of a β-gal substrate solution (5.8 mM o-nitrophenyl-beta-D-galactopyranoside, 1 mM MgCl$_2$, 45 mM 2-mercaptoethanol) which had been dispensed into a 96-well plate in advance, and the plate was incubated at 37° C. for 2 hours. Then, an absorbance in each well was measured using a microplate reader at 420 nm. Based on the resulting value, the transcription activity was calculated according to the following equation:

$$\text{Transcription activity} = [\text{luminescence amount(supernatant-added section)} - \text{luminescence amount(cell lysing agent-added section)}] / [420 \text{ nm absorbance (supernatant-added section)} - 420 \text{ nm absorbance (cell lysing agent-added section)}]$$

Then, based on the calculated transcription activity, an inhibitory effect of a test compound on the ability of TGF-β to promote transcription of a Type I collagen gene was calculated as an inhibition percentage according to the following equation:

$$\text{Inhibition percentage} = [\text{transcription activity}(DMSO \text{ and } TGF\text{-}\beta\text{-added test section}) - \text{transcription activity (compound and } TGF\text{-}\beta\text{-added test section})] / [\text{transcription activity }(DMSO \text{ and } TGF\text{-}\beta\text{-added test section}) - \text{transcription activity}(DMSO \text{ and } TGF\text{-}\beta \text{ non-added test section})] \times 100$$

The inhibition percentages of the present compounds represented by the compound number (1a), (2a), (4a), (5a), (7a) to (10a), (14a), (15a), (21a), (22a), (24a), (25a), (33a), (36a), (1b), (2b), (14b) to (16b), (19b), (20b), (14d), (15d), (21d), (22d), (24d), (25d), (32d), (33d), (36d), (17e) or (18e) were 70 or more. It was found that these compounds can inhibit the ability of TGF-β to promote transcription of a Type I collagen gene, and then can suppress transcription of a Type I collagen gene.

Example 5

Improvement of Chronic Renal Failure by Administration of the Present Compound (1) Preparation of anti-Thy-1 Antibody (IgG)

IgG was purified from an ascites-lyophilized powder (CEDARLANE, lot No. 05122) containing an anti-rat CD90 (Thy1.1) monoclonal antibody using MAbTrap kit (Amersham Biosciences, catalogue No. 17-1128-01).

6 ml of a binding buffer was added to 3 ml of ascites to sufficiently recover it, and this was passed through a 0.22 μm filter. The resulting solution was applied to a pre-bufferized column, and the column was then washed with 10 ml of a binding buffer. Thereafter, the column was eluted with 5 ml of an elution buffer. From washing, each 1 ml was fractionated, and the protein concentration of each fraction was measured using bovine serum albumin as a standard. A single peak was confirmed from an elution pattern, and an IgG fraction was dialyzed against a physiological saline overnight at 4° C. The protein concentration of the resulting anti-Thy-1 antibody (IgG) was calculated.

(2) Administration of anti-Thy-1 Antibody (IgG) and Compound

The present compounds represented by the compound numbers (1a), (4a), (9a), (14a), (21a), (33a), (19b) or (21d) (hereinafter, referred to as the present compound (1a), (4a), (9a), (14a), (21a), (33a), (19b) or the present compound (21d), respectively) and a corn oil which is a medium were weighed. These were mixed using a mortar and a pestle to prepare a 3 mg/kg solution. Using four 7-week old male Wistar rats [Nippon Charles River] per group, 60 μg/ml of the anti-Thy-1 antibody (IgG) or a physiological saline was intravenously injected via a tail vein at 5 ml/kg. Immediately after administration of the anti-Thy-1 antibody (IgG) or a physiological saline, the present compound or a corn oil was repeatedly orally administered for 7 days at 5 ml/kg. A dose of the present compound was 15 mg/kg/day.

(3) Quantization of mRNA of Type I Collagen Gene in Renal Glomerulus

On the next day of final administration, a rat reared as described in the above (2) was slaughtered by collection of whole blood, and kidneys were isolated. A whole RNA was separated from the cortex of the isolated kidney using RNeasy Mini Kit (QIAGEN, catalogue No. 74106). To 5 µl (50 ng) of the separated whole RNA were added 1 µl of 20 µM oligo dT and 4 µl of RNase-free distilled water. After the mixture was incubated at 65° C. for 5 minutes, it was immediately ice-cooled. To 10 µl of the solution were added 4 µl of 5× buffer, 2.4 µl of $MgCl_2$, 1 µl of 10 mM dNTP, 1 µl of RNasin, 1 µl of Improm II and 0.6 µl of RNase-free distilled water (all available from Promega), and a reverse transcription reaction was performed under the condition of at 25° C. for 5 minutes, at 42° C. for 1 hour, and at 70° C. for 15 minutes.

Into 5 µl of the reverse transcription reaction solution were mixed each 2 µl of each 1.25 pmol/µl of primers represented by SEQ ID NOS: 3 and 4, 1.25 µl of a probe (FAM-ctcgccttca tgcgcctgct agc-TAMRA) for detecting DNA of a Type I collagen gene represented by SEQ ID No:5, each 0.25 µl of Rodent GAPDH primers, 0.25 µl of a Rodent GAPDH probe, 12.5 µl of TaqMan Universal PCR Master Mix (all available from Applied Biosystem) and 1.5 µl of sterilized water in a well of Optical 96-Well Reaction Plate (Applied Biosystem, catalogue No. N801-0560). As a standard, in place of 5 µl of the reverse transcription reaction solution, each 5 µl of 500, 250, 125, 62.5, 31.25, 15.625 ng/µl rat renal cortex cDNA which had been prepared in advance was used. Thereafter, using Gene Amp 7900 (Applied Biosystem), PCR was performed under the condition of at 50° C. for 5 minutes, and 40 cycles in which one cycle is at 95° C. for 15 seconds and at 60° C. for 1 minute. For quantization, a standard straight line was made, the Type I collagen and GAPDH amounts of each sample were calculated, and the transcription amount was calculated according to the following equation:

Type I collagen transcription amount=Type I collagen amount/GAPDH amount

For statistical treatment of the resulting result, F-test of a variance ratio was performed between two groups of the anti-Thy-1 antibody and corn oil-administered groups and other each group. When there is no significant difference in variance, Student test (one-tailed) was performed and, when there is a significant difference in variance, Aspin-Welch test (one-tailed) was performed. Results are shown in Table 3.

It was found that the present compound (1a), (4a), (9a), (14a), (21a), (33a), (19b) or (21d) have the ability to improve chronic renal failure.

TABLE 3

| Group | Anti-Thy-1 antibody | Administrated substance | mRNA of collagen gene | Test results |
|---|---|---|---|---|
| Control group | + | Corn oil | 5.6 | — |
| Present compound (1a) administered group | + | Present compound (1a) | 1.9 | $p < 0.01$ |
| Present compound (4a) administered group | + | Present compound (4a) | 3.2 | $p < 0.01$ |
| Present compound (9a) administered group | + | Present compound (9a) | 3.4 | $p < 0.05$ |
| Present compound (14a) administered group | + | Present compound (14a) | 2.2 | $p < 0.01$ |
| Present compound (21a) administered group | + | Present compound (21a) | 1.7 | $p < 0.01$ |
| Present compound (33a) administered group | + | Present compound (33a) | 3.3 | $p < 0.01$ |
| Present compound (19b) administered group | + | Present compound (19b) | 2.9 | $p < 0.05$ |
| Present compound (21d) administered group | + | Present compound (21d) | 2.2 | $p < 0.05$ |
| Normal group | − | Corn oil | 1.7 | $p < 0.01$ |

INDUSTRIAL APPLICABILITY

According to the present invention, it is possible to develop and provide a composition which decreases expression of a Type I collage gene in a tissue to induce a reduction in accumulation of collagen and thereby improves tissue fibrosis (i.e. a collagen accumulation-suppressing agent and a fibrosing disease-treating agent).

The invention claimed is:

1. A cinnamoyl compound represented by the formula (I):

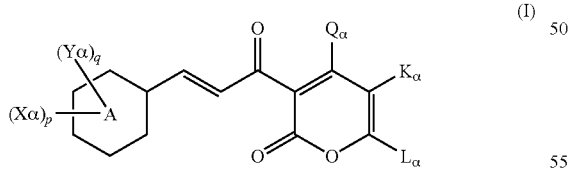

wherein:

(I) A represents a phenyl ring or a pyridyl ring; and in $(Y_\alpha)_q$, $Y_\alpha$ is a substituent on a carbon atom and represents a group included in the following $X_0$ group or $Y_0$ group, q represents 0, 1, 2, 3 or 4, and $Y_\alpha$s are the same or different when q is 2 or more and the adjacent two same or different $Y_\alpha$s together may form a group included in the $Z_0$ group to be fused to the A ring when q is 2 or more; and in $(X_\alpha)_p$, $X_\alpha$ is a substituent on a carbon atom and represents $a_{3\text{-}1}$-$CH_2$—CO—NH- (wherein $a_{3\text{-}1}$ represents a C1-C10 alkoxy group), p represents 1, 2, 3, 4 or 5, and $X_\alpha$s may be the same or different when p is 2 or more; and the sum of p and q is 5 or less;

(1) the $X_0$ group: a $M_a$-group, wherein $M_a$ represents a $R_b$- group (wherein $R_b$ represents a C1-C10 alkyl group optionally substituted with a halogen atom), a halogen atom, a nitro group, a cyano group, a hydroxy group, a $R_c$—$B_a$—$R_d$- group (wherein $R_c$ represents a C1-C10 alkyl group optionally substituted with a halogen atom, $B_a$ represents an oxy group, a thio group, a sulfinyl group or a sulfonyl group, and $R_d$ represents a single bond or a C1-C10 alkylene group), a HOR$_d$- group (wherein $R_d$ is as defined above), a $R_e$—CO—$R_d$- group (wherein $R_e$ represents a hydrogen atom, or a C1-C10 alkyl group optionally substituted with a halogen atom, and $R_d$ is as defined above), a $R_e$—CO—O—$R_d$- group (wherein $R_e$ and $R_d$ are as defined above), a $R_e$O—CO—$R_d$- group (wherein $R_e$ and $R_d$ are as defined above), a HO—CO—CH=CH- group, a $R_e R_e$'N—$R_d$- group (wherein $R_e$ and $R_e$' are the same or different, $R_e$ is as defined above, $R_e$' has the same meaning as $R_e$ has, and $R_d$ is as defined above), a $R_e$—CO—$NR_e'$—$R_d$- group (wherein $R_e$, $R_e'$ and $R_d$ are as defined above), a $R_bO$—CO—N($R_e$)—$R_d$- group (wherein $R_b$, $R_e$ and $R_d$ are as defined above), a $R_eR_e'N$—CO—$R_d$- group (wherein $R_e$, $R_e'$ and $R_d$ are as defined above), a $R_eR_e'N$—CO—$NR_e''$—$R_d$— group (wherein $R_e$, $R_e'$ and $R_e''$ are the same or different, $R_e$ and $R_e'$ are as defined above, $R_e''$ has the same meaning as $R_e$ has, and $R_d$ is as defined above), a $R_eR_e'N$—C(=$NR_e''$)—$NR_e'''$—$R_d$- group (wherein $R_e$, $R_e'$, $R_e''$ and $R_e'''$ are the same or different, $R_e$, $R_e'$ and $R_e''$ are as defined above, $R_e'''$ has the same meaning as $R_e$ has, and $R_d$ is as defined above), a $R_b$—$SO_2$—$NR_e$—$R_d$— group (wherein $R_b$, $R_e$ and $R_d$ are as defined above), a $R_eR_e'N$—$SO_2$—$R_d$— group (wherein $R_e$, $R_e'$ and $R_d$ are as defined above), a C2-C10 alkenyl group or a C2-C10 alkynyl group;

(2) the $Y_0$ group: a $M_{b0}$-$R_d$- group, wherein $M_{b0}$ represents a $M_{c0}$-group wherein $M_{co}$ represents a $M_{do}$-$R_d'$- group (wherein $M_{do}$ represents a 6 to 10-membered aryl group optionally substituted with a $M_a$- group (wherein $M_a$ is as defined above), a 5 to 10-membered heteroaryl group optionally substituted with a $M_a$- group (wherein $M_a$ is as defined above), a 3 to 10-membered cyclic hydrocarbon or heterocyclic group optionally substituted with a $M_a$- group (wherein $M_a$ is as defined above) and optionally containing an unsaturated bond, a $(b_0)$- group

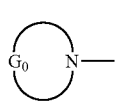

(in the $(b_0)$- group, $G_0$ forms an optionally substituted, saturated or unsaturated, nonaromatic 5 to 14-membered cyclic hydrocarbon or heterocyclic ring), a $(c_0)$- group

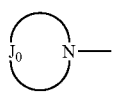

(in the $(C_0)$- group, $J_0$ forms a 5 to 7-membered aromatic ring optionally containing a nitrogen atom), a $(d_0)$- group

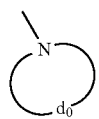

(wherein $d_0$ forms a 5 to 12-membered hydrocarbon ring which is substituted with a carbonyl group or a thiocarbonyl group and further which may be optionally substituted with an oxy group, a thio group, a —$NR_1$- group {wherein $R_1$ represents a hydrogen atom, a C1-C10 alkyl group, a C2-C10 alkyl group substituted with a halogen atom or a $R_2$—$B_1$- group (wherein $R_2$ represents a C1-C10 alkyl group, a C3-C10 alkenyl group or a C3-C10 alkynyl group, and $B_1$ represents an oxy group, a thio group, a sulfinyl group or a sulfonyl group), a C3-C10 alkenyl group, or a C3-C10 alkynyl group}, a sulfinyl group or a sulfonyl group) or a$(e_0)$-group

{wherein $e_0$ forms a 5 to 12-membered hydrocarbon ring optionally substituted with a carbonyl group, a thiocarbonyl group, an oxy group, a thio group, a —$NR_1$- group (wherein $R_1$ is as defined above), a sulfinyl group or a sulfonyl group};
and $R_d'$ is the same as or different from $R_d$ and has the same meaning as $R_d$ has)), a $M_{c0}$-$B_a$- group (wherein $M_{c0}$ and $B_a$ are as defined above), a $M_{c0}$-CO- group (wherein $M_{c0}$ is as defined above), a $M_{c0}$-CO—O- group (wherein $M_{c0}$ is as defined above), a $M_{c0}O$—CO- group (wherein $M_{c0}$ is as defined above), a $M_{c0}R_eN$- group (wherein $M_{c0}$ and $R_e$ are as defined above), a $M_{c0}$-CO—$NR_e$- group (wherein $M_{c0}$ and $R_e$ are as defined above), a $M_{c0}O$—CO—$NR_e$- group (wherein $M_{c0}$ and $R_e$ are as defined above), a $M_{c0}R_eN$—CO- group (wherein $M_{c0}$ and $R_e$ are as defined above), a $M_{c0}R_eN$—CO—$NR_e'$- group (wherein $M_{c0}$, $R_e$ and $R_e'$ are as defined above), a $M_{c0}R_eN$—C(=$NR_e'$)—$NR_e''$- group (wherein $M_{c0}$, $R_e$, $R_e'$ and $R_e''$ are as defined above), a $M_{c0}$-$SO_2$—$NR_e$- group (wherein $M_{c0}$ and $R_e$ are as defined above) or a $M_{c0}R_eN$—$SO_2$- group (wherein $M_{c0}$ and $R_e$ are as defined above), and $R_d$ is as defined above;

(3) the $Z_0$ group: a 5 to 12-membered cyclic hydrocarbon or heterocyclic ring optionally substituted with a halogen atom, a C1-C10 alkoxy group, a C3-C10 alkenyloxy group, a C3-C10 alkynyloxy group, a carbonyl group, a thiocarbonyl group, an oxy group, a thio group, a sulfinyl group or a sulfonyl group, which is an aromatic or nonaromatic and monocyclic or fused ring and which is fused to the A ring;

(II) $Q_\alpha$ represents an optionally substituted hydroxy group, or an optionally substituted amino group;

(III) $K_\alpha$ and $L_\alpha$ are the same or different, and represent a hydrogen atom, or a substituent on a carbon atom, or $K_\alpha$ and $L_\alpha$ may form a C1-C10 alkylene group optionally having a substituent or a C1-C10 alkenylene group optionally having a substituent; and the term "as defined above" used for the same symbols among plural substituents means that the plural substituents independently represent the same meaning as that described above and, among the plural substituents, although the selection range of substituents to be selected is the same, selected substituents may be the same or different as long as they are selected within the range.

2. A cinnamoyl compound represented by the formula (II):

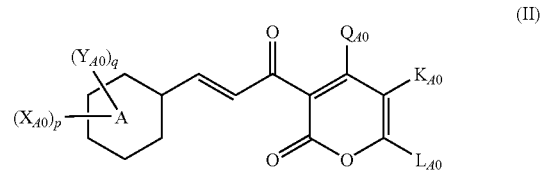

wherein:

(I) A represents a phenyl ring or a pyridyl ring;

(II) in $(X_{A0})_p$, $X_{A0}$ is a substituent on a carbon atom and represents $a_{3-1}$-CH$_2$—CO—NH— (wherein $a_{3-1}$ represents a C1-C10 alkoxy group) and p represents 1, 2, 3, 4 or 5, and when p is 2 or more, $X_{A0}$s are the same or different;

(III) in $(Y_{A0})_q$, $Y_{A0}$ is a substituent on a carbon atom and represents a group included in the following $X_0$ group and $Y_0$ group, q represents 0, 1, 2, 3 or 4, the sum of p (wherein p is as defined above) and q is 5 or less, $Y_{A0}$s are the same as or different when q is 2 or more, and the adjacent two same or different $Y_{A0}$s may form a group included in the $Z_0$ group to be fused to the A ring when q is 2 or more;

(1) the $X_0$ group: a $M_a$- group, wherein $M_a$ represents a $R_b$- group (wherein $R_b$ represents a C1-C10 alkyl group optionally substituted with a halogen atom), a halogen atom, a nitro group, a cyano group, a hydroxy group, a $R_c$—$B_a$—$R_d$- group (wherein $R_c$ represents a C1-C10 alkyl group optionally substituted with a halogen atom, $B_a$ represents an oxy group, a thio group, a sulfinyl group or a sulfonyl group, and $R_d$ represents a single bond or a C1-C10 alkylene group), a HOR$_d$- group (wherein $R_d$ is as defined above), a $R_e$—CO—$R_d$- group (wherein $R_e$ represents a hydrogen atom, or a C1-C10 alkyl group optionally substituted with a halogen atom, and $R_d$ is as defined above), a $R_e$—CO—O—$R_d$- group (wherein $R_e$ and $R_d$ are as defined above), a $R_e$O—CO—$R_d$- group (wherein $R_e$ and $R_d$ are as defined above), a HO—CO—CH=CH- group, a $R_eR_e'$N—$R_d$- group (wherein $R_e$ and $R_e'$ are the same or different, $R_e$ is as defined above, $R_e'$ has the same meaning as $R_e$ has, and $R_d$ is as defined above), a $R_e$—CO—NR$_e'$—$R_d$- group (wherein $R_e$, $R_e'$ and $R_d$ are as defined above), a $R_b$O—CO—N(R$_e$)—$R_d$- group (wherein $R_b$, $R_e$ and $R_d$ are as defined above), a $R_eR_e'$N—CO—$R_d$- group (wherein $R_e$, $R_e'$ and $R_d$ are as defined above), a $R_eR_e'$N—CO—NR$_e''$—$R_d$- group (wherein $R_e$, $R_e'$ and $R_e''$ are the same or different, $R_e$ and $R_e'$ are as defined above, $R_e''$ has the same meaning as $R_e$ has, and $R_d$ is as defined above), a $R_eR_e'$N—C(=NR$_e''$)—NRe'''—$R_d$- group (wherein $R_e$, $R_e'$, $R_e''$ and $R_e'''$ are the same or different, $R_e$, $R_e'$ and $R_e''$ are as defined above, $R_e'''$ has the same meaning as $R_e$ has, and $R_d$ is as defined above), a $R_b$—SO$_2$—NR$_e$—$R_d$- group (wherein $R_b$, $R_e$ and $R_d$ are as defined above), a $R_eR_e'$N—SO$_2$—$R_d$- group (wherein $R_e$, $R_e'$ and $R_d$ are as defined above), a C2-C10 alkenyl group or a C2-C10 alkynyl group;

(2) the $Y_0$ group: a $M_{b0}$-$R_d$- group, wherein $M_{b0}$ represents a $M_{c0}$- group (wherein $M_{c0}$ represents a $M_{d0}$-$R_d'$- group (wherein $M_{d0}$ represents a 6 to 10-membered aryl group optionally substituted with a $M_a$- group (wherein $M_a$ is as defined above), a 5 to 10-membered heteroaryl group optionally substituted with a $M_a$- group (wherein $M_a$ is as defined above), a 3 to 10-membered cyclic hydrocarbon or heterocyclic group which is optionally substituted with a $M_a$- group (wherein $M_a$ is as defined above) and which optionally contains an unsaturated bond, or a $(b_o)$- group

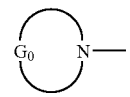

(wherein $(b_o)$ forms as defined above), a $(c_o)$- group

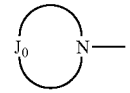

(wherein $(c_o)$ forms as defined above), a $(d_o)$- group

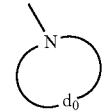

{wherein $d_o$ forms a 5 to 12-membered hydrocarbon ring which is substituted with a carbonyl group or a thiocarbonyl group and further which may be optionally substituted with an oxy group, a thio group, a —NR$_1$- group (wherein $R_1$ is a hydrogen atom, or a C1-C10 alkyl group, or a C2-C10 alkyl group substituted with a halogen atom or a $R_2$—$B_1$-group (wherein $R_2$ represents a C1-C10 alkyl group, a C3-C10 alkenyl group or a C3-C10 alkynyl group, and $B_1$ represents an oxy group, a thio group, a sulfinyl group or a sulfonyl group), or a C3-C10 alkenyl group, or a C3-C10 alkynyl group), a sulfinyl group or a sulfonyl group} or a $(e_0)$- group

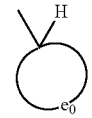

{wherein $e_0$ forms a 5 to 12-membered hydrocarbon ring optionally substituted with a carbonyl group, a thiocarbonyl group, an oxy group, a thio group, a —NR$_1$- group (wherein $R_1$ is as defined above), a sulfinyl group or a sulfonyl group}, and $R_d'$ is the same as or different from $R_d$ and has the same meaning as $R_d$ has)), a $M_{c0}$-$B_a$- group (wherein $M_{c0}$ and $B_a$ are as defined above), a $M_{c0}$-CO- group (wherein $M_{c0}$ is as defined above), a $M_{c0}$-CO—O- group (wherein $M_{c0}$ is as defined above), a $M_{c0}$O—CO- group (wherein $M_{c0}$ is as defined above), a $M_{c0}R_e$N- group (wherein $M_{c0}$ and $R_e$ are as defined above), a $M_{c0}$-CO—NR$_e$- group (wherein $M_{c0}$ and $R_e$ are as defined above), a $M_{c0}$O—CO—NR$_e$- group (wherein $M_{c0}$ and $R_e$ are as defined above), a $M_{c0}R_e$N—CO- group (wherein $M_{c0}$ and $R_e$ are as defined above), a $M_{c0}R_e$N—CO—NR$_e'$- group (wherein $M_{c0}$, $R_e$ and $R_e'$ are as defined above), a $M_{c0}R_e$N—C(=NR$_e'$)—NR$_e''$- group (wherein $M_{c0}$, $R_e$, $R_e'$ and $R_e''$ are as defined above), a $M_{c0}$-SO$_2$—NR$_e$- group (wherein $M_{c0}$ and $R_e$ are as defined above) or a $M_{c0}R_eN$—$SO_2$- group (wherein $M_{co}$ and $R_e$ are as defined above), and $R_d$ is as defined above;

(3) the $Z_0$ group: a 5 to 12-membered cyclic hydrocarbon or heterocyclic ring optionally substituted with a halogen atom, a C1-C10 alkoxy group, a C3-C10 alkenyloxy group, a C3-C10 alkynyloxy group, a carbonyl group, a thiocarbonyl group, an oxy group, a thio group, a sulfinyl group or a sulfonyl group, which is an aromatic or nonaromatic and monocyclic or fused ring and which is fused to the A ring;

(IV) $Q_{40}$ represents a hydroxyl group, a $(b_0)$- group (wherein $(b_0)$ is as defined above), an $A_9$-$B_6$—$B_e$- group (wherein $A_9$ and $B_6$ are as defined above, and $B_c$ represent an oxy group or a —$N((O)_mR_1)$- group (wherein m and $R_1$ are as defined above), provided that $B_c$ is not a sulfonyl group when $A_9$ is a hydrogen atom), an $A_7$"-$SO_2$—$B_c$- group (wherein $A_7$" and $B_c$ are as defined above), an $A_8$-$SO_2$—$B_c$- group (wherein $A_8$ and $B_c$ are as defined above, provided that $A_8$ is not a hydrogen atom), a $R_1R_1'N$—$SO_2$—$B_c$- group (wherein $R_1$, $R_1'$ and $B_c$ are as defined above), a $(b_0)$-$SO_2$—$B_c$- group (wherein $(b_0)$ and $B_c$ are as defined above), an $A_9'$-$B_c$- group (wherein $A_9'$ and $B_c$ are as defined above), a $D_5$-$R_4$—$B_c$- group (wherein $D_5$, $R_4$ and $B_c$ are as defined above), a $M_{c0}$-$B_3$—$B_c$- group (wherein $M_{c0}$, $B_3$ and $B_c$ are as defined above) or a $M_{c0}$-$B_c$- group (wherein $M_{c0}$ and $B_c$ are as defined above);

(V) $K_{A0}$ represents a hydrogen atom, a halogen atom, or a C10 alkyl group, $L_{A0}$ represents a hydrogen atom, or a $M_{b0}$-group ($M_{b0}$ is as defined above), or $K_{A0}$ and $L_{A0}$ may form a C1-C10 alkylene group, or a C1-C10 alkenylene group optionally substituted with single or the same or different plural $M_a$ groups; and the term "as defined above" used for the same symbols among plural substituents means that the plural substituents independently represent the same meaning as that described above and, among the plural substituents, although the selection range of substituents to be selected is the same, selected substituents may be the same or different as long as they are selected within the range.

3. A cinnamoyl compound represented by the formula (III):

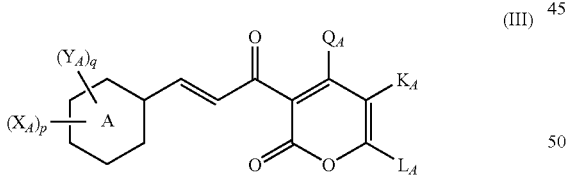

(III)

wherein:

(I) A represents a phenyl ring or a pyridyl ring;

(II) in $(X_A)_p$, $X_A$ is a substituent on a carbon atom and represents $a_{3-1}$-$CH_2$—CO—NH— (wherein $a_{3-1}$ represents a C1-C10 alkoxy group) and p represents 1, 2, 3, 4 or 5, and $X_A$s are the same or different when p is 2 or more;

(III) in $(Y_A)_q$, $Y_A$ is a substituent on a carbon atom and represents a group included in the following X group or Y group, q represents 0, 1, 2, 3 or 4, the sum of p (wherein p is as defined above) and q is 5 or less, $Y_A$s are the same or different when q is 2 or more, and the adjacent two same or different $Y_A$s together may form a group included in the Z group to be fused to the A ring when q is 2 or more, (1) the X group: a $M_a$- group wherein $M_a$ represents a $R_b$- group (wherein $R_b$ represents a C1-C10 alkyl group optionally substituted with a halogen atom), a halogen atom, a nitro group, a cyano group, a $R_c$—$B_a$—$R_d$- group (wherein $R_c$ represents a C1-C10 alkyl group optionally substituted with a halogen atom, $B_a$ represents an oxy group, a thio group, a sulfinyl group or a sulfonyl group, and $R_d$ represents a single bond or a C1-C10 alkylene group), a HOR$_d$- group (wherein $R_d$ is as defined above), a $R_e$—CO—$R_d$- group (wherein $R_e$ represents a hydrogen atom, or a C1-C10 alkyl group optionally substituted with a halogen atom, and $R_d$ is as defined above), a $R_e$—CO—O—$R_d$- group (wherein $R_e$ and $R_d$ are as defined above), a $R_eO$—CO—$R_d$- group (wherein $R_e$ and $R_d$ are as defined above), a HO—CO—CH=CH- group, a $R_eR_e'N$—$R_d$- group (wherein $R_e$ and $R_e'$ are the same or different, $R_e$ is as defined above, $R_e'$ has the same meaning as $R_e$ has, and $R_d$ is as defined above), a $R_e$—CO—$NR_e'$—$R_d$- group (wherein $R_e$, $R_e'$ and $R_d$ are as defined above), a $R_bO$—CO—$N(R_e)$—$R_d$- group (wherein $R_b$, $R_e$ and $R_d$ are as defined above), a $R_eR_e'N$—CO—$R_d$- group (wherein $R_e$, $R_e'$ and $R_d$ are as defined above), a $R_eR_e'N$—CO—$NR_e''$—$R_d$- group (wherein $R_e$, $R_e'$ and $R_e''$ are the same or different, $R_e$ and $R_e'$ are as defined above, $R_e''$ has the same meaning as $R_e$ has, and $R_d$ is as defined above), a $R_eR_e'N$—C(=$NR_e''$)—$NRe'''$—$R_d$- group (wherein $R_e$, $R_e'$, $R_e''$ and $R_e'''$ are the same or different, $R_e$, $R_e'$ and $R_e''$ are as defined above, $R_e'''$ has the same meaning as $R_e$ has, and $R_d$ is as defined above), a $R_b$—$SO_2$—$NR_e$—$R_d$- group (wherein $R_b$, $R_e$ and $R_d$ are as defined above), a $R_eR_e'N$—$SO_2$—$R_d$- group (wherein $R_e$, $R_e'$ and $R_d$ are as defined above), a C2-C10 alkenyl group or a C2-C10 alkynyl group;

(2) the Y group: a $M_b$-$R_d$-group, wherein $M_b$ represents a $M_c$-group (wherein $M_c$ represents a $M_d$-$R_d'$- group (wherein $M_d$ represents a phenyl group optionally substituted with a $M_a$- group (wherein $M_a$ is as defined above), a pyridyl group optionally substituted with a $M_a$- group (wherein $M_a$ is as defined above), a naphthyl group optionally substituted with a $M_a$- group (wherein $M_a$ is as defined above), a (b)- group (wherein (b) is as defined above), a (c)- group (wherein (c) is as defined above), a (d)- group

(d)

(wherein 1 is 2, 3 or 4, $B_b$ represents an oxy group or a thio group) or an (e)- group

(e)

(wherein 1 and $B_b$ are as defined above), and $R_d'$ is the same as or different from $R_d$ and has the same meaning as $R_d$ has)), a $M_c$-$B_a$- group (wherein $M_c$ and $B_a$ are as defined above), a $M_c$-CO- group (wherein $M_c$ is as defined above), a $M_c$-CO—O- group (wherein $M_c$ is as defined above), a M$_c$O—CO- group (wherein M$_c$ is as defined above), a M$_c$R$_e$N- group (wherein M$_e$ and R$_e$ are as defined above), a M$_c$—CO—NR$_e$- group (wherein M$_c$ and R$_e$ are as defined above), a M$_c$—CO—NR$_e$- group (wherein M$_c$ and R$_e$ are as defined above), a M$_c$R$_e$N—CO- group (wherein M$_c$ and R$_e$ are as defined above), a M$_c$R$_e$N—CO—NR$_e$'- group (wherein M$_c$, R$_e$ and R$_e$' are as defined above), a M$_c$R$_e$N—C(=NR$_e$')—NR$_e$"- group (wherein M$_c$, R$_e$, R$_e$' and R$_e$" are as defined above), a M$_c$—SO$_2$—NR$_e$- group (wherein M$_c$ and R$_e$ are as defined above) or a M$_c$R$_e$N—SO$_2$- group (wherein M$_c$ and R$_e$ are as defined above), and R$_d$ is as defined above;

(3) the Z group:

a —N=C(Y$_a$)—Y$_a$'- group (wherein Y$_a$ represents a hydrogen atom, or a C1-C10 alkyl group optionally substituted with a halogen atom, or a C1-C10 alkoxy group, and Y$_a$' represents an oxy group, a thio group, or an imino group optionally substituted with a C1-C10 alkyl group), a —Y$_b$—Y$_b$'—Y$_b$"- group (wherein Y$_b$ and Y$_b$" are the same or different, and represent a methylene group, an oxy group, a thio group, a sulfinyl group, or an imino group optionally substituted with a C1-C10 alkyl group, and Y$_b$' represents a C1-C4 alkylene group optionally substituted with a halogen atom, or a C1-C4 alkylene group optionally having an oxo group) or a —Y$_c$—O—Y$_c$'—O- group (wherein Y$_c$ and Y$_c$' are the same or different, and represent a C1-C10 alkylene group);

(IV) Q$_A$ represents a hydroxyl group, a (b)- group (wherein (b) is as defined above), an A$_9$-B$_6$—B$_c$- group (wherein A$_9$ and B$_6$ are as defined above, and B$_c$ represents an oxy group or a —N((O)$_m$R$_1$)- group (wherein m and R$_1$ are as defined above, provided that B$_c$ is not a sulfonyl group when A$_9$ is a hydrogen atom), an A$_7$"-SO$_2$—B$_c$- group (wherein A$_7$" and B$_c$ are as defined above), an A$_8$-SO$_2$—B$_c$- group (wherein A$_8$ and B$_c$ are as defined above, provided that A$_8$ is not a hydrogen atom), a R$_1$R$_1$'N—SO$_2$—B$_c$- group (wherein R$_1$, R$_1$' and B$_c$ are as defined above), a (b)-SO$_2$—B$_c$- group (wherein (b) and B$_c$ are as defined above), an A$_9$'-B$_c$- group (wherein A$_9$' and B$_c$ are as defined above), a D$_5$-R$_c$—B$_c$- group (wherein D$_5$, R$_4$ and B$_c$ are as defined above), a M$_c$-B$_3$—B$_c$- group (wherein M$_c$, B$_3$ and B$_c$ are as defined above) or a M$_c$-B$_c$- group (wherein M$_c$ and B$_c$ are as defined above);

(V) K$_A$ represents a hydrogen atom, a halogen atom or a C1-C10 alkyl group, L$_A$ represents a hydrogen atom, a C1-C10 alkyl group or a M$_b$-group (M$_b$ is as defined above), or K$_A$ and L$_A$ may form a C1-C10 alkylene group or a —C(M$_a$')=C(M$_a$")-C(M$_a$''')=C(M$_a$'''')- group (M$_a$', M$_a$", M$_a$''' and M$_a$'''' are the same or different, are the same as or different from M$_a$, and represent a hydrogen atom or M$_a$); and the term "as defined above" used for the same symbols among plural substituents means that the plural substituents independently represent the same meaning as that described above and, among the plural substituents, although the selection range of substituents to be selected is the same, selected substituents may be the same or different as long as they are selected within the range.

4. A cinnamoyl compound represented by the formula (IV):

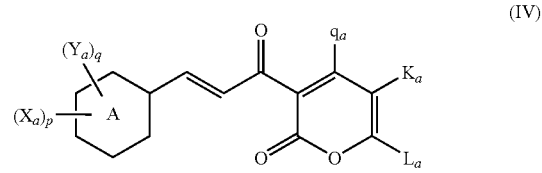

wherein:

A represents a phenyl ring or a pyridyl ring,

X$_a$ is a substituent on a carbon atom, and represents a$_{3-1}$-CH$_2$—CO—NH— (wherein a$_{3-1}$ represents a C1-C10 alkoxy group)

p represents 1, 2 or 3, and when p is 2 or more, X$_a$s are the same or different;

Y$_a$ represents a halogen atom, a nitro group, a r$_0$CO—NH- group (wherein r$_0$ is a C1-C10 alkyl group), a C1-C10 alkyl group or a C1-C10 alkoxy group;

q represents 0, 1 or 2, and when q is 2 or more, Y$_a$s are the same or different;

q$_a$ represents a r$_a$-O- group {wherein r$_a$ represents a hydrogen atom, a C1-C10 alkyl group, a C3-C10 alkenyl group, a C3-C10 alkynyl group, a C1-C10 alkyl group substituted with a r$_0$r$_0$'N—CH$_2$- group (wherein r$_0$ is as defined above and r$_0$' is the same as the different from r$_0$ and has the same meaning as r$_0$ has), a rOCH$_2$- group (wherein r is a hydrogen atom or a C1-C10 alkyl group), a r$_0$-CO- group (wherein r$_0$ is as defined above), a C1-C10 alkoxycarbonyl group, a carboxy group, an aminocarbonyl group or a cyano group, or a r$_3$-r$_1$- group (wherein r$_3$ represents a phenyl group or a pyridyl group, and r$_1$ is a C1-C10 alkylene group)}; a piperidino group; a morpholino group; or a r$_4$r$_4$'N- group (wherein r$_4$ and r$_4$' are the same or different, and represent a hydrogen atom, a C1-C10 alkyl group, a C3-C10 alkenyl group, a C3-C10 alkynyl group, or a C2-C10 alkyl group substituted with a C1-C10 alkoxy group, provided that r$_4$ and r$_4$' are not a hydrogen atom at the same time);

K$_a$ represents a hydrogen atom, a halogen atom or a C1-C10 alkyl group, and L$_a$ represents a hydrogen atom or a C1-C10 alkyl group; or K$_a$ and L$_a$ together may form a C1-C10 alkylene group or a 1,3-butadienylene group;

the term "as defined above" used for the same symbols among plural substituents means that the plural substituents independently represent the same meaning as that described above and, among the plural substituents, although the selection range of substituents to be selected is the same, selected substituents may be the same or different as long as they are selected within the range.

5. A cinnamoyl compound represented by the formula (V):

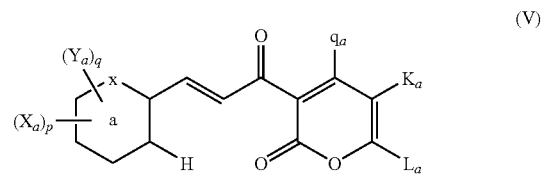

wherein:

a represents a phenyl ring or a pyridyl ring;

x represents a methine group or a nitrogen atom;

$X_a$ is a substituent on a carbon atom, and represents $a_{3-1}$-$CH_2$—CO—NH- (wherein $a_{3-1}$ represents a C1-C10 alkoxy group)

p represents 1, 2 or 3, and when p is 2 or more, $X_a$s are the same or different;

$Y_a$ represents a halogen atom, a nitro group, a $r_0$CO—NH- group (wherein $r_0$ a C1-C10 alkyl group), a C1-C10 alkyl group or a C1-C10 alkoxy group;

q represents 0, 1 or 2, and when q is 2 or more, $Y_a$s are the same or different;

$q_a$ represents a $r_a$-O- group {wherein $r_a$ represents a hydrogen atom, a C1-C10 alkyl group, a C3-C10 alkenyl group, a C3-C10 alkynyl group, a C1-C10 alkyl group substituted with a $r_0r_0'$N—$CH_2$- group (wherein $r_0$ is as defined above and $r_0'$ is the same as the different from $r_0$ and has the same meaning as $r_0$ has), a $rOCH_2$- group (wherein r is a hydrogen atom or a C1-C10 alkylene group), a $r_0$-CO- group (wherein $r_0$ is as defined above), a C1-C10 alkoxycarbonyl group, a carboxy group, an aminocarbonyl group or a cyano group, or a $r_3$-$r_1$- group (wherein $r_3$ represents a phenyl group or a pyridyl group, and $r_1$ is a C1-C10 alkylene group)}; a piperidino group; a morpholino group; or a $r_4r_4'$N- group (wherein $r_4$ and $r_4'$ are the same or different, and represent a hydrogen atom, a C1-C10 alkyl group, a C3-C10 alkenyl group, a C3-C10 alkynyl group, or a C2-C10 alkyl group substituted with a C1-C10 alkoxy group, provided that $r_4$ and $r_4'$ are not a hydrogen atom at the same time);

$t_a$ represents a $r_b$- group (wherein $r_b$ is the same as or different from $r_a$, and has the same meaning as $r_a$ has) or a $r_3'$- group (wherein $r_3'$ is the same as or different from $r_3$, and has the same meaning as $r_3$ has);

$K_a$ represents a hydrogen atom, a halogen atom or a C1-C10 alkyl group, and $L_a$ represents a hydrogen atom or a C1-C10 alkyl group; or $K_a$ and $L_a$ together may form a C1-C10 alkylene group or a 1,3-butadienylene group;

the term "as defined above" used for the same symbols among plural substituents means that the plural substituents independently represent the same meaning as that described above and, among the plural substituents, although the selection range of substituents to be selected is the same, selected substituents may be the same or different as long as they are selected within the range.

6. A 2H-pyran-2-one compound represented by the formula (VI):

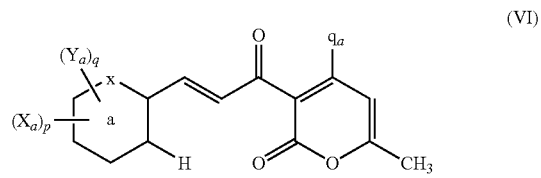

(VI)

wherein:

a represents a phenyl ring or a pyridyl ring;

x represents a methine group or a nitrogen atom;

$X_a$ is a substituent on a carbon atom, and represents $a_{3-1}$-$CH_2$—CO——NH- (wherein $a_{3-1}$ represents a C1-C10 alkoxy group)

p represents 1, 2 or 3, and when p is 2 or more, $X_a$s are the same or different;

$Y_a$ represents a halogen atom, a nitro group, a $r_0$CO—NH- group (wherein $r_0$ is a C1-C10 alkyl group), a C1-C10 alkyl group or a C1-C10 alkoxy group;

q represents 0, 1 or 2, and when q is 2 or more, $Y_a$s are the same or different;

$q_a$ represents a $r_a$-O- group {wherein $r_a$ represents a hydrogen atom, a C1-C10 alkyl group, a C3-C10 alkenyl group, a C3-C10 alkynyl group, a C1-C10 alkyl group substituted with a $r_0r_0'$N—$CH_2$- group (wherein $r_0$ is as defined above and $r_0'$ is the same as the different from $r_0$ and has the same meaning as $r_0$ has), a $rOCH_2$- group (wherein r is a hydrogen atom or a C1-C10 alkyl group), a $r_0$-CO- group (wherein $r_0$ is as defined above), a C1-C10 alkoxycarbonyl group, a carboxy group, an aminocarbonyl group or a cyano group, or a $r_3$-$r_1$- group (wherein $r_3$ represents a phenyl group or a pyridyl group, and $r_1$ is a C1-C10 alkylene group)}; a piperidino group; a morpholino group; or a $r_4r_4'$N- group (wherein $r_4$ and $r_4'$ are the same or different, and represent a hydrogen atom, a C1-C10 alkyl group, a C3-C10 alkenyl group, a C3-C10 alkynyl group, or a C2-C10 alkyl group substituted with a C1-C10 alkoxy group, provided that $r_4$ and $r_4'$ are not a hydrogen atom at the same time);

the term "as defined above" used for the same symbols among plural substituents means that the plural substituents independently represent the same meaning as that described above and, among the plural substituents, although the selection range of substituents to be selected is the same, selected substituents may be the same or different as long as they are selected within the range.

7. A 2H-pyran-2-one compound represented by the formula (VII):

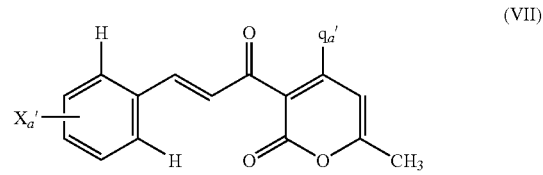

(VII)

wherein:

$X_a'$ represents $a_{3-1}$-$CH_2$—CO—NH— (wherein $a_{3-1}$ represents a C1-C10 alkoxy group).

8. A 2H-1-benzopyran-2-one compound represented by the formula (VIII):

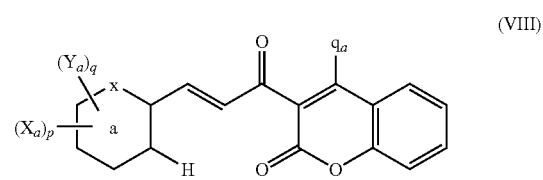

(VIII)

wherein:

a represents a phenyl ring or a pydridyl ring;

x represents a methine group or a nitrogen atom;

$X_a$ is a substituent on a carbon atom, and represents $a_{3-1}$-$CH_2$—CO—NH— (wherein $a_{3-1}$ represents a C1-C10 alkoxy group)

p represents 1, 2 or 3, and when p is 2 or more, $X_a$s are the same or different;

$Y_a$ represents a halogen atom, a nitro group, a $r_0CO-NH-$ group (wherein $r_0$ is a C1-C10 alkyl group), a C1-C10 alkyl group or a C1-C10 alkoxy group;

q represents 0, 1 or 2, and when q is 2 or more, $Y_a$s are the same or different;

$q_a$ represents a $r_a$-O- group {wherein $r_a$ represents a hydrogen atom, a C1-C10 alkyl group, a C3-C10 alkenyl group, a C3-C10 alkynyl group, a C1-C10 alkyl group substituted with a $r_0r_0'N-CH_2$- group (wherein $r_0$ is as defined above and $r_0'$ is the same as the different from $r_0$ and has the same meaning as $r_0$ has), a $rOCH_2$- group (wherein r is a hydrogen atom or a C1-C10 alkyl group), a $r_0$-CO- group (wherein $r_0$ is as defined above), a C1-C10 alkoxycarbonyl group, a carboxy group, an aminocarbonyl group or a cyano group, or a $r_3$-$r_1$- group (wherein $r_3$ represents a phenyl group or a pyridyl group, and $r_1$ is a C1-C10 alkylene group)}; a piperidino group; a morpholino group; or a $r_4r_4'N$- group (wherein $r_4$ and $r_4'$ are the same or different, and represent a hydrogen atom, a C1-C10 alkyl group, a C3-C10 alkenyl group, a C3-C10 alkynyl group, or a C2-C10 alkyl group substituted with a C1-C10 alkoxy group, provided that $r_4$ and $r_4'$ are not a hydrogen atom at the same time);

$t_a$ represents a $r_b$- group (wherein $r_b$ is the same as or different from $r_a$, and has the same meaning as $r_a$ has) or a $r_3'$- group (wherein $r_3'$ is the same as or different from $r_3$, and has the same meaning as $r_3$ has);

$K_a$ represents a hydrogen atom, a halogen atom or a C1-C10 alkyl group, and $L_a$ represents a hydrogen atom or a C1-C10 alkyl group; or $K_a$ and $L_a$ together may form a C1-C10 alkylene group or a 1,3-butadienylene group;

the term "as defined above" used for the same symbols among plural substituents means that the plural substituents independently represent the same meaning as that described above and, among the plural substituents, although the selection range of substituents to be selected is the same, selected substituents may be the same or different as long as they are selected within the range.

9. A 2H-1-benzopyran-2-one compound represented by the formula (IX):

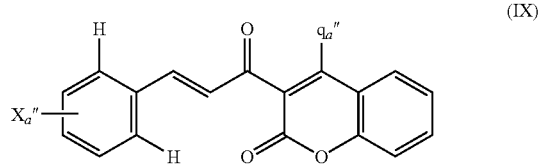

wherein:

$X_a''$ represents $a_{3-1}$-$CH_2$—CO—NH— (wherein $a_{3-1}$ represents a C1-C10 alkoxy group), and $q_a''$ represents a hydroxy group, a C1-C10 alkoxy group or a piperidino group.

10. A 2H-pyran-2-one compound represented by the formula (X):

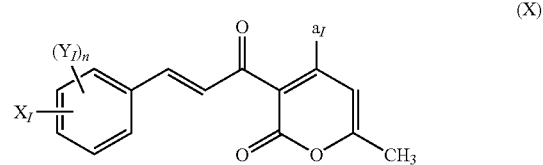

wherein:

$X_1$ represents $a_{3-1}$-$CH_2$—CO—NH— (wherein $a_{3-1}$ represents a C1-C10 alkoxy group), $Y_1$ represents a halogen atom, a nitro group, a C1-C4 alkyl group or a C1-C4 alkoxy group, n represents 0, 1 or 2 and, when n is 2, $Y_1$s may be different.

11. A 2H-1-benzopyran-2-one compound represented by the formula (XI):

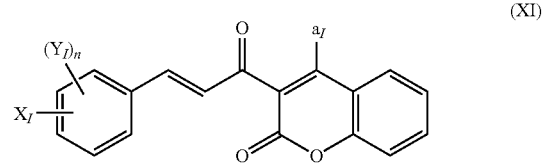

wherein:

$X_1$ represents $a_{3-1}$-$CH_2$—CO—NH— (wherein $a_{3-1}$ represents a C1-C10 alkoxy group), $Y_1$ represents a halogen atom, a nitro group, a C1-C4 alkyl group or a C1-C4 alkoxy group, n represented 0, 1 or 2 and, when n is 2, $Y_1$s may be different.

12. A 2H-pyran-2-one compound represented by the formula (XII):

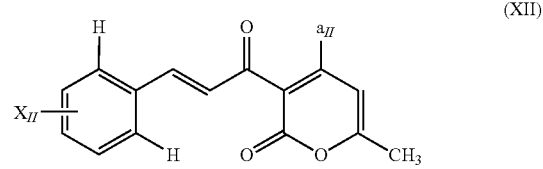

wherein:

$X_{11}$ represents $a_{3-1}$-$CH_2$—CO—NH— (wherein $a_{3-1}$ represents a C1-C10 alkoxy group), and $a_{11}$ represents a hydroxy group, a methoxy group or a morpholino group.

13. A 2H-1-benzopyran-2-one compound represented by the formula (XIII):

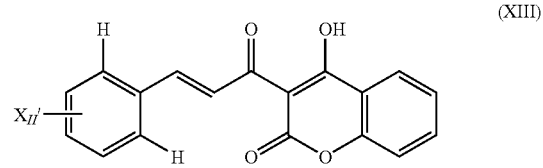

wherein:

$X_{11}'$ represents $a_{3-1}$-$CH_2$—CO—NH— (wherein $a_{3-1}$ represents a C1-C10 alkoxy group).

14. The 2H-pyran-2-one compound according to claim 1 represented by the formula (XVIII):

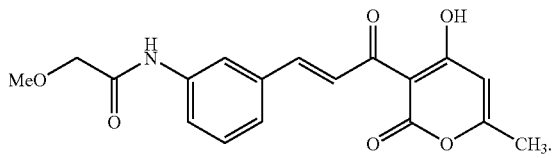
(XVIII)

15. The 2H-1-benzopyran-2-one compound according to claim 1 represented by the formula (XXV):

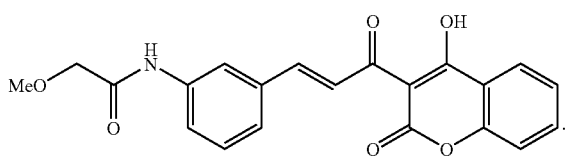
(XXV)

16. A process for producing a cinnamoyl compound represented by the formula (XLVII"):

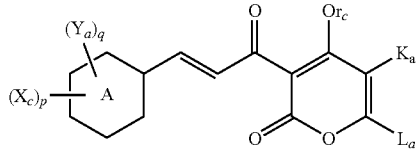
(XLVII")

wherein A, $X_c$, $Y_a$, p, q, $r_c$, $K_a$ and $L_a$ are as defined below, and the term "as defined above (or below)" used for the same symbols among plural substituents means that the plural substituents independently represent the same meaning as that described above (or below) and, among the plural substituents, although the selection range of substituents to be selected is the same, selected substituents may be the same or different as long as they are selected within the range; which comprises reacting a cinnamoyl compound represented by the formula (XLVII):

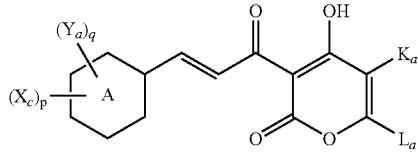
(XLVII)

wherein
A represents a phenyl ring or a pyridyl ring,
$X_c$ is a substituent on a carbon atom, and represents $a_{3-1}$-$CH_2$—CO—N— (wherein $a_{3-1}$ represents a C1-C10 alkoxy group)
p represents 1, 2 or 3, and when p is 2 more, $X_c$s are the same or different;
$Y_a$ represents a halogen atom, a nitro group, a $r_0$CO—NH-group (wherein $r_0$ is a C1-C10 alkyl group), a C1-C10 alkyl group or a C1-C10 alkoxy group;
q represents 0, 1 or 2, and when q is 2 or more, $Y_a$s are the same or different;
$K_a$ represents a hydrogen atom, a halogen atom or a C1-C10 alkyl group, and $L_a$ represents a hydrogen atom or a C1-C10 alkyl group, or
$K_a$ and $L_a$ together may form a C1-C10 alkylene group or a 1,3-butadienylene group, and
the term "as defined above" used for the same symbols among plural substituents means that the plural substituents independently represent the same meaning as that described above and, among the plural substituents, although the selection range of substituents to be selected is the same, selected substituents may be the same or different as long as they are selected within the range, with a compound represented by the formula (XLVII'):

$$r_c\text{-V} \qquad (XLVII')$$

wherein $r_c$ represents a $t_c'$- group {wherein $t_c'$ represents a C1-C10 alkyl group; a C3-C10 alkenyl group; a C3-C10 alkynyl group; a C1-C10 alkyl group substituted with a $r_0r_0'$N—$CH_2$- group (wherein $r_0$ is as defined above and $r_0'$ is the same as the different from $r_0$ and has the same meaning as $r_0$ has), a r$OCH_2$- group (wherein r is a hydrogen atom or a C1-C10 alkyl group), a $r_0$-CO- group (wherein $r_0$ is as defined above), a C1-C10 alkoxycarbonyl group, an aminocarbonyl group or a cyano group; or a $r_3$-$r_1$- group (wherein $r_3$ represents a phenyl group or a pyridyl group, and $r_1$ is a C1-C10 alkylene group)}, and V represents a leaving group, and
the term "as defined above" used for the same symbols among plural substituents means that the plural substituents independently represent the same meaning as that described above and, among the plural substituents, although the selection range of substituents to be selected is the same, selected substituents may be the same or different as long as they are selected within the range.

17. A process for producing a cinnamoyl compound represented by the formula (XLVIII'):

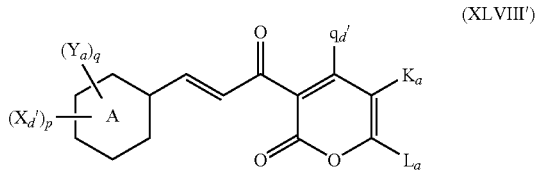
(XLVIII')

wherein:
A is as defined below,
$X_d'$ is a substituent on a carbon atom, and represents $a_{3-1}$-$CH_2$—CO—NH— (wherein $a_{3-1}$ represents a C1-C10 alkoxy group)
p is as defined below and, and when p is 2 or more, $X_d$'s are the same or different,
$Y_a$ and q are as defined below,
$q_d'$ represents a $r_d''$-O- group {wherein $r_d''$ represents a hydrogen atom; a C1-C10 alkyl group; a C3-C10 alkenyl group; a C3-C10 alkynyl group; a C1-C10 alkyl group substituted with a $r_0r_0'$N—$CH_2$- group (wherein $r_0$ and $r_0'$ are as defined below), a r$OCH_2$- group (wherein r is as defined below), a $r_0$-CO- group (wherein $r_0$ is as defined below), a carboxy group, an aminocarbonyl group or a cyano group; or a $r_3$-$r_1$- group (wherein $r_3$ represents a phenyl group or a pyridyl group, and $r_1$ is as defined below)}, a piperidino group, a morpholino group, or a $r_4r_4'N-$ group (wherein $r_4$ and $r_4'$ are as defined below, provided that they are not hydrogen atom at the same time), $K_a$ and $L_a$ are as defined below, and the term "as defined above (or below)" used for the same symbols among plural substituents means that the plural substituents independently represent the same meaning as that described above (or below) and, among the plural substituents, although the selection range of substituents to be selected is the same, selected substituents may be the same or different as long as they are selected within the range;

which comprises hydrolyzing a cinnamoyl compound represented by the formula (XLVIII):

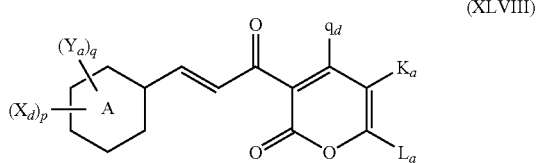

(XLVIII)

wherein:

A represents a benzene ring or a pyridine ring, $X_d$ is a substituent on a carbon atom, and represents an $a_{0d}$-$r_1$-b-$r_1'$- group {wherein $a_{0d}$ represents a $r_2O$—CO- group (wherein $r_2$ represents a C1-C10 alkyl group, or a C2-C10 alkyl group substituted with a hydroxy group), $r_1$ represents a C1-C10 alkylene group, $r_1'$ represents a single bond or a C1-C10 alkylene group, and b represents an oxy group, a thio group, a sulfinyl group, a sulfonyl group or an imino group}, a $r_0O$—COCO—NH- group (wherein $r_0$ represents a C1-C10 alkyl group), an $a_{3d}$-z-NH- group (wherein $a_{3d}$ represents a C1-C10 alkyl group substituted with a C1-C10 alkoxycarbonyl group, and z represents a carbonyl group or a sulfonyl group), or an $a_{4d}$-NHCO- group {wherein $a_{4d}$ represents a C1-C10 alkyl group substituted with a $r_0O$—CO- group (wherein $r_0$ is as defined above), or a $r_0O$—CO-($r_0O$—COCH$_2$)CH- group (wherein $r_0$ is as defined above)}, p represents 1, 2 or 3, and when p is 2 or more, $X_d$s are the same or different, $Y_a$ represents a halogen atom, a nitro group, a $r_0CO$—NH- group (wherein $r_0$ is as defined above), a C1-C10 alkyl group or a C1-C10 alkoxy group, q represents 0, 1 or 2, and when q is 2 or more, $Y_a$ s are the same or different;

$q_d$ represents a $r_d$—O- group {wherein $r_d$ represents a hydrogen atom, a C1-C10 alkyl group, a C3-C10 alkenyl group, a C3-C10 alkynyl group, a C1-C10 alkyl group substituted with a $r_0r_0'N$—CH$_2$- group (wherein $r_0$ is as defined above, and $r_0'$ is the same as or different from $r_0$ and has the same meaning as $r_0$ has), a rOCH$_2$- group (wherein r is as defined above), a $r_0$-CO- group (wherein $r_0$ is as defined above), a C1-C10 alkoxycarbonyl group, a carboxy group, an aminocarbonyl group or a cyano group, or a $r_3$-$r_1$-group (wherein $r_3$ represents a phenyl group or a pyridyl group, and $r_1$ is as defined above)}; a piperidino group; a morpholino group; or a $r_4r_4'N$- group (wherein $r_4$ and $r_4'$ represent a hydrogen atom, a C1-C10 alkyl group, a C3-C10 alkenyl group, a C3-C10 alkynyl group, or a C2-C10 alkyl group substituted with a C1-C10 alkoxy group, provided that they are not a hydrogen atom at the same time), $K_a$ represents a hydrogen atom, a halogen atom or a C1-C10 alkyl group, and $L_a$ represents a hydrogen atom or a C1-C10 alkyl group, or $K_a$ and $L_a$ together may form a C1-C10 alkylene group or a 1,3-butadienylene group, the term "as defined above" used for the same symbols among plural substituents means that the plural substituents independently represent the same meaning as that described above and, among the plural substituents, although the selection range of substituents to be selected is the same, selected substituents may be the same or different as long as they are selected within the range.

18. A process for producing a cinnamoyl compound represented by the formula (XLIX″):

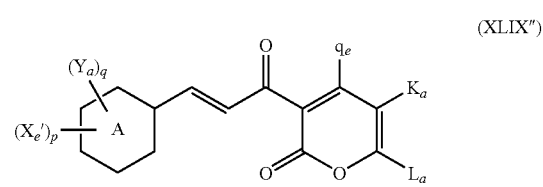

(XLIX″)

wherein $X_e'$ is a substituent on a carbon atom and represents $a_{3-1}$-CH$_2$—CO—NH— (wherein $a_{3-1}$ represents a C1-C10 alkoxy group), and A, $Y_a$, p, q, $q_e$, $K_a$ and $L_a$ are as defined below, and the term "as defined above (or below)" used for the same symbols among plural substituents means that the plural substituents independently represent the same meaning as that described above (or below) and, among the plural substituents, although the selection range of substituents to be selected is the same, selected substituents may be the same or different as long as they are selected within the range;

which comprises reacting a cinnamoyl compound represented by the formula (XLIX):

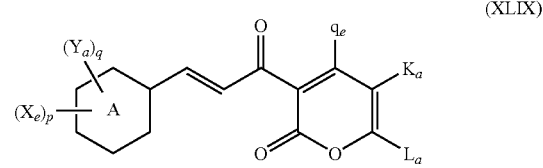

(XLIX)

wherein:

A represents a benzene ring or a pyridine ring, $X_e$ is a substituent on a carbon atom, and represents a H-b″- group (wherein b″ represents an oxy group or a thio group), p represents 1, 2 or 3 and, when p is 2 or more, $X_e$s are the same or different, $Y_a$ represents a halogen atom, a nitro group, a $r_0CO$—NH- group (wherein $r_0$ is a C1-C10 alkyl group), a C1-C10 alkyl group or a C1-C10 alkoxy group, q represents 0, 1 or 2, and when q is 2 or more, $Y_a$ s are the same or different;

$q_e$ represents a $r_e$-O- group {wherein $r_e$ represents a C1-C10 alkyl group, a C3-C10 alkenyl group, a C3-C10 alkynyl group, a C1-C10 alkyl group substituted with a $r_0r_0'N$—CH$_2$- group (wherein $r_0$ is as defined above, and $r_0'$ is the same as or different from $r_0$ and has the same meaning as $r_0$ has), a rOCH$_2$- group (wherein r represents a hydrogen atom or a C1-C10 alkyl group), a $r_0$-CO- group (wherein $r_0$ is as defined above), a C1-C10 alkoxycarbonyl group, an aminocarbonyl group or a cyano group, or a $r_3$-$r_1$- group (wherein $r_3$ represents a phenyl group or a pyridyl group, and $r_1$ represents a C1-C10 alkylene group)}; a piperidino group; a morpholino group; or a $r_4r_4'$N- group (wherein $r_4$ and $r_4'$ represent a hydrogen atom, a C1-C10 alkyl group, a C3-C10 alkenyl group, a C3-C10 alkynyl group, or a C2-C10 alkyl group substituted with a C1-C10 alkoxy group, provided that they are not a hydrogen atom at the same time), $K_a$ represents a hydrogen atom, a halogen atom or a C1-C10 alkyl group, and $L_a$ represents a hydrogen atom or a C1-C10 alkyl group, or $K_a$ and $L_a$ together may form a C1-C10 alkylene group or a 1,3-butadienylene group, and the term "as defined above" used for the same symbols among plural substituents means that the plural substituents independently represent the same meaning as that described above and, among the plural substituents, although the selection range of substituents to be selected is the same, selected substituents may be the same or different as long as they are selected within the range, with a compound represented by the formula (XLIX'):

$$a_{0e}\text{-}r_1''\text{-}V' \qquad (XLIX')$$

wherein $a_{0e}$ represents a methyl group substituted with a C1-C10 alkylthio group, a methyl group substituted with a C1-C10 alkylsulfinyl group, a methyl group substituted with a C1-C10 alkylsulfonyl group, a C2-C10 alkenyl group, a C2-C10 alkynyl group, a $r_2$O—CO- group (wherein $r_2$ represents a C1-C10 alkyl group, or a C2-C10 alkyl group substituted with a hydroxy group), a rr'N—CO- group (wherein r and r' are the same or different, and represent a hydrogen atom or a C1-C10 alkyl group), an $a_1$-NH—CO- group (wherein $a_1$ represents a C2-C10 alkyl group substituted with a C1-C10 alkoxy group), an $a_1'$-CO- group (wherein $a_1'$ represents a morpholino group), a rr'N—CH$_2$- group (wherein r is as defined above, r' is the same as or different from r and has the same meaning as r has), a $r_0$-(O)$_l$—CONH—CH$_2$- group (wherein $r_0$ is as defined above, and l represents 0 or 1), a r-OCH$_2$- group (wherein r is as defined above), a $r_0$—CO- group (wherein $r_0$ is as defined above) or a cyano group, $r_1''$ is the same as or different from $r_1$ and has the same meaning as $r_1$ has, and V' represents a leaving group or a hydroxy group, or 1,3-propanesultone or 1,4-butanesultone the term "as defined above" used for the same symbols among plural substituents means that the plural substituents independently represent the same meaning as that described above and, among the plural substituents, although the selection range of substituents to be selected is the same, selected substituents may be the same or different as long as they are selected within the range.

19. A composition comprising a compound according to claim 1 and an inert carrier.

20. A method for treating tissue fibrosis, which comprises administering an effective amount of a compound according to claim 1 to a mammal in need thereof.

21. A method for growing hair, which comprises administering an effective amount of a compound according to claim 1 to a mammal in need thereof.

22. A method for treating chronic renal failure, which comprises administering a compound according to claim 1 to a mammal in need thereof.

23. A composition comprising a compound according to claim 2 and an inert carrier.

24. A composition comprising a compound according to claim 3 and an inert carrier.

25. A composition comprising a compound according to claim 4 and an inert carrier.

26. A composition comprising a compound according to claim 10 and an inert carrier.

27. A composition comprising a compound according to claim 11 and an inert carrier.

* * * * *

SEQUENCE LISTING

<160> NUMBER OF SEQ ID NOS: 5

<210> SEQ ID NO 1
<211> LENGTH: 32
<212> TYPE: DNA
<213> ORGANISM: Artificial
<220> FEATURE:
<223> OTHER INFORMATION: oligonucleotide

<400> SEQUENCE: 1

-continued

```
<210> SEQ ID NO 2
<211> LENGTH: 28
<212> TYPE: DNA
<213> ORGANISM: Artificial
<220> FEATURE:
<223> OTHER INFORMATION: oligonucleotide

<400> SEQUENCE: 2
ccaaaagctt gcagtcgtgg ccagtacc                                              28

<210> SEQ ID NO 3
<211> LENGTH: 19
<212> TYPE: DNA
<213> ORGANISM: Artificial
<220> FEATURE:
<223> OTHER INFORMATION: oligonucleotide

<400> SEQUENCE: 3
atggtggcag ccagtttga                                                        19

<210> SEQ ID NO 4
<211> LENGTH: 22
<212> TYPE: DNA
<213> ORGANISM: Artificial
<220> FEATURE:
<223> OTHER INFORMATION: oligonucleotide

<400> SEQUENCE: 4
caggtacgca atgctgttct tg                                                    22

<210> SEQ ID NO 5
<211> LENGTH: 23
<212> TYPE: DNA
<213> ORGANISM: Artificial
<220> FEATURE:
<223> OTHER INFORMATION: oligonucleotide

<400> SEQUENCE: 5
ctcgccttca tgcgcctgct agc                                                   23
```